US008440691B2

(12) United States Patent
Gomtsyan et al.

(10) Patent No.: US 8,440,691 B2
(45) Date of Patent: May 14, 2013

(54) TETRAHYDROQUINOLINYL COMPOUNDS THAT INHIBIT VANILLOID RECEPTOR SUBTYPE 1 (VR1) RECEPTOR AND USES THEREOF

(75) Inventors: Arthur Gomtsyan, Vernon Hills, IL (US); Erol K. Bayburt, Gurnee, IL (US); Robert G. Schmidt, Jr., Waukegan, IL (US); Chih-Hung Lee, Vernon Hills, IL (US); Brian S. Brown, Evanston, IL (US); Tammie K. Jinkerson, Kenosha, WI (US); John R. Koenig, Chicago, IL (US); Jerome F. Daanen, Racine, WI (US); Steven P. Latshaw, Round Lake Beach, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 12/875,839

(22) Filed: Sep. 3, 2010

(65) Prior Publication Data
US 2011/0152250 A1 Jun. 23, 2011

Related U.S. Application Data

(62) Division of application No. 11/285,448, filed on Nov. 22, 2005, now Pat. No. 7,812,019.

(60) Provisional application No. 60/630,636, filed on Nov. 24, 2004.

(51) Int. Cl.
*A61K 31/47* (2006.01)
*A61K 31/445* (2006.01)
*A61K 31/415* (2006.01)
*C07D 217/00* (2006.01)
*C07D 215/00* (2006.01)
*C07D 211/00* (2006.01)
*C07D 231/56* (2006.01)

(52) U.S. Cl.
USPC ........... 514/307; 514/311; 514/320; 514/405; 546/139; 546/152; 546/184; 548/361.1

(58) Field of Classification Search ............... 514/307, 514/311, 320, 405; 546/139, 152, 184; 548/361.1
See application file for complete search history.

(56) References Cited

U.S. PATENT DOCUMENTS
5,374,643 A  12/1994 Atwal et al.

FOREIGN PATENT DOCUMENTS
| EP | 0587180 A2 | 3/1994 |
| EP | 0386836 B1 | 1/1997 |
| WO | WO-9808818 | 3/1998 |
| WO | WO-0136403 A1 | 5/2001 |
| WO | WO03097586 A1 | 11/2003 |
| WO | WO2004078744 A3 | 9/2004 |
| WO | WO2007050732 A1 | 5/2007 |

OTHER PUBLICATIONS

Vasil'eva et al. CAS Accession No. 1978:563368.*
Bognar rezso et al., "Flavanoids XII. Synthesis of 4-ureldoflavan and bis (4flavanyl) urea," Acts Chim Acad. Sci, 1963, 223-224, vol. 35.
Caterina, M. J. et al., "Impaired Nociception and Pain Sensation in Mice Lacking the Capsaicin Receptor," Science, 2000, vol. 288, pp. 306-313.
Caterina, M. J. et al., "The Capsaicin Receptor: A Heat-Activated Ion Channel in the Pain Pathway," Nature, 1997, vol. 389 (6653), pp. 816-824.
Caterina, M. J. et al., "The Vanilloid Receptor: A Molecular Gateway to the Pain Pathway," Annual Review of Neuroscience, 2001, vol. 24, pp. 487-517.
Collier, H.O. et al., "The Abdominal Constriction Response and its Suppression by Analgesic Drugs in the Mouse," British Journal of Pharmacology and Chemotherapy, 1968, vol. 32 (2), pp. 295-310.
Dade J., et al., "Synthesis of 2-Substituated Trifluoromethylquinolines for the Evaluation of Leishmanicidal Activity," Chemical & Pharmaceutical Bulletin, 2001, vol. 49 (4), pp. 480-483.
Database Beilstein Beilstein Institute for Organic Chemistry, Frank Furt-Main, DE; XP002507218 Database accession No. brn 355828 abstract & Webster et al: J.Chem.Soc. , 1965, pp. 4785-4789.
Davis, J. B. et al., "Vanilloid Receptor-1 is Essential for Inflammatory Thermal Hyperalgesia," Nature, 2000, vol. 405 (6783), pp. 183-187.
Fowler, C.J., "Intravesical Treatment of Overactive Bladder," Urology, 2000, vol. 55, pp. 60-64.
Hayes, P. et al., "Cloning and Functional Expression of a Human Orthologue of Rat Vanilloid Receptor-1," Pain, 2000, vol. 88, pp. 205-215.
International Search Report for application No. PCT/US05/042545, Mailed on Feb. 19, 2009, 3 pages.
Nolano, M. et al., "Topical Capsaicin in Humans: Parallel Loss of Epidermal Nerve Fibers and Pain Sensation," Pain, 1999, vol. 81, pp. 135-145.
Patini G.A., et al., "Bloisosterism: A Rational Approach in Drug Design," Chemical Reviews, 1996, vol. 96 (8), pp. 3147-3176.
Pircio, A. W. et al., "A New Method for the Evaluation of Analgesic Activity Using Adjuvant-Induced Arthritis in the Rat," European Journal of Pharmacology, 1975, vol. 31 (2), pp. 207-215.
Berge, S. M. et al., "Pharmaceutical Salts," Journal of Pharmaceutical Sciences, 1977, vol. 66 (1), pp. 1-19.
Poste, G. et al., "Lipid Vesicles as Carriers for Introducing Biologically Active Materials into Cells," Methods in Cell Biology, 1976, vol. 14, pp. 33-71.

* cited by examiner

Primary Examiner — Joseph Kosack

(57) ABSTRACT

Compounds that are antagonists of the VR1 receptor, having formula (I)

or a pharmaceutically acceptable salt, prodrug, or salt of a prodrug thereof, wherein $A_1$, $A_2$, $A_3$, $A_4$, $R^7$, $R^8$, $R^9$, X, Y, Z, L, n, and m, are as defined herein, and are useful in disorders prevented or ameliorated by inhibiting the VR1 receptor.

18 Claims, No Drawings

TETRAHYDROQUINOLINYL COMPOUNDS THAT INHIBIT VANILLOID RECEPTOR SUBTYPE 1 (VR1) RECEPTOR AND USES THEREOF

This application is a Divisional of U.S. application Ser. No. 11/285,448 filed on Nov. 22, 2005, which claims priority to U.S. Provisional Application Ser. No. 60/630,636 filed on Nov. 24, 2004.

FIELD OF THE INVENTION

The present invention relates to compounds of formula (I), which are useful for treating disorders caused by or exacerbated by vanilloid receptor activity, pharmaceutical compositions containing compounds of formula (I) and methods to treat or prevent pain, inflammatory thermal hyperalgesia, bladder overactivity, and urinary incontinence, using the compounds of formula (I).

BACKGROUND OF INVENTION

Nociceptors are primary sensory afferent (C and Aδ fibers) neurons that are activated by a wide variety of noxious stimuli including chemical, mechanical, thermal, and proton (pH<6) modalities. The lipophillic vanilloid, capsaicin, activates primary sensory fibers via a specific cell surface capsaicin receptor, cloned as VR1. The intradermal administration of capsaicin is characterized by an initial burning or hot sensation followed by a prolonged period of analgesia. The analgesic component of VR1 receptor activation is thought to be mediated by a capsaicin-induced desensitization of the primary sensory afferent terminal. Thus, the long lasting anti-nociceptive effect of capsaicin has prompted the clinical use of capsaicin analogs as analgesic agents. Further, capsazepine, a capsaicin receptor antagonist can reduce inflammation-induced hyperalgesia in animal models. VR1 receptors are also localized on sensory afferents, which innervate the bladder. Capsaicin or resiniferatoxin has been shown to ameliorate incontinence symptoms upon injection into the bladder.

The VR1 receptor has been called a "polymodal detector" of noxious stimuli since it can be activated in several ways. The receptor channel is activated by capsaicin and other vanilloids and thus is classified as a ligand-gated ion channel. VR1 receptor activation by capsaicin can be blocked by the competitive VR1 receptor antagonist, capsazepine. The channel can also be activated by protons. Under mildly acidic conditions (pH 6-7), the affinity of capsaicin for the receptor is increased, whereas at pH<6, direct activation of the channel occurs. In addition, when membrane temperature reaches 43° C., the channel is opened. Thus heat can directly gate the channel in the absence of ligand. The capsaicin analog, capsazepine, which is a competitive antagonist of capsaicin, blocks activation of the channel in response to capsaicin, acid, or heat.

The channel is a nonspecific cation conductor. Both extracellular sodium and calcium enter through the channel pore, resulting in cell membrane depolarization. This depolarization increases neuronal excitability, leading to action potential firing and transmission of a noxious nerve impulse to the spinal cord. In addition, depolarization of the peripheral terminal can lead to release of inflammatory peptides such as, but not limited to, substance P and CGRP, leading to enhanced peripheral sensitization of tissue.

Recently, two groups have reported the generation of a "knock-out" mouse lacking the VR1 receptor. Electrophysiological studies of sensory neurons (dorsal root ganglia) from these animals revealed a marked absence of responses evoked by noxious stimuli including capsaicin, heat, and reduced pH. These animals did not display any overt signs of behavioral impairment and showed no differences in responses to acute non-noxious thermal and mechanical stimulation relative to wild-type mice. The VR1 (−/−) mice also did not show reduced sensitivity to nerve injury-induced mechanical or thermal nociception. However, the VR1 knock-out mice were insensitive to the noxious effects of intradermal capsaicin, exposure to intense heat (50-55° C.), and failed to develop thermal hyperalgesia following the intradermal administration of carrageenan.

The compounds of the present invention are novel VR1 antagonists and have utility in treating pain and urinary disorders, especailly acute pain, chronic pain, inflammatory pain, osteoarthritic pain, cancer pain, lower back pain, bladder overactivity and urinary incontinence.

SUMMARY OF THE PRESENT INVENTION

The present invention discloses chromanylurea compounds of formula (I), a method for inhibiting the VR1 receptor in mammals using these compounds, pharmaceutical compositions including these compounds, and methods for controlling pain and urinary disorders in mammals, especailly acute pain, chronic pain, inflammatory pain, osteoarthritic pain, cancer pain, lower back pain, bladder overactivity and urinary incontinence, using these compounds. More particularly, the present invention is directed to compounds of formula (I)

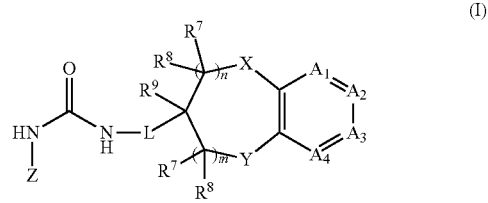

or a pharmaceutically acceptable salt, prodrug, or salt of a prodrug thereof, wherein $A_1$ is N or $CR^1$;

$A_2$ is N or $CR^2$;

$A_3$ is N or $CR^3$;

$A_4$ is N or $CR^4$; provided that only one or two of $A_1, A_2, A_3$ and $A_4$ can be N;

$R^1, R^2, R^3$ and $R^4$ are each independently selected from the group consisting of alkyl, alkenyl, alkynyl, haloalkyl, halogen, hydrogen, hydroxy, alkoxy, —$OR_c$, haloalkoxy, —$NR_AR_B$, —$C(O)R_a$, —$C(O)OH$, —$C(O)Oalkyl$, —$S(alkyl)$, —$S(O)alkyl$, —$S(O)_2R_a$, $R_c$, —O-alkyl-$R_c$ and -alkyl-$R_c$;

X is O or $NR^5$;

Y is O, $NR^6$, S or a bond;

L is a bond or $C_{1-10}$ alkyl;

$R^5$ and $R^6$ are each independently selected from the group consisting of hydrogen, alkyl, alkenyl, haloalkyl, —$C(O)R_a$, —$S(O)_2R_a$, $R_c$, and -alkyl-$R_c$;

$R_a$ is alkyl, haloalkyl, —$NH_2$, —$N(H)(alkyl)$, —$N(alkyl)_2$, $R_c$, or -alkyl-$R_c$;

m is 0, 1, 2, 3 or 4;

n is 0, 1, 2, 3 or 4; provided that when Y is a bond, then the sum of m and n is 1, 2, 3 or 4, or when Y is O, $NR^6$ or S, then the sum of m and n is 0, 1, 2 or 3;

$R^7$ and $R^8$, at each occurrence, are independently selected from the group consisting of hydrogen, alkyl, alkenyl, aryl, heteroaryl, cycloalkyl, cycloalkenyl, and -alkyl-$R_c$, wherein the aryl, heteroaryl, cycloalkyl and cycloalkenyl are each independently unsubstituted or substituted with 1, 2, 3 or 4 substituents selected from the group consisting of alkyl, haloalkyl, halogen, hydroxy, alkoxy, haloalkoxy, —NH$_2$, —N(H)(alkyl), —N(alkyl)$_2$, —N(H)C(O)alkyl, —N(alkyl)C(O)alkyl, —N(H)C(O)Oalkyl, —N(alkyl)C(O)Oalkyl, —C(O)alkyl, —C(O)OH, —C(O)Oalkyl, —C(O)NH$_2$, —C(O)N(H)(alkyl), —C(O)N(alkyl)$_2$, —S(alkyl), —S(O)alkyl, —S(O)$_2$alkyl, —S(O)$_2$N(H)$_2$, —S(O)$_2$N(H)(alkyl) and —S(O)$_2$N(alkyl)$_2$;

$R^9$ is hydrogen, alkyl, haloalkyl, hydroxy, alkoxy or haloalkoxy;

$R_A$ and $R_B$ are independently selected from the group consisting of hydrogen, alkyl, haloalkyl, $R_c$ and -alkyl-$R_c$, Z is a monocyclic or bicyclic ring selected from the group consisting of cycloalkyl, cycloalkenyl, heterocycle, heteroaryl and aryl; wherein each Z is independently unsubstituted or substituted with 1, 2, 3 or 4 substituents selected from the group consisting of alkyl, haloalkyl, halogen, hydroxy, alkoxy, haloalkoxy, —NH$_2$, —N(H)(alkyl), —N(alkyl)$_2$, —C(O)alkyl, —C(O)OH, —C(O)Oalkyl, —C(O)NH$_2$, —C(O)N(H)(alkyl), —C(O)N(alkyl)$_2$, —S(alkyl), —S(O)alkyl, —S(O)$_2$alkyl, —S(O)$_2$N(H)$_2$, —S(O)$_2$N(H)(alkyl), —S(O)$_2$N(alkyl)$_2$, $R_c$, and alkoxyalkyl;

provided that when $A_1$ is $CR^1$, $A_2$ is $CR^2$, $A_3$ is $CR^3$, $A_4$ is $CR^4$, Y is a bond, L is a bond, X is O, and the sum of m and n is 2, 3 or 4, then Z is a bicyclic ring selected from the group consisting of cycloalkyl, cycloalkenyl, heterocycle and heteroaryl; wherein each Z is independently unsubstituted or substituted with 1, 2, 3 or 4 substituents selected from the group consisting of alkyl, haloalkyl, halogen, hydroxy, alkoxy, haloalkoxy, —NH$_2$, —N(H)(alkyl), —N(alkyl)$_2$, —C(O)alkyl, —C(O)OH, —C(O)Oalkyl, —C(O)NH$_2$, —C(O)N(H)(alkyl), —C(O)N(alkyl)$_2$, —S(alkyl), —S(O)alkyl, —S(O)$_2$alkyl, —S(O)$_2$N(H)$_2$, —S(O)$_2$N(H)(alkyl), —S(O)$_2$N(alkyl)$_2$, $R_c$, and alkoxyalkyl; and $R_c$ at each occurrence is independently a monocyclic or bicyclic ring, independently selected from the group consisting of cycloalkyl, cycloalkenyl, heterocycle, heteroaryl and aryl; wherein each $R_c$ is independently unsubstituted or substituted with 1, 2, 3 or 4 substituents selected from the group consisting of alkyl, haloalkyl, halogen, oxo, hydroxy, alkoxy, haloalkoxy, —NH$_2$, —N(H)(alkyl), —N(alkyl)$_2$, —N(H)C(O)alkyl, —N(alkyl)C(O)alkyl, —N(H)C(O)Oalkyl, —N(alkyl)C(O)Oalkyl, —C(O)alkyl, —C(O)OH, —C(O)Oalkyl, —C(O)NH$_2$, —C(O)N(H)(alkyl), —C(O)N(alkyl)$_2$, —S(alkyl), —S(O)alkyl, —S(O)$_2$alkyl, —S(O)$_2$N(H)$_2$, —S(O)$_2$N(H)(alkyl) and —S(O)$_2$N(alkyl)$_2$.

DETAILED DESCRIPTION OF THE INVENTION (1) Compounds and Methods of the Invention The present invention relates to compounds having formula (I) as described above.

The invention includes compounds having the formula (I) in which Z is a bicyclic ring selected form the group consisting of cycloalkenyl, cycloalkyl, heterocycle and heteroaryl. Preferred compounds include those in which Z is heteroaryl, selected from the group consisting of benzimidazolyl, indazolyl, isoquinolinyl, and quinolinyl.

The present invention includes compounds in which Z is indazolyl; $R^7$ and $R^8$, at each occurrence, are independently selected from the group consisting of hydrogen, alkyl, alkenyl, aryl, heteroaryl, cycloalkyl, cycloalkenyl, and -alkyl-$R_c$, in which $R_c$ at each occurrence is independently a monocyclic or bicyclic ring, independently selected from the group consisting of cycloalkyl, cycloalkenyl, heterocycle, heteroaryl and aryl; wherein each $R_c$ is independently unsubstituted or substituted with 1, 2, 3 or 4 substituents selected from the group consisting of alkyl, haloalkyl, halogen, oxo, hydroxy, alkoxy, haloalkoxy, —NH$_2$, —N(H)(alkyl), —N(alkyl)$_2$, —N(H)C(O)alkyl, —N(alkyl)C(O)alkyl, —N(H)C(O)Oalkyl, —N(alkyl)C(O)Oalkyl, —C(O)alkyl, —C(O)OH, —C(O)Oalkyl, —C(O)NH$_2$, —C(O)N(H)(alkyl), —C(O)N(alkyl)$_2$, —S(alkyl), —S(O)alkyl, —S(O)$_2$alkyl, —S(O)$_2$N(H)$_2$, —S(O)$_2$N(H)(alkyl) and —S(O)$_2$N(alkyl)$_2$ and $A_1$ is $CR^1$; $A_2$ is $CR^2$; $A_3$ is $CR^3$; and $A_4$ is $CR^4$; wherein R', $R^2$, $R^3$ and $R^4$ are each independently selected from the group consisting of alkyl, alkenyl, alkynyl, haloalkyl, halogen, hydrogen, hydroxy, alkoxy, —O$R_c$, haloalkoxy, —NR$_A$R$_B$, —C(O)R$_a$, —C(O)OH, —C(O)Oalkyl, —S(alkyl), —S(O)alkyl, —S(O)$_2$R$_a$, R$_c$, —O-alkyl-R$_c$ and -alkyl-R$_c$; and R$_c$ is as described above; preferably where L is a bond; X is O; Y is a bond; m is 0; and n is 2. Other preferred compound sin this subgenus are those in which L is a bond; X is NR$^5$ and R$^5$ is independently selected from the group consisting of hydrogen, alkyl, alkenyl, haloalkyl, —C(O)R$_a$, —S(O)$_2$R$_a$, R$_c$, and -alkyl-R$_c$, where R$_c$ is as described above; Y is a bond; m is 0; and n is 3. Other preferred compounds include those in which L is a bond; X is NR$^5$ and R$^5$ is each independently selected from the group consisting of hydrogen, alkyl, alkenyl, haloalkyl, —C(O)R$_a$, —S(O)$_2$R$_a$, R$_c$, and -alkyl-R$_c$, wherein R$_c$ is as described above; Y is a bond; m is 0; and n is 2; or those in which m is 1; and n is 1. Other preferred compounds include those in which L is C$_{1-10}$ alkyl; X is O; Y is a bond; m is 1; and n is 0; or those in which m is 2; and n is 0. Other preferred compounds include those in which L is C$_{1-10}$ alkyl; X is NR$^5$; R$^5$ is each independently selected from the group consisting of hydrogen, alkyl, alkenyl, haloalkyl, —C(O)R$_a$, —S(O)$_2$R$_a$, R$_c$, and -alkyl-R$_c$; Y is a bond; m is 1; and n is 0. Other compounds comprise those in which L is C$_{1-10}$ alkyl; X is NR$^5$; R$^5$ is each independently selected from the group consisting of hydrogen, alkyl, alkenyl, haloalkyl, —C(O)R$_a$, —S(O)$_2$R$_a$, R$_c$, and -alkyl-R$_c$; Y is O; m is 0; and n is 1. Other compounds included in the present invention are those in which L is C$_{1-10}$ alkyl; X is O; Y is NR$^6$; R$^6$ is each independently selected from the group consisting of hydrogen, alkyl, alkenyl, haloalkyl, —C(O)R$_a$, —S(O)$_2$R$_a$, R$_c$, and -alkyl-R$_c$ and, R$_c$, is as described above; m is 1; and n is 0. Other compounds are those in which L is C$_{1-10}$ alkyl; X is NR$^5$; R$^5$ is as described above; Y is a bond; m is 2; and n is 0. Also, compounds where L is C$_{1-10}$ alkyl; X is O; Y is O; m is 1; and n is 0 are included The present invention also includes compounds where Z is isoquinolinyl;

$R^7$ and $R^8$, at each occurrence, are independently selected from the group consisting of hydrogen, alkyl, alkenyl, aryl, heteroaryl, cycloalkyl, cycloalkenyl, and -alkyl-R$_c$ as described in claim 1; $A_1$ is $CR^1$; $A_2$ is $CR^2$; $A_3$ is $CR^3$; and $A_4$ is $CR^4$; wherein R', $R^2$, $R^3$ and $R^4$ are as described above. Preferred compounds in this group include those in which L is a bond; X is O; Y is a bond; m is 0; and n is 2. Other preferred compounds include those in which L is a bond; X is O; Y is a bond; m is 1; and n is 1. The present invention also includes compounds where Z is quinolinyl; $R^7$ and $R^8$, at each occurrence, are independently selected from the group consisting of hydrogen, alkyl, alkenyl, aryl, heteroaryl, cycloalkyl, cycloalkenyl, and -alkyl-R$_c$ as described in claim 1; $A_1$ is $CR^1$; $A_2$ is $CR^2$; $A_3$ is $CR^3$; and $A_4$ is $CR^4$; wherein $R^1$, $R^2$, $R^3$ and $R^4$ are as described above. Preferred compounds in this group are those in which L is a bond; X is O; Y is a bond; m is 0; and n is 2.

The present invention also comprises compounds where Z is isoquinolinyl;

$R^7$ and $R^8$, at each occurrence, are independently selected from the group consisting of hydrogen, alkyl, alkenyl, aryl, heteroaryl, cycloalkyl, cycloalkenyl, and -alkyl-$R_c$ as described in claim 1; $A_1$ is $CR^1$; $A_2$ is $CR^2$; $A_3$ is $CR^3$; and $A_4$ is $CR^4$; wherein $R^1$, $R^2$, $R^3$ and $R^4$ are as described above. Preferably where L is $C_{1-10}$ alkyl; X is $NR^5$; $R^5$ is as described above; Y is a bond; m is 2; and n is 0.

Compounds and compositions of the invention are useful for modulating the effects of vanilloid receptor activity, and more particularly the receptor type VR1. In particular, the compounds and compositions of the invention can be used for treating and preventing disorders modulated by VR1. Typically, such disorders can be ameliorated by selectively modulating the VR1 receptor in a mammal, preferably by administering a compound or composition of the invention, either alone or in combination with another active agent, for example, as part of a therapeutic regimen. The compounds of the invention, including but not limited to those specified in the examples, possess an affinity for VR1 s. As VR1 ligands, the compounds of the invention can be useful for the treatment and prevention of a number of diseases or conditions mediated by the VR1 activity.

For example, VR1 have been shown to play a significant role in the release of inflammatory peptides such as, but not limited to, substance P and CGRP, leading to enhanced peripheral sensitization of tissue. As such, VR1 ligands are suitable for the treatment of disorders associated with several types of pain and with inflammation. Further, capsazepine, a capsaicin receptor antagonist can reduce inflammation-induced hyperalgesia in animal models. Therefore the compounds and compositions of the present invention are useful for treatment of disorders like acute pain, chronic pain, inflammatory pain, osteoarthritic pain, cancer pain, lower back pain.

VR1s are also localized on sensory afferents, which innervate the bladder. Capsaicin or resiniferatoxin has been shown to ameliorate incontinence symptoms upon injection into the bladder. Therefore, VR1 ligands are suitable for the treatment of disorders associated with urinary incontinence and bladder dysfunction.

(2) Definition of Terms

As used throughout this specification and the appended claims, the following terms have the following meanings:

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylbutyl, 3-methylhexyl, 3,3-dimethylbutyl, 2,2-dimethylpentyl, 2,3-dimethylpentyl, n-heptyl, n-octyl, n-nonyl, and n-decyl.

The term "alkynyl" as used herein, refers to a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl" as used herein, means an alkoxy group, as defined herein, appended to the parent molecular moiety through an alkyl group, as defined herein.

The term "aryl" as used herein, means a phenyl group, a bicyclic aryl or a tricyclic aryl. The bicyclic aryl or the tricyclic aryl is a hydrocarbon fused ring system containing zero heteroatom wherein one or more of the fused rings is a phenyl group. Bicyclic aryl is a phenyl group fused to a monocyclic cycloalkyl group, as defined herein, a monocyclic cycloalkenyl group, as defined herein, or another phenyl group. Tricyclic aryl is a bicyclic aryl fused to a monocyclic cycloalkyl group, as defined herein, a monocyclic cycloalkenyl group, as defined herein, or another phenyl group. The phenyl group, the bicyclic aryls and the tricyclic aryls of the present invention are appended to the parent moiety through any substitutable atoms in the phenyl group, the bicyclic aryls and the tricyclic aryls respectively. The phenyl group, the bicyclic aryls and the tricyclic aryls of the present invention can be unsubstituted or substituted. Representative examples of aryl include, but are not limited to, anthracenyl, azulenyl, fluorenyl, 2,3-dihydro-1H-inden-1-yl, 2,3-dihydro-1H-inden-4-yl, inden-1-yl, inden-4-yl, naphthyl, phenyl, 5,6,7,8-tetrahydronaphthalen-1-yl, 1,2,3,4-tetrahydronaphthalen-2-yl and tetrahydronaphthyl.

The term "cycloalkyl" or "cycloalkane" as used herein, means a monocyclic cycloalkyl or a bicyclic cycloalkyl. The monocyclic cycloalkyl is a saturated hydrocarbon ring system having three to eight carbon atoms and zero heteroatom. Examples of monocyclic cycloalkyls include cyclopropyl, cyclobutyl, cyclopentyl, cyclohexyl, cycloheptyl, and cyclooctyl. The bicyclic cycloalkyl is a fused ring system wherein the monocyclic cycloalkyl ring is fused to another monocyclic cycloalkyl group, as defined herein The monocyclic cycloalkyls and the bicyclic cycloalkyls of the present invention can be unsubstituted or substituted, and are connected to the parent molecula moiety through any substitutable carbon atom of the monocyclic cycloalkyls and the bicyclic cycloalkyls respectively.

The term "cycloalkenyl" or "cycloalkene" as used herein, means a monocyclic cycloalkenyl or a bicyclic cycloalkenyl. The monocyclic cycloalkenyl is a non-aromatic, partially unsaturated hydrocarbon ring system, having 4, 5, 6, 7 or 8 carbon atoms and zero heteroatom. The 4-membered ring systems have one double bond, the 5-or 6-membered ring systems have one or two double bonds, and the 7- or 8-membered ring systems have one, two or three double bonds. Representative examples of monocyclic cycloalkenyl groups include, but not limited to, cyclobutenyl, cyclopentenyl, and cyclohexenyl. The bicyclic cycloalkenyl is a hydrocarbon fused ring system wherein the monocyclic cycloalkenyl ring is fused to a monocyclic cycloalkyl group, as defined herein, or another monocyclic cycloalkenyl group, as defined herein. Representative examples of the bicyclic cycloalkenyls include, but not limited to, 4,5,6,7-tetrahydro-3aH-indene, octahydronaphthalenyl and 1,6-dihydro-pentalene. The monocyclic cycloalkenyls and the bicyclic cycloalkenyls of the present invention can be unsubstituted or substituted, and are attached to the parent molecular moiety through any substitutable carbon atom of the monocyclic cycloalkenyls and the bicyclic cycloalkenyls respectively.

The term "halo" or "halogen" as used herein, means —Cl, —Br, —I or —F.

The term "haloalkoxy" as used herein, refers to an alkoxy group, as defined herein, in which one, two, three, four, five or six hydrogen atoms are replaced by halogen. Representative examples of haloalkoxy include, but are not limited to, chloromethoxy, 2-fluoroethoxy, trifluoromethoxy, 2-chloro-3-fluoropentyloxy, and pentafluoroethoxy.

The term "haloalkyl" as used herein, refers to an alkyl group, as defined herein, in which one, two, three or four, five, or six hydrogen atoms are replaced by halogen. Representative examples of haloalkyl include, but are not limited to, chloromethyl, 2-fluoroethyl, trifluoromethyl, pentafluoroethyl, and 2-chloro-3-fluoropentyl.

The term "heterocycle" or "heterocyclic" as used herein, refers to a monocyclic heterocycle or a bicyclic heterocycle. The monocyclic heterocycle is a non-aromatic, saturated or partially unsaturated hydrocarbon ring system containing at least one heteroatom selected from the group consisting of oxygen, nitrogen and sulfur. Monocyclic ring systems are exemplified by a 4-membered ring containing three carbon atoms and one heteroatom selected from oxygen, nitrogen and sulfur, or a 5-, 6-, 7-, or 8-membered ring containing one, two, three or four heteroatoms wherein the heteroatoms are independently selected from nitrogen, oxygen and sulfur, and the remaining atoms are carbon atoms. The 5-membered ring has 0 or 1 double bond. The 6-membered ring has 0, 1 or 2 double bonds. The 7- or 8-membered ring has 0, 1, 2 or 3 double bonds. The monocyclic heterocycle of the present invention can be unsubstituted or substituted. Representative examples of unsubstituted and substituted monocyclic ring systems include, but are not limited to, azetidinyl, azepanyl, azepinyl, diazepinyl, dioxolanyl, dioxanyl, dithianyl, imidazolinyl, imidazolidinyl, isothiazolinyl, isothiazolidinyl, isoxazolinyl, isoxazolidinyl, morpholinyl, 3-oxo-morpholinyl, oxadiazolinyl, oxadiazolidinyl, oxazolinyl, 2-oxo-oxazolinyl, oxazolidinyl, piperazinyl, piperidinyl (piperidyl), pyranyl, pyrazolinyl, pyrazolidinyl, pyrrolinyl, pyrrolidinyl, tetrahydrofuryl, tetrahydropyranyl, tetrahydropyridyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, 1,4-diazepanyl and trithianyl. Bicyclic heterocycle is a monocyclic heterocycle fused to a phenyl group, a monocyclic cycloalkenyl group, as defined herein, a monocyclic cycloalkyl group, as defined herein, or a monocyclic heterocycle group. The bicyclic heterocycles of the present invention can be unsubstituted or substituted. Representative examples of bicyclic heterocycles include but are not limited to, benzodioxinyl, benzopyranyl, benzothiopyranyl, 2,3-dihydroindolyl, indolizinyl, tetrahydroisoquinolinyl, tetrahydroquinolinyl, 3-azabicyclo[3.2.0]heptyl, 3,6-diazabicyclo[3.2.0]heptyl, octahydrocyclopenta[c]pyrrolyl, hexahydro-1H-furo[3,4-c]pyrrolyl, and octahydropyrrolo[3,4-c]pyrrolyl. The monocyclic heterocycles and the bicyclic heterocycles of the present invention are connected to the parent molecular moiety through any substitutable carbon or nitrogen atom in the monocyclic heterocycles and the bicyclic heterocycles respectively. The nitrogen heteroatom may or may not be quaternized, and the nitrogen or sulfur heteroatom may or may not be oxidized. In addition, the nitrogen containing heterocyclic rings may or may not be N-protected.

The term "heteroaryl" as used herein, means a monocyclic heteroaryl or a bicyclic heteroaryl. The monocyclic heteroaryl is an aromatic, five- or six-membered ring where at least one atom is selected from the group consisting of N, O, and S, and the remaining atoms are carbon. The five membered rings have two double bonds, and the six membered rings have three double bonds. The bicyclic heteroaryl is a monocyclic heteroaryl fused to a phenyl group, a monocyclic cycloalkyl, as defined herein, a monocyclic cycloalkenyl, as defined herein, a monocyclic heterocycle, as defined herein, or a monocyclic heteroaryl. Representative examples of monocyclic and bicyclic heteroaryls include, but not limited to, benzothienyl, benzoxazolyl, benzimidazolyl, benzoxadiazolyl, 6,7-dihydro-1,3-benzothiazolyl, furanyl (furyl), imidazolyl, imidazo[1,2-a]pyridinyl, indazolyl, indolyl, isoindolyl, isoxazolyl, isoquinolinyl, isothiazolyl, naphthyridinyl, oxadiazolyl, oxazolyl, pyridoimidazolyl, pyridyl, pyridazinyl, pyrimidinyl, pyrazinyl, pyrazolyl, pyrrolyl, quinolinyl, thiazolyl, thienyl, triazolyl, thiadiazolyl, tetrazolyl, 1,2,3,4-tetrahydro-1,8-naphthyridin-2-yl, and 5,6,7,8-tetrahydroquinolin-5-yl. The monocyclic and the bicyclic heteroaryls of the present invention can be substituted or unsubstituted, and are connected to the parent molecular moiety through any substitutable carbon or nitrogen atom in the monocyclic and the bicyclic heteroaryls respectively. In addition, the nitrogen heteroatom may or may not be quaternized, the nitrogen and the sulfur atoms in the group may or may not be oxidized. Also, the nitrogen containing rings may or may not be N-protected.

The term "heteroatom" as used herein, refers to nitrogen, oxygen and sulfur atoms.

The term "hydroxy" or "hydroxyl" as used herein, means an —OH group.

The term "oxo" as used herein, means an =O group.

(3) Preparation of Compounds of the Present Invention

The compounds and processes of the present invention will be better understood in connection with the following synthetic Schemes and Examples, which illustrate a means by which the compounds of the present invention can be prepared.

Scheme 1

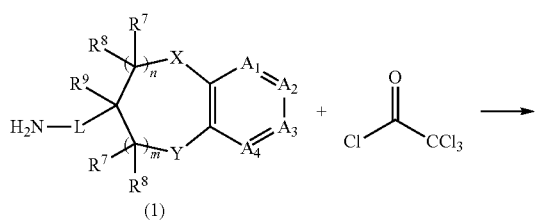

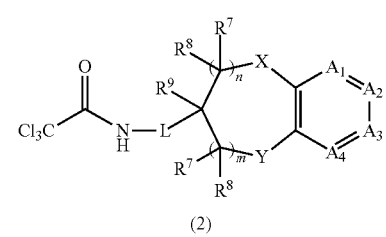

-continued (2) Z—NH₂ ⟶

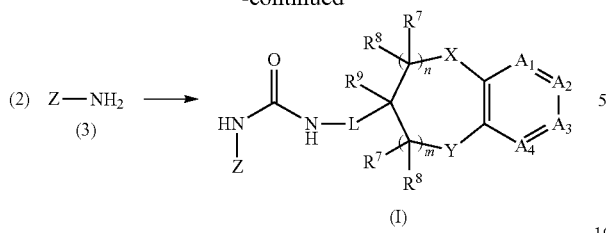

(I)

Ureas of general formula (I), wherein X, Y, Z, $A_1$, $A_2$, $A_3$, $A_4$, m, n, L, $R^7$, $R^8$ and $R^9$ as defined in formula (I), can be prepared as described in Scheme 1. The amines of general formula (1), purchased commercially or prepared using standard chemistry known to those skilled in the art, can be treated with trichloracetyl chloride and a base such as, but not limited to, triethylamine in a solvent such as dichloromethane to provide trichloroacetamides of general formula (2). The reaction can be carried out at ambient temperature for a period of about 1 hour to about 24 hours. Trichloroacetamides of general formula (2) can be treated with amines of general formula (3) and a non-nucleophilic base such as, but not limited to, 1,8-diazabicyclo[5.4.0]undec-7-ene (DBU) in a solvent such as, but not limited to, acetonitrile to provide ureas of general formula (1). The reaction can be performed at a temperature from about room temperature to about the reflux temperature of the solvent employed, for a period of about 30 minutes to about 10 hours.

Scheme 2

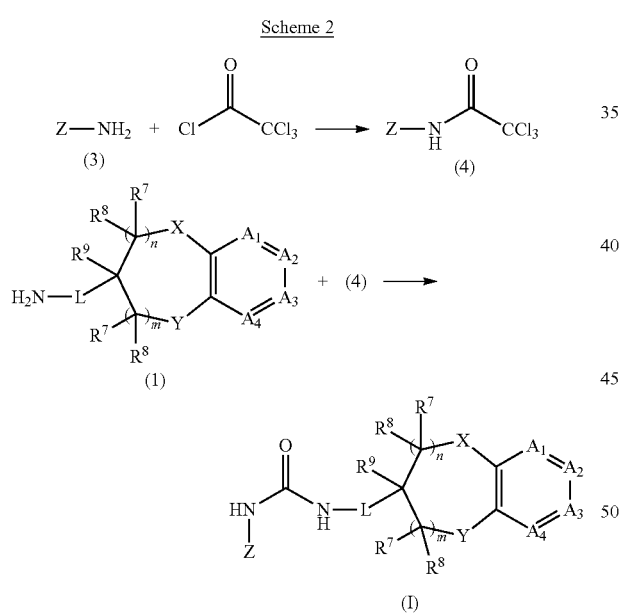

Ureas of general formula (I), wherein X, Y, Z, $A_1$, $A_2$, $A_3$, $A_4$, m, n, L, $R^7$, $R^8$ and $R^9$ are as defined in formula (I), can also be prepared as described in Scheme 2. The amines of general formula (3), purchased commercially or prepared using standard chemistry known to those skilled in the art, can be treated with trichloracetyl chloride using the conditions for the transformation of compounds of formula (1) to compounds of formula (2) as described in Scheme 1. The trichloroacetamides of general formula (4) can be converted to ureas of formula (I) by treatment with amines of formula (1), using the conditions as outlined in Scheme (1) for the conversion of compounds of formula (2) to compounds of formula (I).

Scheme 3

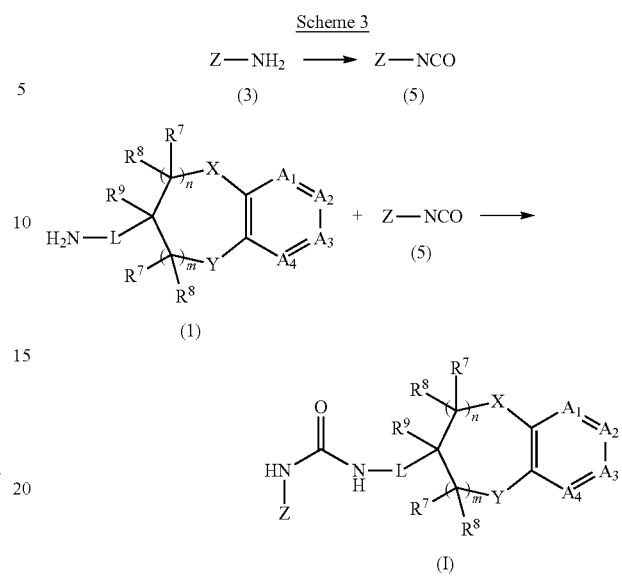

Ureas of general formula (I), wherein X, Y, Z, $A_1$, $A_2$, $A_3$, $A_4$, m, n, L, $R^7$, $R^8$ and $R^9$ are as defined in formula (I), may be prepared as described in Scheme 3. Amines of general formula (3) can be treated with phosgene or triphosgene and 4-(dimethylamino)pyridine (DMAP) in a solvent such as, but not limited to, dichloromethane to provide isocyanates of general formula (5). The reaction is generally performed at a temperature from about −10° C. to about room temperature for a period of about 1 hour to about 24 hours Amines of general formula (1) can be treated with isocyanates of general formula (5) in a solvent such as, but not limited to, dichloromethane, acetonitrile, toluene or tetrahydrofuran or a combination thereof to provide ureas of general formula (4). The reaction is generally performed at a temperature from about room temperature to about 40 C., for a period of about 1 hour to about 24 hours.

Scheme 4

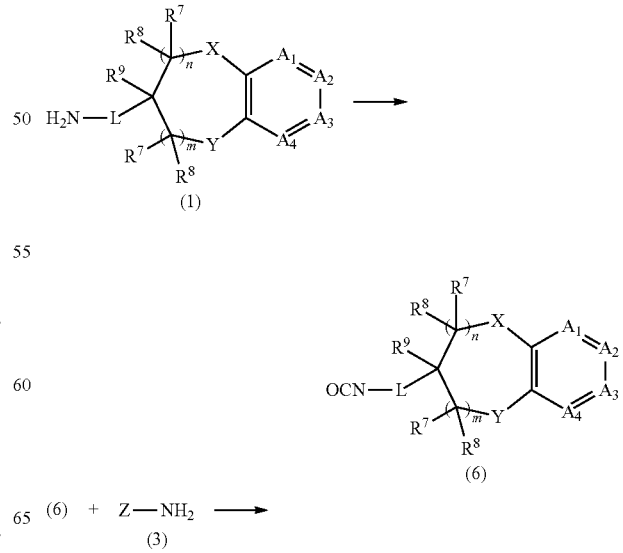

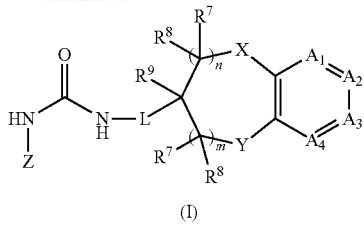

(I)

Ureas of general formula (I), wherein X, Y, Z, $A_1$, $A_2$, $A_3$, $A_4$, m, n, L, $R^7$, $R^8$ and $R^9$ are as defined in formula (I), can be prepared as described in Scheme 3. Amines of general formula (1) can be treated with phosgene or triphosgene and 4-(dimethylamino)pyridine (DMAP) using conditions for the transformation of compounds of formula (3) to compounds of formula (5) as described in Scheme 2. Isocyanates of general formula (6) can be treated with amines of general formula (3) in a solvent such as, but not limited to, dichloromethane, acetonitrile, toluene or tetrahydrofuran or a combination thereof to provide ureas of general formula (I). The reaction is generally performed at a temperature from about room temperature to about 40 C, for a period of about 1 hour to about 24 hours.

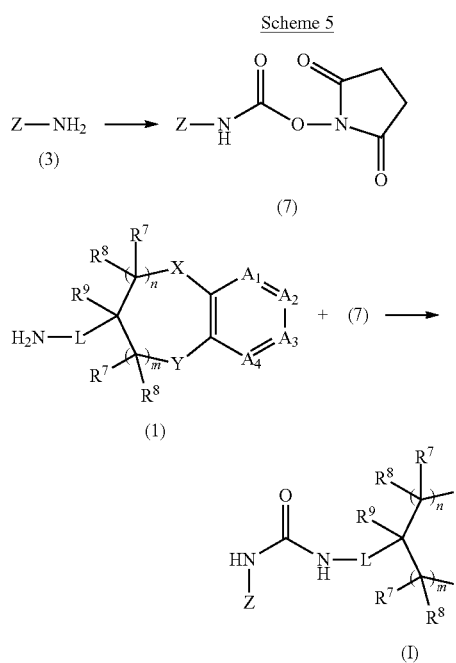

Ureas of formula (I), wherein X, Y, Z, $A_1$, $A_2$, $A_3$, $A_4$, m, n, L, $R^7$, $R^8$ and $R^9$ are as defined in formula (I), can be prepared as described in Scheme 5. Amines of formula (3) can be converted to compounds of formula (7) by reacting with disuccinimidylcarbonate in a solvent such as, but not limited to, acetonitrile, dichloromethane, or tetrahydrofuran, at a temperature from about room temperature to about 50° C., for a period of about 2 hours to about 48 hours.

Compounds of formula (7) can be converted to ureas of formula (I) by treatment with amines of formula (1) in the presence of a base such as, but not limited to, diisopropylethylamine or triethylamine, in a solvent such as, but not limited to, N,N-dimethylformamide. The reaction can be performed at a temperature from about room temperature to about 50° C., for a period of about 2 hours to about 24 hours.

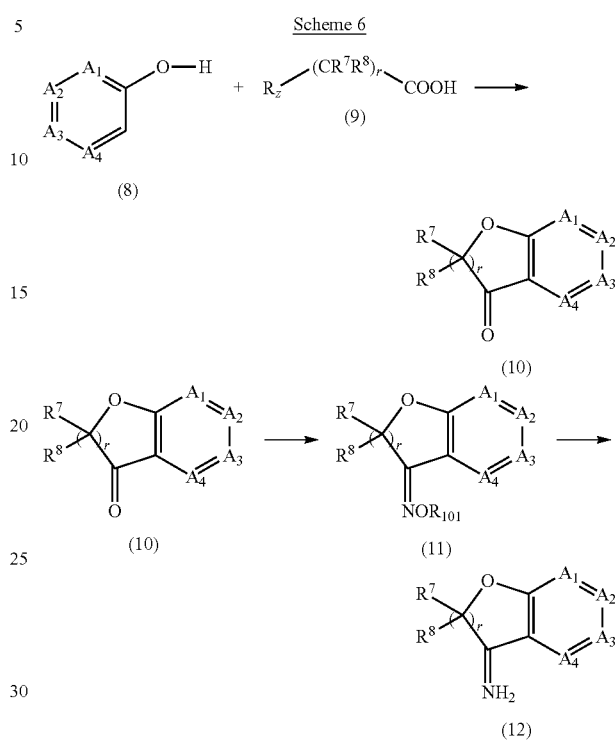

Amines of formula (12) wherein $A_1$, $A_2$, $A_3$, $A_4$, $R^7$ and $R^8$ are as defined in formula (I) and r is 2 or 3, can be obtained from alcohols of formula (8) as shown in Scheme 6. Alcohols of formula (8) can be converted to ketones of formula (10) by (a) treating with acids of formula (9) wherein $R_z$ is Cl, Br or I, in the presence of a base such as, but not limited to, metal hydroxide (for example sodium hydroxide, potassium hydroxide and the like) or metal hydrides (for example sodium hydride and the like) in a solvent such as, but not limited to, water, dichloromethane, or tetrahydrofuran, and (b) treating product from step (a) with an acid such as polyphosphoric acid. The transformation in step (a) can be performed at a temperature from about room temperature to about 100° C. for a period of about 1 hour to about 24 hours. Step (b) is generally performed at a temperature from about 60° C. to about 120° C. for a period of about 30 minutes to about 5 hours.

Ketones of formula (10) can be converted to oximes of formula (11) wherein $R_{101}$ is hydrogen or methyl, by reaction with hydroxylamine hydrochloride or methoxyamine hydrochloride in the presence of a base such as, but not limited to, pyridine or triethylamine, and optionally in the presence of a solvent such as, but not limited to, dichloromethane, acetonitrile or tetrahydrofuran. The reaction can be carried out at a temperature from about room temperature to about 50° C. for a period of about 1 hour to about 18 hours. Oximes of formula (11) wherein $R_{101}$ is hydrogen can be converted to oximes of formula (11) wherein $R_{101}$ is acetyl by treatment with acetic anhydride and a base such as, but not limited to, pyridine. The reaction can be conducted optionally in a solvent and at about room temperature.

Oximes of formula (11) wherein $R_{101}$ is methyl or acetyl can be converted to amines of formula (12) when stirred in the presence of a hydrogen source such as hydrogen gas, and a catalyst such as 10% palladium in carbon, optionally in the presence of ammonia. The reaction can be conducted in an alcoholic solvent such as, but not limited to, methanol. The reaction is generally performed under a pressure of about 60 p.s.i. and at a temperature of about room temperature to about 50° C., for a period of about 1 hour to about 12 hours.

Alternatively, conversion of (11) to (12) can also be facilitated in a hydrogen source such as hydrogen gas and a catalyst such as Raney nickel, in a solvent such as, but not limited to, methanol or ethanol, and optionally in the presence of ammonia. The reaction is generally conducted at a temperature from about room temperature to about 50° C.

Alternatively, ketones of formula (10) wherein r is 2 or 3 and $A_1$, $A_2$, $A_3$, $A_4$, $R^7$ and $R^8$ are as defined in formula (I) can be obtained from alcohols of formula (8) as shown in Scheme (7) by (a) reacting with compounds of formula (13) wherein $R_z$ is Br, Cl or I, in the presence of a base such as, but not limited to, organic amines (for example, triethylamine, diisopropylethylamine, N-methylimidazole, pyridine and the like) or alkali metal carbonates (for example sodium carbonate and the like) in a solvent such as, but not limited to, acetonitrile, dichloromethane or ethyl acetate, (b) treating the product from step (a) with an acid in a solvent such as, but not limited to, acetonitrile, dichloromethane or tetrahydrofuran, and (c) treating the product of step (b) with an oxidizing agent in a solvent such as, but not limited to, acetonitrile, dichloromethane or tetrahydrofuran.

Step (a) can be performed at a temperature from about room temperature to about 100° C. for a period of about 1 hour to about 12 hours.

Examples of the acid employed in step (b) include, but are not limited to, hydrochloric acid, sulfuric acid or nitric acid. The reaction can be performed at a temperature from about room temperature to about 50° C. for a period of about 1 hour to about 10 hours.

Examples of the oxidizing agent used in step (c) include, but are not limited to, pyridinium chlorochromate or manganese dioxide. The reaction can be performed at a temperature from about room temperature to about 50° C. for a period of about 1 hour to about 10 hours.

Scheme 7

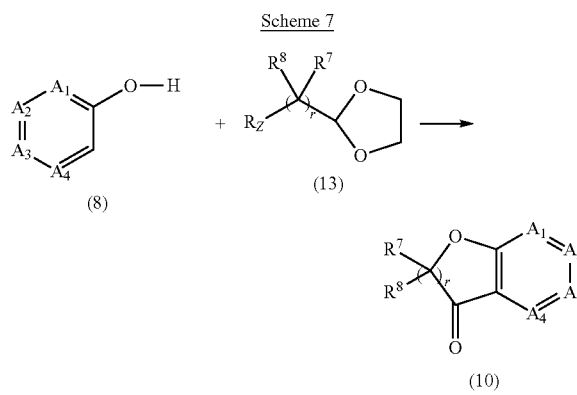

Scheme 8

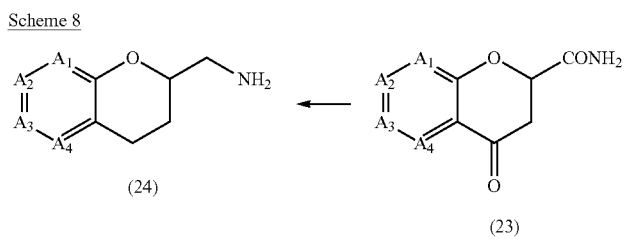

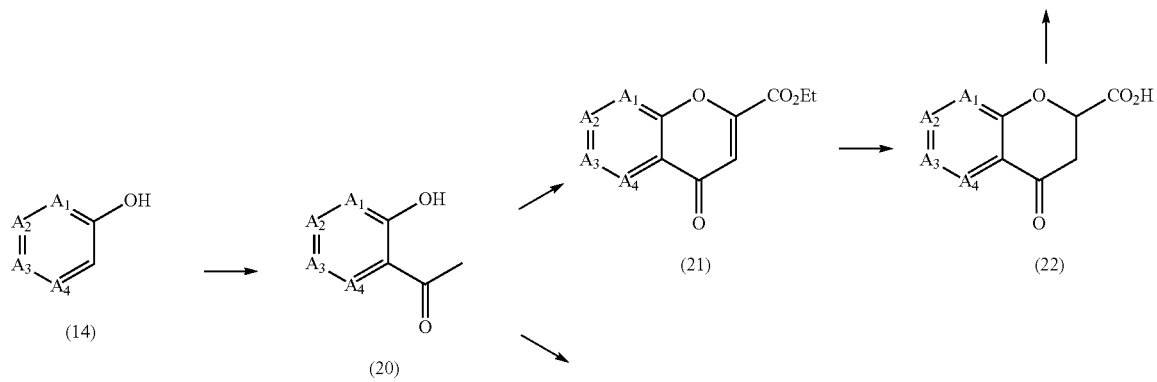

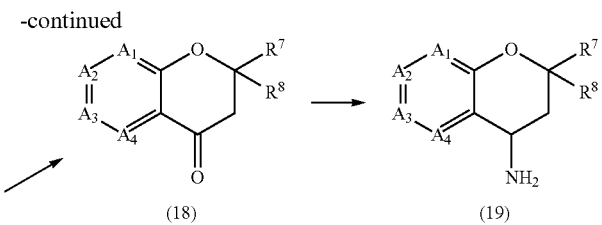

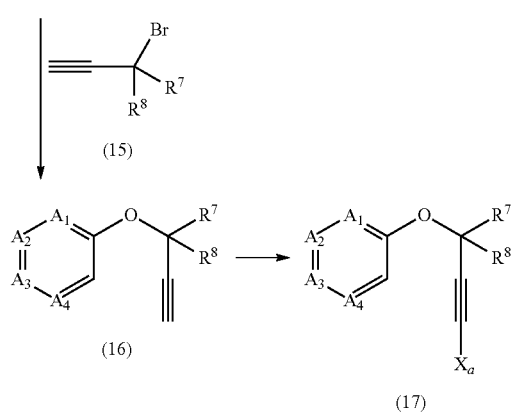

Amines of formula (19) wherein $A_1, A_2, A_3, A_4, R^7$ and $R^8$ are as defined in formula (I), can be prepared as shown in Scheme 8.

Phenols of formula (14) when reacted with propargyl bromides of formula (15), in the presence of a base such as, but not limited to potassium carbonate, can be converted to propargyl compounds of formula (16). Halogenation of propargyl compounds of formula (16) can be achieved by reacting with an halogenating agent such as, but not limited to, N-chlorosuccinimide or N-bromosuccinimide, in the presence of catalytic amount of silver acetate, and in a solvent such as, but not limited to, acetone, to afford halides of formula (17) wherein $X_a$ is Cl or Br. The reaction is generally carried out at elevated temperature such as, but not limited to, the reflux temperature of the solvent employed. Cyclization of the halides of formula (17) to provide chromanones of formula (18) can be facilitated in the presence of an acid such as, but not limited to, concentrated sulfuric acid or a mixture of sulfuric acid and methanesulfonic acid. The reaction can be conducted at ambient temperature to about 50° C. Alternatively, chromanones of formula (18) can be obtained from halides of formula (17) under neutral conditions at elevated temperature. Typically, the reaction mixture is refluxed in ethylene glycol. Chromanones of formula (18) can also be obtained from the treatment of acetophenones of formula (20) with ketones of formula $R_7C(O)R_8$, in the presence of a base such as, but not limited to, pyrrolidine. The reaction is generally performed in a solvent such as, but not limited to, toluene, at reflux. Conversion of chormanones of formula (18) to amines of formula (19) can be achieved using the reaction conditions as described in Scheme 6 for the conversion of (10) to (12).

Amines of formula (24) can be prepared from phenols of formula (14) as shown in Scheme 8.

Treatment of compounds of phenols of formula (14) with sodium acetate in refluxing acetic anhydride, followed by heating with aluminum chloride, provides the acetophenones of formula (20). Upon treatment with diethyl oxalate, in the presence of a base such as, but not limited to, sodium ethoxide, acetophenones of formula (20) can be transformed to esters of formula (21). The reaction is generally conducted in a solvent such as, but not limited to, ethanol, and at a temperature of about 60° C. to about 90° C. Esters of formula (21) can be converted to acids of formula (22) in the presence of glacial acetic acid and a hydrogen source such as, but not limited to, hydrogen gas, and a catalyst such as, but not limited to, Pd/C. The reaction is generally performed at a temperature of about 50° C. to about 80° C. Acids of formula (22) can be converted to amides of formula (23) by (a) treating the acid with oxalyl chloride in the presence of catalytic amount of N,N-dimethylformamide at ambient temperature; and (b) treating the product of step (a) with ammonia in dioxane at ambient temperature. Reduction of the amides to amines of formula (24) can be accomplished by treatment with a reducing agent such as, but not limited to, lithium aluminum hydride, at a temperature of about 40° C. to about 70° C. The reaction is generally conducted in a solvent such as, but not limited to, tetrahydrofuran.

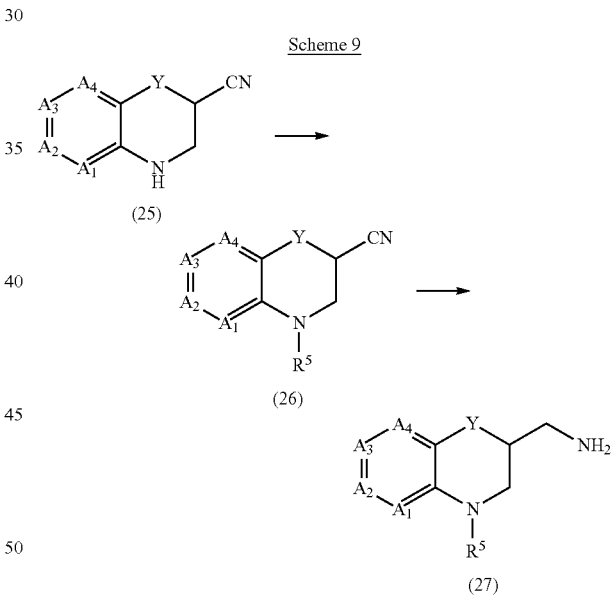

Scheme 9

Amines of formula (27) can be obtained from nitriles of formula (25) wherein Y is O or S, and $R_5, A_1, A_2, A_3,$ and $A_4$ are as defined in formula (I) as depicted in Scheme 9.

Alkylation of nitriles of formula (25) with halides of formula $R^5X_1$, and $X_1$-alkyl-$R_c$, wherein $X_1$ is Cl, I or Br, and $R^5$ is alkyl, alkenyl, haloalkyl or $R_c$ and $R_c$ is as defined in formula (I), in the presence of a base such as, but not limited to, diisopropylethylamine and in a solvent such as, but not limited to, acetonitrile, provides nitriles of formula (26) wherein $R^5$ is alkyl, alkenyl, haloalkyl, $R_c$ or -alkyl-$R_1$ and $R_c$ is as defined in formula (I). The reaction can be facilitated in a microwave reactor at elevated temperature.

Acylation of nitriles of formula (25) to compounds of formula (26) wherein $R^5$ is —C(O)$R_a$ and $R_a$ is as defined in formula (I) can be achieved by treatment with acid chlorides of formula $R_aCOCl$ or acid anhydride of formula $(R_aCO)_2O$ in the presence of a base such as, but not limited to, triethylamine, at a temperature of 0° C. to about room temperature.

Sulfonylation of nitriles of formula (25) to compounds of formula (26) wherein $R^5$ is $-S(O)_2R_a$ and $R_a$ is as defined in formula (I) can be achieved by treatment with anhydrides such as trifluoromethanesulfonic anhydride, in the presence of a base such as, but not limited to, triethylamine, and in a solvent such as, but not limited to, dichloromethane, at a temperature of 0° C. to about room temperature.

Conversion of compounds of formula (26) wherein $R^5$ is as defined in formula (I) to amines of formula (27) can be achieved by treatment with ammonia in methanol, in the presence of a hydrogen source such as, but not limited to, hydrogen gas, and a catalyst such as Raney Nickel. The reaction is generally performed under a pressure of about 60 p.s.i. and at a temperature of about room temperature.

Reductive amination of aldehydes of formula (28) with amines of formula $C_6H_5CH_2NH_2$, in the presence of a reducing agent such as, but not limited to, sodium triacetoxy borohydride, and an acid such as, but not limited to, glacial acetic acid, provides amines of formula (29).

Removal of the benzyl protective group in compounds of formula (29) followed by protection with tert-butoxycarbonyl group provides compounds of formula (30). The benzyl group can be removed by shaking in 30 psi of hydrogen and catalytic amount of palladium hydroxide and in a solvent such as, but not limited to, ethanol, at about 50° C. Protection of the amines with tert-butoxycarbonyl group can be facilitated by stirring with di-tert-butyl carbonate and a base such as, but not limited to, triethyl amine, in a solvent such as, but not limited to, tetrahydrofuran. Partial reduction of the compounds of formula (30) affords tetrahydroquinolines of formula (31). Such conversion can be facilitated with stirring the compounds of formula (30) with 30 psi hydrogen in the presence of palladium hydroxide, and in a solvent such as, but not limited to, ethanol. Derivatization of compounds of formula (31) using the reaction conditions as described in Scheme 9 for the conversion of (25) to (26), affords compounds of formula (32). Removal of the tert-butoxycarbonyl group of (31) and (32) can be achieved by treatment with an acid such as, but not limited to, trifluoroacetic acid, in a solvent such as, but not limited to, dichloromethane, to provide compounds of formula (33) wherein $R^5$ is as defined in formula (I).

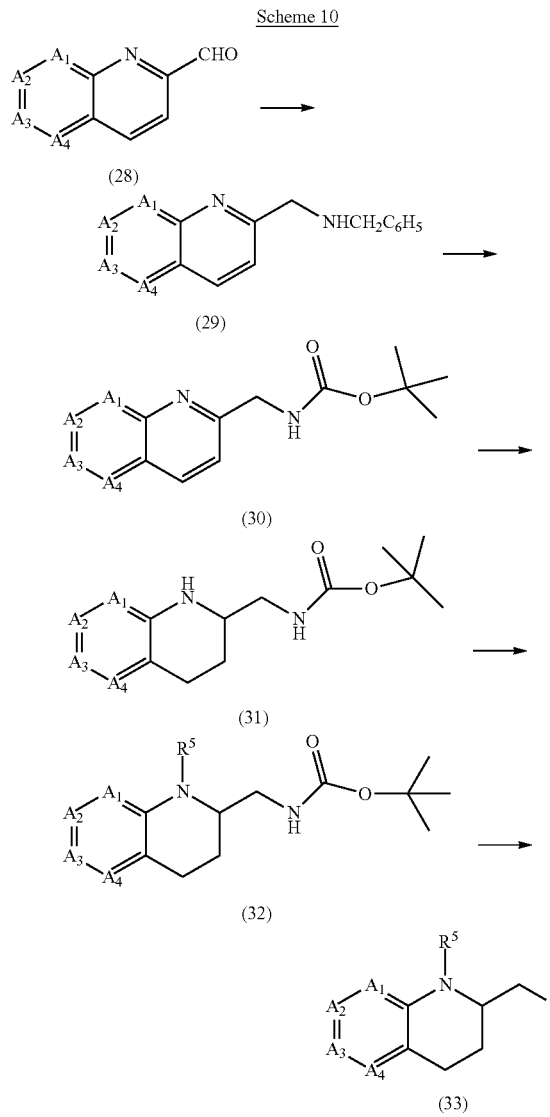

Scheme 10

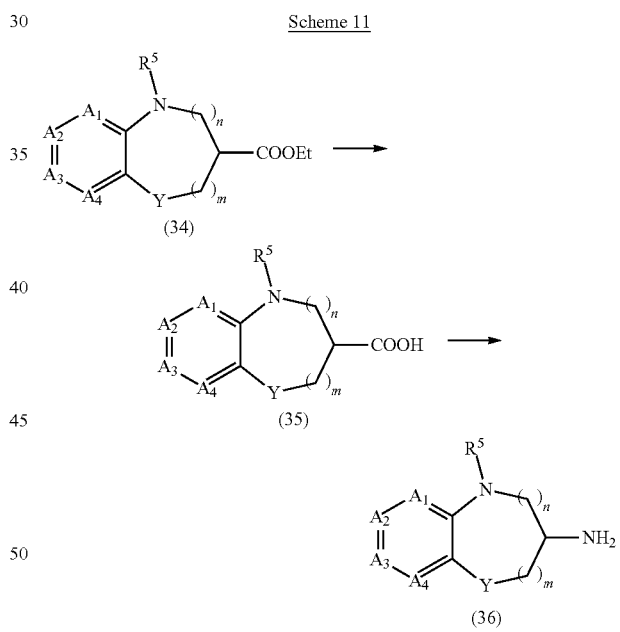

Scheme 11

Compounds of formula (33) wherein $R^5$, $A_1$, $A_2$, $A_3$, and $A_4$ are as defined in formula (I) can be prepared from aldehydes of formula (28) as shown in Scheme 10.

Amines of formula (36) wherein $A_1$, $A_2$, $A_3$, $A_4$, and $R^5$ are as defined as formula (I), Y is a bond, m is 1 and n is 1, or m is 0 and n is 2 can be prepared from the corresponding acids of formula (35) by treatment with tert-butanol and an azide such as, but not limited to, diphenylphosphorazide, and in the presence of an amine such as, but not limited to, triethyl amine, at reflux.

Acids of formula (35) wherein Y is a bond, m is 1 and n is 1 or Y is a bond, m is 0 and n is 2, can be prepared from the hydrolyzing the corresponding esters of formula (34) using reaction conditions known to one skilled in the art. For example, treatment of the esters with a base such as, but not limited to, lithium hydroxide, in a mixed solvent of tetrahydrofuran and water, at a temperature of about 0° C. to about 60° C., affords acids of formula (35).

Acids of formula (35) wherein Y is a bond, m is 0 and n is 2, can be prepared from the partial reduction of the corresponding quinoline 4-carboxylic acid using the reaction conditions for the conversion of (30) to (31) as described in Scheme 10.

Esters of formula (34) wherein Y is a bond, m is 1 and n is 1 can be prepared from the corresponding quinoline-3-carboxylic acid ethyl ester by (a) heating in the presence of phosphorus oxychloride; and (b) treating the product from step (a) with hydrogen, palladium on carbon, and in a solvent such as, but not limited to, ethanol.

Scheme 12

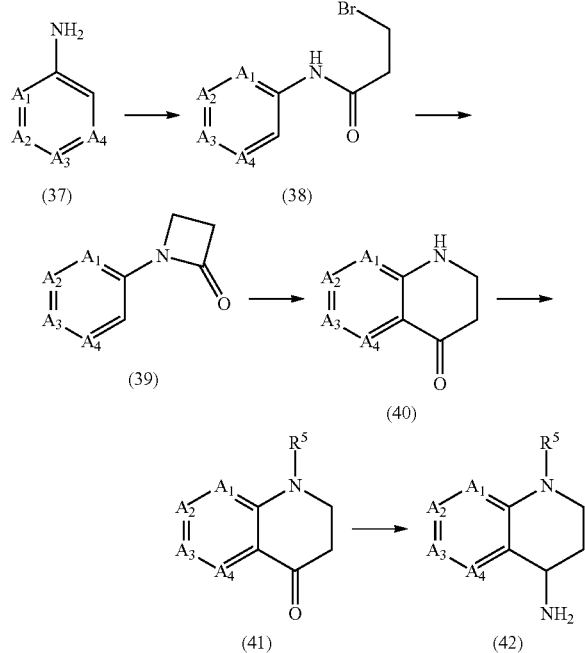

Amines of formula (42) wherein $R^5$, $A_1$, $A_2$, $A_3$, and $A_4$ are as defined in formula (I) can be prepared from amines of formula (37) as shown in Scheme 12.

Acylation of amines of formula (37) with 3-bromopropionyl chloride in the presence of a base such as, but not limited to, potassium carbonate, in a solvent such as, but not limited to, dichloromethane, provides compounds of formula (38). Cyclization of compounds of formula (38) is facilitated by potassium tert-butoxide and in a solvent such as, but not limited to, N,N-dimethylformamide. Treatment of compounds of formula (39) with trifluoromethanesulfonic acid in a solvent such as, but not limited to, dichloromethane, at a temperature of about 50° C. to about 80° C., provides ketones of formula (40). Derivatization of compounds of formula (40) to compounds of formula (41) wherein $R_5$ is alkyl, alkenyl, haloalkyl, —C(O)$R_a$, —S(O)$_2R_a$, $R_c$, and -alkyl-$R_c$ and wherein $R_c$ and $R_a$ are as defined in formula (I) can be achieved using reaction conditions as described in Scheme 9 for the conversion of (25) to (26).

The compounds of formula (40) and (41) wherein $R_5$ is alkyl, alkenyl, haloalkyl, —C(O)$R_a$, —S(O)$_2R_a$, $R_c$, and -alkyl-$R_c$ and wherein $R_c$ and $R_a$ are as defined in formula (I) can be converted to the corresponding amines of formula (42) using the reaction conditions as described Scheme 6 for the conversion of (10) to (12).

(4) EXAMPLES

The following Examples are intended as an illustration of and not a limitation upon the scope of the invention as defined in the appended claims.

Example 1

N-(7-tert-butyl-3,4-dihydro-2H-chromen-4-yl)-N'-1H-indazol-4-ylurea

Example 1A 7-tert-Butyl-chroman-4-one

A. 3-tert-butyl-phenol (1.50 g, 10 mmol), 2-(2-bromoethyl)-[1,3]dioxane (1.38 g, 10 mmol) and potassium carbonate (2.15 g, 11 mmol) in 20 ml acetonitrile was heated to reflux for 16 hours. After cooling, the solvent was removed under reduced pressure and the residue partitioned between diethyl ether and water. The isolated organic layer was washed with water, dried with magnesium sulfate, filtered and the solvent removed under reduced pressure to give 2.97 g of crude 2-[2-(3-tert-butyl-phenoxy)-ethyl]-[1,3]dioxane, which was used without further purification.

B. The intermediate from step A was dissolved in 20 ml tetrahydrofuran. Concentrated hydrochloric acid (20 mL) was added, and the reaction mixture was stirred at ambient temperature for 4 hours, diluted with diethyl ether and washed with water. The isolated organic layer was dried with magnesium sulfate, filtered and the solvent removed under reduced pressure to give 2.87 g of crude 7-tert-butyl-chroman-4-ol which was used without further purification.

C. The crude 7-tert-butyl-chroman-4-ol from step B was dissolved in 50 ml dichloromethane. Pyridinium chlorochromate (4.31 g, 20 mmol) was added and the reaction mixture was stirred at ambient temperature for 3 hours, diluted with hexanes and filtered through a pad of celite. Solvent was removed from the filtrate under reduced pressure and the residue filtered through a pad of silica gel, eluting with 20% ethyl acetate:hexanes. Removal of solvent gave 2.37 g of crude product, which was chromatographed on silica gel with an eluent of 10% ethyl acetate:hexanes to give 1.50 g of the title compound (73% for 3 steps). $^1$H NMR (300 MHz, CDCl$_3$) δ 7.83 (d, 1H, J=8.1 Hz), 7.07 (dd, 1H, J=8.3 and 1.9 Hz), 6.97 (d, 1H, J=1.7 Hz), 4.62 (m, 2H), 2.78 (m, 2H), 1.31 (s, 9H). MS (DCI) m/e 205 (M+H)$^+$.

Example 1B 7-tert-Butyl-chroman-4-one O-methyl-oxime

The product of Example 1A (1.50 g, 7.3 mmol) and methoxyamine hydrochloride (0.69 g, 8 mmol) were dissolved in 7 mL of pyridine. The reaction mixture was stirred at ambient temperature for 16 hours, and the pyridine removed under reduced pressure. The residue was taken in diethyl ether and sequentially washed with water and 1N aqueous hydrochloric acid. The isolated organic layer was then dried with magnesium sulfate, filtered and the solvent removed under reduced pressure to give 1.53 g of the title compound, which was used without further purification. MS (DCI) m/e 234 (M+H)$^+$

Example 1C

7-tert-Butyl-chroman-4-ylamine

The product of Example 1B (1.53 g) was taken into a solution of 20% ammonia in methanol, and hydrogenated for 4 hours at 60 psi at 50° C. in the presence of 1.55 g of 10% palladium on carbon as catalyst. The reaction mixture was filtered to remove catalyst, and the solvent removed under reduced pressure to give 1.40 g of the title compound (93% for two steps). $^1$H NMR (300 MHz, CDCl$_3$) δ 7.25 (d, 1H, J=6.8 Hz), 6.96 (dd, 1H, J=2.0 and 8.1 Hz), 6.85 (d, 1H, J=2.0 Hz), 4.18-4.32 (m, 2H), 4.04 (t, 1H), 2.11-2.21 (m, 1H), 1.80-1.90 (m, 1H), 1.29 (s, 9H). MS (DCI) m/e 206 (M+H)$^+$.

Example 1D

4-[3-(7-tert-Butyl-chroman-4-yl)-ureido]-indazole-1-carboxylic acid methyl ester A mixture of the product of Example 1C, (513 mg, 2.5 mmol), the product of Example 24D (830 mg, 2.5 mmol), and diisopropylethylamine (390 mg, 0.52 ml, 3 mmol) in 5 ml dimethylformamide was stirred at ambient temperature for 16 hours, diluted with water, and the percipitate collected by filtration to give 1.00 g of the title compound (95% yield). $^1$H NMR (300 MHz, DMSO-d$_6$) δ 8.78 (s, 1H), 8.36 (s, 1H), 7.88 (d, 1H, J=7.1 Hz), 7.69 (d, 1H, J=8.5 Hz), 7.50 (t, 1H, J=8.1 Hz), 7.23 (d, 1H, J=8.5 Hz), 6.97 (dd, 1H, J=2.0 and 8.1 Hz), 6.84 (d, 1H, J=7.2 Hz), 6.79 (d, 1H, J=2.0 Hz), 4.85 (m, 1H), 4.26 (m, 1H), 4.09-4.19 (m, 1H), 4.03 (s, 3H), 2.09 (m, 2H), 1.24 (s, 9H). MS (ESI) m/e 423 (M+H)$^+$.

Example 1E

N-(7-tert-butyl-3,4-dihydro-2H-chromen-4-yl)-N'-1H-indazol-4-ylurea

A solution of the product of Example 1D (1.00 g, 2.37 mmol) in a mixture of 5 mL methanol and 5 mL tetrahydrofuran was treated with 5M sodium hydroxide (2 mL) in methanol, and stirred at ambient temperature for 90 minutes. The reaction mixture was diluted with water, and the resulting precipitate was collected by filtration to give 0.75 g of the title compound (86% yield). $^1$H NMR (300 MHz, DMSO-d$_6$) δ 13.00 (broad s, 1H), 8.59 (s, 1H), 8.03 (s, 1H), 7.66 (d, J=7.5 Hz, 1H), 7.20 (m, 2H), 7.10-6.90 (m, 4H), 4.91 (m, 1H), 4.30-4.12 (m, 2H), 2.20-2.00 (m, 2H), 1.22 (s, 9H). MS (ESI) m/e 365 (M+H)$^+$. Calc'd. For C$_{17}$H$_{16}$N$_4$O$_2$.1.0; H$_2$O: C, 65.95; H, 6.85; N, 14.65. Found: C, 65.93, H, 6.69, N, 14.41.

Example 2

N-(7-tert-butyl-3,4-dihydro-2H-chromen-4-yl)-N'-quinolin-5-ylurea

A solution of phosgene (20% in toluene, 2.9 mL, 5.5 mmol) was added to 30 mL of dichloromethane and cooled to 0° C., treated with dropwise addition of a solution of 4-dimethylaminopyridine (1.43 g, 11.7 mL) in 15 mL of dichloromethane. A thick white suspension formed. A solution of 5-aminoquinoline in 15 mL of dichloromethane was then added dropwise to this suspension. The reaction mixture was allowed to warm to ambient temperature and stirred overnight. At the end of this time, a solution formed, and the solvent was removed under reduced pressure. The residue was titurated with 50 mL of diethyl ether to give an approximately 0.1 M solution of 5-isocyanato-isoquinoline.

6 mL of the 5-isocyanato-isoquinoline solution was added to the product of Example 1C (123 mg, 0.6 mmol). The reaction mixture was stirred overnight, and the precipitate formed was collected by filtration and washed with diethyl ether to give 132 mg of the title compound (55% yield). $^1$H NMR (300 MHz, DMSO-d$_6$) δ ppm 8.89 (dd, J=4.0 and 1.4 Hz, 1H), 8.56 (s, 1H), 8.46 (dd, J=8.6 and 1.5 Hz, 1H), 8.15 (dd, J=6.1 and 2.71 Hz, 1H), 7.65-7.71 (m, 2H), 7.55 (dd, J=8.6 and 4.2 Hz, 1H), 7.24 (d, J=8.1 Hz, 1H), 7.06 (d, J=7.1 Hz, 1H), 6.97 (dd, J=8.0 and 1.9 Hz, 1H), 6.79 (d, J=2.0 Hz, 1 H), 4.83-4.89 (m, 1H), 4.23-4.31 (m, 1H), 4.14 (ddd, J=11.3, 8.9, and 2.9 Hz, 1H), 4.02 (d, J=1.7 Hz, 1H), 1.99-2.15 (m, 2H), 1.25 (s, 9H). MS (ESI) m/e 376 (M+H)$^+$. Calcd. For C$_{23}$H$_{25}$N$_3$O$_2$.0.7; H$_2$O: C, 71.18; H, 6.86; N, 10.83. Found: C, 71.14; H, 6.65; N, 10.61.

Example 3

N-(7-tert-butyl-3,4-dihydro-2H-chromen-4-yl)-N'-quinolin-8-ylurea

Example 3A

2,2,2-Trichloro-N-quinolin-8-yl-acetamide

A solution of 8-aminoquinoline (2.88 g, 20 mmol) in dichloromethane (100 mL) was treated sequentially with triethylamine (3.1 mL, 2.23 g, 22 mmol) and trichloroacetyl chloride (2.5 mL, 4.0 g, 22 mmol). The reaction mixture was allowed to stir at ambient temperature for 16 hours, and the solvent removed under reduced pressure. The residue was taken into ethyl acetate, washed sequentially with water and saturated aqueous ammonium chloride. The isolated organic layers were dried with magnesium sulfate, filtered and the solvent removed under reduced pressure to give 5.79 g of the title compound (99% yield) which was used without further purification. $^1$H NMR (300 MHz, DMSO-d$_6$) δ 11.18 (br s, 1H, NH), 9.00 (dd, 1H, J=4.4 and 1.7 Hz), 8.53 (m, 2H), 7.89 (d, 1H, 7.1 Hz), 7.73 (m, 2H). MS (ESI) m/e 289 (M+H)$^+$.

Example 3B

N-(7-tert-butyl-3,4-dihydro-2H-chromen-4-yl)-N'-quinolin-8-ylurea

A mixture of the product of Example 3A (145 mg, 0.5 mmol), the product of Example 1C (103 mg, 0.5 mmol) and 1,8-diazabicyclo[5.4.0]undec-7-ene (DBU, 190 mg, 1.25 mmol) in acetonitrile (15 mL) was heated at reflux for 3.5 hours, cooled, and the acetonitrile removed under reduced pressure. The residue was taken up in ethyl acetate and washed with water. The isolated organic layer was dried with magnesium sulfate, filtered and the solvent removed under reduced pressure. The resulting residue was purified by reverse-phase HPLC (acetonitrile/water) to give 27 mg of the title compound (14% yield). $^1$H NMR (300 MHz, DMSO-d$_6$) δ ppm 9.37 (s, 1H), 8.83 (dd, J=4.1 and 1.7 Hz, 1H), 8.54 (dd, J=7.3 and 1.9 Hz, 1H), 8.34 (dd, J=8.5 and 1.7 Hz, 1H), 7.91 (d, J=7.8 Hz, 1H), 7.55-7.60 (m, 1H), 7.46-7.53 (m, 2H), 7.22 (d, J=8.1 Hz, 1H), 6.94 (dd, J=8.1 and 2.0 Hz, 1H), 6.77 (d, J=2.0 Hz, 1H), 4.87-4.93 (m, 1H), 4.22-4.29 (m, 1H), 4.12-4.20 (m, 1H), 2.07-2.16 (m, 1H), 1.91-2.00 (m, 1H), 1.24 (s, 9H). MS (ESI) m/e 376 (M+H)$^+$. Calcd. For $C_{23}H_{25}N_3O_2 \cdot 0.35$; $CF_3CO_2H$, C, 68.53; H, 6.15; N, 10.12. Found C, 68.33; H, 6.00; N, 10.00.

Example 4

N-1H-indazol-4-yl-N'-[7-(trifluoromethyl)-3,4-dihydro-2H-chromen-4-yl]urea

Example 4A 4-(3-Trifluoromethyl-phenyl)-butyric acid

To a solution of sodium hydroxide (4.0 g, 100 mmol) in water (50 mL) was added 3-trifluoromethyl-phenol (5.4 g, 33.4 mmol) and the mixture was refluxed for 6 hrs. The pH of the solution was kept at about 10 by adding more of aqueous sodium hydroxide. The mixture was cooled to ambient temperature and extracted with ethyl acetate. The aqueous layer was treated with 3N HCl and extracted with ethyl acetate. The combined organic layers was concentrated to obtain 2.5 g of the title compound, which was used directly in the next step. $^1$H NMR (300 MHz, $d_6$-DMSO) δ 12.40 (broad s, 1H), 7.51 (t, J 7.5 Hz, 1H), 7.24 (m, 3H), 4.23 (t, J 6.0 Hz, 2H), 2.71 (t, J 6.0 Hz, 2H).

Example 4B

7-Trifluoromethyl-chroman-4-one

Polyphosphoric acid (10 mL) was heated in water bath and the product of Example 4A (~2.5 g) was added. After stirring for 30 min this mixture was poured onto ice and extracted twice with diethyl ether. The combined organic layers were washed with water, aqueous $NaHCO_3$, and water and concentrated. The residue was chromatographed on silica gel, and eluted with 9:1 ethyl acetate:hexanes to afford the title compound (0.84 g, 12% for 2 steps) as a white solid. $^1$H NMR (300 MHz, DMSO-$d_6$) δ 7.96 (d, J 7.5 Hz, 1H), 7.40 (m, 2H), 4.62 (t, J 6.0 Hz, 2H), 2.88 (t, J 6.0 Hz, 2H). MS (DCI/$NH_3$) m/e 234 $(M+NH_4)^+$.

Example 4C

7-Trifluoromethyl-chroman-4-one O-methyl-oxime

A solution of the product of Example 4B (0.84 g, 3.88 mmol) and methoxyl amine hydrochloride (0.65 g, 7.78 mmol, 2 eq.) in pyridine (10 mL) was stirred for 18 hrs at ambient temperature and concentrated under vacuum. The residue was dissolved in diethyl ether and washed sequentially with water, 1N HCl and water. The isolated organic layer was concentrated and the residue chromatographed on silica gel, eluting with 5:95 ethyl acetate:hexanes to afford the title product (0.71 g, 74%). $^1$H NMR (300 MHz, DMSO-$d_6$) δ 8.60 (d, J 7.5 Hz, 1H, major), 8.00 (d, J 7.5 Hz, 1H, minor), 7.28 (m, 2H), 4.40 (t, J 6.0 Hz, 2H, major), 4.24 (t, J 6.0 Hz, 2H, minor), 3.98 (s, 3H, minor), 3.96 (s, 3H, major), 2.87 (t, J 6.0 Hz, 2H, minor), 2.70 (t, J 6.0 Hz, 2H, major). MS (DCI/$NH_3$) m/e 246 $(M+H)^+$.

Example 4D

7-Trifluoromethyl-chroman-4-ylamine

The title compound was prepared according to the procedure described in Example 1C substituting the product of Example 4C for the product of Example 1B. $^1$H NMR (300 MHz, $CDCl_3$) δ 7.43(d, 1H, J=8.1 Hz), 7.1(d, 1H, J=8.1 Hz), 7.0(s, 1H), 4.22-4.37 (m, 2H), 4.08 (t, 1H, J=5.4 Hz), 2.12-2.22 (m, 1H), 1.82-1.92 (m, 1H). MS (DCI) m/e 218 $(M+H)^+$.

Example 4E

4-[3-(7-Trifluoromethyl-chroman-4-yl)-ureido]-indazole-1-carboxylic acid methyl ester The title compound was prepared using the procedure as described in Example 1D, substituting the product of Example 4D for the product of Example 1C. $^1$H NMR (300 MHz, DMSO-$d_6$) δ 8.92 (s, 1H), 8.40 (s, 1H), 7.85 (d, 1H, J=7.1 Hz), 7.71 (d, 1H, J=8.5 Hz), 7.54 (m, 2H), 7.26 (d, 1H, J=7.8 Hz), 7.14 (s, 1H), 6.95 (d, 1H, J=8.1 Hz), 5.03 (m, 1H), 4.38 (m, 1H), 4.27 (m, 1H), 4.03 (s, 3H), 2.19 (m, 1H), 2.09 (m, 1H). MS (ESI) m/e 435 $(M+H)^+$.

Example 4F

N-1H-indazol-4-yl-N'-[7-(trifluoromethyl)-3,4-dihydro-2H-chromen-4-yl]urea

The title compound was prepared using the procedure as described in Example 1E, substituting the product of Example 4E for the product of Example 1D. $^1$H NMR (300 MHz, DMSO-$d_6$) δ 13.00 (broad s, 1H), 8.67 (s, 1H), 8.04 (s, 1H), 7.67 (d, J=7.5 Hz, 1H), 7.55 (d, J=7.5 Hz, 1H), 7.22 (m, 2H), 7.10 (m, 2H), 7.00 (d, J=7.5 Hz, 1H), 5.00 (m, 1H), 4.41-4.20 (m, 2H), 2.22-2.00 (m, 2H). S (ESI) m/e 377 $(M+H)^+$. Calcd. For $C_{18}H_{15}N_4O_2F_3 \cdot 0.7$; $H_2O$: C, 55.59; H, 4.25; N, 14.40. Found: C, 55.51; H, 3.98; N, 14.65.

Example 5

N-isoquinolin-5-yl-N'-[7-(trifluoromethyl)-3,4-dihydro-2H-chromen-4-yl]urea

A solution of phosgene (20% in toluene, 2.9 mL, 5.5 mmol) in dichloromethane (30 mL) at 0° C. was treated with dropwise addition of 4-dimethylaminopyridine (1.43 g, 11.7 ml) in dichloromethane (15 mL). A thick white suspension formed. A solution of 5-aminoisoquinoline in 15 mL of dichloromethane was then added dropwise to this suspension. The reaction mixture was allowed to warm to ambient temperature and stirred overnight. At the end of this time, a solution formed, and the solvent was removed under reduced pressure. The residue was titurated with 50 mL of diethyl ether to give an approximately 0.1 M solution of 5-isocyanato-isoquinoline.

3 ml of the 5-isocyanato-isoquinoline solution was added to the product of Example 4D (49 mg, 0.3 mmol) and stirred at ambient temperature overnight, and the precipitate formed was collected by filtration and washed with diethyl ether to give 23 mg of the title compound (23% yield). $^1$H NMR (300 MHz, DMSO-$d_6$) δ 9.28 (s, 1H), 8.63 (s, 1H), 8.55 (d, J=6.0 Hz, 1H), 8.32 (m, 1H), 7.90 (d, J=6.0 Hz, 1H), 7.77 (d, J=7.5 Hz, 1H), 7.60 (m, 1H), 7.30-7.12 (m, 3H), 5.02 (m, 1H), 4.42-4.20 (m, 2H), 2.30-2.00 (m, 2H). MS (ESI) m/e 388 $(M+H)^+$. Calcd. For $C_{20}H_{16}N_3O_2F_3 \cdot 0.2$; $H_2O$: C, 62.01; H, 4.16; N, 10.85. Found: C, 61.29; H, 3.94; N, 10.64.

Example 6

N-quinolin-5-yl-N'-[7-(trifluoromethyl)-3,4-dihydro-2H-chromen-4-yl]urea

The title compound was prepared using the procedure as described for Example 5, substituting 5-aminoquinoline for 5-aminoisoquinoline. $^1$H NMR (300 MHz, DMSO-d$_6$) δ 8.90 (m, 1H), 8.63 (s, 1H), 8.45 (m, 1H), 8.11 (t, J=4.0 Hz, 1H), 7.68 (d, J=4.0 Hz, 2H), 7.57 (m, 2H), 7.23 (m, 1H), 7.12 (m, 1H), 5.02 (m, 1H), 4.42-4.20 (m, 2H), 2.30-2.00 (m, 2H). MS (ESI) m/e 388 (M+H)$^+$. Calcd. For C$_{20}$H$_{16}$N$_3$O$_2$F$_3$.0.25; H$_2$O: C, 61.30; H, 4.24; N, 10.72. Found: C, 61.25; H, 3.99; N, 10.55.

Example 7

N-1H-indazol-4-yl-N'-(6-methyl-3,4-dihydro-2H-chromen-4-yl)urea

Example 7A

6-Methyl-chroman-4-one O-methyl-oxime

The title compound was prepared following the procedure as described in Example 1B, substituting 6-methyl-chroman-4-one for the product of Example 1B. MS (DCI) m/e 192 (M+H)$^+$.

Example 7B

6-Methyl-chroman-4-ylamine

A solution of the product of Example 7A (4.24 g) in 50 mL of a mixture of 20% ammonia in methanol was treated with 40 g Raney Nickle under 60 psi hydrogen for 4 hours at ambient temperature. The reaction mixture was filtered, and the solvent evaporated under reduced pressure. The residue was taken in diethyl ether, washed sequentially with water and saturated aqueous sodium bicarbonate, dried with magnesium sulfate, filtered and concentrated to give 2.22 g of the title compound. $^1$H NMR (300 MHz, CDCl$_3$) δ 7.11 (s, 1H), 6.95 (d, 1H, J=8.5 Hz), 6.71 (d, 1H, J=8.5 Hz), 4.22 (m, 2H), 4.01 (m, 1H), 2.27 (s, 3H), 2.10-2.21 (m, 1H), 1.78-1.88 (m, 1H). MS (DCI) m/e 164 (M+H)$^+$.

Example 7C

4-[3-(6-Methyl-chroman-4-yl)-ureido]-indazole-1-carboxylic acid methyl ester

The title compound was prepared using the procedure as described in Example 1D, substituting the product of Example 7B for the product of Example 1C. $^1$H NMR (300 MHz, DMSO-d$_6$) δ 8.83 (s, 1H), 8.38 (s, 1H), 7.89 (d, 1H, J=7.1 Hz), 7.69 (d, 1H, J=8.5 Hz), 7.51 (m, 1H), 7.11 (d, 1H, J=2.0 Hz), 7.00 (dd, 1H, J=8.3 and 2.2 Hz), 6.86 (d, 1H, J=7.5 Hz), 6.71 (d, 1H, J=8.5 Hz), 4.86 (m, 1H), 4.25 (m, 1H), 4.12 (m, 1H), 4.03 (s, 3H), 2.22 (s, 3H), 2.12 (m, 1H), 2.03 (m, 1H). MS (ESI) m/e 381 (M+H)$^+$.

Example 7D

N-1H-indazol-4-yl-N'-(6-methyl-3,4-dihydro-2H-chromen-4-yl)urea

The title compound was prepared using the procedure as described in Example 1E, substituting the product of Example 7C for the product of Example 1D. $^1$H NMR (300 MHz, DMSO-d$_6$) δ 13.00 (broad s, 1H), 8.56 (s, 1H), 8.02 (s, 1H), 7.67 (d, J=7.5 Hz, 1H), 7.20 (m, 1H), 7.12-6.94 (m, 3H), 6.86 (d, J=7.5 Hz, 1H), 6.70 (d, J=7.5 Hz, 1H), 4.92 (m, 1H), 4.33-4.00 (m, 2H), 2.22 (s, 3H), 2.20-1.93 (m, 2H). MS (ESI) m/e 323 (M+H)$^+$. Calcd. For C$_{18}$H$_{18}$N$_4$O$_2$.0.9; H$_2$O 0.25 NaCl: C, 61.21; H, 5.65; N, 15.86. Found: C, 61.02; H, 5.74; N, 15.84.

Example 8

N-isoquinolin-5-yl-N'-(6-methyl-3,4-dihydro-2H-chromen-4-yl)urea

The title compound was prepared using the procedure as described in Example 5, substituting the product of Example 7B for the product of Example 4D. $^1$H NMR (300 MHz, DMSO-d$_6$) δ 9.26 (s, 1H), 8.60 (s, 1H), 8.56 (d, J=6.0 Hz, 1H), 8.40 (m, 1H), 7.90 (d, J=6.0 Hz, 1H), 7.78 (d, J=7.5 Hz, 1H), 7.61 (m, 1H), 7.13 (m, 2H), 7.00 (m, 1H), 6.73 (d, J=7.5 Hz, 1H), 4.85 (m, 1H), 4.33-4.06 (m, 2H), 2.21 (s, 3H), 2.20-1.95 (m, 2H). MS (ESI) m/e 334 (M+H)$^+$. Calcd. For C$_{20}$H$_{19}$N$_3$O$_2$.0.2; H$_2$O, C, 71.28; H, 5.80; N, 12.47. Found C, 71.45; H, 5.57; N, 12.31.

Example 9

N-(6-methyl-3,4-dihydro-2H-chromen-4-yl)-N'-quinolin-5-ylurea

This compound was made following the procedure of Example 5, except substituting 5-aminoquinoline for 5-aminoisoquinoline and 6-methyl-chroman-4-ylamine for 7-trifluoromethyl-chroman-4-ylamine. $^1$H NMR (300 MHz, DMSO-d$_6$) δ 8.90 (m, 1H), 8.60 (s, 1H), 8.47 (m, 1H), 8.18 (m, 1H), 7.68 (m, 2H), 7.57 (m, 1H), 7.16 (m, 1H), 7.08 (d, J=7.5 Hz, 1H), 7.00 (m, 1H), 6.71 (d, J=7.5 Hz, 1H), 4.93 (m, 1H), 4.31-4.10 (m, 2H), 2.21 (s, 3H), 2.20-1.93 (m, 2H). MS (ESI) m/e 334 (M+H)$^+$. Calcd. For C$_{20}$H$_{19}$N$_3$O$_2$.0.1; H$_2$O: C, 71.67; H, 5.77; N, 12.54. Found: C, 71.65; H, 5.83; N, 12.30.

Example 10

N-(6-fluoro-3,4-dihydro-2H-chromen-4-yl)-N'-1H-indazol-4-ylurea

Example 10A

6-Fluoro-chroman-4-one O-methyl-oxime

The title compound was prepared using the procedure as described in Example 1B, substituting 6-fluoro-chroman-4-one for the product of Example 1A. MS (DCI) m/e 196 (M+H)$^+$.

Example 10B

6-Fluoro-chroman-4-ylamine

The title compound was prepared using the procedure as described in Example 7B, substituting the product of Example 10A for the product of Example 7A. $^1$H NMR (300 MHz, CDCl$_3$) δ 7.03 (dd, 1H, J=9.1 and 3.1 Hz), 6.85 (m, 1H), 6.74 (m, 1H), 4.15-4.29 (m, 2H), 4.02 (m, 1H), 2.10-2.20 (m, 1H), 1.79-1.89 (m, 1H). MS (DCI) m/e 168 (M+H)$^+$.

Example 10C

4-[3-(6-Fluoro-chroman-4-yl)-ureido]-indazole-1-carboxylic acid methyl ester

The title compound was prepared using the procedure as described in Example 1D, substituting the product of Example 10B for the product of Example 1C. $^1$H NMR (300 MHz, DMSO-d$_6$) δ 8.86 (s, 1H), 8.40 (s, 1H), 7.93 (s, 1H), 7.86 (d, 1H, J=7.5 Hz), 7.72 (d, 1H, J=7.5 Hz), 7.51 (m, 1H), 7.15-6.80 (m, 3H), 4.91 (m, 1H), 4.30-4.13 (m, 2H), 4.03 (s, 3H), 2.20-1.97 (m, 2H). MS (DCI) m/e 385 (M+H)$^+$.

Example 10D

N-(6-fluoro-3,4-dihydro-2H-chromen-4-yl)-N'-1H-indazol-4-ylurea

The title compound was prepared using the procedure as described in Example 1E, substituting the product of Example 10C for the product of Example 1D. $^1$H NMR (300 MHz, DMSO-d$_6$) δ 13.00 (broad s, 1H), 8.60 (s, 1H), 8.02 (s, 1H), 7.67 (d, J=7.5 Hz, 1H), 7.21 (m, 1H), 7.08-7.00 (m, 3H), 6.92-6.80 (m, 2H), 4.92 (m, 1H), 4.35-4.11 (m, 2H), 2.20-1.93 (m, 2H). MS (DCI) m/e 327 (M+H)$^+$. Calcd. For C$_{17}$H$_{15}$N$_4$O$_2$F.0.1; H$_2$O: C, 62.23; H, 4.67; N, 17.07. Found: C, 62.31; H, 4.46; N, 16.74.

Example 11

N-(6-fluoro-3,4-dihydro-2H-chromen-4-yl)-N'-isoquinolin-5-ylurea

The title compound was prepared using the procedure as described in Example 5, substituting the product of Example 10B for the product of Example 4D. $^1$H NMR (300 MHz, DMSO-d$_6$) δ 9.23 (s, 1H), 8.61 (s, 1H), 8.53 (d, J=6.0 Hz, 1H), 8.37 (m, 1H), 7.91 (d, J=6.0 Hz, 1H), 7.78 (d, J=7.5 Hz, 1H), 7.60 (m, 1H), 7.18 (m, 2H), 7.05 (m, 1H), 6.83 (m, 1H), 4.92 (m, 1H), 4.38-4.10 (m, 2H), 2.20-1.95 (m, 2H). MS (ESI) m/e 338 (M+H)$^+$. Calcd. For C$_{19}$H$_{16}$N$_3$O$_2$F.0.2; H$_2$O: C, 66.93; H, 4.85; N, 12.32. Found: C, 66.94; H, 4.57; N, 12.18.

Example 12

N-(6-fluoro-3,4-dihydro-2H-chromen-4-yl)-N'-quinolin-5-ylurea

The title compound was prepared using the procedure as described in Example 5, substituting 5-aminoquinoline for 5-aminoisoquinoline and substituting the product of Example 10B for the product of Example 4D. $^1$H NMR (300 MHz, DMSO-d$_6$) δ 8.90 (m, 1H), 8.62 (s, 1H), 8.46 (m, 1H), 8.12 (m, 1H), 7.68 (m, 2H), 7.57 (m, 1H), 7.18-7.00 (m, 3H), 6.83 (m, 1H), 4.91 (m, 1H), 4.33-4.06 (m, 2H), 2.20-1.95 (m, 2H). MS (ESI) m/e 336 (M−H)$^+$. Calcd. For C$_{19}$H$_{16}$N$_3$O$_2$F.0.2 NaCl: C, 65.38; H, 4.62; N, 12.04. Found C, 65.31; H, 4.51; N, 11.77.

Example 13

N-(6-chloro-7-methyl-3,4-dihydro-2H-chromen-4-yl)-N'-1H-indazol-4-ylurea

Example 13A

6-Chloro-7-methyl-chroman-4-one O-methyl-oxime

The compound was prepared using the procedure as described in Example 1B, substituting 6-chloro-7-methyl-chroman-4-one for the product of Example 1A. MS (DCI) m/e 226 (M+H)$^+$.

Example 13B

6-Chloro-7-methyl-chroman-4-ylamine

The title compound was prepared using the procedure as described in Example 7B, substituting the product of Example 13A for the product of Example 7A. $^1$H NMR (300 MHz, CDCl$_3$) δ 7.27 (s, 1H), 6.68 (s, 1H), 4.15-4.29 (m, 2H), 3.98 (m, 1H), 2.29 (s, 3H), 2.07-2.17 (m, 1H), 1.75-1.85 (m, 1H). MS (DCI) m/e 198 (M+H)$^+$.

Example 13C

4-[3-(6-Chloro-7-methyl-chroman-4-yl)-ureido]-indazole-1-carboxylic acid methyl ester The title compound was prepared using the procedure as described in Example 1D, substituting the product of Example 13B for the product of Example 1C. $^1$H NMR (300 MHz, DMSO-d$_6$) δ 8.88 (s, 1H), 8.40 (s, 1H), 7.85 (d, 1H, J=7.5 Hz), 7.70 (d, 1H, J=8.1 Hz), 7.51 (t, 1H, J=8.1 Hz), 7.31 (s, 1H), 6.89 (d, 1H, J=7.5 Hz), 6.83 (s, 1H), 4.90 (m, 1H), 4.26 (m, 1H), 4.18 (m, 1H), 4.03 (s, 3H), 2.26 (s, 3H), 2.08-2.18 (m, 1H), 1.95-2.05 (m, 1H). MS (ESI) m/e 415 (M+H)$^+$.

Example 13D

N-(6-chloro-7-methyl-3,4-dihydro-2H-chromen-4-yl)-N'-1H-indazol-4-ylurea

The title compound was prepared using the procedure as described in Example 1E, substituting the product of Example 13C for the product of Example 1D. $^1$H NMR (300 MHz, DMSO-d$_6$) δ 13.00 (broad s, 1H), 8.62 (s, 1H), 8.03 (s, 1H), 7.63 (d, J=7.5 Hz, 1H), 7.30 (s, 1H), 7.21 (m, 1H), 7.08 (d, J=7.5 Hz, 1H), 6.91 (d, J=7.5 Hz, 1H), 6.82 (s, 1H), 4.92 (m, 1H), 4.32-4.11 (m, 2H), 2.23 (s, 3H), 2.20-1.93 (m, 2H). MS (DCI) m/e 357 (M+H)$^+$. Calcd. For C$_{18}$H$_{17}$ClN$_4$O$_2$.0.3; H$_2$O.0.1; C$_4$H$_8$O: C, 59.82; H, 5.02; N, 15.17. Found: C, 59.75; H, 4.76; N, 15.00.

Example 14

N-(6-chloro-7-methyl-3,4-dihydro-2H-chromen-4-yl)-N'-isoquinolin-5-ylurea

The title compound was prepared using the procedure as described in Example 5, substituting the product of Example 13B for the product of Example 4D. $^1$H NMR (300 MHz, DMSO-d$_6$) δ 9.28 (s, 1H), 8.61 (s, 1H), 8.55 (d, J=6.0 Hz, 1H), 8.37 (m, 1H), 7.89 (d, J=6.0 Hz, 1H), 7.74 (d, J=7.5 Hz, 1H), 7.61 (m, 1H), 7.32 (s, 1H), 7.18 (d, J=7.5 Hz, 1H), 6.83 (s, 1H), 4.90 (m, 1H), 4.34-4.11 (m, 2H), 2.23 (s, 3H), 2.20-1.90 (m, 2H). MS (ESI) m/e 368 (M+H)$^+$. Calcd. For C$_{20}$H$_{18}$N$_3$O$_2$Cl.0.25; H$_2$O.0.1diethyl ether: C, 64.52; H, 5.18; N, 11.07. Found C, 64.28; H, 4.85; N, 10.84.

Example 15

N-(6-chloro-7-methyl-3,4-dihydro-2H-chromen-4-yl)-N'-quinolin-5-ylurea

The title compound was prepared using the procedure as described in Example 5, substituting 5-aminoquinoline for 5-aminoisoquinoline and substituting the product of Example 13B for the product of Example 4D. $^1$H NMR (300 MHz, DMSO-d$_6$) δ 8.90 (m, 1H), 8.62 (s, 1H), 8.47 (m, 1H), 8.12

(m, 1H), 7.70 (m, 2H), 7.58 (m, 1H), 7.31 (s, 1H), 7.07 (d, J=7.5 Hz, 1H), 7.18-7.00 (m, 3H), 6.82 (s, 1H), 4.91 (m, 1H), 4.33-4.10 (m, 2H), 2.24 (s, 3H), 2.20-1.92 (m, 2H). MS (ESI) m/e 368 (M−H)+. Calcd. For $C_{20}H_{18}N_3O_2Cl.0.2; H_2O$: C, 64.67; H, 4.99; N, 11.31. Found: C, 64.85; H, 4.90; N, 11.02.

Example 16

N-3,4-dihydro-2H-chromen-4-yl-N'-1H-indazol-4-ylurea

Example 16A

Chroman-4-one O-methyl-oxime

The title compound was prepared using the procedure as described in Example 1B, substituting chroman-4-one for the product of Example 1A. $^1$H NMR (300 MHz, $d_6$-DMSO) δ 7.79 (dd, J=1.0 and 7.5 Hz, 1H), 7.28 (m, 1H), 6.90 (m, 2H), 4.18 (t, J 6.0 Hz, 2H), 3.90 (s, 3H, minor), 3.88 (s, 3H, major), 2.82 (t, J 6.0 Hz, 2H). MS (DCI/NH$_3$) m/e 178 (M+H)+.

Example 16B

Chroman-4-ylamine

The title compound was prepared using the procedure as described in Example 7B, substituting the product of Example 16A for the product of Example 7A. $^1$H NMR (300 MHz, DMSO-$d_6$) δ ppm 7.32 (dd, J 1.0 and 7.5 Hz, 1H), 7.05 (m, 1H), 6.81 (m, 1H), 6.70 (dd, J 1.0 and 7.5 Hz, 1H), 4.27-4.08 (m, 2H), 3.83 (t, J 6.0 Hz, 1H), 2.03-1.66 (m, 4H). MS (DCI/NH$_3$) m/e 150 (M+H)+.

Example 16C 4-(-Chroman-4-yl-ureido)-indazole-1-carboxylic acid methyl ester The title compound was prepared according to the procedure as described in Example 1D, substituting the product of Example 16B for the product of Example 1C. $^1$H NMR (300 MHz, DMSO-$d_6$) δ 8.82 (s, 1H), 8.40 (s, 1H), 7.88 (d, J 7.5 Hz, 1H), 7.70 (d, J 7.5 Hz, 1H), 7.52 (m, 1H), 7.32 (d, J 7.5 Hz, 1H), 7.20 (m, 1H), 6.86 (m, 3H), 4.90 (m, 1H), 4.35-4.10 (m, 2H), 4.00 (s, 3H), 2.10-1.92 (m, 2H). MS (DCI/NH$_3$) m/e 150 (M+H)+.

Example 16D

N-3,4-dihydro-2H-chromen-4-yl-N'-1H-indazol-4-ylurea

The title compound was prepared according to the procedure as described in Example 1E, substituting the product of Example 16C for the product of Example 1D. $^1$H NMR (300 MHz, DMSO-$d_6$) δ 13.00 (broad s, 1H), 8.58 (s, 1H), 8.03 (s, 1H), 7.65 (d, J=7.5 Hz, 1H), 7.30 (d, J=7.5 Hz, 1H), 7.20 (m, 2H), 7.05 (d, J=6 Hz, 1H), 6.95-6.80 (m, 3H), 4.90 (m, 1H), 4.30-4.17 (m, 2H), 2.20-2.00 (m, 2H). MS (DCI) m/e 309 (M+H)+. Calcd. For $C_{17}H_{16}N_4O_2.0.6; H_2O$: C, 63.98; H, 5.43; N, 17.56. Found: C, 63.85; H, 5.07; N, 17.62.

Example 17

N-(6-methyl-3,4-dihydro-2H-chromen-4-yl)-N'-quinolin-8-ylurea

The title compound was prepared using the procedure as described in Example 3B, substituting the product of Example 7B for the product of Example 1C. $^1$H NMR (300 MHz, DMSO-$d_6$) δ ppm 9.39 (s, 1H), 8.84 (dd, J=4.0 and 1.7 Hz, 1H), 8.56 (dd, J=7.1 and 2.0 Hz, 1H), 8.35 (dd, J=8.5 and 1.7 Hz, 1H), 7.93 (d, J=7.8 Hz, 1H), 7.47-7.61 (m, 3H), 7.09 (s, 1H), 6.97 (dd, J=8.3 and 2.2 Hz, 1H), 6.69 (d, J=8.5 Hz, 1H), 4.88-4.95 (m, 1H), 4.21-4.28 (m, 1H), 4.14 (ddd, J=11.3, 8.9, and 2.9 Hz, 1H), 2.51 (s, 3H), 2.20 (s, 3 H), 2.05-2.17 (m, 1H), 1.89-2.00 (m, 1H). MS (ESI) m/e 334 (M+H)+. Calcd. For $C_{20}H_{19}N_3O_2.0.33 CF_3CO_2H$: C, 66.88; H, 5.25; N, 11.33. Found: C, 67.06; H, 5.09; N, 11.07.

Example 18

N-(6-fluoro-3,4-dihydro-2H-chromen-4-yl)-N'-quinolin-8-ylurea

The title compound was prepared using the procedure as described in Example 3B, substituting the product of Example 10B for the product of Example 1C. $^1$H NMR (300 MHz, DMSO-$d_6$) δ ppm 9.42 (s, 1H), 8.83-8.88 (m, 1H), 8.55 (dd, J=6.8 and 2.0 Hz, 1H), 8.36 (dd, J=8.3 and 1.5 Hz, 1H), 7.97 (d, J=7.8 Hz, 1H), 7.55-7.64 (m, 1H), 7.48-7.55 (m, 2H), 7.11 (dd, J=9.3 and 2.9 Hz, 1H), 7.02 (td, J=8.6 and 3.2 Hz, 1H), 6.83 (dd, J=9.0 and 4.9 Hz, 1H), 4.92-4.99 (m, 1H), 4.14-4.30 (m, 2H), 2.09-2.20 (m, 1H), 1.91-2.01 (m, 1H). MS (ESI) m/e 338 (M+H)+. Calcd. For $C_{20}H_{19}N_3O_2.0.1 CF_3CO_2H$: C, 66.12; H, 4.65; N, 12.05. Found: C, 65.97; H, 4.63; N, 11.99.

Example 19

N-(7-tert-butyl-3,4-dihydro-2H-chromen-4-yl)-N'-(3-methylisoquinolin-5-yl)urea

A solution of phosgene (20% in toluene, 2.9 mL, 5.5 mmol) of dichloromethane (30 mL) was cooled to 0° C. and treated dropwise with a solution of 4-dimethylaminopyridine (1.43 g, 11.7 mL) in dichloromethane (15 mL). A thick white suspension formed. A solution of 3-methyl-isoquinolin-5-ylamine (0.79 g, 5 mmol) in tetrahydrofuran (20 mL) was then added dropwise to this suspension. The reaction mixture was allowed to warm to ambient temperature and stirred overnight, the solvent was removed under reduced pressure, and the residue titurated with 50 mL of diethyl ether to give an approximately 0.1 M solution of 3-methyl-5-isocyanato-isoquinoline.

6 mL of the 3-methyl-5-isocyanato-isoquinoline solution was added to the product of Example 1C (123 mg, 0.6 mmol). The reaction mixture was stirred overnight, and the percipitate formed was collected by filtration and washed with diethyl ether to give 0.15 g of the title compound (64% yield). $^1$H NMR (300 MHz, DMSO-$d_6$) δ ppm 9.17 (s, 1 H), 8.46 (s, 1 H), 8.34 (d, J=6.8 Hz, 1 H), 7.66-7.73 (m, 2 H), 7.51 (t, J=8.0 Hz, 1 H), 7.25 (d, J=8.5 Hz, 1 H), 7.12 (d, J=7.1 Hz, 1 H), 6.98 (dd, J=8.0, 1.9 Hz, 1 H), 6.80 (d, J=2.0 Hz, 1 H), 4.82-4.89 (m, 1 H), 4.24-4.31 (m, 1 H), 4.10-4.18 (m, 1 H), 2.63 (s, 3 H), 1.99-2.14 (m, 2 H), 1.25 (s, 9 H). MS (ESL+) m/e 390 (M+H)+. Calc'd. For $C_{24}H_{27}N_3O_2.0.5; H_2O$: C, 72.34; H, 7.08; N, 10.54. Found C, 72.52; H, 7.23; N, 10.53.

Example 20

N-(6-fluoro-3,4-dihydro-2H-chromen-4-yl)-N'-(3-methylisoquinolin-5-yl)urea

The title compound was prepared using the procedure as described for Example 19, substituting the product of Example 10B for the product of Example 1C. $^1$H NMR (300 MHz, DMSO-d$_6$) δ ppm 7.13-7.18 (m, 2 H), 7.71 (d, J=10.5 Hz, 2 H), 9.18 (s, 1 H), 8.53 (s, 1 H), 4.17 (ddd, J=11.3, 8.4, 3.0 Hz, 1 H), 8.30 (d, J=6.4 Hz, 1 H), 4.93 (q, J=6.1 Hz, 1 H), 7.05 (td, J=8.6, 3.4 Hz, 1 H), 4.25-4.33 (m, 1 H), 2.10-2.21 (m, 1 H), 7.52 (t, J=8.0 Hz, 1 H), 6.85 (dd, J=9.0, 4.9 Hz, 1 H), 2.02 (ddd, J=13.4, 6.8, 2.9 Hz, 1 H), 2.64 (s, 3 H). MS (ESL$^+$) m/e 352 (M+H)$^+$. Calc'd. For C$_{20}$H$_{18}$N$_3$O$_2$.0.1; H$_2$O.0.1 Et$_2$O: C, 67.95; H, 5.37; N, 11.65. Found C, 67.88; H, 5.33; N, 11.56.

Example 21

N-(6-methyl-3,4-dihydro-2H-chromen-4-yl)-N'-(3-methylisoquinolin-5-yl)urea

The title compound was prepared using the procedure as described for Example 19, substituting the product of Example 7B for the product of Example 1C. $^1$H NMR (300 MHz, DMSO-d$_6$) δ ppm 8.49 (s, 1 H), 9.17 (s, 1 H), 8.34 (d, J=7.8 Hz, 1 H), 7.67-7.73 (m, 2 H), 7.52 (t, J=8.0 Hz, 1 H), 7.10-7.15 (m, 2 H), 7.01 (dd, J=8.3, 2.2 Hz, 1 H), 6.72 (d, J=8.5 Hz, 1 H), 4.83-4.90 (m, 1 H), 4.22-4.30 (m, 1 H), 4.12 (ddd, J=11.4, 9.0, 2.7 Hz, 1 H), 2.63 (s, 3 H), 2.23 (s, 3 H), 2.10 (dd, J=9.7, 4.2 Hz, 1 H), 2.02 (tt, J=5.4, 2.9 Hz, 1 H). MS (ESI$^+$) m/e 348 (M+H)$^+$. Calc'd. For C$_{21}$H$_{21}$N$_3$O$_2$.0.1; H$_2$O.0.1 Et$_2$O: C, 72.07; H, 6.27; N, 11.78. Found C, 72.20; H, 6.25; N, 11.78.

Example 22

N-[(1-benzyl-1,2,3,4-tetrahydroquinolin-2-yl)methyl]-N'-1H-indazol-4-ylurea

Example 22A tert-butyl 2-{[({[1-(methoxycarbonyl)-1H-indazol-4-yl]amino}carbonyl)amino]methyl}-3,4-dihydroquinoline-1 (2H)-carboxylate To a solution of 2-aminomethyl-3,4-dihydro-2H-quinoline-1-carboxylic acid tert-butyl ester (0.6 g, 2.29 mmol) in N,N-dimethylformamide (15 mL) and diisopropylethylamine was added the product of Example 24D (0.69 g, 2.1 mmol) and the mixture was stirred for 2 hrs at room temperature. Water was added to the reaction mixture and the organic phase was separated from the aqueous phase. The isolated organic phase was diluted with ethyl acetate and washed twice with water. Organic layer was separated and concentrated to afford the title compound (0.72 g, 73%) as an amorphous solid. $^1$H NMR (300 MHz, DMSO-d$_6$) δ 8.91 (s, 1H), 8.40 (s, 1H), 7.78 (d, J=7.5 Hz, 1H), 7.67 (d, J=7.5 Hz, 1H), 7.49 (m, 2H), 7.15 (m, 2H), 7.00 (m, 1H), 6.40 (m, J=6.0 Hz, 1H), 4.60 (m, 1H), 4.02 (s, 3H), 3.27 (m, 1H), 3.00 (m, 1H), 2.78-2.51 (m, 2H), 2.12 (m, 1H), 1.65 (m, 1H), 1.40 (s, 9H); MS (DCI/NH$_3$) m/e 480 (M+H)$^+$.

Example 22B methyl 4-({[(1,2,3,4-tetrahydroquinolin-2-ylmethyl)amino]carbonyl}amino)-1H-indazole-1-carboxylate A solution of the product of Example 22A (0.72 g, 1.5 mmol) in dichloromethane (10 mL) was treated with trifluoroacetic acid (2 mL) at 0° C., stirred for 18 hrs, and concentrated under vacuo. Toluene was added to the resulting residue and concentrated to obtain the title compound (0.72 g, 99%) as a pink trifluoroacetate salt. $^1$H NMR (300 MHz, DMSO-d$_6$) δ 9.04 (s, 1H), 8.44 (s, 1H), 7.81 (d, J=7.5 Hz, 1H), 7.70 (d, J=7.5 Hz, 1H), 7.46 (m, 1H), 6.92 (m, 2H), 6.60 (m, 3H), 4.02 (s, 3H), 3.40 (m, 2H), 3.22 (m, 1H), 2.72 (m, 2H), 1.90 (m, 1H), 1.64 (m, 1H).

Example 22C methyl 4-[({[(1-benzyl-1,2,3,4-tetrahydroquinolin-2-yl)methyl]amino}carbonyl)amino]-1H-indazole-1-carboxylate A mixture of the product of Example 22B (0.72 g, 1.5 mmol), benzyl bromide (0.26 g, 1.5 mmol) and potassium carbonate (3.0 g in 3 mL of H$_2$O) in tetrahydrofuran (6 mL) was stirred at room temperature for 72 hrs, diluted with ethyl acetate, washed with water and partitioned. The isolated organic layer was concentrated and the residue was chromatographed on silica gel, eluting with 60%-100% ethyl acetate/hexanes to afford the title compound (0.58 g, 72%) as an amorphous solid. $^1$H NMR (300 MHz, d$_6$-DMSO) 9.00 (s, 1H), 8.42 (s, 1H), 7.80 (d, J=7.5 Hz, 1H), 7.68 (d, J=7.5 Hz, 1H), 7.48 (m, 1H), 7.28 (m, 5H), 6.95 (d, J=7.5 Hz, 1H), 6.83 (m, 1H), 6.58 (m, J=6.0 Hz, 1H), 6.50 (m, 1H), 6.36 (d, J=7.5 Hz, 1H), 4.64 (m, 2H), 4.01 (s, 3H), 3.57 (m, 1H), 3.41-3.20 (m, 2H), 2.90 (m, 1H), 2.67 (m, 1H), 2.03 (m, 1H), 1.82 (m, 1H); MS (DCI/NH$_3$) m/e 470 (M+H)$^+$.

Example 22D

N-[(1-benzyl-1,2,3,4-tetrahydroquinolin-2-yl)methyl]-N'-1H-indazol-4-ylurea

A solution of the product of Example 22C (0.55 g, 1.17 mmol) in methanol (5 mL) was treated with a solution of NaOH in methanol (5M, 1 mL), and stirred for 2 hrs at ambient temperature. Water was added to the reaction mixture filtered. The isolated solid was washed with water and dried under vacuo to afford the title compound (0.32 g, 65%) as a white solid.

$^1$H NMR (300 MHz, DMSO-d$_6$) δ 13.00 (broad s, 1H), 8.75 (s, 1H), 8.10 (s, 1H), 7.59 (d, J=7.5 Hz, 1H), 7.25 (m, 6H), 7.03 (d, J=7.5 Hz, 1H), 6.95 (d, J=7.5 Hz, 1H), 6.83 (m, 1H), 6.60 (m, J=6.0 Hz, 1H), 6.48 (m, 1H), 6.36 (d, J=7.5 Hz, 1H), 4.64 (m, 2H), 3.57 (m, 1H), 3.41-3.20 (m, 2H), 2.92 (m, 1H), 2.67 (m, 1H), 2.05 (m, 1H), 1.82 (m, 1H); MS (DCI/NH$_3$) m/e 412 (M+H)$^+$. Anal. Calc'd. For C$_{25}$H$_{25}$N$_5$O.0.7; H$_2$O: C, 70.80; H, 6.27; N, 16.51. Found: C, 70.67; H, 6.19; N, 16.26.

Example 23

N-(1-benzyl-1,2,3,4-tetrahydroquinolin-3-yl)-N'-1H-indazol-4-ylurea

Example 23A tert-butyl 1-benzyl-1,2,3,4-tetrahydroquinolin-3-ylcarbamate

A mixture of (1,2,3,4-tetrahydroquinolin-3-yl)-carbamic acid tert-butyl ester (507 mg, 2.04 mmol) and potassium carbonate (367 mg, 2.65 mmol) in ethanol (15 mL) was treated with benzyl bromide (367 mg, 2.14 mmol) and stirred overnight at ambient temperature. The reaction mixture was partitioned between ethyl acetate (100 mL) and water (100 mL). The isolated organic phase was washed with brine and dried over anhydrous sodium sulfate, filtered and concentrated. The resulting oil was chromatographed on silica gel, eluting with 5-to-50% ethyl acetate in hexane to afford the title compound (529 mg, 77%) as a white solid. $^1$H NMR (300 MHz, DMSO-$d_6$) δ: 1.38 (s, 9H), 2.65-2.75 (dd, 1H), 2.83-2.92 (dd, 1H), 3.11-3.22 (dd, 1H), 3.35-3.42 (dd, 1H), 3.77-3.90 (m, 1H), 4.39-4.51 (q, 2H), 6.45-6.52 (m, 2H), 6.82-6.94 (m, 3H), 7.20-7.34 (m, 5H). MS (ESI) m/z 222.2, 283.1, 339.1 (M+H)$^+$.

Example 23B 1-benzyl-1,2,3,4-tetrahydroquinolin-3-amine

Trifluoroacetic acid (3 mL) was added to a solution of (1-benzyl-1,2,3,4-tetrahydroquinolin-3-yl)-carbamic acid tert-butyl ester (481 mg, 1.42 mmol) in dichloromethane (6 mL), stirred for 30 minutes at ambient temperature, and concentrated. A solution of the resulting oil in methanol (10 mL) was treated with potassium carbonate (393 mg, 2.84 mmol), stirred for an hour at room temperature, and concentrated to afford the title compound as yellow residue. MS (DCI/NH$_3$) m/z: 239.1 [M+H]$^+$.

Example 23C

N-(1-benzyl-1,2,3,4-tetrahydroquinolin-3-yl)-N'-1H-indazol-4-ylurea

A solution of the product of Example 23B and diisopropylethylamine (0.3 mL, 1.72 mmol) in N,N-dimethylformamide (10 mL) was treated with the product of Example 24D (472 mg, 1.42 mmol) under nitrogen atmosphere at ambient temperature, stirred at room temperature for 30 minutes, diluted with water (100 mL), and filtered. The isolated solid was washed with water and air-dried. A mixture of the solid and a solution of methanol (25 mL), water (3 mL) and triethylamine (0.4 mL, 2.87 mmol) was refluxed for an hour, cooled to room temperature, diluted with water (200 mL), and filtered. The isolated solid was rinsed with water and air-dried. The wet cake was vacuum dried to constant weight to afford the title compound (483 mg, 85%) as a white solid. $^1$H NMR (300 MHz, DMSO-$d_6$) δ: 2.68-2.76 (dd, 1H), 3.09-3.17 (dd, 1H), 3.57 (dd, 1H), 4.24 (m, 1H), 4.46-4.61 (q, 2H), 6.51-6.58 (m, 3H), 6.92-7.06 (m, 3H), 7.16-7.21 (m, 2H), 7.23-7.33 (m, 4H), 7.65 (d, 1H), 8.06 (s, 1H), 8.81 (s, 1H), 12.98 (s, 1H). MS (ESI) m/z 222.1, 398.2 (M+H)$^+$. Anal. Calc'd for $C_{24}H_{23}N_5O.0.9; H_2O$: C, 69.68; H, 6.04; N, 16.93. Found: C, 69.73; H, 5.74; N, 16.67.

Example 24

4-(2,5-dioxo-pyrrolidin-1-yloxycarbonylamino)-indazole-1-carboxylic acid methyl ester Example 24A 4-nitro-1H-indazole 2-Methyl-3-nitroaniline (20 g) in acetic acid (~200 mL) was treated with NaNO$_2$ (20 g) in water (50 mL) at 4° C. (mechanical stirring). The reaction mixture was allowed to warm to room temperature and stir overnight. The solvent was removed under reduced pressure. The residue was treated with water (700 mL) and the mixture was filtered. The solid was dried at 45° C. in a vacuum oven overnight to provide the title compound. $^1$H NMR (DMSO-$d_6$) δ 8.56 (s, 1H), 8.2-8.05 (dd, 2H), 7.6 (t, 1H).

Alternatively, to a 4-necked 5-L jacketed round bottom flask fitted with a mechanical stirrer and a thermocouple was charged the nitroaniline (100 g, 1.0 equiv.) and acetic acid (2000 mL). The solution was cooled to 14° C. A chilled to about 1° C. (ice-water bath) solution of sodium nitrite (100 g, 2.2 equiv.) in water (250 mL) was added quickly in one portion. The internal temperature rose from 14° C. to 27.6° C. over 5 min., stayed at this temperature for 5 min. before gradually cooling to 15° C. The mixture was stirred for 24 h after which it was concentrated in vacuo to an approximate volume of 500 mL. The residue was re-slurried in water (1800 mL) at ambient temperature for 21 hours. The orange solid was filtered, washed with water (3×250 mL), and dried in a vacuum oven at 70° C. to afford 97.0 g of the title compound as a bright orange solid.

Example 24B methyl 4-nitro-1H-indazole-1-carboxylate

NaH (0.3 g, 12.5 mmol) in N,N-dimethylformamide (5 mL) was treated with the product of Example 24A (1.33 g, 10 mmol) at 0° C. The reaction mixture was allowed to warm to room temperature and stir for 1 hour. The mixture was treated with methyl chloroformate (0.9 mL) and stirred at room temperature for 3 hours. The mixture was treated with water and filtered to provide the title compound as a solid. $^1$H NMR (300 MHz, DMSO-$d_6$) δ 4.19 (s, 3H), 7.9 (t, 1H), 8.38 (d, 1H), 8.62 (d, 1H), 8.85 (s, 1H).

Alternatively, to a 3-necked 2-L jacketed flask fitted with a mechanical stirrer, a thermocouple, and an addition funnel was charged 95.2 g of the product of Example 24A and N,N-dimethylformamide (650 mL). The dark solution was cooled to 10° C. and DBU (96.0 g, 1.1 equiv.) was added via addition funnel so that the internal temperature did not go beyond 15° C. After cooling the mixture back to 10° C., methyl chloroformate (108.5 g, 2.0 equiv.) was added via addition funnel so that the internal temperature did not go beyond 25° C. After 1 hour stirring at 10° C., aqueous 10% potassium phosphate diacid in water (500 mL) was added and the mixture was stirred for 15 hours. The resulting brown solid was filtered and the reaction vessel rinsed with aqueous 10% potassium phosphate diacid in water (2×150 mL). The rinses were added to the solid on the filter. The resulting solid was washed with aqueous 10% potassium phosphate diacid in water (2×200 mL), water (2×200 mL), dried in a vacuum oven at 70° C. to afford 122.2 g of a dark brown solid. The solid was reslurried in isopropyl acetate (2000 mL) for 2 hours. The solid was filtered, washed with fresh isopropyl acetate (2×250 mL), and dried in a vacuum oven at 70° C. to afford 110.2 g of the title compound as a light brown solid.

Example 24C methyl 4-amino-1H-indazole-1-carboxylate

The product of Example 24B (1.66 g, 7.5 mmol) and 10% Pd/C were combined in ethanol (20 mL) and exposed to a hydrogen atmosphere. The reaction mixture was heated at 80° C. for 20 minutes, allowed to cool to room temperature, and filtered through Celite. The filtrate was evaporated to provide title compound. $^1$H NMR (300 MHz, DMSO-$d_6$) δ 6.1 (s, 2H), 6.41 (dd, 1H), 7.21 (m, 2H), 8.42 (s, 1H).

Alternatively, to the reaction vessel was charged the product of Example 24B, MeOH (2000 mL), and 5% Pd/C (10.6 g). The mixture was pressured with $H_2$ (40 psi) and shaken at ambient temperature. The reaction was completed in 1.5 hours. The mixture was filtered to obtain the product in MeOH. Conc., 37% HCl (100 mL) was added to the reaction mixture. The product solution was concentrated to furnish a light brown solid. The solid was reslurried in isopropyl alcohol (200 mL) for 15 minutes. The solid was filtered and washed with fresh isopropyl alcohol (3×50 mL), and dried in a vacuum oven to provide 94.9 g of 4-aminoindazole-1-carboxylic acid methyl ester, HCl salt as a light brown solid.

Example 24D 4-(2,5-dioxo-pyrrolidin-1-yloxycarbonylamino)-indazole-1-carboxylic acid methyl ester The product of Example 24C (1.9 g, 10 mmol) and disuccinimidylcarbonate (2.8 g, 11 mmol) were mixed in acetonitrile (100 mL) for 48 hours under nitrogen atmosphere. The solid was isolated by filtration, washed with acetonitrile (10 mL) and dried under vacuum at ambient temperature to give the title compound (2.56 g, 77%) as off-white solid.

Example 25

N-(2,3-dihydro-1,4-benzodioxin-2-ylmethyl)-N'-1H-indazol-4-ylurea

The product of Example 24D (635 mg, 1.9 mmol) was added to a solution of 1-(2,3-dihydro-1,4-benzodioxin-2-yl)methanamine (315 mg, 1.9 mmol) and diisopropylethylamine (0.34 mL, 1.9 mmol) in N,N-dimethylformamide (5 mL) under nitrogen atmosphere at ambient temperature. After 30 minutes the reaction solution was diluted with water (50 mL), the resulting precipitate was filtered off, washed with water and air-dried. The wet cake was added to a solution of methanol (25 mL), water (3 mL) and triethylamine (0.54 mL, 3.8 mmol). The mixture was refluxed for an hour, cooled to room temperature, diluted with water (100 mL), collected the white precipitate by filtration, rinsed with water and air-dried. The wet cake was vacuum dried to constant weight to provide the title compound (568 mg, 92%) as a white solid. $^1$H NMR (300 MHz, DMSO-$d_6$) δ: 3.41-3.56 (m, 2H), 3.98 (dd, 1H), 4.26-4.33 (m, 1H), 4.36 (dd, 1H), 6.68 (t, 1H), 6.81-6.94 (m, 4H), 7.06 (d, 1H), 7.20 (t, 1H), 7.62 (d, 1H), 8.09 (s, 1H), 8.80 (s, 1H), 13.00 (s, 1H). MS (ESI) m/z: 325.1 (M+H)$^+$; Anal. Calc'd for $C_{17}H_{16}N_4O_3$: C, 62.95; H, 4.97; N, 17.27. Found: C, 62.66; H, 4.83; N, 16.99.

Example 26

N-(1-benzyl-2,3,4,5-tetrahydro-1H-1-benzazepin-5-yl)-N'-1H-indazol-4-ylurea

Example 26A

A mixture of 0.45 g (2.80 mmol) of 1,2,3,4-tetrahydrobenzo[b]azepin-5-one and 0.5 g (2.94 mmol) benzyl bromide in 4 mL of acetonitrile and 1 mL (5.74 mmol) of diisopropylethylamine was heated in a microwave oven at 180° C. for 30 minutes. The mixture was cooled to about room temperature and partitioned between ethyl acetate and sodium bicarbonate solution. The organic phase was concentrated, and the residue was chromatographed on silica gel, eluted with 5 to 50% ethyl acetate in hexane to provide 662 mg (94% yield) of Example 26A as a yellow solid. $^1$H NMR (300 MHz, DMSO-$d_6$) δ ppm 7.56 (dd, 1H), 7.22-7.36 (m, 6H), 6.90 (d, 1H), 6.76 (t, 1H), 4.73 (s, 2H), 3.27-3.31 (m, 2H), 2.69 (t, 2H), 2.06-2.15 (m, 2H). MS (DCI) m/e 252.1 (M+H)$^+$.

Example 26B

A mixture of 0.61 g (2.41 mmol) of Example 26A and 0.22 g (2.65 mmol) methoxyl amine hydrochloride in 10 mL pyridine was stirred overnight at ambient temperature, concentrated and partitioned between ethyl acetate and sodium bicarbonate solution. The organic phase was concentrated and the residue was chromatographed on silica gel, eluting with 0 to 50% ethyl acetate in hexane to provide 0.62 g (92% yield) of Example 26B as a yellow oil. $^1$H NMR (300 MHz, DMSO-$d_6$) δ ppm 7.23-7.36 (m, 6H), 7.16 (t, 1H), 6.84 (d, 1H), 6.78 (t, 1H), 4.47 (s, 2H), 3.88 (s, 3H), 3.12 (t, 2H), 2.68 (t, 2H), 1.78-1.86 (m, 2H). MS (DCI) m/e 281.1 (M+H)$^+$.

Example 26C 0.59 g (2.09 mmol) of Example 26B was added to 20 mL 20% ammonia in methanol and 1.0 g Raney nickel in a Parr shaker. The reactor was sealed and flushed with nitrogen, and then was pressurized with 60-psi hydrogen. The mixture was shaken at ambient temperature for 13 hours. After the reactor was flushed with nitrogen, the Raney nickel was filtered off and washed with methanol. The filtrate was concentrated to a yellow oil to provide 0.47 g (89% yield) of Example 26C. $^1$H NMR (300 MHz, DMSO-$d_6$) δ ppm 7.30-7.40 (m, 5H), 7.23 (t, 1H), 7.09 (t, 1H), 6.97 (d, 1H), 6.92 (t, 1H), 4.31-4.39 (m, 1H), 4.15-4.23 (m, 2H), 2.87-2.97 (m, 1H), 2.60-2.68 (m, 1H), 1.99-2.17 (m, 2H), 1.75-1.85 (m, 1H), 1.41-1.62 (m, 2H), 1.27-1.37 (m, 1H). MS (DCI) m/e 253.2 (M+H)$^+$.

Example 26D

N-(1-benzyl-2,3,4,5-tetrahydro-1H-1-benzazepin-5-yl)-N'-1H-indazol-4-ylurea

A mixture of 0.47 g (1.86 mmol) of Example 26C and 0.62 g (1.86 mmol) Example 24D in 10 mL of N,N-dimethylformamide and 0.33 mL (1.89 mmol) of diisopropylethylamine was stirred for an hour at ambient temperature, diluted with water, filtered off the precipitate and rinsed with water. The wet cake was added to 30 mL of methanol, 4 mL water, and 0.52 mL (3.73 mmol) of triethylamine. The mixture was refluxed for two hours, cooled and diluted with water, filtered off the precipitate and rinsed with water. The wet cake was vacuum dried to constant weight, yielding 0.73 g (95% yield) of title compound as a white solid. $^1$H NMR (300 MHz, DMSO-$d_6$) δ ppm 13.01 (s, 1H), 8.80 (s, 1H), 8.12 (s, 1H), 7.63 (d, 1H), 7.47 (d, 2H), 7.32 (t, 2H), 7.12-7.27 (m, 4H), 7.04 (t, 2H), 6.94 (t, 2H), 5.21 (ddd, 1H), 4.38-4.47 (m, 1H), 4.23-4.32 (m, 1H), 2.96-3.06 (m, 1H), 2.71-2.79 (m, 1H), 1.86-1.97 (m, 1H), 1.51-1.71 (m, 3H). MS (ESI) m/e 412.2 (M+H)$^+$. Calcd. for $C_{25}H_{25}N_5O.0.27H_2O$: C, 72.12; H, 6.18; N, 16.82;
Found C, 72.20; H, 6.37; N, 16.48.

Example 27

N-(2,3-dihydro-1-benzofuran-2-ylmethyl)-N'-1H-indazol-4-ylurea

Example 27A

A mixture of 0.5 g (3.05 mmol) of 2,3-dihydro-benzofuran-2-carboxylic acid and 0.83 g (6.09 mmol) of isobutyl chloroformate in 20 mL of tetrahydrofuran and 1.43 mL (10.3 mmol) of triethylamine was stirred for an hour at ambient temperature and filtered. The filtrate was added to 61 mL (30.5 mmol) of 0.5 M ammonia in dioxane and stirred overnight at ambient temperature, filtered and concentrated. The residue was chromatographed on silica gel, eluting with 20 to 80% ethyl acetate in hexane. The residue obtained was again chromatographed on silica gel with 0 to 10% methanol in dichloromethane to provide 0.26 g (52% yield) of Example 27A as a light yellow solid. $^1$H NMR (300 MHz, DMSO-d$_6$) δ ppm 7.52 (s, 1H), 7.37 (s, 1H), 7.21 (d, 1H), 7.12 (t, 1H), 6.85 (t, 1H), 6.82 (d, 1H), 5.06 (dd, 1H), 3.45 (dd, 1H), 3.21 (dd, 1H). MS (DCI) m/e 164.0 (M+H)$^+$.

Example 27B

A mixture of 4.65 mL (4.65 mmol) of 1.0 M lithium aluminum hydride in tetrahydrofuran and 0.25 g (1.55 mmol) of Example 27A in 10 mL of tetrahydrofuran was stirred for two hours at ambient temperature, then refluxed for two hours. The mixture was chilled to 0° C., and added 0.3 mL water dropwise, 10 mL tetrahydrofuran, 0.3 ml 3N sodium hydroxide, and 0.8 mL water. The slurry was filtered and the solid was rinsed with ethyl acetate. The filtrate was concentrated to provide 0.14 g (61% yield) of Example 27B. $^1$H NMR (300 MHz, DMSO-d$_6$) δ ppm 7.17 (d, 1H), 7.05 (t, 1H), 6.78 (t, 1H), 6.72 (d, 1H), 4.65-4.74 (m, 1H), 3.18 (dd, 1H), 2.96 (dd, 1H), 2.76 (d, 2H). MS (DCI) m/e 150.0 (M+H)$^+$.

Example 27C

N-(2,3-dihydro-1-benzofuran-2-ylmethyl)-N'-1H-indazol-4-ylurea

A mixture of 0.14 g (0.95 mmol) of Example 27B and 0.32 g (0.95 mmol) Example 24D in 9 mL of N,N-dimethylformamide and 0.17 mL (0.98 mmol) of diisopropylethylamine was stirred for an hour at ambient temperature, diluted with water, and filtered. The wet cake was added to 12 mL methanol, 1 mL water, and 0.27 mL (1.94 mmol) of triethylamine. The mixture was refluxed for two hours, cooled to ambient temperature, and partitioned between ethyl acetate and water. The organic layer was filtered through silica gel and rinsed with ethyl acetate. The filtrate was concentrated to a yellow solid and vacuum dried to constant weight, yielding 0.18 g (62% yield) of the titled compound. $^1$H NMR (300 MHz, DMSO-d$_6$) δ ppm 12.99 (s, 1H), 8.78 (s, 1H), 8.08 (s, 1H), 7.64 (d, 1H), 7.22 (d, 1H), 7.19 (d, 1H), 7.03-7.13 (m, 2H), 6.84 (d, 1H), 6.79 (d, 1H), 6.68 (t, 1H), 4.85-4.94 (m, 1H), 3.55 (ddd, 1H), 3.39 (dt, 1H), 3.28 (dd, 1H), 2.97 (dd, 1H). MS (ESI) m/e 309.1 (M+H)$^+$. Calcd. for $C_7H_{16}N_4O_2 \cdot 0.38C_4H_8O_2$: C, 65.08; H, 5.61; N, 16.39. Found C, 65.36; H, 5.47; N, 16.20.

Example 28

N-(3,4-dihydro-2H-chromen-2-ylmethyl)-N'-1H-indazol-4-ylurea

Example 28A 2.0 g (10.5 mmol) of 4-oxo-4H-chromene-2-carboxylic acid was added to 25 mL of acetic acid and 200 mg of 10% palladium on carbon (dry) in a Parr shaker. The reactor was sealed and flushed with nitrogen, and then was pressurized with 60-psi hydrogen. The mixture was shaken at 70° C. for 2.5 hours. After cooling the reactor was flushed with nitrogen, the palladium was filtered off and washed with acetic acid, and the filtrate was concentrated to a yellow oil. The yellow oil was chromatographed on silica gel, eluting with 0 to 10% methanol in ethyl acetate, yielding 2.04 g of Example 28A as a yellow solid. $^1$H NMR (300 MHz, DMSO-d$_6$) δ ppm 12.94 (br s, 1H), 7.03-7.11 (m, 2H), 6.82 (td, 1H), 6.79 (d, 1H), 4.76 (dd, 1H), 2.79 (dt, 1H), 2.62 (dt, 1H), 2.10-2.20 (m, 1H), 2.01-2.08 (m, 1H). MS (DCI) m/e 196.0 (M+NH$_4$)$^+$.

Example 28B 1.0 g (5.6 mmol) Example 28A was added to 20 mL of dichloromethane, and then 1.47 mL (16.9 mmol) oxalyl chloride and a few drops of N,N-dimethylformamide were added. Stirred for 30 minutes at ambient temperature and concentrated. The residue was dissolved in dichloromethane and added to 80 mL of 0.5 M ammonia in dioxane. The mixture was stirred overnight, filtered, and concentrated. The residue was chromatographed on silica gel, eluting with 50 to 100% ethyl acetate in hexane to provide 0.77 g (77% yield) of Example 28B as a white solid. $^1$H NMR (300 MHz, DMSO-d$_6$) δ ppm 7.40 (s, 1H), 7.35 (s, 1H), 7.04-7.12 (m, 2H), 6.80-6.86 (m, 2H), 4.46 (dd, 1H), 2.80 (ddd, 1H), 2.67 (dt, 1H), 2.10-2.20 (m, 1H), 1.83-1.95 (m, 1H). MS (DCI) m/e 178.0 (M+H)$^+$.

Example 28C 12.4 mL (12.4 mmol) 1.0 M lithium aluminum hydride in tetrahydrofuran was added to 0.73 g (4.12 mmol) of Example 28B in 20 mL tetrahydrofuran. The mixture was stirred for 3.5 hours at ambient temperature, refluxed for two hours, chilled to 0° C., and added 1.0 mL water dropwise, 30 mL tetrahydrofuran, 1.0 mL 15% sodium hydroxide, and 2.0 mL water. The slurry was filtered and the solids rinsed with ethyl acetate. The filtrate was concentrated to provide Example 28C as a colorless oil (0.67 g). $^1$H NMR (300 MHz, DMSO-d$_6$) δ ppm 7.00-7.06 (m, 2H), 6.78 (td, 1H), 6.72 (dd, 1H), 3.82-3.91 (m, 1H), 2.66-2.82 (m, 4H), 1.96-2.05 (m, 1H), 1.47-1.68 (m, 3H). MS (DCI) m/e 164.0 (M+H)$^+$.

Example 28D

N-(3,4-dihydro-2H-chromen-2-ylmethyl)-N'-1H-indazol-4-ylurea

A mixture of 0.34 g (2.10 mmol) of Example 28C and 0.7 g (2.10 mmol) of Example 24D in 10 mL of N,N-dimethylformamide and 0.37 mL (2.12 mmol) of diisopropylethylamine was stirred for an hour at ambient temperature, diluted with water, filtered off the precipitate and rinsed with water. The wet cake was added to 40 mL methanol, 3 mL water, and 0.59 mL (4.23 mmol) triethylamine. The mixture was refluxed for two hours, cooled and diluted with water, filtered off the precipitate and rinsed with water. The wet cake was vacuum dried to constant weight, yielding 0.54 g (80% yield) of the titled compound as a white solid. $^1$H NMR (300 MHz, DMSO-d$_6$) δ ppm 12.99 (s, 1H), 8.79 (s, 1H), 8.09 (s, 1H), 7.65 (d, 1H), 7.20 (t, 1H), 7.03-7.11 (m, 3H), 6.82 (td, 1H), 6.79 (dd, 1H), 6.66 (t, 1H), 4.08-4.16 (m, 1H), 3.37-3.53 (m, 2H), 2.75-2.87 (m, 2H), 1.97-2.05 (m, 1H), 1.64-1.78 (m, 1H). MS (ESI) m/e 323.1 (M+H)$^+$. Calcd. for $C_{18}H_{18}N_4O_2 \cdot 0.1H_2O$: C, 66.69; H, 5.66; N, 17.28. Found C, 66.71; H, 5.44; N, 17.21.

Example 29

N-[(1-benzyl-2,3-dihydro-1H-indol-2-yl)methyl]-N'-1H-indazol-4-ylurea

Example 29A

A mixture of 0.65 g (4.0 mmol) 2,3-dihydro-1H-indole-2-carboxylic acid and 2.05 g (12.0 mmol) benzyl bromide in 3 mL acetonitrile and 2.79 mL (16.0 mmol) diisopropylethylamine was heated in a microwave oven at 180° C. for 15 minutes, cooled to about room temperature and partitioned between ethyl acetate and water. The organic phase was concentrated. The residue was chromatographed on silica gel, eluting with 5 to 20% ethyl acetate in hexane to provide 1.496 g of Example 29A as a yellow oil. $^1$H NMR (300 MHz, DMSO-d$_6$) δ ppm 7.22-7.38 (m, 10H), 7.01 (d, 1H), 6.96 (t, 1H), 6.58 (t, 1H), 6.43 (d, 1H), 5.10 (s, 2H), 4.52 (d, 1H), 4.34 (dd, 1H), 4.21 (d, 1H), 3.39 (dd, 1H), 3.05 (dd, 1H). MS (ESI) m/e 344.4 (M+H)$^+$.

Example 29B

A mixture of 1.496 g of Example 29A and 11 mL of N,N-dimethylformamide and 11 mL of 30% ammonium hydroxide was stirred for 3 days at ambient temperature, diluted with water, and extracted with ethyl acetate and dichloromethane sequentially. The combined organic phases were concentrated. The residue was chromatographed on silica gel, eluting with 40 to 100% ethyl acetate in hexane, yielding 0.48 g (48% yield) of Example 29B as a white solid. $^1$H NMR (300 MHz, DMSO-d$_6$) δ ppm 7.46 (s, 1H), 7.31 (d, 4H), 7.22-7.28 (m, 1H), 7.13 (s, 1H), 6.99 (d, 1H), 6.94 (t, 1H), 6.56 (t, 1H), 6.41 (d, 1H), 4.53 (d, 1H), 4.10 (d, 1H), 4.06 (t, 1H), 3.27 (dd, 1H), 2.93 (dd, 1H). MS (DCI) m/e 253.1 (M+H)$^+$.

Example 29C 5.75 mL (5.75 mmol) of 1.0 M lithium aluminum hydride in tetrahydrofuran was added to 0.48 g (1.92 mmol) of Example 29B in 20 mL tetrahydrofuran. The mixture was stirred for 2.5 hours at ambient temperature, refluxed for one hour, chilled to 0° C., and followed by the addition of 0.5 mL of water dropwise, 15 mL of tetrahydrofuran, 0.5 ml of 15% sodium hydroxide, and 1.0 mL water. The slurry was filtered and the solid was rinsed with ethyl acetate. The filtrate was concentrated to provide 0.47 g of Example 29C as an orange oil. $^1$H NMR (300 MHz, DMSO-d$_6$) δ ppm 7.27-7.35 (m, 4H), 7.21-7.26 (m, 1H), 6.99 (d, 1H), 6.90 (t, 1H), 6.52 (t, 1H), 6.34 (d, 1H), 4.44 (d, 1H), 4.21 (d, 1H), 3.56-3.66 (m, 1H), 3.03 (dd, 1H), 2.87 (dd, 1H), 2.68-2.80 (m, 2H), 1.40-1.64 (m, 2H). MS (DCI) m/e 239.1 (M+H)$^+$.

Example 29D

N-[(1-benzyl-2,3-dihydro-1H-indol-2-yl)methyl]-N'-1H-indazol-4-ylurea

A mixture of 0.47 g of Example 29C and 0.64 g (1.92 mmol) of Example 24D in 10 mL of N,N-dimethylformamide and 0.34 mL (1.95 mmol) of diisopropylethylamine was stirred for an hour at ambient temperature, diluted with water and filtered. The wet cake was rinsed with water and added to 50 mL methanol, 5 mL water, and 0.54 mL (3.87 mmol) triethylamine. The mixture was refluxed for two hours, cooled and diluted with water, filtered off the precipitate and rinsed with water. The solid was purified on reverse phase preparative liquid chromatography with 20 to 100% acetonitrile in water (with 0.1% trifluoroacetic acid). The trifluoroacetic acid salt isolated was dissolved in methanol and treated with 0.54 mL (3.87 mmol) of triethylamine, precipitated with water, filtered and the wet cake rinsed with water and vacuum dried to constant weight, yielding 0.43 g (56% yield) of title compound as an off-white solid. $^1$H NMR (300 MHz, DMSO-d$_6$) δ ppm 12.97 (s, 1H), 8.79 (s, 1H), 8.07 (s, 1H), 7.62 (d, 1H), 7.29-7.38 (m, 4H), 7.16-7.26 (m, 2H), 7.01-7.06 (m, 2H), 6.95 (t, 1H), 6.57 (t, 1H), 6.44-6.49 (m, 2H), 4.57 (d, 1H), 4.26 (d, 1H), 3.75-3.85 (m, 1H), 3.57 (ddd, 1H), 3.33-3.40 (m, 1H), 3.09 (dd, 1H), 2.85 (dd, 1H). MS (ESI) m/e 398.1 (M+H)$^+$. Calcd. for C$_{24}$H$_{23}$N$_5$O.0.23H$_2$O: C, 71.77; H, 5.89; N, 17.44. Found C, 71.83; H, 5.77; N, 17.17.

Example 30

N-[(4-benzyl-3,4-dihydro-2H-1,4-benzoxazin-2-yl)methyl]-N'-1H-indazol-4-ylurea

Example 30A

A mixture of 0.36 g (2.26 mmol) of 3,4-dihydro-2H-benzo[1,4]oxazine-2-carbonitrile and 0.41 g (2.37 mmol) of benzyl bromide in 4 mL acetonitrile and 0.79 mL (4.54 mmol) of diisopropyl-ethylamine was heated in a microwave oven at 140° C. for one hour, cooled to about room temperature and partitioned between ethyl acetate and water. The organic phase was concentrated to an oil, and chromatographed on silica gel, eluting with 10 to 50% ethyl acetate in hexane to provide 0.44 g (78% yield) of Example 30A as an orange solid. $^1$H NMR (300 MHz, DMSO-d$_6$) δ ppm 7.31-7.38 (m, 4H), 7.23-7.39 (m, 1H), 6.79-6.86 (m, 2H), 6.72 (dd, 1H), 6.63 (td, 1H), 5.66 (t, 1H), 4.48-4.60 (m, 2H), 3.66 (qd, 2H). MS (DCI) m/e 251.1 (M+H)$^+$.

Example 30B 0.44 g (1.75 mmol) of Example 30A was added to 20 mL of 20% ammonia in methanol and 2.0 g of Raney nickel in a Parr shaker. The reactor was sealed and flushed with nitrogen, and then was pressurized with 60-psi hydrogen. The mixture was shaken at ambient temperature for 90 minutes. After the reactor was flushed with nitrogen, the Raney nickel was filtered off and washed with methanol, and the filtrate was concentrated to provide 0.40 g (90% yield) of Example 30B. $^1$H NMR (300 MHz, DMSO-d$_6$) δ ppm 7.22-7.36 (m, 5H), 6.62-6.72 (m, 3H), 6.48-6.54 (m, 1H), 4.46 (q, 2H), 4.01 (ddd, 1H), 4.43 (dd, 1H), 3.17 (dd, 1H), 2.74 (qd, 2H), 1.57 (br s, 2H). MS (DCI) m/e 255.1 (M+H)$^+$.

Example 30C

N-[(4-benzyl-3,4-dihydro-2H-1,4-benzoxazin-2-yl)methyl]-N'-1H-indazol-4-ylurea

A mixture of 0.40 g (1.58 mmol) of Example 30B and 0.53 g (1.58 mmol) of Example 24D in 10 mL N,N-dimethylformamide and 0.30 mL (1.72 mmol) diisopropylethylamine was stirred for an hour at ambient temperature and partitioned between ethyl acetate and water. The organic layer was filtered through silica gel and rinsed with ethyl acetate. The filtrate was concentrated to a brown oil, then added 50 mL methanol, 5 mL water, and 0.44 mL (3.16 mmol) triethylamine. The solution was refluxed for two hours, cooled to ambient temperature, and partitioned between ethyl acetate and water. The organic layer was washed with brine and dried over sodium sulfate, filtered and the filtrate concentrated to a brown residue. A solution of the residue in 1:1 methanol: ethanol was added to water and freeze-dried to provide 0.62 g (94% yield) of title compound as an off-white powder. $^1$H NMR (300 MHz, DMSO-$d_6$) δ ppm 12.98 (s, 1H), 8.78 (s, 1H), 8.09 (s, 1H), 7.61 (d, 1H), 7.27-7.35 (m, 4H), 7.17-7.26 (m, 2H), 7.06 (d, 1H), 6.78 (dd, 1H), 6.63-6.75 (m, 3H), 6.53-6.58 (m, 1H), 4.49 (q, 2H), 4.23-4.30 (m, 1H), 3.37-3.53 (m, 2H), 3.20-3.28 (m, 2H). MS (ESI) m/e 414.1 (M+H)$^+$. Calcd. for $C_{24}H_{23}N_5O_2 \cdot 0.35H_2O$: C, 68.67; H, 5.69; N, 16.68. Found C, 68.71; H, 5.62; N, 16.53.

Example 31

N-(1-benzyl-1,2,3,4-tetrahydroquinolin-4-yl)-N'-1H-indazol-4-ylurea

Example 31A 4.35 g (25.1 mmol) quinoline-4-carboxylic acid was added to 125 mL methanol and 8.7 g Raney nickel in a Parr shaker. The reactor was sealed and flushed with nitrogen, and then was pressurized with 60-psi hydrogen. The mixture was shaken at ambient temperature for 19 hours. After the reactor was flushed with nitrogen, the Raney nickel was filtered off and washed with methanol, and the filtrate was concentrated to provide 5.25 g of Example 31A. $^1$H NMR (300 MHz, DMSO-$d_6$) δ ppm 12.26 (br s, 1H), 6.94 (d, 1H), 6.88 (t, 1H), 6.39-6.48 (m, 2H), 5.76 (s, 1H), 3.61 (t, 1H), 3.10-3.25 (m, 2H), 2.00-2.10 (m, 1H), 1.74-1.87 (m, 1H). MS (DCI) m/e 178.1 (M+H)$^+$.

Example 31B

A mixture of 1.45 g (8.18 mmol) of Example 31A, 1.54 g (9.00 mmol) benzyl bromide in 30 mL ethanol and 2.83 g (20.5 mmol) potassium carbonate was stirred at ambient temperature overnight, treated with water, and the pH was adjusted to about 6 with the addition of 1N hydrochloric acid. The mixture was extracted with ethyl acetate and the organic phase concentrated and chromatographed on silica gel, eluting with 20 to 100% ethyl acetate in hexane to provide 1.379 g (63% yield) of Example 31B as a yellow solid. $^1$H NMR (300 MHz, DMSO-$d_6$) δ ppm 12.41 (s, 1H), 7.27-7.33 (m, 2H), 7.18-7.25 (m, 3H), 7.00-7.03 (m, 1H), 6.90-6.95 (m, 1H), 6.46-6.52 (m, 2H), 4.50 (q, 2H), 3.72 (t, 1H), 3.43-3.52 (m, 1H), 2.13-2.22 (m, 1H), 1.94-2.05 (m, 1H). MS (DCI) m/e 267.8 (M+H)$^+$.

Example 31C

A mixture of 1.07 g (4.0 mmol) of Example 31B, 1.21 g (4.4 mmol) diphenyl phosphoryl azide in 30 mL tent-butanol and 0.37 mL (4.8 mmol) triethylamine was refluxed 90 minutes, stirred at ambient temperature overnight, and concentrated. The residue was chromatographed on silica gel, eluting with 5 to 30% ethyl acetate in hexane, yielding 0.69 g (51% yield) of Example 31C as a colorless oil. $^1$H NMR (300 MHz, DMSO-$d_6$) δ ppm 7.22-7.36 (m, 5H), 7.01 (d, 1H), 6.92 (t, 1H), 6.51 (t, 1H), 6.43 (d, 1H), 4.66 (q, 1H), 4.48 (s, 2H), 3.39 (q, 2H), 1.88-1.99 (m, 2H), 1.43 (s, 9H). MS (DCI) m/e 339.1 (M+H)$^+$.

Example 31D

A solution of 0.69 g (2.03 mmol) Example 31C in 10 mL dichloromethane and 2 mL trifluoroacetic acid was stirred overnight at ambient temperature, and concentrated. The residue was dissolved in 10 mL methanol and treated with 281 mg (2.03 mmol) potassium carbonate. The mixture was stirred for 30 minutes at ambient temperature, filtered and the filtrate concentrated. The residue was chromatographed on silica gel with 1% triethylamine in dichloromethane, yielding 0.36 g (74% yield) of Example 31D as a yellow oil. $^1$H NMR (300 MHz, DMSO-$d_6$) δ ppm 7.49 (br s, 2H), 7.21-7.36 (m, 6H), 7.05 (t, 1H), 6.59 (t, 1H), 6.53 (d, 1H), 4.47-4.59 (m, 2H), 4.36 (t, 1H), 3.35-3.54 (m, 2H), 2.01-2.17 (m, 2H). MS (DCI) m/e 239.2 (M+H)$^+$.

Example 31E

N-(1-benzyl-1,2,3,4-tetrahydroquinolin-4-yl)-N'-1H-indazol-4-ylurea

A mixture of 0.36 g (1.51 mmol) of Example 31D, 0.50 g (1.51 mmol) of Example 24D in 10 mL N,N-dimethylformamide and 0.27 mL (1.55 mmol) diisopropylethylamine was stirred for an hour at ambient temperature, and partitioned between ethyl acetate and water. The organic layer was filtered through silica gel and rinsed with ethyl acetate. The filtrate was concentrated. The residue was treated with 50 mL methanol, 5 mL water, and 0.43 mL (3.09 mmol) triethylamine, refluxed for two hours, cooled and diluted with water and filtered. The wet cake was rinsed with water and vacuum dried to constant weight, yielding 0.39 g (64% yield) of title compound as an off-white solid. $^1$H NMR (300 MHz, DMSO-$d_6$) δ ppm 13.00 (s, 1H), 8.58 (s, 1H), 8.02 (s, 1H), 7.71 (d, 1H), 7.16-7.38 (m, 7H), 7.06 (d, 1H), 7.01 (t, 1H), 6.73 (d, 1H), 6.54-6.59 (m, 2H), 4.84 (q, 1H), 4.50-4.62 (m, 2H), 3.41-3.47 (m, 2H), 2.01-2.10 (m, 2H). MS (ESI) m/e 398.3 (M+H)$^+$. Calcd. for $C_{24}H_{23}N_5O \cdot 0.47H_2O$: C, 71.01; H, 5.94; N, 17.25. Found C, 70.94; H, 5.75; N, 17.47.

Example 32

N-(3,4-dihydro-2H-1,4-benzoxazin-2-ylmethyl)-N'-1H-indazol-4-ylurea 0.38 g (0.92 mmol) of Example 30C was added to 10 mL methanol and 76 mg 20% palladium hydroxide on carbon (wet) in a Parr shaker. The reactor was sealed and flushed with nitrogen, and then was pressurized with 50-psi hydrogen. The mixture was shaken at 50° C. for 24 hours. After cooling, the reactor was flushed with nitrogen, and the palladium was filtered off and washed with methanol. The filtrate was concentrated to a brown residue. The residue was dissolved in 1:1 methanol:acetonitrile and to which was water and freeze-dried to provide 0.31 g of title compound as a beige powder. $^1$H NMR (300 MHz, DMSO-$d_6$) δ ppm 12.99 (s, 1H), 8.78 (s, 1H), 8.09 (s, 1H), 7.63 (d, 1H), 7.20 (t, 1H), 7.06 (d, 1H), 6.56-6.72 (m, 4H), 6.49 (td, 1H), 5.75 (s, 1H), 4.06-4.13 (m, 1H), 3.35-3.51 (m, 3H), 3.06 (dd, 1H). MS (ESI) m/e 324.1 (M+H)$^+$. Calcd. for $C_{17}H_pN_5O_2 \cdot 0.07H_2O \cdot 0.38CH_4O$: C, 61.98; H, 5.58; N, 20.79. Found C, 61.98; H, 5.39, N, 20.72.

Example 33

N-isoquinolin-5-yl-N'-(8-piperidin-1-yl-3,4-dihydro-2H-chromen-4-yl)urea

Example 33A

A solution of 6-chloro-chroman-4-one (0.91 g, 5 mmol) in 12 ml of concentrated sulfuric acid was treated with N-bromosuccinimide (0.94 g, 5.3 mmol) and stirred at ambient temperature for 3 hours. The reaction mixture was poured onto ice and extracted with diethyl ether. The combined organic layers were dried with magnesium sulfate, filtered and the solvent evaporated under reduced pressure to give 1.42 g of Example 33A which was used without further purification. $^1$H NMR (300 MHz, CHLOROFORM-D) δ ppm 7.83 (d, J=2.71 Hz, 1 H), 7.71 (d, J=2.71 Hz, 1 H), 4.62-4.68 (m, 2 H), 2.83-2.88 (m, 2 H). MS (DCI) m/e 261.8 (M+H)$^+$ (Br+Cl pattern)

Example 33B

A solution of Example 33A (1.66 g, 6.3 mmol) in 6 ml pyridine was treated with methoxyl amine hydrochloride (0.84 g, 10 mmol) and stirred at ambient temperature for 3 days. The pyridine was removed under reduced pressure, and the residue partitioned between water and diethyl ether. The mixture was extracted with diethyl ether, and the combined organic layers dried with magnesium sulfate and filtered. The solvent was removed under reduced pressure to give 1.50 g of Example 33B which was used without further purification. $^1$H NMR (300 MHz, CHLOROFORM-D) δ ppm 7.86 (d, J=2.37 Hz, 1 H), 7.48 (d, J=2.71 Hz, 1 H), 4.23-4.32 (m, 2 H), 4.00 (s, 3 H), 2.86-2.92 (m, 2 H). MS (DCI) m/e 291.8 (M+H)$^+$ (Br+Cl pattern)

Example 33C

A mixture of Example 33B (1.20 g, 4.1 mmol), piperidine (0.43 g, 0.5 ml, 5 mmol), sodium tert-butoxide (0.60 g, 6.2 mmol), tris(dibenzylidineacetone)dipalladium(0) (0.11 g, 0.12 mmol), and 2,2'-bis(diphenylphosphino)-1,1'-binaphthalene (0.22 g, 0.36 mmol) in 12 ml of 1,4-dioxane was heated in a microwave reactor (Personal Chemistry) to 170 C for 30 minutes. After cooling, the reaction mixture was diluted with hexanes, filtered through a pad of silica gel with 10% ethyl acetate in hexanes, and the filtrate evaporated under reduced pressure. The residue was purified by flash chromatography using 5% ethyl acetate in hexanes as eluent to provide Example 33C. $^1$H NMR (300 MHz, CHLOROFORM-D) δ ppm 7.56 (s, 1 H), 6.84 (s, 1 H), 4.24 (m, 2 H), 3.98 (s, 3 H), 2.95 (br, 4 H), 2.88 (m, 2H), 1.73 (br, 4 H), 1.57 (br, 2 H). MS (DCI) m/e 295 (M+H)$^+$ (Cl pattern)

Example 33D

Example 33C (0.24 g, 0.81 mmol), 40 mg of 10% palladium on carbon, and 12 ml of 20% ammonia in methanol were shaken under hydrogen at 40 psi and ambient temperature for 5 hours. LC/MS showed a mixture of starting material, intermediate, and product at this point. 200 mg additional palladium on carbon was added, and the reaction continued for an additional 16 hours. LC/MS showed complete reaction at this point.

The catalyst was removed by filtration and the filtrate evaporated under reduced pressure to give the HCl salt of Example 33D. The HCl salt was neutralized with aqueous sodium bicarbonate, extracted with diethyl ether, and the solvent evaporated to give 70 mg of Example 33D. $^1$H NMR (300 MHz, CHLOROFORM-D) δ ppm 6.98 (m, 1 H), 6.80-6.91 (m, 2 H), 4.29-4.38 (m, 2 H), 4.04-4.14 (m, 1 H), 2.87-3.02 (m, 4 H), 2.49 (br, 2 H, NH$_2$), 2.09-2.24 (m, 1 H), 1.83-1.95 (m, 1 H), 1.68-1.80 (m, 4 H), 1.50-1.63 (m, 2 H). MS (DCI) m/e 233 (M+H)$^+$ Example 33E N-isoquinolin-5-yl-N'-(8-piperidin-1-yl-3,4-dihydro-2H-chromen-4-yl)urea A solution of phosgene (20% in toluene, 5.8 ml, 11 mmol) was added to 50 ml methylene chloride and cooled to 0° C. 4-Dimethylaminopyridine (2.86 g, 23.4 mmol) in 30 ml methylene chloride was added dropwise. A thick white suspension formed. A solution of 5-aminoisoquinoline (1.44 g, 10 mmol) in 30 ml methylene chloride was then added dropwise to this suspension. The reaction was allowed to warm to ambient temperature and stirred overnight. At the end of this time, a solution formed, and the solvent was removed under reduced pressure. The residue was triturated with 50 ml diethyl ether to give an approximately 0.1 M solution of 5-isocyanato-isoquinoline.

3 ml of the 5-isocyanato-isoquinoline solution was added to Example 33D (70 mg, 0.3 mmol). The reaction was stirred overnight, and the precipitate that formed was collected by filtration and washed with diethyl ether to give 56 mg of N-isoquinolin-5-yl-N'-(8-piperidin-1-yl-3,4-dihydro-2H-chromen-4-yl)urea. $^1$H NMR (300 MHz, DMSO-d$_6$) δ ppm 9.27 (s, 1 H), 8.51-8.63 (m, 2 H), 8.39 (d, J=7.46 Hz, 1 H), 7.88 (d, J=6.10 Hz, 1H), 7.71-7.78 (m, 1 H), 7.61 (t, J=7.97 Hz, 1 H), 7.13 (d, J=7.12 Hz, 1 H), 6.94 (dd, J=6.44, 3.05 Hz, 1 H), 6.72-6.86 (m, 2 H), 4.88 (m, 1 H), 4.26-4.39 (m, 1 H), 4.11-4.23 (m, 1 H), 2.81-2.94 (m, 4 H), 1.99-2.15 (m, 2 H), 1.63 (br s, 4 H), 1.52 (br s, 2 H). MS (ESI) m/e 403 (M+H)$^+$. Calcd. For $C_{24}H_{26}N_4O_2$.0.33 tetrahydrofuran: C, 71.23; H, 6.92; N, 13.12. Found C, 71.17; H, 6.86; N, 13.06.

Example 34

N-3,4-dihydro-2H-chromen-3-yl-N'-isoquinolin-5-ylurea 3-aminochroman hydrochloride (0.37 g, 2 mmol) was neutralized with aqueous sodium bicarbonate, extracted with diethyl ether, dried with magnesium sulfate, and the solvent evaporated to give 2-aminochroman.

A solution of phosgene (20% in toluene, 5.8 ml, 11 mmol) was added to 50 ml methylene chloride and cooled to 0° C. 4-Dimethylaminopyridine (2.86 g, 23.4 mmol) in 30 ml methylene chloride was added dropwise. A thick white suspension formed. A solution of 5-aminoisoquinoline (1.44 g, 10 mmol) in 30 ml methylene chloride was then added dropwise to this suspension. The reaction was allowed to warm to ambient temperature and stirred overnight. At the end of this time, a solution formed, and the solvent was removed under reduced pressure. The residue was triturated with 50 ml diethyl ether to give an approximately 0.1 M solution of 5-isocyanato-isoquinoline.

20 ml of this solution was added to the 3-aminochroman, and the reaction stirred overnight. The precipitate that formed was collected by filtration, and was purified using reverse-phase HPLC (acetonitrile-water with 0.1% trifluoroacetic acid as eluent) to give 70 mg of the titled compound as the trifluoroacetate salt. $^1$H NMR (300 MHz, DMSO-D6) δ ppm 9.54 (s, 1 H), 8.89 (s, 1 H), 8.60 (d, J=6.44 Hz, 1 H), 8.52 (d, J=6.78 Hz, 1 H), 8.15 (d, J=6.44 Hz, 1 H), 7.92 (d, J=8.14 Hz, 1 H), 7.77 (t, J=7.97 Hz, 1 H), 7.10-7.17 (m, 2 H), 6.98 (d, J=7.46 Hz, 1 H), 6.83-6.93 (m, 2 H), 4.19-4.28 (m, 1 H), 4.08-4.19 (m, 2 H), 3.16 (dd, J=16.44, 5.26 Hz, 1 H), 2.75 (dd, J=16.44, 3.56 Hz, 1 H). MS (ESI) m/e 320 (M+H)$^+$. Calcd.

For $C_{19}H_{17}N_3O_2 \cdot 1.4$trifluoroacetic acid: C, 54.66; H, 3.87; N, 8.77. Found C, 54.74; H, 3.77; N, 8.82.

Example 35

(+)—N-isoquinolin-5-yl-N'-[7-(trifluoromethyl)-3,4-dihydro-2H-chromen-4-yl]urea

Example 35A

3-Trifluoromethylphenol (8.75 g, 6.5 ml, 54 mmol), propargyl bromide (7.1 ml of 80% in toluene, 64 mmol), and potassium carbonate (8.83 g, 64 mmol) were stirred together in 100 ml of acetonitrile at ambient temperature for four days. The solvent was removed under reduced pressure, and the residue taken in water and extracted with diethyl ether. The organic layers were combined, dried with magnesium sulfate, and filtered. The solvent was evaporated under reduced pressure to give 11.24 g of Example 35A which was used without further purification. $^1$H NMR (300 MHz, CHLOROFORM-D) δ ppm 7.42 (t, J=7.97 Hz, 1 H), 7.20-7.29 (m, 2 H), 7.13-7.19 (m, 1 H), 4.74 (d, J=2.37 Hz, 2 H), 2.54 (t, J=2.37 Hz, 1 H)

Example 35B

Example 35A (5.00 g, 25 mmol) was dissolved in 100 ml acetone. N-chlorosuccinimide (4.00 g, 40 mmol) and silver acetate (334 mg, 2 mmol) were added, and the reaction heated to reflux for 3 hours. After cooling, the silver salts were removed by filtration and the filtrate evaporated under reduced pressure. The residue was taken up in diethyl ether, washed with water, dried with magnesium sulfate, and filtered. The solvent was removed under reduced pressure to give 7.98 g of Example 35B which was used without further purification. $^1$H NMR (300 MHz, CDCl$_3$) δ ppm 7.42 (t, J=7.97 Hz, 1 H) 7.26 (m, 1 H), 7.19 (s, 1 H), 7.11-7.16 (m, 1 H), 4.74 (s, 2 H)

Example 35C

Example 35B (0.94 g, 4 mmol) was dissolved in 25 ml of concentrated sulfuric acid. The reaction was stirred at ambient temperature for 30 minutes, then poured onto ice. The mixture was extracted with diethyl ether, and the combined organic layers washed with saturated aqueous sodium bicarbonate, dried with magnesium sulfate and filtered. The solvent was removed under reduced pressure to give 0.73 g of Example 35C containing the 5-trifluoromethyl regioisomer as an impurity. $^1$H NMR (300 MHz, d$_6$-DMSO) δ 7.96 (d, J=7.5 Hz, 1H), 7.40 (m, 2H), 4.62 (t, J=6.0 Hz, 2H), 2.88 (t, J=6.0 Hz, 2H). MS (DCI) m/e 234 (M+NH$_4$)$^+$ Example 35D Example 35C (1.29 g, 6 mmol) was dissolved in 6 ml pyridine. Methoxylamine hydrochloride (1.00 g, 12 mmol) was added and the reaction stirred at ambient temperature for 1 day. The pyridine was removed under reduced pressure, and the residue partitioned between water and diethyl ether. The mixture was extracted with diethyl ether, and the combined organic layers dried with magnesium sulfate. The solvent was removed under reduced pressure and the residue purified by flash chromatography using 5% ethyl acetate in hexanes to give 0.81 g of Example 35D. $^1$H NMR (300 MHz, CHLOROFORM-D) δ ppm 8.00 (d, J=7.46 Hz, 1 H), 7.10-7.18 (m, 2 H), 4.18-4.27 (m, 2 H), 4.01 (s, 3 H), 2.89-2.95 (m, 2 H)MS (DCI) m/e 246 (M+H)$^+$.

Example 35E

Example 35D (0.80 g, 3.2 mmol), 180 mg of 10% palladium on carbon, and 30 mL of 20% ammonia in methanol were shaken under hydrogen at 40 psi and ambient temperature for 1 hour. The catalyst was removed by filtration and the solvent evaporated under reduced pressure to give 0.70 g of Example 35E which was used without further purification. $^1$H NMR (300 MHz, CDCl$_3$), δ ppm 7.45 (d, J=8.14 Hz, 1 H), 7.14 (d, J=7.80 Hz, 1 H), 7.08 (s, 1 H), 4.22-4.37 (m, 2 H), 4.07-4.17 (m, 1 H), 2.41 (br, 2 H, NH$_2$), 2.13-2.27 (m, 1 H), 1.84-1.96 (m, 1 H). MS (CI) m/e 218 (M+H)$^+$ Example 35F A solution of phosgene (20% in toluene, 5.8 ml, 11 mmol) was added to 50 ml methylene chloride and cooled to 0° C. 4-Dimethylaminopyridine (2.86 g, 23.4 mmol) in 30 ml methylene chloride was added dropwise. A thick white suspension formed. A solution of 5-aminoisoquinoline (1.44 g, 10 mmol) in 30 ml methylene chloride was then added dropwise to this suspension. The reaction was allowed to warm to ambient temperature and stirred overnight. At the end of this time, a solution formed, and the solvent was removed under reduced pressure. The residue was triturated with 50 ml diethyl ether to give an approximately 0.1 M solution of 5-isocyanato-isoquinoline. 32 ml of this solution was added to Example 35E (0.70 g, 3.2 mmol), and the reaction stirred overnight. The precipitate that formed was collected by filtration to give 0.43 g of Example 35F. $^1$H NMR (300 MHz, DMSO-d$_6$) δ ppm 9.28 (s, 1 H), 8.65 (s, 1 H), 8.54 (d, J=6.10 Hz, 1 H), 8.31-8.37 (m, 1 H), 7.90 (d, J=6.10 Hz, 1 H), 7.76 (d, J=8.14 Hz, 1 H), 7.55-7.66 (m, 2 H), 7.24-7.29 (m, 1 H), 7.13-7.22 (m, 2 H), 5.03 (m, 1 H) 4.38 (m, 1 H) 4.27 (m, 3.22 Hz, 1 H) 2.14-2.26 (m, 1 H) 2.08 (m, 1 H). MS (ESI) m/e 388 (M+H)$^+$.

Example 35G (+)—N-isoquinolin-5-yl-N'-[7-(trifluoromethyl)-3,4-dihydro-2H-chromen-4-yl]urea Example 35F was resolved by chiral HPLC (Column: Chiracel OD (5 cm ID×50 cm); mobile phase: 80:10:10 hexanes:ethanol:methanol) to give a total of 295 mg of title compound. $[\alpha]_D$=+47.7 degrees (c=0.88, 1:1 ethanol:dimethylsulfoxide). $^1$H NMR (300 MHz, DMSO-d$_6$) δ ppm 9.28 (s, 1 H), 8.64 (s, 1 H), 8.54 (d, J=6.10 Hz, 1 H), 8.35 (d, J=6.78 Hz, 1 H), 7.89 (d, J=6.10 Hz, 1 H), 7.76 (d, J=8.14 Hz, 1 H), 7.55-7.66 (m, 2 H), 7.26 (d, 1 H), 7.13-7.22 (m, 2 H), 4.99-5.07 (m, 1 H), 4.34-4.43 (m, 1 H), 4.27 (m, 1 H) 2.15-2.27 (m, 1 H) 2.02-2.13 (m, 1 H). MS (ESI) m/e 388 (M+H)$^+$Calcd. For $C_{20}H_{16}N_3O_2F_3 \cdot 0.3H_2O$: C, 61.16; H, 4.26; N, 10.70. Found C, 61.40; H, 3.97; N, 10.33.

Example 36

(−)—N-isoquinolin-5-yl-N-[7-(trifluoromethyl)-3,4-dihydro-2H-chromen-4-yl]urea

Example 35F was resolved by chiral HPLC (Column: Chiracel OD (5 cm ID×50 cm); mobile phase: 80:10:10 hexanes:ethanol:methanol) to give a total of 270 mg of title compound. [α]$_D$=−44.8 degrees (c=1.005, 1:1 ethanol:dimethylsulfoxide). $^1$H NMR (300 MHz, DMSO-d$_6$) δ ppm 9.28 (s, 1 H), 8.64 (s, 1 H), 8.54 (d, J=6.10 Hz, 1 H), 8.35 (dd, J=7.63, 1.19 Hz, 1 H), 7.89 (d, J=6.10 Hz, 1 H), 7.76 (d, J=8.14 Hz, 1 H), 7.54-7.66 (m, 2 H), 7.26 (d, J=8.14 Hz, 1 H), 7.13-7.23 (m, 2 H), 4.99-5.07 (m, 1 H), 4.34-4.43 (m, 1 H), 4.27 (m, 1 H), 2.15-2.27 (m, 1 H), 2.02-2.13 (m, 1 H). MS (ESI) m/e 388 (M+H)$^+$. Calcd. For C$_{20}$H$_{16}$N$_3$O$_2$F$_3$: C, 62.01; H, 4.16; N, 10.85. Found C, 61.82; H, 4.04; N, 10.46.

Example 37

N-1H-indazol-4-yl-N'-[8-(trifluoromethyl)-3,4-dihydro-2H-chromen-4-yl]urea

Example 37A

2-Trifluoromethylphenol (3.57 g, 22 mmol), propargyl bromide (2.9 ml of 80% in toluene, 26 mmol), and potassium carbonate (3.59 g, 26 mmol) were stirred together in 40 ml of acetonitrile at ambient temperature for 24 hours. The solvent was removed under reduced pressure, and the residue taken in water and extracted with diethyl ether. The organic layers were combined, dried with magnesium sulfate, and filtered. The solvent was evaporated under reduced pressure to give 4.23 g of Example 37A which was used without further purification. $^1$H NMR (300 MHz, CDCl$_3$) δ ppm 7.59 (d, J=7.46 Hz, 1 H), 7.51 (t, J=7.97 Hz, 1 H), 7.17 (d, J=8.48 Hz, 1 H), 7.06 (t, J=7.63 Hz, 1 H), 4.80 (d, J=2.37 Hz, 2 H), 2.54 (t, J=2.37 Hz, 1 H)

Example 37B

Example 37A (3.00 g, 15 mmol) was dissolved in 75 ml acetone. N-chlorosuccinimide (2.40 g, 18 mmol) and silver acetate (167 mg, 1 mmol) were added, and the reaction mixture heated to reflux for 3 hours. After cooling, the silver salts were removed by filtration and the filtrate evaporated under reduced pressure. The residue was taken up in diethyl ether, washed with water, dried with magnesium sulfate, and filtered. The solvent was removed under reduced pressure to give 4.88 g of Example 37B which was used without further purification. $^1$H NMR (300 MHz, CDCl$_3$) δ ppm 7.59 (d, J=7.80 Hz, 1 H), 7.52 (t, J=7.97 Hz, 1 H), 7.04-7.15 (m, 2 H), 4.80 (s, 2 H).

Example 37C

Example 37B (4.88 g, 20.8 mmol) was dissolved in 100 ml of concentrated sulfuric acid at 0 C. The reaction mixture was stirred at ambient temperature for 2.5 hours, then poured onto ice. The mixture was extracted with diethyl ether, and the combined organic layers washed with saturated aqueous sodium bicarbonate, dried with magnesium sulfate and filtered. The solvent was removed under reduced pressure, and the residue purified via flash chromatography, eluting with 10% ethyl acetate in hexanes to provide 0.55 g of Example 37C along with 0.52 g of recovered starting material. $^1$H NMR (300 MHz, CDCl$_3$) δ ppm 8.10 (dd, J=7.80, 1.70 Hz, 1 H), 7.77 (d, J=8.48 Hz, 1 H), 7.10 (t, J=7.46 Hz, 1 H), 4.61-4.70 (m, 2 H), 2.83-2.92 (m, 2 H). MS (DCI) m/e 234 (M+NH$_4$)$^+$

Example 37D

A solution of Example 37C (0.55 g, 2.5 mmol) in 6 ml pyridine was treated with methoxylamine hydrochloride (0.42 g, 5 mmol) and stirred at ambient temperature for 16 hours. The pyridine was removed under reduced pressure, and the residue partitioned between water and ethyl acetate. The mixture was extracted with ethyl acetate, and the combined organic layers dried with magnesium sulfate, and filtered. The solvent was removed under reduced pressure to give 0.61 g of Example 37D which was used without further purification. $^1$H NMR (300 MHz, CDCl$_3$) δ ppm 8.09 (d, J=6.78 Hz, 1 H), 7.54 (d, J=7.46 Hz, 1 H), 6.99 (t, J=8.31 Hz, 1 H), 4.31 (t, J=6.27 Hz, 2 H), 4.00 (s, 3 H), 2.95 (t, J=6.27 Hz, 2 H). MS (CI) m/e 246 (M+H)$^+$.

Example 37E

Example 37D (0.61 g, 2.5 mmol), 120 mg of 10% palladium on carbon, and 20 ml of 20% ammonia in methanol were shaken under hydrogen at 60 psi and ambient temperature for 2.5 hours. The catalyst was removed by filtration and the solvent evaporated under reduced pressure. The residue was taken in diethyl ether, extracted with 1N hydrochloric acid, and the acid extracts made basic with 10 N aqueous sodium hydroxide solution. The aqueous extracts were extracted with diethyl ether. The organic layers were combined, dried with magnesium sulfate, filtered, and the solvent removed under reduced pressure to give 0.50 g of Example 37E. $^1$H NMR (300 MHz, CDCl$_3$) δ ppm 7.51 (d, J=7.12 Hz, 1 H), 7.45 (d, J=7.80 Hz, 1 H), 6.94 (t, J=7.46 Hz, 1 H), 4.30-4.44 (m, 2 H), 4.08-4.19 (m, 1 H), 2.16-2.27 (m, 1 H), 2.21 (br, 2 H, NH$_2$), 1.85-1.98 (m, 1 H). MS (CI) m/e 218 (M+H)$^+$

Example 37F methyl 4-[({[8-(trifluoromethyl)-3,4-dihydro-2H-chromen-4-yl]amino}carbonyl)amino]-1H-indazole-1-carboxylate Example 37E (0.50 g, 2.3 mmol), Example 24D (0.76 g, 2.3 mmol), and diisopropylethylamine (0.44 g, 0.6 ml, 3.4 mmol) were dissolved in 4 ml of N,N-dimethylformamide. The reaction was stirred at ambient temperature for 16 hours, and diluted with water. The precipitate formed was collected by filtration and air-dried to give 0.68 g of the titled compound which was used without further purification. $^1$H NMR (300 MHz, DMSO-d$_6$) δ ppm 8.88 (s, 1 H), 8.39 (s, 1 H), 7.85 (d, J=7.80 Hz, 1 H), 7.71 (d, J=8.48 Hz, 1 H), 7.62 (d, J=7.80 Hz, 1 H), 7.53-7.58 (m, 2 H), 7.08 (t, J=7.63 Hz, 1 H), 6.98 (d, J=7.80 Hz, 1 H), 4.98-5.05 (m, 1 H), 4.41-4.49 (m, 1 H), 4.27-4.35 (m, 1 H), 4.03 (s, 3 H), 2.07-2.23 (m, 2 H). MS (ESI) m/e 435 (M+H)$^+$

Example 37G

N-1H-indazol-4-yl-N'-[8-(trifluoromethyl)-3,4-dihydro-2H-chromen-4-yl]urea

A solution of Example 37F (0.68 g, 1.56 mmol) in a mixture of 5 ml tetrahydrofuran and 5 ml methanol was treated with sodium hydroxide (5M in methanol, 3 ml, 15 mmol), and the reaction stirred at ambient temperature for 2 hours. The reaction mixture was diluted with water, and the precipitate that formed was collected by filtration. After drying, the solid was purified using reverse-phase HPLC (acetonitrile-water with 0.1% trifluoroacetic acid as eluent) to provide 0.29 g of title compound. $^1$H NMR (300 MHz, DMSO-d$_6$) δ ppm 13.01 (s, 1 H), 8.59 (s, 1 H), 8.03 (s, 1 H), 7.67 (d, J=7.46 Hz, 1 H), 7.62 (d, J=7.80 Hz, 1 H), 7.55 (d, J=7.80 Hz, 1 H), 7.22 (t, J=7.80 Hz, 1 H), 7.04-7.11 (m, 2 H), 6.96 (d, J=7.80 Hz, 1 H), 4.96-5.03 (m, 1 H), 4.41-4.49 (m, 1 H), 4.30 (m, 1 H), 2.18 (m, 1 H), 2.06-2.13 (m, 1 H). MS (ESI) m/e 377 (M+H)$^+$. Calcd. For $C_{18}H_{15}N_4O_2F_3$.0.15 trifluoroacetic acid: C, 55.87; H, 3.88; N, 14.24. Found C, 55.95; H, 3.82; N, 14.28.

Example 38

(−)—N-1H-indazol-4-yl-N'-[7-(trifluoromethyl)-3,4-dihydro-2H-chromen-4-yl]urea

Example 38A methyl 4-[({[7-(trifluoromethyl)-3,4-dihydro-2H-chromen-4-yl]amino}carbonyl)amino]-1H-indazole-1-carboxylate Example 35E (0.44 g, 2 mmol), Example 24D (0.66 g, 2 mmol), and diisopropylethylamine (0.39 g, 0.54 ml, 3 mmol) were dissolved in 4 ml of N,N-dimethylformamide. The reaction mixture was stirred at ambient temperature for 16 hours, and diluted with water. The precipitate that formed was collected by filtration and air-dried to give 0.69 g of the titled compound which was used without further purification. $^1$H NMR (300 MHz, DMSO-$d_6$) δ ppm 8.92 (s, 1 H), 8.40 (s, 1 H), 7.81-7.88 (m, 1 H), 7.71 (d, J=8.48 Hz, 1 H), 7.46-7.59 (m, 2 H), 7.23-7.29 (m, 1 H), 7.14 (s, 1 H), 6.95 (d, J=7.80 Hz, 1 H), 5.03 (q, J=6.56 Hz, 1 H), 4.38 (td, J=7.46, 3.39 Hz, 1 H), 4.22-4.34 (m, 1 H), 4.03 (s, 3 H), 2.05-2.20 (m, 2 H). MS (ESI) m/e 435 (M+H)$^+$.

Example 38B

A solution of Example 38A (0.69 g, 1.59 mmol) in a mixture of 3 ml tetrahydrofuran and 3 ml methanol was treated with sodium hydroxide (5M in methanol, 3 ml, 15 mmol) and stirred at ambient temperature for 2 hours. The reaction was diluted with water, and the precipitate that formed was collected by filtration to give 0.55 g of Example 38B. $^1$H NMR (300 MHz, DMSO-$d_6$) δ ppm 13.00 (br s, 1 H), 8.69 (s, 1 H), 8.06 (s, 1 H), 7.67 (d, J=7.80 Hz, 1 H), 7.55 (d, J=8.14 Hz, 1 H), 7.18-7.28 (m, 2 H), 7.05-7.15 (m, 2 H), 7.00 (d, J=7.80 Hz, 1 H), 5.02 (q, J=6.33 Hz, 1 H), 4.32-4.43 (m, 1 H), 4.26 (ddd, J=11.19, 7.97, 3.22 Hz, 1 H), 2.12-2.27 (m, 1 H), 2.00-2.12 (m, J=10.21, 6.82, 3.48, 3.22 Hz, 1 H). MS (ESI) m/e 377 (M+H)$^+$.

Example 38C (−)—N-1H-indazol-4-yl-N'-[7-(trifluoromethyl)-3,4-dihydro-2H-chromen-4-yl]urea Example 38B was resolved by chiral HPLC (Column: Chiracel OJ (5 cm ID×50 cm); mobile phase: 80:10:10 hexanes:ethanol:methanol) to give a total of 356 mg of title compound.

$[α]_D$=−54.2 degrees (c=0.815, 1:1 ethanol:dimethylsulfoxide). $^1$H NMR (300 MHz, DMSO-$d_6$) δ ppm 13.00 (s, 1 H), 8.63 (s, 1 H), 8.04 (s, 1 H), 7.67 (d, J=7.46 Hz, 1 H), 7.55 (d, J=8.14 Hz, 1 H), 7.19-7.28 (m, 2 H), 7.05-7.15 (m, 2 H), 6.93 (d, J=7.80 Hz, 1 H), 4.97-5.06 (m, 1 H), 4.32-4.42 (m, 1 H), 4.26 (ddd, J=11.27, 7.88, 3.22 Hz, 1 H), 2.13-2.26 (m, 1 H), 2.01-2.12 (m, J=10.38, 6.91, 6.78, 3.39, 3.05 Hz, 1 H). MS (ESI) m/e 377 (M+H)$^+$. Calcd. For $C_{18}H_{15}N_4O_2F_3$: C, 57.45; H, 4.02; N, 14.89. Found C, 57.13; H, 3.89; N, 14.76.

Example 39

(+)—N-1H-indazol-4-yl-N'-[7-(trifluoromethyl)-3,4-dihydro-2H-chromen-4-yl]urea

Example 38B was resolved by chiral HPLC (Column: Chiracel OJ (5 cm ID×50 cm); mobile phase: 80:10:10 hexanes:ethanol:methanol) to give a total of 349 mg of title compound.

$[α]_D$=+54.7 degrees (c=1.010, 1:1 ethanol:dimethylsulfoxide). $^1$H NMR (300 MHz, DMSO-$d_6$) δ ppm 13.02 (s, 1 H), 8.63 (s, 1 H), 8.04 (s, 1 H), 7.67 (d, J=6.78 Hz, 1 H), 7.55 (d, J=8.14 Hz, 1 H), 7.18-7.29 (m, 2 H), 7.05-7.15 (m, 2 H), 6.93 (d, J=8.14 Hz, 1 H), 5.02 (q, J=6.55 Hz, 1 H), 4.33-4.42 (m, 1 H), 4.26 (ddd, J=11.36, 7.97, 3.05 Hz, 1 H), 2.13-2.25 (m, 1 H), 2.01-2.12 (m, J=6.91, 6.91, 6.70, 3.22 Hz, 1 H). MS (ESI) m/e 377 (M+H)$^+$. Calcd. For $C_{18}H_{15}N_4O_2F_3$: C, 57.45; H, 4.02; N, 14.89. Found C, 57.51; H, 3.91; N, 14.74.

Example 40

N-1H-indazol-4-yl-N'-(8-piperidin-1-yl-3,4-dihydro-2H-chromen-4-yl)urea

Example 40A methyl 4-({[(8-piperidin-1-yl-3,4-dihydro-2H-chromen-4-yl)amino]carbonyl}amino)-1H-indazole-1-carboxylate A solution of Example 33D (0.37 g, 1.6 mmol), Example 24D (0.53 g, 1.6 mmol), and diisopropylethylamine (0.52 g, 0.7 ml, 4 mmol) in 4 ml of N,N-dimethylformamide was stirred at ambient temperature for 16 hours, then diluted with water. The precipitate that formed was collected by filtration and air-dried to give 0.54 g of Example 40A which was used without further purification. $^1$H NMR (300 MHz, DMSO-$d_6$) δ ppm 8.80 (s, 1 H), 8.37 (s, 1 H), 7.88 (d, J=8.14 Hz, 1 H), 7.69 (d, J=8.48 Hz, 1 H), 7.50 (t, J=8.14 Hz, 1 H), 6.88-6.94 (m, 1 H), 6.79-6.88 (m, 3 H), 4.87 (d, J=7.46 Hz, 1 H), 4.28-4.37 (m, 1 H), 4.11-4.20 (m, 1 H), 4.03 (s, 3 H), 2.82-2.96 (m, 4 H), 2.08 (ddd, J=17.97, 8.99, 4.92 Hz, 2 H), 1.63 (br s, 4 H), 1.52 (br s, 2 H). MS (ESI) m/e 450 (M+H)$^+$

Example 40B

N-1H-indazol-4-yl-N'-(8-piperidin-1-yl-3,4-dihydro-2H-chromen-4-yl)urea

A solution of Example 40A (0.54 g, 1.2 mmol) in a mixture of 5 ml tetrahydrofuran and 5 ml methanol was treated with sodium hydroxide (5M in methanol, 2.4 ml, 12 mmol) and stirred at ambient temperature for 45 minutes. The reaction mixture was diluted with water, and the precipitate that formed was collected by filtration to give 329 mg of title compound. $^1$H NMR (300 MHz, DMSO-$d_6$) δ ppm 12.96 (br s, 1 H), 8.56 (s, 1 H), 8.00-8.03 (m, 1 H), 7.69 (d, J=7.80 Hz, 1 H), 7.18-7.27 (m, 1 H), 7.06 (d, J=8.48 Hz, 1 H), 6.78-6.94 (m, 4 H), 4.83-4.88 (m, 1 H), 4.30-4.37 (m, 1 H), 4.11-4.20 (m, 1 H), 2.82-2.91 (m, 4 H), 1.98-2.14 (m, 2 H), 1.63 (br s, 4 H), 1.52 (br s, 2 H). MS (ESI) m/e 392 (M+H)$^+$ Calcd. For $C_{22}H_{25}N_5O_2$.0.2 tetrahydrofuran.0.1$H_2O$: C, 67.17; H, 6.63; N, 17.18. Found C, 67.09; H, 6.45; N, 17.04.

Example 41

N-1H-indazol-4-yl-N'-(8-morpholin-4-yl-3,4-dihydro-2H-chromen-4-yl)urea

Example 41A

Example 33B (1.02 g, 3.5 mmol), morpholine (0.37 g, 0.37 ml, 4.2 mmol), sodium tert-butoxide (0.51 g, 5.3 mmol), tris(dibenzylidineacetone)dipalladium(0) (0.18 g, 0.2 mmol), and 2,2'-bis(diphenylphosphino)-1,1'-binaphthalene (0.37 g, 0.6 mmol) were combined in 40 ml toluene. The reaction mixture was heated to reflux for four hours, at which point an additional 0.10 g of tris(dibenzylidineacetone)dipalladium (0) was added, continued to reflux for 16 hours longer, cooled, diluted with diethyl ether, and filtered through celite. The filtrate was evaporated under reduced pressure and the residue purified by flash chromatography using 20% ethyl acetate in hexanes as eluent to give 0.63 g of Example 41A. $^1$H NMR (300 MHz, CHLOROFORM-D) δ ppm 7.60 (d, J=2.71 Hz, 1 H), 6.87 (s, 1 H), 4.25 (t, J=6.27 Hz, 2 H), 3.99 (s, 3 H), 3.86-3.91 (m, 4 H), 3.02-3.10 (m, 4 H), 2.89 (t, J=6.27 Hz, 2 H). MS (CI) m/e 297 (M+H)$^+$ (Cl pattern)

Example 41B

Example 41A (0.63 g, 2.1 mmol), 0.7 g 10% palladium on carbon, and 20 ml of 20% ammonia in methanol were shaken under 60 psi hydrogen at 50 C for 18 hours. After filtering off the catalyst, the solvent was evaporated under reduced pressure to give 0.55 g of Example 41B, which was used without further purification. $^1$H NMR (300 MHz, DMSO-d$_6$) δ ppm 8.36 (br s, 2 H, NH$_2$), 7.14 (dd, J=6.78, 2.71 Hz, 1 H), 6.856.94 (m, 2 H), 4.44 (t, J=5.26 Hz, 1 H), 4.22-4.32 (m, 2 H), 3.66-3.74 (m, 4 H), 2.87-2.97 (m, 4 H), 2.16-2.30 (m, 1 H), 2.10 (td, J=9.75, 4.58 Hz, 1 H). MS (CI) m/e 235 (M+H)$^+$

Example 41C methyl 4-({[(8-morpholin-4-yl-3,4-dihydro-2H-chromen-4-yl)amino]carbonyl}amino)-1H-indazole-1-carboxylate Example 41B (0.55 g), Example 24D (0.70 g, 2.1 mmol), and diisopropylethylamine (0.65 g, 0.9 ml, 5 mmol) were dissolved in 10 ml of N,N-dimethylformamide. The reaction was stirred at ambient temperature for 16 hours, then diluted with water. The precipitate that formed was collected by filtration and air-dried to give 0.93 g of Example 41C which was used without further purification. $^1$H NMR (300 MHz, DMSO-d$_6$) δ ppm 8.85 (s, 1 H), 8.39 (s, 1 H), 7.88 (d, J=7.80 Hz, 1 H), 7.69 (d, J=8.14 Hz, 1 H), 7.50 (t, J=8.14 Hz, 1 H), 6.92-7.00 (m, 1 H), 6.85 (ddd, J=18.23, 7.88, 2.03 Hz, 3 H), 4.85-4.92 (m, 1 H), 4.28-4.38 (m, 1 H), 4.11-4.22 (m, 1 H), 4.03 (s, 3 H), 3.68-3.78 (m, 4 H), 2.91-2.98 (m, 4 H), 2.00-2.15 (m, 2 H). MS (ESI) m/e 452 (M+H)$^+$

Example 41D

N-1H-indazol-4-yl-N'-(8-morpholin-4-yl-3,4-dihydro-2H-chromen-4-yl)urea

Example 41C (0.93 g, 2 mmol) was dissolved in a mixture of 10 ml tetrahydrofuran and 5 ml methanol. Sodium hydroxide (5M in methanol, 4 ml, 20 mmol) was added, and the reaction stirred at ambient temperature for 1 hour. The reaction mixture was diluted with water, and the precipitate that formed was collected by filtration to give 0.57 g of title compound. $^1$H NMR (300 MHz, DMSO-d$_6$) δ ppm 13.00 (s, 1 H), 8.54 (s, 1 H), 8.01 (s, 1 H), 7.69 (d, J=7.80 Hz, 1 H), 7.18-7.25 (m, 1 H), 7.06 (d, J=8.48 Hz, 1 H), 6.92-6.99 (m, 1 H), 6.80-6.90 (m, 3 H), 4.84-4.90 (m, 1 H), 4.30-4.38 (m, 1 H), 4.09-4.20 (m, 1 H), 3.73 (t, J=4.41 Hz, 4 H), 3.60 (m, 0.2 H, tetrahydrofuran), 2.95 (m, 4 H), 1.99-2.15 (m, 2 H), 1.76 (m, 0.2 H, tetrahydrofuran). MS (ESI) m/e 394 (M+H)$^+$. Calcd. For C$_{21}$H$_{23}$N$_5$O$_3$.0.1 tetrahydrofuran.0.2H$_2$O: C, 63.58; H, 6.03; N, 17.32. Found C, 63.68; H, 5.68; N, 17.10.

Example 42

N-(8-tert-butyl-3,4-dihydro-2H-chromen-4-yl)-N'-1H-indazol-4-ylurea

Example 42A 2-tert-butylphenol (15.02 g, 15.4 ml, 100 mmol), propargyl bromide (14.3 ml of 80% in toluene, 128 mmol), and potassium carbonate (17.66 g, 128 mmol) were stirred together in 200 ml of acetonitrile at ambient temperature for 5 days. The solvent was removed under reduced pressure, and the residue taken into water and extracted with diethyl ether. The organic layers were combined, dried with magnesium sulfate, and filtered. The solvent was evaporated under reduced pressure to give 18.86 g of Example 42A which was used without further purification. $^1$H NMR (300 MHz, CHLOROFORM-D) δ ppm 7.30 (dd, J=7.80, 1.70 Hz, 1 H), 7.15-7.22 (m, 1 H), 6.90-6.98 (m, 2 H), 4.73 (d, J=2.37 Hz, 2 H), 2.48 (t, J=2.37 Hz, 1 H), 1.39 (s, 9 H). MS (DCI) m/e 206 (M+NH$_4$)$^+$

Example 42B

Example 42A (18.86 g, 100 mmol) was dissolved in 400 ml acetone. N-chlorosuccinimide (16.02 g, 120 mmol) and silver acetate (1.67 g, 10 mmol) were added, and the reaction mixture heated to reflux for 4 hours. After cooling, the silver salts were removed by filtration and the filtrate evaporated under reduced pressure. The residue was taken up in diethyl ether, washed with water and saturated aqueous sodium bicarbonate, dried with magnesium sulfate, and filtered. The solvent removed under reduced pressure to give 26.13 g of Example 42B which was used without further purification. $^1$H NMR (300 MHz, CHLOROFORM-D) δ ppm 7.30 (dd, J=7.97, 1.53 Hz, 1 H), 7.19 (td, J=7.71, 1.86 Hz, 1 H), 6.91-6.97 (m, 2 H), 4.73 (s, 2 H), 1.38 (s, 9 H). MS (DCI) m/e 223 (M+H)$^+$

Example 42C

Example 42B (25.8 g) in 250 ml ethylene glycol was heated to reflux for 4 hours. The reaction mixture was cooled, poured into water, and extracted with diethyl ether. The organic layers were combined, washed with 1N sodium hydroxide and saturated ammonium carbonate sequentially, dried with magnesium sulfate, and filtered. Removal of solvent under reduced pressure gave a residue. The residues were filtered through a pad of silica gel with 1:1 methylene chloride:hexanes, and the filtrate evaporated under reduced pressure to give 13.51 g of Example 42C. $^1$H NMR (300 MHz, CHLOROFORM-D) δ ppm 7.81 (dd, J=7.80, 1.70 Hz, 1 H), 7.47 (dd, J=7.63, 1.86 Hz, 1 H), 6.95 (t, J=7.80 Hz, 1 H), 4.51-4.58 (m, 2 H), 2.79-2.85 (m, 2 H), 1.39 (s, 9 H). MS (DCI) m/e 205 (M+H)$^+$

Example 42D

Example 42C (13.51 g, 66 mmol) was dissolved in 100 ml pyridine. Methoxylamine hydrochloride (10 g, 120 mmol)

was added and the reaction mixture stirred at ambient temperature for 16 hours. The pyridine was removed under reduced pressure, and the residue partitioned between water and diethyl ether. The mixture was extracted with diethyl ether, and the combined organic layers washed with 1N sodium hydroxide and 1N hydrochloric acid sequentially, dried with magnesium sulfate, and filtered. The solvent was removed under reduced pressure to give 14.44 g of Example 42D which was used without further purification. $^1$H NMR (300 MHz, CHLOROFORM-D) δ ppm 7.79 (dd, J=7.80, 1.70 Hz, 1 H), 7.21-7.27 (m, 1 H), 6.87 (t, J=7.80 Hz, 1 H), 4.18 (t, J=6.27 Hz, 2 H), 3.98 (s, 3 H), 2.91 (t, J=6.27 Hz, 2 H), 1.36 (s, 9 H). MS (DCI) m/e 234 (M+H)$^+$

Example 42E

Example 42D (14.44 g, 61.9 mmol), 1.5 g of 10% palladium on carbon, and 400 ml of 20% ammonia in methanol were shaken under hydrogen at 60 psi and ambient temperature for 2.5 hours. The catalyst was removed by filtration and the solvent evaporated under reduced pressure, giving 13.50 g of Example 42E which was used without further purification. $^1$H NMR (300 MHz, CHLOROFORM-D) δ ppm 7.14-7.24 (m, 3 H) 6.81-6.89 (m, 1 H) 4.22-4.29 (m, 2 H) 4.11 (t, J=5.09 Hz, 1 H) 2.10-2.25 (m, 1 H) 1.90 (td, J=9.16, 4.07 Hz, 1 H) 1.34-1.37 (m, 9 H). MS (DCI) m/e 206 (M+H)$^+$

Example 42F methyl 4-({[(8-tert-butyl-3,4-dihydro-2H-chromen-4-yl)amino]carbonyl}amino)-1H-indazole-1-carboxylate Example 42E (12.32 g, 60 mmol), Example 24D (19.94 g, 60 mmol), and diisopropylethylamine (11.63 g, 16 ml, 90 mmol) were dissolved in 100 ml of N,N-dimethylformamide. The reaction was stirred at ambient temperature for 16 hours, and diluted with water. The precipitate that formed was collected by filtration, air-dried, and then triturated with a mixture of diethyl ether and hexanes to give 20.6 g of the titled compound. $^1$H NMR (300 MHz, DMSO-d$_6$) δ ppm 8.77 (s, 1 H), 8.35 (s, 1 H), 7.89 (d, J=7.46 Hz, 1 H), 7.69 (d, J=8.48 Hz, 1 H), 7.46-7.55 (m, 1 H), 7.16 (dd, J=8.14, 2.37 Hz, 2 H), 6.83-6.93 (m, 2 H), 4.86-4.92 (m, 1 H), 4.32-4.40 (m, 1 H), 4.09-4.20 (m, 1 H), 4.03 (s, 3 H), 2.09 (ddd, J=17.88, 8.90, 4.75 Hz, 2 H), 1.34 (s, 9 H). MS (ESI) m/e 423 (M+H)$^+$

Example 42G

N-(8-tert-butyl-3,4-dihydro-2H-chromen-4-yl)-N'-1H-indazol-4-ylurea

Example 42F (20.6 g, 48 mmol) was dissolved in a mixture of 100 ml tetrahydrofuran and 75 ml methanol. Sodium hydroxide (5M in methanol, 50 ml, 250 mmol) was added, and the reaction mixture stirred at ambient temperature for 30 minutes. The reaction mixture was diluted with water, and the precipitate that formed was collected by filtration, giving 15.70 g of the titled compound. $^1$H NMR (300 MHz, DMSO-d$_6$) δ ppm 13.00 (s, 1 H), 8.51 (s, 1 H), 8.01 (s, 1 H), 7.69 (d, J=7.46 Hz, 1 H), 7.13-7.25 (m, 3 H), 7.06 (d, J=8.14 Hz, 1 H), 6.83-6.94 (m, 2 H), 4.84-4.91 (m, 1 H), 4.37 (dt, J=10.85, 4.24 Hz, 1 H), 4.06-4.19 (m, 1 H), 1.99-2.14 (m, 2 H), 1.35 (s, 9 H). MS (ESI) m/e 365 (M+H)$^+$

Example 43

N-[8-chloro-7-(trifluoromethyl)-3,4-dihydro-2H-chromen-4-yl]-N'-1H-indazol-4-ylurea

Example 43A

2-Chloro-3-trifluoromethylphenol (4.91 g, 3.3 ml, 25 mmol), propargyl bromide (3.6 ml of 80% in toluene, 32 mmol), and potassium carbonate (4.42 g, 32 mmol) were stirred together in 40 ml of acetonitrile at ambient temperature for 6 days. The solvent was removed under reduced pressure, and the residue taken in water and extracted with diethyl ether. The organic layers were combined, dried with magnesium sulfate and filtered. The solvent was evaporated under reduced pressure to give 5.63 g of Example 43A which was used without further purification. $^1$H NMR (300 MHz, CHLOROFORM-D) δ ppm 7.26-7.38 (m, 3 H), 4.83 (d, J=2.37 Hz, 2 H), 2.56 (t, J=2.54 Hz, 1 H)

Example 43B

Example 43A (5.35 g, 22.8 mmol) was dissolved in 120 ml acetone. N-chlorosuccinimide (3.87 g, 29 mmol) and silver acetate (0.33 g, 2 mmol) were added, and the reaction heated to reflux for 5.5 hours. After cooling, the silver salts were removed by filtration and the filtrate evaporated under reduced pressure. The residue was taken up in diethyl ether, washed with water, dried with magnesium sulfate, and filtered. The solvent was removed under reduced pressure to give 6.06 g of Example 43B which was used without further purification. $^1$H NMR (300 MHz, CHLOROFORM-D) δ ppm 7.31-7.39 (m, 3 H), 4.83 (s, 2 H)

Example 43C

Example 43B (5.96 g, 22 mmol) was dissolved in a mixture of 50 ml methanesulfonic acid and 150 mL concentrated sulfuric acid. The reaction was stirred at ambient temperature for 16 hours, then poured onto ice and extracted with diethyl ether. The combined organic layers were washed with saturated aqueous sodium bicarbonate, dried with magnesium sulfate, and filtered. The solvent was removed under reduced pressure to give 4.70 g of crude product.

The crude product was filtered through a pad of silica gel with 10% ethyl acetate in hexanes. After removing the solvent under reduced pressure, the residue was taken in diethyl ether, washed with 1N sodium hydroxide, dried with magnesium sulfate, and filtered. The solvent was evaporated to give 1.43 g of Example 43C. $^1$H NMR (300 MHz, CDCl$_3$) δ ppm 7.91 (d, J=8.48 Hz, 1 H), 7.33-7.40 (m, 1 H), 4.67-4.75 (m, 2 H), 2.86-2.94 (m, 2 H)

Example 43D

Example 43C (1.43 g, 5.7 mmol) was dissolved in 35 ml pyridine. Methoxylamine hydrochloride (0.83 g, 10 mmol) was added and the reaction stirred at ambient temperature for 3 days. The pyridine was removed under reduced pressure, and the residue taken into diethyl ether. The ether solution was washed with water and 1N hydrochloric acid sequentially, dried with magnesium sulfate, and filtered. The solvent was evaporated under reduced pressure to give 1.29 g of Example 43D which was used without further purification. $^1$H NMR (300 MHz, CDCl$_3$) δ ppm 7.89-7.94 (m, 1 H), 7.23-7.27 (m, 1 H), 4.32-4.38 (m, 2 H), 4.02 (s, 3 H), 2.91-2.97 (m, 2 H). MS (DCI) m/e 280 (M+H)$^+$

Example 43E

Example 43D (1.29 g, 4.6 mmol) was dissolved in 40 ml of 20% ammonia in methanol, and hydrogenated using 4 g of Raney nickel, under 60 psi hydrogen at ambient temperature for four hours. The catalyst was removed by filtration, and the filtrate evaporated under reduced pressure. The residue was taken in diethyl ether, washed with water and saturated aqueous ammonium chloride sequentially, dried with magnesium sulfate, and filtered. The solvent was evaporated under reduced pressure to give 0.85 g of Example 43E. $^1$H NMR (300 MHz, CDCl$_3$) δ ppm 7.31-7.39 (m, 1 H), 7.20-7.28 (m, 1 H), 4.36-4.50 (m, 2 H), 2.14-2.30 (m, J=13.52, 8.86, 4.75, 4.41 Hz, 2 H), 1.88-2.00 (m, 1 H). MS (DCI) m/e 252 (M+H)$^+$

Example 43F methyl 4-[({[8-chloro-7-(trifluoromethyl)-3,4-dihydro-2H-chromen-4-yl]amino}carbonyl)amino]-1H-indazole-1-carboxylate Example 43E (0.85 g, 3.4 mmol), Example 24D (1.13 g, 3.4 mmol), and diisopropylethylamine (0.90 g, 1.25 ml, 7 mmol) were dissolved in 15 ml of N,N-dimethylformamide. The reaction mixture was stirred at ambient temperature for 3 days, and diluted with water. The precipitate that formed was collected by filtration, and air-dried to give 1.10 g of the titled compound which was used without further purification. $^1$H NMR (300 MHz, DMSO-d$_6$) δ ppm 8.99 (s, 1 H), 8.42 (s, 1 H), 7.83 (d, J=7.46 Hz, 1 H), 7.72 (d, J=8.14 Hz, 1 H), 7.51 (t, J=7.97 Hz, 2 H), 7.36-7.43 (m, 1 H), 6.99 (d, J=8.14 Hz, 1 H), 5.10 (d, J=6.78 Hz, 1 H), 4.37-4.51 (m, 2 H), 4.03 (s, 3 H), 2.09-2.24 (m, 2 H). MS (ESI) m/e 469 (M+H)$^+$

Example 43G

N-[8-chloro-7-(trifluoromethyl)-3,4-dihydro-2H-chromen-4-yl]-N'-1H-indazol-4-ylurea Example 43F (1.10 g, 2.48 mmol) was dissolved in a mixture of 5 ml tetrahydrofuran and 5 ml methanol. Sodium hydroxide (5M in methanol, 4 ml, 20 mmol) was added, and the reaction stirred at ambient temperature for 40 minutes. The reaction was diluted with water, and the precipitate that formed was collected by filtration, giving 0.85 g of title compound. $^1$H NMR (300 MHz, DMSO-d$_6$) δ ppm 13.01 (s, 1 H), 8.69 (s, 1 H), 8.06 (s, 1 H), 7.65 (d, J=7.46 Hz, 1 H), 7.47-7.53 (m, 1 H), 7.34-7.42 (m, 1 H), 7.23 (t, J=7.80 Hz, 1 H), 7.09 (d, J=8.14 Hz, 1 H), 6.97 (d, J=8.14 Hz, 1 H), 5.04-5.12 (m, 1 H), 4.51 (ddd, J=11.02, 7.63, 3.05 Hz, 1 H), 4.36-4.45 (m, 1 H), 2.08-2.23 (m, 2 H). MS (ESI) m/e 411 (M+H)$^+$. Calcd. For C$_{18}$H$_{14}$N$_4$O$_2$ClF$_3$.0.4NaOH.0.35tetrahydrofuran: C, 51.55; H, 3.84; N, 12.39. Found C, 51.77; H, 3.48; N, 12.10.

Example 44

(+)—N-(8-tert-butyl-3,4-dihydro-2H-chromen-4-yl)-N'-1H-indazol-4-ylurea

Example 42G was resolved by chiral HPLC (Column: Chiracel OD (5 cm ID×50 cm); mobile phase: 90:5:5 hexanes:ethanol:methanol) to give title compound.

[α]$_D$=+114 degrees (c=1.110, ethanol). $^1$H NMR (300 MHz, DMSO-d$_6$) δ ppm 8.55 (s, 1 H), 8.02 (s, 1 H), 7.69 (d, J=7.12 Hz, 1 H), 7.13-7.24 (m, 3 H), 7.06 (d, J=8.14 Hz, 1 H), 6.95 (d, J=7.12 Hz, 1 H), 6.86 (t, J=7.63 Hz, 1 H), 4.84-4.92 (m, 1 H), 4.32-4.41 (m, 1 H), 4.09-4.19 (m, 1 H), 1.99-2.14 (m, 2 H), 1.35 (s, 9 H). MS (ESI) m/e 365 (M+H)$^+$. Calcd. For C$_{21}$H$_{24}$N$_4$O$_2$.0.5H$_2$O: C, 67.54; H, 6.75; N, 15.00. Found C, 67.35; H, 6.47; N, 14.88.

Example 45

(−)—N-(8-tert-butyl-3,4-dihydro-2H-chromen-4-yl)-N'-1H-indazol-4-ylurea

Example 42G was resolved by chiral HPLC (Column: Chiracel OD (5 cm ID×50 cm); mobile phase: 90:5:5 hexanes:ethanol:methanol) to give title compound.

[α]$_D$=−107 degrees (c=1.075, ethanol). $^1$H NMR (300 MHz, DMSO-d$_6$) δ ppm 8.55 (s, 1 H), 8.02 (s, 1 H), 7.69 (d, J=7.46 Hz, 1 H), 7.13-7.25 (m, 3 H), 7.06 (d, J=8.14 Hz, 1 H), 6.95 (d, J=7.12 Hz, 1 H), 6.82-6.90 (m, 1 H), 4.85-4.92 (m, 1 H), 4.32-4.41 (m, 1 H), 4.09-4.19 (m, 1 H), 1.99-2.15 (m, 2 H), 1.35 (s, 9 H). MS (ESI) m/e 365 (M+H)$^+$. Calcd. For C$_2$H$_{24}$N$_4$O$_2$.0.6H$_2$O: C, 67.22; H, 6.77; N, 14.93. Found C, 67.18; H, 6.42; N, 14.92.

Example 46

N-1H-indazol-4-yl-N'-[8-(trifluoromethoxy)-3,4-dihydro-2H-chromen-4-yl]urea

Example 46A

2-Trifluoromethoxyphenol (5.0 g, 28 mmol), propargyl bromide (4 ml of 80% in toluene, 36 mmol), and potassium carbonate (4.97 g, 36 mmol) were stirred together in 70 ml of acetonitrile at ambient temperature for 2 days. The solvent was removed under reduced pressure, and the residue taken in water and extracted with diethyl ether. The organic layers were combined, dried with magnesium sulfate, and filtered. The solvent was evaporated under reduced pressure to give 5.60 g of Example 46A which was used without further purification. $^1$H NMR (300 MHz, CDCl$_3$) δ ppm 7.23-7.30 (m, 2 H), 7.13-7.19 (m, 1 H), 6.95-7.04 (m, 1 H), 4.77 (d, J=2.37 Hz, 2 H), 2.53 (t, J=2.37 Hz, 1 H).

Example 46B

Example 46A (5.60 g, 26 mmol) was dissolved in 125 ml acetone. N-chlorosuccinimide (4.00 g, 30 mmol) and silver acetate (0.42 g, 2.5 mmol) were added, and the reaction mixture heated to reflux for 4 hours. After cooling to ambient temperature, the silver salts were removed by filtration and the filtrate evaporated under reduced pressure. The residue was taken up in diethyl ether, washed with water, dried with magnesium sulfate, and filtered. The solvent was removed under reduced pressure to give 5.80 g of Example 46B which was used without further purification. $^1$H NMR (300 MHz, CHLOROFORM-D) δ ppm 7.24-7.30 (m, 2 H), 7.09-7.15 (m, 1 H), 7.01 (td, J=7.80, 1.36 Hz, 1 H), 4.77 (s, 2 H). MS (DCI) m/e 268 (M+NH$_4$)$^+$

Example 46C

Example 46B (25.8 g) in 250 ml ethylene glycol was heated to reflux for 4 hours. The reaction mixture was cooled, poured into water, and extracted with diethyl ether. The organic layers were dried with magnesium sulfate, filtered, and concentrated under reduced pressure. The residue was taken in hexanes, washed with 1N sodium hydroxide, and concentrated. The residue was purified by flash chromatography using 10% ethyl acetate in hexanes as eluent to provide 1.20 g of Example 46C. $^1$H NMR (300 MHz, CDCl$_3$) δ ppm 7.86 (dd, J=8.14, 1.70 Hz, 1 H), 7.44 (d, J=7.80 Hz, 1 H), 6.98-7.05 (m, 1 H), 4.60-4.66 (m, 2 H), 2.84-2.90 (m, 2 H).

Example 46D

Example 46C (1.20 g, 5.17 mmol) was dissolved in 10 ml pyridine. Methoxylamine hydrochloride (0.67 g, 8 mmol) was added and the reaction stirred at ambient temperature for 3 days. The pyridine was removed under reduced pressure, and the residue partitioned between water and diethyl ether. The mixture was extracted with diethyl ether, and the combined organic layers washed with 1N hydrochloric acid and saturated aqueous sodium bicarbonate sequentially. The organic layer was then dried with magnesium sulfate, and filtered. The solvent was removed under reduced pressure to give 1.05 g of Example 46D which was used without further purification. $^1$H NMR (300 MHz, CDCl$_3$) δ ppm 7.85 (dd, J=8.14, 1.36 Hz, 1 H), 7.16-7.24 (m, 1 H), 6.91 (t, J=8.14 Hz, 1 H), 4.23-4.31 (m, 2 H), 3.99 (s, 3 H), 2.93 (t, J=6.27 Hz, 2 H). MS (DCI) m/e 262 (M+H)$^+$.

Example 46E

Example 46D (1.05 g, 4.25 mmol), 0.25 g of 10% palladium on carbon, and 50 ml of 20% ammonia in methanol were shaken under hydrogen at 60 psi and ambient temperature for 18 hours. The catalyst was removed by filtration and the solvent evaporated under reduced pressure. The residue was taken in diethyl ether, extracted with 1N hydrochloric acid, and the acid extracts made basic with 10 N sodium hydroxide solution. The combined basic aqueous extracts were then extracted with diethyl ether. The organic layers were combined, dried with magnesium sulfate and filtered. The solvent was removed under reduced pressure to give 0.67 g of Example 46E. $^1$H NMR (300 MHz, CDCl$_3$) δ ppm 7.21-7.30 (m, 1 H), 7.11 (d, J=8.14 Hz, 1 H), 6.87 (t, J=7.97 Hz, 1 H), 4.26-4.40 (m, 2 H), 4.04-4.12 (m, 1 H), 2.10-2.23 (m, 1 H), 1.82-1.93 (m, 1 H). MS (DCI) m/e 234 (M+H)$^+$.

Example 46F methyl 4-[({[8-(trifluoromethoxy)-3,4-dihydro-2H-chromen-4-yl]amino}carbonyl)amino]-1H-indazole-1-carboxylate Example 49E (0.61 g, 2.6 mmol), Example 24D (0.83 g, 2.6 mmol), and diisopropylethylamine (0.52 g, 0.7 ml, 4 mmol) were dissolved in 10 ml of N,N-dimethylformamide. The reaction was stirred at ambient temperature for 16 hours, and diluted with water. The precipitate that formed was collected by filtration, and air-dried to give 1.03 g of the titled compound which was used without further purification. $^1$H NMR (300 MHz, DMSO-D6) δ ppm 8.87 (s, 1 H), 8.39 (s, 1 H), 7.86 (d, J=7.80 Hz, 1 H), 7.71 (d, J=8.48 Hz, 1 H), 7.51 (t, J=8.14 Hz, 1 H), 7.37 (d, J=7.80 Hz, 1 H), 7.29 (d, J=8.14 Hz, 1 H), 6.90-7.03 (m, 2 H), 5.00 (d, J=7.12 Hz, 1 H), 4.37-4.46 (m, 1 H), 4.20-4.32 (m, 1 H), 4.03 (s, 3 H), 2.06-2.21 (m, 2 H). MS (ESI) m/e 451 (M+H)$^+$.

Example 46G

N-1H-indazol-4-yl-N'-[8-(trifluoromethoxy)-3,4-dihydro-2H-chromen-4-yl]urea

Example 46F (1.03 g, 1.5 mmol) was dissolved in a mixture of 5 ml tetrahydrofuran and 10 ml methanol. Sodium hydroxide (5M in methanol, 2 ml, 10 mmol) was added, and the reaction mixture stirred at ambient temperature for 40 minutes. The reaction mixture was diluted with water, and the precipitate that formed was collected by filtration, giving 0.82 g of titled compound. $^1$H NMR (300 MHz, DMSO-d$_6$) δ ppm 13.00 (s, 1 H), 8.60 (s, 1 H), 8.04 (s, 1 H), 7.67 (d, J=7.12 Hz, 1 H), 7.37 (d, J=7.80 Hz, 1 H), 7.19-7.32 (m, 2 H), 7.08 (d, J=8.14 Hz, 1 H), 6.91-7.03 (m, 2 H), 4.91-5.02 (m, 1 H), 4.38-4.46 (m, 1 H), 4.25 (ddd, J=11.44, 8.56, 3.05 Hz, 1 H), 2.04-2.20 (m, 2 H). MS (ESI) m/e 393 (M+H)$^+$. Calcd. For C$_{18}$H$_{15}$N$_4$O$_3$F$_3$: C, 55.11; H, 3.85; N, 14.28. Found C, 54.92; H, 3.74; N, 14.04.

Example 47

N-[8-fluoro-7-(trifluoromethyl)-3,4-dihydro-2H-chromen-4-yl]-N'-1H-indazol-4-ylurea

Example 47A

2-Fluoro-3-trifluoromethylphenol (4.39 g, 24 mmol), propargyl bromide (3.6 ml of 80% in toluene, 32 mmol), and potassium carbonate (4.42 g, 32 mmol) were stirred together in 50 ml of acetonitrile at ambient temperature for 6 days. The solvent was removed under reduced pressure, and the residue taken in water and extracted with diethyl ether. The organic layers were combined, dried with magnesium sulfate, and filtered. The solvent was evaporated under reduced pressure to give 5.05 g of Example 47A which was used without further purification. $^1$H NMR (300 MHz, CDCl$_3$) δ ppm 7.32 (td, J=7.71, 1.86 Hz, 1 H), 7.14-7.26 (m, 2 H), 4.81 (d, J=2.37 Hz, 2 H), 2.56 (t, J=2.37 Hz, 1 H)

Example 47B

Example 43A (5.05 g, 23 mmol) was dissolved in 100 ml acetone. N-chlorosuccinimide (3.74 g, 28 mmol) and silver acetate (0.33 g, 2 mmol) were added, and the reaction heated to reflux for 4.5 hours. After cooling, the silver salts were removed by filtration and the filtrate evaporated under reduced pressure. The residue was triturated with hexanes and filtered. The filtrate evaporated under reduced pressure to give 4.97 g of Example 47B which was used without further purification. $^1$H NMR (300 MHz, CHLOROFORM-D) δ ppm 7.17-7.32 (m, 3 H), 4.81 (s, 2 H)

Example 47C

Example 47B (4.97 g, 19.7 mmol) was dissolved in 100 ml of concentrated sulfuric acid. The reaction mixture was stirred at ambient temperature for 16 hours, then poured onto ice and extracted with diethyl ether. The combined organic layers were washed with saturated aqueous sodium bicarbonate, dried with magnesium sulfate, and filtered. The solvent was removed under reduced pressure, to give crude product.

The crude product was taken in diethyl ether, washed with two portions of 1N sodium hydroxide, dried with magnesium sulfate, and filtered through a pad of silica gel. Evaporation of the filtrate gave 1.80 g of Example 47C. $^1$H NMR (300 MHz, CDCl$_3$) δ ppm 7.76 (d, J=8.48 Hz, 1 H), 7.07 (m, 1 H), 4.66-4.72 (m, 2 H), 2.88-2.95 (m, 2 H)

Example 47D

Example 47C (1.80 g, 7.7 mmol) was dissolved in 15 ml pyridine. Methoxylamine hydrochloride (1.00 g, 12 mmol) was added and the reaction mixture stirred at ambient temperature for 16 hours. The pyridine was removed under reduced pressure, and the residue taken into diethyl ether. The ether solution was washed with water, 1N hydrochloric acid and saturated aqueous sodium bicarbonate sequentially, dried with magnesium sulfate, and filtered. The solvent was evaporated under reduced pressure to give crude product.

The crude product was filtered through a pad of silica gel with hexanes, and the solvent evaporated to give 1.00 g of Example 47D. $^1$H NMR (300 MHz, CHLOROFORM-D) δ ppm 7.74 (d, J=7.80 Hz, 1 H), 7.09 (dd, J=8.48, 6.44 Hz, 1 H), 4.29-4.35 (m, 2 H), 4.02 (s, 3 H), 2.95 (t, J=6.27 Hz, 2 H). MS (DCI) m/e 264 (M+H)$^+$

Example 47E

Example 47D (1.00 g, 3.8 mmol), 0.20 g of 10% palladium on carbon, and 30 ml of 20% ammonia in methanol were shaken under hydrogen at 60 psi and ambient temperature for 18 hours. The catalyst was removed by filtration and the solvent evaporated under reduced pressure to give 0.63 g of Example 47E. $^1$H NMR (300 MHz, CDCl$_3$) δ ppm 7.15-7.21 (m, 1 H), 7.02-7.13 (m, 1 H), 4.30-4.45 (m, 2 H), 4.10 (t, J=5.42 Hz, 1 H), 2.11-2.25 (m, 1 H), 1.84-1.98 (m, J=13.90, 6.10, 6.10, 3.39 Hz, 1 H). MS (DCI) m/e 236 (M+H)$^+$.

Example 47F methyl 4-[({[8-fluoro-7-(trifluoromethyl)-3,4-dihydro-2H-chromen-4-yl]amino}carbonyl)amino]-1H-indazole-1-carboxylate Example 43E (0.63 g, 2.7 mmol), Example 24D (0.86 g, 2.7 mmol), and diisopropylethylamine (0.65 g, 0.9 ml, 5 mmol) were dissolved in 10 ml of N,N-dimethylformamide. The reaction mixture was stirred at ambient temperature for 24 hours, then diluted with water. The precipitate that formed was collected by filtration, and air-dried to give 0.87 g of the titled compound which was used without further purification. $^1$H NMR (300 MHz, DMSO-d$_6$) δ ppm 8.99 (s, 1 H), 8.42 (s, 1 H), 7.83 (d, J=7.46 Hz, 1 H), 7.72 (d, J=8.48 Hz, 1 H), 7.51 (t, J=8.14 Hz, 1 H), 7.31-7.39 (m, 1 H), 7.19-7.29 (m, 1 H), 6.98 (d, J=8.14 Hz, 1 H), 5.03-5.13 (m, 1 H), 4.34-4.50 (m, 2 H), 4.03 (s, 3 H), 2.09-2.24 (m, 2 H). MS (ESI) m/e 453 (M+H)$^+$.

Example 47G

N-[8-fluoro-7-(trifluoromethyl)-3,4-dihydro-2H-chromen-4-yl]-N'-1H-indazol-4-ylurea Example 47F (0.87 g, 1.9 mmol) was dissolved in a mixture of 5 ml tetrahydrofuran and 5 ml methanol. Sodium hydroxide (5M in methanol, 2 ml, 10 mmol) was added, and the reaction stirred at ambient temperature for 40 minutes. The mixture was diluted with water, and the precipitate that formed was collected by filtration, giving 0.68 g of titled compound. $^1$H NMR (300 MHz, DMSO-d$_6$) δ ppm 13.01 (br s, 1 H), 8.75 (s, 1 H), 8.05-8.08 (m, 1 H), 7.65 (d, J=7.46 Hz, 1 H), 7.32-7.37 (m, 1 H), 7.16-7.28 (m, 2 H), 7.09 (d, J=8.14 Hz, 1 H), 6.94-7.05 (m, 1 H), 5.07 (d, J=6.10 Hz, 1 H), 4.47 (ddd, J=11.10, 7.71, 3.22 Hz, 1 H), 4.33-4.41 (m, J=7.37, 7.37, 3.56, 3.39 Hz, 1 H), 2.18-2.27 (m, 1 H), 2.12 (qd, J=7.06, 3.22 Hz, 1 H). MS (ESI) m/e 395 (M+H)$^+$. Calcd. For C$_{18}$H$_{14}$N$_4$O$_2$F$_4$.0.25H$_2$O: C, 54.21; H, 3.66; N, 14.05. Found C, 54.25; H, 3.80, N, 13.76.

Example 48

N-(8-cyclohexyl-3,4-dihydro-2H-chromen-4-yl)-N'-1H-indazol-4-ylurea

Example 48A 2-cyclohexylphenol (5.29 g, 30 mmol), propargyl bromide (4.2 ml of 80% in toluene, 38 mmol), and potassium carbonate (5.24 g, 38 mmol) were stirred together in 70 ml of acetonitrile at ambient temperature for 5 days. The solvent was removed under reduced pressure, and the residue taken into water and extracted with diethyl ether. The organic layers were combined, dried with magnesium sulfate, and filtered. The solvent was evaporated under reduced pressure to give 6.60 g of Example 48A which was used without further purification. $^1$H NMR (300 MHz, CDCl$_3$) δ ppm 7.12-7.24 (m, 2 H), 6.91-7.00 (m, 2 H), 4.71 (d, J=2.37 Hz, 2 H), 2.90-3.02 (m, 1 H), 2.49 (t, J=2.37 Hz, 1 H), 1.72-1.87 (m, 5 H), 1.34-1.47 (m, 4 H), 1.22-1.32 (m, 1 H). MS (DCI) m/e 232 (M+NH$_4$)$^+$.

Example 48B

Example 48A (6.60 g, 30.8 mmol) was dissolved in 120 ml acetone. N-chlorosuccinimide (4.94 g, 37 mmol) and silver acetate (0.5 g, 3 mmol) were added, and the reaction heated to reflux for 4 hours. Thin-layer chromatography showed starting material present, so an additional 9.94 g of N-chlorosuccinimide was added, and the reaction mixture was refluxed for 16 hours longer.

After cooling, the silver salts were removed by filtration and the filtrate evaporated under reduced pressure. The residue was taken up in diethyl ether, washed with water and saturated aqueous sodium bicarbonate sequentially, dried with magnesium sulfate, and filtered. The solvent was removed under reduced pressure to give 7.55 g of Example 48B which was used without further purification. $^1$H NMR (300 MHz, CDCl$_3$) δppm 7.12-7.23 (m, 2 H), 6.90-7.00 (m, 2 H), 4.71 (s, 2 H), 2.88-3.01 (m, 1 H), 1.81-1.84 (m, 5 H), 1.70-1.79 (m, 1 H), 1.34-1.47 (m, 4 H), 1.18-1.33 (m, 1 H). MS (DCI) m/e 266 (M+NH$_4$)$^+$.

Example 48C

Example 48B (7.55 g, 30 mmol) in 100 ml ethylene glycol was heated to reflux for 2.5 hours. The reaction mixture was cooled, poured into water, and extracted with diethyl ether. The organic layers were combined, dried with magnesium sulfate, and filtered. The solvent was evaporated under reduced pressure. The residue was purified by flash chromatography using 10% ethyl acetate in hexanes as eluent, giving 3.15 g of Example 48C. $^1$H NMR (300 MHz, CDCl$_3$) δ ppm 7.76 (dd, J=7.80, 1.70 Hz, 1 H), 7.38 (dd, J=7.46, 1.70 Hz, 1 H), 6.97 (t, J=7.63 Hz, 1 H), 4.51-4.57 (m, 2 H), 2.87-2.98 (m, 1 H), 2.75-2.85 (m, 2 H), 1.73-1.89 (m, 5 H), 1.33-1.47 (m, 4 H), 1.26-1.31 (m, 1 H). MS (DCI) m/e 231 (M+H)$^+$.

Example 48D

Example 48C (3.15 g, 13.7 mmol) was dissolved in 25 ml pyridine. Methoxyamine hydrochloride (2.00 g, 24 mmol) was added and the reaction stirred at ambient temperature for 5 days. The pyridine was removed under reduced pressure, and the residue partitioned between water and diethyl ether. The mixture was extracted with diethyl ether, and the combined organic layers washed with 1N hydrochloric acid and saturated aqueous sodium bicarbonate sequentially, dried with magnesium sulfate, and filtered. The solvent was removed under reduced pressure to give 3.23 g of Example 48D which was used without further purification. $^1$H NMR (300 MHz, CDCl$_3$) δ ppm 7.75 (dd, J=8.14, 1.70 Hz, 1 H), 7.16 (dd, J=7.63, 1.53 Hz, 1 H), 6.89 (t, J=7.80 Hz, 1 H), 4.20 (t, J=6.27 Hz, 2 H), 3.97 (s, 3 H), 2.89 (t, J=6.10 Hz, 2 H), 1.71-1.87 (m, 5 H), 1.32-1.45 (m, 4 H), 1.21-1.26 (m, 1 H). MS (DCI) m/e 260 (M+H)$^+$.

Example 48E

Example 48D (3.23 g, 12.5 mmol), 0.60 g of 10% palladium on carbon, and 60 ml of 20% ammonia in methanol were shaken under hydrogen at 60 psi and ambient temperature for 16 hours. The catalyst was removed by filtration and the solvent evaporated under reduced pressure, giving 2.88 g of Example 48E which was used without further purification. $^1$H NMR (300 MHz, CDCl$_3$) δ ppm 7.06-7.16 (m, 2 H), 6.84-6.90 (m, 1 H), 4.22-4.29 (m, 2 H), 4.05 (t, J=5.26 Hz, 1 H), 2.81-2.95 (m, 1 H), 2.07-2.21 (m, J=13.44, 8.01, 5.21, 5.21 Hz, 1 H), 1.71-1.87 (m, 7 H), 1.31-1.46 (m, 4 H). MS (DCI) m/e 215 (M−NH$_2$)$^+$ 232 (M+H)$^+$.

Example 48F methyl 4-({[(8-cyclohexyl-3,4-dihydro-2H-chromen-4-yl)amino]carbonyl}amino)-1H-indazole-1-carboxylate Example 48E (1.16 g, 5 mmol), Example 24D (1.66 g, 5 mmol), and diisopropylethylamine (1.29 g, 1.8 ml, 10 mmol) were dissolved in 20 ml of N,N-dimethylformamide. The reaction mixture was stirred at ambient temperature for 24 hours, then diluted with water. The precipitate that formed was collected by filtration to give 2.00 g of the titled compound which was used without further purification. $^1$H NMR (300 MHz, DMSO-d$_6$) δ ppm 8.77 (s, 1 H), 8.36 (s, 1 H), 7.88 (d, J=7.46 Hz, 1 H), 7.69 (d, J=8.48 Hz, 1 H), 7.50 (t, J=8.14 Hz, 1 H), 7.12 (t, J=7.12 Hz, 2 H), 6.84-6.91 (m, 2 H), 4.85-4.92 (m, 1 H), 4.27-4.38 (m, 1 H), 4.09-4.21 (m, 1 H), 4.03 (s, 3 H), 2.80-2.92 (m, 1 H), 1.99-2.15 (m, 2 H), 1.73 (br, 5 H), 1.27-1.41 (m, 5 H). MS (ESI) m/e 449 (M+H)$^+$.

Example 48G

N-(8-cyclohexyl-3,4-dihydro-2H-chromen-4-yl)-N'-1H-indazol-4-ylurea

Example 48F (2.00 g, 4.46 mmol) was dissolved in a mixture of 12 ml tetrahydrofuran and 12 ml methanol. Sodium hydroxide (5M in methanol, 5 ml, 25 mmol) was added, and the reaction mixture stirred at ambient temperature for 40 minutes, diluted with water, and the precipitate that formed was collected by filtration, giving 1.49 g of the titled compound. $^1$H NMR (300 MHz, DMSO-d$_6$) δ ppm 12.99 (s, 1 H), 8.51 (s, 1 H), 8.01 (s, 1 H), 7.69 (d, J=7.46 Hz, 1 H), 7.17-7.25 (m, 1 H), 7.03-7.15 (m, 3 H), 6.87 (t, J=7.46 Hz, 2 H), 4.84-4.91 (m, 1 H), 4.26-4.39 (m, 1 H), 4.10-4.24 (m, 1 H), 2.87 (m, 1 H), 1.98-2.14 (m, 2 H), 1.66-1.85 (br, 6 H), 1.28-1.41 (m, 4 H). MS (ESI) m/e 391 (M+H)$^+$. Calcd. For C$_{23}$H$_{26}$N$_4$O$_2$.0.2 tetrahydrofuran.0.7H$_2$O: C, 68.47; H, 7.00; N, 13.42. Found C, 68.58; H, 6.86; N, 13.25.

Example 49

N-1H-indazol-4-yl-N'-[7-(trifluoromethoxy)-3,4-dihydro-2H-chromen-4-yl]urea

Example 49A

3-Trifluoromethoxyphenol (4.45 g, 25 mmol), propargyl bromide (3.6 ml of 80% in toluene, 32 mmol), and potassium carbonate (4.42 g, 32 mmol) were stirred together in 50 ml of acetonitrile at ambient temperature for 6 days. The solvent was removed under reduced pressure, and the residue taken in water and extracted with diethyl ether. The organic layers were combined, dried with magnesium sulfate, and filtered. The solvent was evaporated under reduced pressure to give 5.00 g of Example 49A which was used without further purification. $^1$H NMR (300 MHz, CHLOROFORM-D) δ ppm 7.31 (t, J=8.48 Hz, 1 H), 6.90 (m, 6.87-6.93 2 H), 6.85 (s, 1 H), 4.70 (d, J=2.71 Hz, 2 H), 2.55 (t, J=2.37 Hz, 1 H)

Example 49B

Example 49A (5.00 g, 23 mmol) was dissolved in 120 ml acetone. N-chlorosuccinimide (3.87 g, 29 mmol) and silver acetate (0.33 g, 2 mmol) were added, and the reaction mixture heated to reflux for 5.5 hours. After cooling, the silver salts were removed by filtration and the filtrate evaporated under reduced pressure. The residue was taken up in diethyl ether, washed with water, dried with magnesium sulfate, and filtered. The solvent was removed under reduced pressure to give 5.88 g of Example 49B which was used without further purification. $^1$H NMR (300 MHz, CHLOROFORM-D) δ ppm 7.31 (t, J=8.31 Hz, 1 H), 6.81-6.91 (m, 3 H), 4.70 (s, 2 H)

Example 49C

Example 49B (5.88 g, 23 mmol) was heated to reflux in 100 ml of ethylene glycol for five hours, cooled, and poured into water. The mixture was extracted with diethyl ether. The combined organic layers were dried with magnesium sulfate and filtered. The solvent was evaporated under reduced pressure. The residue was purified by flash chromatography using 10% ethyl acetate in hexanes as eluent to give 1.49 g of Example 49C. $^1$H NMR (300 MHz, CDCl$_3$) δ ppm 6.77-6.88 (m, 3 H), 4.54-4.60 (m, 2 H), 2.80-2.85 (m, 2 H). MS (DCI) m/e 233 (M+H)$^+$.

Example 49D

Example 49C (1.49 g, 6.4 mmol) was dissolved in 12 ml pyridine. Methoxylamine hydrochloride (0.83 g, 10 mmol) was added and the reaction mixture stirred at ambient temperature for 3 days. The pyridine was removed under reduced pressure, and the residue taken into diethyl ether. The ether solution was washed with 1N hydrochloric acid and saturated aqueous sodium bicarbonate sequentially, dried with magnesium sulfate, and filtered. The solvent was evaporated under reduced pressure to give 1.56 g of Example 49D which was used without further purification. $^1$H NMR (300 MHz, CHLOROFORM-D) δ ppm 6.71-6.81 (m, 3 H), 4.20-4.25 (m, 2 H), 3.99 (s, 3 H), 2.87-2.93 (m, 2 H). MS (DCI) m/e 262 (M+H)$^+$.

Example 49E

Example 49D (1.56 g, 6 mmol), 0.38 g of 10% palladium on carbon, and 70 ml of 20% ammonia in methanol were shaken under hydrogen at 60 psi and ambient temperature for 28 hours. The catalyst was removed by filtration and the solvent evaporated under reduced pressure. The residue was taken in to diethyl ether and extracted with 1N hydrochloric acid. The aqueous extracts were combined and made basic with 10N sodium hydroxide and extracted with diethyl ether. The organic extracts were combined, dried with magnesium sulfate, and filtered. The solvent was evaporated under reduced pressure to give 0.57 g of Example 49E. $^1$H NMR (300 MHz, CDCl$_3$) δ ppm 7.33 (d, J=8.48 Hz, 1 H), 6.76 (d, J=8.48 Hz, 1 H), 6.69 (s, 1 H), 4.20-4.35 (m, 2 H), 4.07 (t, J=5.26 Hz, 1 H), 2.07-2.22 (m, 1 H), 1.79-1.93 (m, 1 H). MS (DCI) m/e 217 (M−NH$_2$)$^+$234 (M+H)$^+$ Example 49F methyl 4-[({[7-(trifluoromethoxy)-3,4-dihydro-2H-chromen-4-yl]amino}carbonyl)amino]-1H-indazole-1-carboxylate Example 49E (0.57 g, 2.4 mmol), Example 24D (0.80 g, 2.4 mmol), and diisopropylethylamine (0.65 g, 0.9 ml, 5 mmol) were dissolved in 10 ml of N,N-dimethylformamide. The reaction mixture was stirred at ambient temperature for 16 hours, and diluted with water. The precipitate that formed was collected by filtration, and air-dried to give 0.67 g of the titled compound which was used without further purification. $^1$H NMR (300 MHz, DMSO-d$_6$) δ ppm 8.87 (s, 1 H), 8.39 (s, 1 H), 7.86 (d, J=7.12 Hz, 1 H), 7.70 (d, J=8.48 Hz, 1 H), 7.42-7.54 (m, 2 H), 6.81-6.96 (m, 3 H), 4.90-5.00 (m, 1 H), 4.29-4.40 (m, 1 H), 4.22 (ddd, J=11.27, 8.22, 3.22 Hz, 1 H), 4.03 (s, 3 H), 2.03-2.19 (m, 2 H). MS (ESI) m/e 451 (M+H)$^+$ Example 49G N-1H-indazol-4-yl-N'-[7-(trifluoromethoxy)-3,4-dihydro-2H-chromen-4-yl]urea Example 46F (0.67 g, 1.5 mmol) was dissolved in a mixture of 5 ml tetrahydrofuran and 5 ml methanol. Sodium hydroxide (5M in methanol, 2 ml, 10 mmol) was added, and the reaction stirred at ambient temperature for 40 minutes. The reaction mixture was diluted with water, and the precipitate that formed was collected by filtration, giving 0.53 g of titled compound. $^1$H NMR (300 MHz, DMSO-d$_6$) δ ppm 13.03 (s, 1 H), 8.60 (s, 1 H), 8.03 (s, 1 H), 7.68 (d, J=7.12 Hz, 1 H), 7.45 (d, J=8.81 Hz, 1 H), 7.18-7.26 (m, 1 H), 7.08 (d, J=8.14 Hz, 1 H), 6.81-6.96 (m, 3 H), 4.88-4.98 (m, 1 H), 4.29-4.40 (m, 1 H), 4.21 (ddd, J=11.53, 8.48, 3.05 Hz, 1 H), 2.01-2.18 (m, 2 H). MS (ESI) m/e 393 (M+H)$^+$. Calcd. For C$_{18}$H$_{15}$N$_4$O$_3$F$_3$: C, 55.11; H, 3.85; N, 14.28. Found C, 55.44, H, 3.75, N, 14.01.

Example 50

N-isoquinolin-5-yl-N'-{[1-(2-phenylethyl)-1,2,3,4-tetrahydroquinolin-2-yl]methyl}urea Example 50A A solution of phosgene (20% in toluene, 10.2 mL, 19.3 mmol) was added to dichlormethane (120 mL) at 0° C. under N$_2$ and allowed to equilibrate for 15 minutes before addition of a solution of 4-N,N-dimethylaminopyridine (5.1595 g, 42.2 mmol) in dichloromethane (20 mL). After 20 minutes, a solution of 5-aminoisoquinoline (2.5070 g, 17.4 mmol) in dichloromethane (40 mL) was added. The reaction mixture was allowed to warm to ambient temperature and stirred for 17 hours. The mixture was then condensed in vaco to a thick paste which was suspended in ether and filtered. The filtrate was diluted up to 150 mL with ether for a 0.1 M solution of Example 50A in ether.

Example 50B

The product from Example 50A (125 mL, 14.4 mmol) was poured into a solution of 2-aminomethyl-1-N-boc-1,2,3,4-tetrahydroquinoline (3.23 g, 12.3 mmol) in ether (50 mL) at ambient temperature and stirred for 4.5 hours. The reaction mixture was filtered and the precipitate was washed with ether and dried under vacuum to afford Example 50B (2.9493 g, 55%) as a white solid. $^1$H NMR (300 MHz, DMSO-d$_6$) δ ppm 9.26 (s, 1 H) 8.62 (s, 1 H) 8.53 (d, J=6.10 Hz, 1 H) 8.27 (d, J=7.46 Hz, 1 H) 7.89 (d, J=6.10 Hz, 1 H) 7.72 (d, J=7.80 Hz, 1 H) 7.59 (t, J=7.97 Hz, 1 H) 7.52 (d, J=7.80 Hz, 1 H) 7.13 (t, J=7.12 Hz, 2 H) 7.02 (m, 1 H) 6.65 (t, J=6.10 Hz, 1 H) 4.58 (m, 1 H) 3.30 (m, 1 H) 3.01 (m, 1 H) 2.72 (m, 1 H) 2.59 (m, 1 H) 2.15 (m, 1 H) 1.65 (m, 1 H) 1.40 (s, 9 H). MS (DCI) m/z 171 (100%, (M−262)$^+$), 433 (10%, (M+H)$^+$).

Example 50C

Trifluoroacetic acid (5 mL) was added to a solution of the product from Example 50B (1.2413 g, 2.87 mmol) in dichloromethane (50 mL) and stirred for 20 hours at ambient temperature. The reaction solution was concentrated and taken up in ethyl acetate and washed with aqueous saturated NaCHO$_3$ solution, then water and condensed to give Example 50C (0.8788 g, 92%) as a pale yellow solid. $^1$H NMR (300 MHz, DMSO-d$_6$) δ ppm 9.26 (s, 1 H) 8.74 (s, 1 H) 8.53 (d, J=6.10 Hz, 1 H) 8.31 (m, 1 H) 7.95 (d, J=6.10 Hz, 1 H) 7.72 (d, J=8.14 Hz, 1 H) 7.59 (t, J=7.97 Hz, 1 H) 6.84 (m, 3 H) 6.51 (d, J=7.12 Hz, 1 H) 6.44 (t, J=6.78 Hz, 1 H) 5.70 (s, 1 H) 3.38 (m, 2 H) 3.18 (m, 1 H) 2.69 (m, 2 H) 1.87 (m, 1 H) 1.63 (m, 1 H). MS (DCI) m/z 163 (100%, (M−169)$^+$), 333 (10%, (M+H)$^+$).

Example 50D

N-isoquinolin-5-yl-N'-{[1-(2-phenylethyl)-1,2,3,4-tetrahydroquinolin-2-yl]methyl}urea The product from Example 50C (52.1 mg, 0.16 mmol) was suspended in dichloroethane (5 mL) in a flask equipped with a stir bar and septum then flushed with N$_2$ and cooled in an ice bath to 0° C. In succession a solution of phenylacetaldehyde (42.1 mg, 0.35 mmol) in dichloroethane (0.5 mL), a suspension of sodium triacetoxy borohydride (70.7 mg, 0.33 mmol) and glacial acetic acid (0.07 mL, 1.19 mmol) were added then the reaction mixture was allowed to warm to ambient temperature. The reaction mixture cleared after 2 hours. LC/MS indicated reaction was not complete. Continued to stir 17 hours and checked via LC/MS-same as 2 hour sample. Another portion of sodium triacetoxy borohydride (36.0 mg, 0.17 mmol) was added and stirred for 4.5 hours. The reaction mixture was quenched with aqueous saturated NaHCO$_3$ solution (10 mL) and extracted with ethyl acetate (3×10 mL). The combined organic fractions were dried (MgSO$_4$), filtered and concentrated in vacuo. The crude product was purified via column chromatography on silica gel (4% methanol/dichloromethane) to afford the title compound (29.5 mg, 42%) as an off white solid. $^1$H NMR (300 MHz, DMSO-d$_6$) δ ppm 9.26 (s, 1 H) 8.69 (s, 1 H) 8.52 (d, J=5.76 Hz, 1 H) 8.26 (d, J=6.78 Hz, 1 H) 7.91 (d, J=6.10 Hz, 1 H) 7.74 (d, J=8.14 Hz, 1 H) 7.60 (t, J=7.97 Hz, 1 H) 7.24 (m, 6 H) 7.05 (t, J=8.48 Hz, 1 H) 6.95

(d, J=7.12 Hz, 1 H) 6.73 (t, J=8.48 Hz, 1 H) 6.51 (t, J=6.78 Hz, 1 H) 3.72 (m, 1 H) 3.45 (m, 1 H) 3.32 (m, 2 H) 3.13 (m, 1 H) 2.83 (m, 3 H) 2.62 (d, J=3.05 Hz, 1 H) 1.90 (m, 1 H) 1.59 (m, 1 H). MS (ESI) m/z 437 (M+H)$^+$, 435 (M−H)$^-$. Calcd. For $C_{28}H_{28}N_4O\cdot0.35$; $C_2H_4O_2$: C, 75.34; H, 6.48; N, 12.24. Found C, 75.58; H, 6.46; N, 11.84.

Example 51

N-[(1-benzyl-1,2,3,4-tetrahydroquinolin-2-yl)methyl]-N'-isoquinolin-5-ylurea

A solution of the product from Example 50C (0.1113 g, 0.33 mmol), benzaldehyde (0.08 mL, 0.79 mmol) and glacial acetic acid (0.15 mL, 2.55 mmol) in dichloroethane (10 mL) was stirred for 17 hours at ambient temperature to form the imine intermediate. Solid sodium triacetoxy borohydride (0.1411 g, 0.67 mmol) was added and continued to stir at ambient temperature. Checked reaction mixture at 2 and 4 hours intervals; some product formation but major component was the imine intermediate. An additional portion of solid sodium triacetoxy borohydride (0.1722 g, 0.81 mmol) and glacial acetic acid (0.1 mL, 1.7 mmol) were added and the mixture stirred an additional 17 hours. Although the reaction was incomplete, it was quenched with water (20 mL) and diluted with ethyl acetate. The aqueous phase was extracted with ethyl acetate (2×15 mL). The combined organic fractions were washed with brine (1×30 mL), dried (MgSO$_4$), filtered and concentrated in vacuo. The crude material was purified via column chromatography on silica gel (2% methanol/dichloromethane) to afford the title compound (9.9 mg, 7%) as an off white solid. $^1$H NMR (300 MHz, DMSO-d$_6$) δ ppm 9.26 (s, 1 H) 8.70 (s, 1 H) 8.54 (d, J=6.10 Hz, 1 H) 8.23 (d, J=6.78 Hz, 1 H) 7.92 (d, J=6.10 Hz, 1 H) 7.74 (d, J=8.14 Hz, 1 H) 7.58 (t, J=7.97 Hz, 1 H) 7.25 (m, 5 H) 6.96 (d, J=6.10 Hz, 1 H) 6.86 (t, J=7.63 Hz, 1 H) 6.79 (t, J=5.76 Hz, 1 H) 6.48 (t, J=6.78 Hz, 1 H) 6.35 (d, J=8.14 Hz, 1 H) 4.65 (q, 2 H) 3.56 (m, 1 H) 3.40 (m, 1 H) 3.23 (m, 1 H) 2.93 (m, 1 H) 2.69 (m, 1 H) 2.07 (m, 1 H) 1.86 (m, 1 H). MS (ESI) m/z 423 (M+H)$^+$, 421 (M−H)$^-$. Calcd For $C_{27}H_{26}N_4O\cdot0.25$ dichloromethane: C, 73.76; H, 6.02; N, 12.63. Found C, 73.92; H, 6.11; N, 12.55.

Example 52

N-isoquinolin-5-yl-N'-{[1-(3-phenylpropyl)-1,2,3,4-tetrahydroquinolin-2-yl]methyl}urea The product from Example 50C (0.24 g, 0.53 mmol) and sodium triacetoxy borohydride (0.2547 g, 1.20 mmol) were suspended in dichloroethane (5 mL). The reaction flask was equipped with stir bar and septum, then flushed with N$_2$. Hydrocinnamaldehyde (0.11 mL, 0.83 mmol) was added followed by glacial acetic acid (0.2 mL, 3.4 mmol). The reaction mixture was diluted with an additional 5 mL dichloroethane. After 2 hours of stirring at ambient temperature, the reaction was quenched with water (20 mL) and partitioned between ethyl acetate/water. The aqueous phase was extracted with ethyl acetate (2×15 mL). The combined organic fractions were washed with aqueous saturated NaHCO$_3$ (1×25 mL), water (1×25 mL), and brine (1×25 mL), dried (MgSO$_4$), filtered and concentrated in vaco. The crude material was purified via column chromatography (2% to 5% methanol/dichloromethane) to afford the title compound (0.1926 g, 81%) as a white solid. $^1$H NMR (300 MHz, DMSO-d$_6$) δ ppm 9.27 (s, 1 H) 8.70 (s, 1 H) 8.54 (d, J=5.76 Hz, 1 H) 8.27 (d, J=7.46 Hz, 1 H) 7.92 (d, J=6.10 Hz, 1 H) 7.74 (d, J=8.14 Hz, 1 H) 7.60 (t, J=7.97 Hz, 1 H) 7.19 (m, 5 H) 6.93 (m, 2 H) 6.76 (t, J=5.93 Hz, 1 H) 6.48 (m, 2 H) 3.49 (m, 2 H) 3.25 (m, 2 H) 3.13 (m, 1 H) 2.82 (m, 1 H) 2.62 (m, 3 H) 1.80 (m, 4 H). MS (ESI) m/z 451 (M+H)$^+$, 449 (M−H)$^-$. Calcd For $C_{29}H_{30}N_4O$: C, 77.30; H, 6.71; N, 12.43. Found C, 77.20; H, 6.32; N, 12.21.

Example 53

N-1H-indazol-4-yl-N'-{[1-(2-phenylethyl)-1,2,3,4-tetrahydroquinolin-2-yl]methyl}urea Example 53A methyl 4-{[({[1-(2-phenylethyl)-1,2,3,4-tetrahydroquinolin-2-yl]methyl}amino)carbonyl]amino}-1H-indazole-1-carboxylate The product from Example 22B (0.2486 g, 0.50 mmol) and sodium triacetoxy borohydride (0.2235 g, 1.05 mmol) were suspended in dichloroethane (10 mL). The reaction flask was equipped with stir bar and septum, then flushed with N$_2$. Phenylacetaldehyde (0.10 mL, 0.85 mmol) was added followed by glacial acetic acid (0.2 mL, 3.4 mmol). After 1 hour of stirring at ambient temperature, the reaction mixture was quenched with water (20 mL) then partitioned between ethyl acetate/water. The aqueous phase was extracted with ethyl acetate (2×15 mL). The combined organic fractions were washed sequentially with aqueous saturated NaHCO$_3$ (1×25 mL), water (1×25 mL), and brine (1×25 mL), dried (MgSO$_4$), filtered and concentrated in vaco. The crude material was purified via column chromatography (2% to 5% methanol/dichloromethane) to afford the titled compound (0.1913 g, 79%) as a white solid. $^1$H NMR (300 MHz, DMSO-d$_6$) δ ppm 8.99 (s, 1 H) 8.43 (s, 1 H) 7.80 (d, J=7.80 Hz, 1 H) 7.69 (d, J=8.48 Hz, 1 H) 7.48 (t, J=8.14 Hz, 1 H) 7.25 (m, 5 H) 7.04 (m, 1 H) 6.95 (d, J=7.46 Hz, 1 H) 6.71 (d, J=8.14 Hz, 1 H) 6.51 (t, J=6.95 Hz, 2 H) 4.03 (s, 3 H) 3.72 (m, 1 H) 3.37 (m, 3 H) 3.13 (m, 1 H) 2.82 (m, 3 H) 2.59 (m, 1 H) 1.89 (m, 1 H) 1.55 (m, 1 H). MS (ESI) m/z 484 (M+H)$^+$, 482 (M−H)$^-$.

Example 53B

N-1H-indazol-4-yl-N'-{[1-(2-phenylethyl)-1,2,3,4-tetrahydroquinolin-2-yl]methyl}urea The product from Example 53A (0.1913 g, 0.40 mmol) was dissolved in methanol (5 mL). A NaOH solution (1.0 mL, 5 M in methanol) was added and stirred for 30 minutes. The reaction mixture was then diluted with water until a precipitate formed. The solid was collected by filtration, washed with water and dried under vacuum to afford the title compound (0.1294 g, 76%) as a tan solid. $^1$H NMR (300 MHz, DMSO-d$_6$) δ ppm 12.98 (s, 1 H) 8.69 (s, 1 H) 8.07 (s, 1 H) 7.60 (d, J=7.46 Hz, 1 H) 7.24 (m, 6 H) 7.04 (m, 2 H) 6.94 (d, J=6.44 Hz, 1 H) 6.71 (d, J=8.14 Hz, 1 H) 6.51 (t, J=6.95 Hz, 2 H) 3.71 (m, 1 H) 3.37 (m, 3 H) 3.11 (m, 1 H) 2.83 (m, 3 H) 2.62 (m, 1 H) 1.87 (m, 1 H) 1.54 (m, 1 H). MS (ESI) m/z 426 (M+H)$^+$, 424 (M−H)$^-$. Calcd For $C_{26}H_{27}N_5O$: C, 73.39; H, 6.40; N, 16.46. Found C, 73.22; H, 6.36; N, 16.30.

Example 54

N-1H-indazol-4-yl-N'-{[1-(3-phenylpropyl)-1,2,3,4-tetrahydroquinolin-2-yl]methyl}urea

Example 54A methyl 4-{[({[1-(3-phenylpropyl)-1,2,3,4-tetrahydroquinolin-2-yl]methyl}amino)carbonyl]amino}-1H-indazole-1-carboxylate The title compound was prepared using the procedure as described in Example 53A, substituting hydrocinnamaldehyde (0.10 mL, 0.76 mmol) for phenylacetaldehyde. The crude material was purified via column chromatography on silica gel (50% to 80% ethyl acetate/Hex) to afford the titled compound (0.1430 g, 70%) as an off white solid. $^1$H NMR (300 MHz, DMSO-$d_6$) δ ppm 9.00 (s, 1 H) 8.44 (s, 1 H) 7.82 (d, J=7.46 Hz, 1 H) 7.69 (d, J=8.14 Hz, 1 H) 7.49 (t, J=8.14 Hz, 1 H) 7.19 (m, 5 H) 6.93 (m, 2 H) 6.49 (m, 3 H) 4.03 (s, 3 H) 3.48 (m, 2 H) 3.25 (m, 2 H) 3.13 (m, 1 H) 2.82 (m, 1 H) 2.62 (m, 3 H) 1.87 (m, 3 H) 1.66 (m, 1 H). MS (ESI) m/z 498 (M+H)$^+$, 496 (M−H)$^−$.

Example 54B

N-1H-indazol-4-yl-N'-{[1-(3-phenylpropyl)-1,2,3,4-tetrahydroquinolin-2-yl]methyl}urea The title compound was prepared using the procedure as described in Example 53B, substituting Example 54A (0.1430 g, 0.29 mmol) for Example 53A. The crude material collected by filtration was rinsed with ether to afford the title compound (0.0785 g, 61%) as a white solid. $^1$H NMR (300 MHz, DMSO-$d_6$) δ ppm 12.98 (s, 1 H) 8.70 (s, 1 H) 8.08 (s, 1 H) 7.61 (d, J=7.12 Hz, 1 H) 7.21 (m, 6 H) 7.06 (d, J=8.14 Hz, 1 H) 6.94 (m, 2 H) 6.49 (m, 3 H) 3.48 (m, 2 H) 3.25 (m, 2 H) 3.11 (m, 1 H) 2.81 (m, 1 H) 2.62 (m, 3 H) 1.90 (m, 3 H) 1.67 (m, 1 H). MS (ESI) m/z 440 (M+H)$^+$, 438 (M−H)$^−$. Calcd For $C_{27}H_{29}N_5O \cdot 0.25$; $C_4H_{10}O$: C, 73.42; H, 6.93; N, 15.29. Found C, 73.12; H, 6.61; N, 15.50.

Example 55

N-1H-indazol-4-yl-N'-({1-[(trifluoromethyl)sulfonyl]-1,2,3,4-tetrahydroquinolin-2-yl}methyl)urea

Example 55A methyl 4-({[({1-[(trifluoromethyl)sulfonyl]-1,2,3,4-tetrahydroquinolin-2-yl}methyl)amino]carbonyl}amino)-1H-indazole-1-carboxylate The product from Example 22B (0.2034 g, 0.54 mmol) was dissolved in dichloromethane (50 mL). The reaction flask was equipped with stir bar and septum, flushed with N$_2$ and cooled to −78° C. in a dry ice/acetone bath. triethyl amine (0.11 mL, 0.79 mmol) and trifluoromethanesulfonic anhydride (0.15 mL, 0.89 mmol) were added and stirred at −78° C. for 5 minutes. The reaction mixture was removed from the cold bath and stirred for 18.5 hours at ambient temperature, filtered and concentrated in vacuo. The crude material was purified via column chromatography on sica gel (2% to 5% methanol/dichloromethane) to afford the titled compound (0.0927 g, 34%) as an off white solid. $^1$H NMR (300 MHz, DMSO-$d_6$) δ ppm 8.99 (s, 1 H) 8.40 (s, 1 H) 7.71 (dd, J=8.31, 3.90 Hz, 2 H) 7.47 (m, 2 H) 7.29 (m, 3 H) 6.56 (t, J=6.10 Hz, 1 H) 4.57 (m, 1 H) 4.03 (s, 3 H) 3.28 (m, 1 H) 3.09 (m, 1 H) 2.85 (m, 1 H) 2.66 (m, 1 H) 2.40 (m, 1 H) 1.70 (m, 1 H). MS (ESI) m/z 512 (M+H)$^+$, 510 (M−H)$^−$.

Example 55B

N-1H-indazol-4-yl-N'-({1-[(trifluoromethyl)sulfonyl]-1,2,3,4-tetrahydroquinolin-2-yl}methyl)urea The title compound (0.0422 g, 52%) was prepared using the procedure as described in Example 53B, substituting Example 55A (0.0927 g, 0.18 mmol) for Example 53A. $^1$H NMR (400 MHz, DMSO-$d_6$) δ ppm 12.96 (s, 1 H) 8.67 (s, 1 H) 8.05 (s, 1 H) 7.52 (d, J=7.67 Hz, 1 H) 7.45 (m, 1 H) 7.28 (m, 3 H) 7.19 (t, J=7.98 Hz, 1 H) 7.06 (d, J=8.29 Hz, 1 H) 6.54 (t, J=5.98 Hz, 1 H) 4.55 (m, 1 H) 3.33 (m, 1 H) 3.07 (m, 1 H) 2.84 (m, 1 H) 2.63 (m, 1 H) 2.39 (m, 1 H) 1.70 (m, 1 H). MS (ESI) m/z 454 (M+H)$^+$, 452 (M−H)$^−$.

Example 56

N-{[1-(cyclohexylmethyl)-1,2,3,4-tetrahydroquinolin-2-yl]methyl}-N'-1H-indazol-4-ylurea

Example 56A methyl 4-{[({[1-(cyclohexylmethyl)-1,2,3,4-tetrahydroquinolin-2-yl]methyl}amino)carbonyl]amino}-1H-indazole-1-carboxylate The title compound was prepared using the procedure as described in Example 53A, substituting cyclohexane carbaldehyde (0.16 mL, 1.33 mmol) for phenylacetaldehyde. The crude material was purified via column chromatography (2% methanol/dichloromethane) to afford the desired compound (0.2637 g, 64%) as a white solid. $^1$H NMR (300 MHz, DMSO-$d_6$) δ ppm 9.00 (s, 1 H) 8.44 (s, 1 H) 7.79 (d, J=7.46 Hz, 1 H) 7.69 (d, J=8.48 Hz, 1 H) 7.48 (t, J=8.14 Hz, 1H) 6.94 (m, 2 H) 6.49 (m, 3 H) 4.03 (s, 3 H) 3.41 (m, 2 H) 3.23 (m, 1 H) 3.08 (m, 1 H) 2.90 (m, 2 H) 2.63 (m, 1 H) 1.96 (m, 1 H) 1.68 (m, 8 H) 1.14 (m, 4 H). MS (ESI) m/z 476 (M+H)$^+$, 474 (M−H)$^−$.

Example 56B

N-{[1-(cyclohexylmethyl)-1,2,3,4-tetrahydroquinolin-2-yl]methyl}-N'-1H-indazol-4-ylurea The title compound was prepared using the procedure as described in Example 53B, substituting Example 56A (0.2637 g, 0.55 mmol) for Example 53A. The crude material was rinsed with ether to afford the title compound (0.2064 g, 90%) as a white solid. $^1$H NMR (300 MHz, DMSO-$d_6$) δ ppm 12.98 (s, 1 H) 8.69 (s, 1 H) 8.08 (s, 1 H) 7.59 (d, J=7.46 Hz, 1 H) 7.20 (t, J=7.97 Hz, 1 H) 7.06 (d, J=8.14 Hz, 1 H) 6.94 (m, 2 H) 6.48 (m, 3 H) 3.40 (dd, J=14.58, 4.07 Hz, 2 H) 3.21 (m, 1 H) 2.97 (m, 3 H) 2.61 (dd, J=16.28, 3.39 Hz, 1 H) 1.94 (m, 1 H) 1.72 (m, 7 H) 1.03 (m, 5 H). MS (ESI) m/z 418 (M+H)$^+$, 416 (M−H)$^−$. Calcd For $C_{25}H_{31}N_5O$: C, 71.91; H, 7.48; N, 16.77. Found C, 71.81; H, 7.61; N, 16.34.

Example 57

N-1H-indazol-4-yl-N'-[(1-propyl-1,2,3,4-tetrahydroquinolin-2-yl)methyl]urea

Example 57A methyl 4-[({[(1-propyl-1,2,3,4-tetrahydroquinolin-2-methyl]amino}carbonyl)amino]-1H-indazole-1-carboxylate The product from Example 22B (0.3145 g, 0.83 mmol) and sodium triacetoxy borohydride (0.5441 g, 1.39 mmol) were suspended in dichloroethane (15 mL). The reaction flask was equipped with stir bar and spetum, then flushed with $N_2$. Propionaldehyde (0.10 mL, 1.39 mmol) was added followed by glacial acetic acid (0.30 mL, 5.10 mmol). After 2.5 hour of stirring at ambient temperature, the reaction mixture was quenched with water then partitioned between ethyl acetate/water. The aqueous phase was extracted with ethyl acetate. The combined organic fractions were washed with aqueous saturated $NaHCO_3$, water, and brine, dried ($MgSO_4$), filtered and concentrated in vaco. The crude material was purified via column chromatography (2% to 5% methanol/dichloromethane) to afford Example 57A (0.2780 g, 79%) as an off white solid. $^1$H NMR (300 MHz, DMSO-$d_6$) δ ppm 9.00 (s, 1 H) 8.44 (s, 1 H) 7.81 (d, J=7.80 Hz, 1 H) 7.69 (d, J=8.14 Hz, 1 H) 7.48 (t, J=8.14 Hz, 1 H) 6.95 (m, 2 H) 6.54 (m, 2 H) 6.46 (t, J=6.78 Hz, 1 H) 4.04 (s, 3 H) 3.43 (m, 2 H) 3.32 (m, 2 H) 3.13 (m, 2 H) 2.80 (m, 1 H) 2.60 (m, 1 H) 1.97 (m, 1 H) 1.61 (m, 3 H) 0.90 (t, J=7.46 Hz, 3 H). MS (ESI) m/z 422 (M+H)$^+$, 420 (M−H)$^-$.

Example 57B

N-1H-indazol-4-yl-N'-[(1-propyl-1,2,3,4-tetrahydroquinolin-2-yl)methyl]urea

The title compound was prepared using the procedure as described in Example 53B, substituting Example 57A (0.2534 g, 0.60 mmol) for Example 53A. The crude material was rinsed with ether to afford the title compound (0.1852 g, 85%) as an off white solid. $^1$H NMR (300 MHz, DMSO-$d_6$) δ ppm 12.98 (s, 1 H) 8.70 (s, 1 H) 8.08 (s, 1 H) 7.61 (d, J=7.46 Hz, 1 H) 7.20 (t, J=7.97 Hz, 1 H) 7.06 (d, J=8.48 Hz, 1 H) 6.96 (m, 2 H) 6.53 (m, 2 H) 6.46 (t, J=7.12 Hz, 1 H) 3.44 (m, 2 H) 3.31 (m, 1 H) 3.13 (m, 2 H) 2.82 (m, 1 H) 2.60 (m, 1 H) 1.97 (m, 1 H) 1.61 (m, 3 H) 0.90 (t, J=7.46 Hz, 3 H). MS (ESI) m/z 364 (M+H)$^+$, 362 (M−H)$^-$. Calcd For $C_{21}H_{25}N_5O$: C, 69.40; H, 6.93; N, 19.27. Found C, 69.08; H, 6.91; N, 19.32.

Example 58

N-1H-indazol-4-yl-N'-{[1-(pyridin-2-ylmethyl)-1,2,3,4-tetrahydroquinolin-2-yl]methyl}urea The product from Example 22B (0.2540 g, 0.67 mmol), 2-(bromomethyl)pyridine hydrobromide (0.8648 g, 0.67 mmol), and potassium carbonate (0.8351 g, 6.04 mmol) were dissolved in tetrahydrofuran/water (35 mL/10 mL) and heated at 70° C. for 22 hours. The reaction mixture was concentrated in vacuo. The residue was dissolved in methanol (5 mL). A NaOH solution (1 mL 5 M in methanol) was added and stirred for 30 minutes at ambient temperature. The reaction mixture was concentrated in vacuo, and the residue taken up in dichloromethane and washed with water (3×20 mL), dried ($MgSO_4$) and filtered. The filtrate was concentrated in vacuo to a brown residue. The crude product was purified using reverse-phase HPLC (acetonitrile-water with 0.1% trifluoroacetic acid as eleuent), isolating the trifluoroacetic acid salt of the titlted compound (0.0935 g, 34%) as a white solid. $^1$H NMR (300 MHz, DMSO-$d_6$) δ ppm 12.98 (s, 1 H) 8.73 (s, 1 H) 8.66 (d, J=4.41 Hz, 1 H) 8.08 (s, 1 H) 7.97 (t, J=7.12 Hz, 1 H) 7.57 (d, J=7.46 Hz, 1 H) 7.45 (m, 2 H) 7.18 (t, J=8.14 Hz, 1 H) 7.05 (m, 1 H) 6.99 (d, J=7.46 Hz, 1 H) 6.88 (m, 1 H) 6.60 (t, J=5.76 Hz, 1 H) 6.53 (t, J=6.95 Hz, 1 H) 6.31 (d, J=7.80 Hz, 1 H) 4.80 (s, 2 H) 3.64 (m, 1 H) 3.39 (m, 1 H) 3.25 (m, 1 H) 2.91 (m, 1 H) 2.72 (m, 1 H) 2.06 (m, 1 H) 1.92 (m, 1 H). MS (ESI) m/z 413 (M+H)$^+$, 411 (M−H)$^-$. Calcd For $C_{24}H_{24}N_6O.1.9$; $C_2HF_3O_2$: C, 53.07; H, 4.15; N, 13.36. Found C, 53.15; H, 4.14; N, 13.49.

Example 59

N-isoquinolin-5-yl-N'-(1,2,3,4-tetrahydroquinolin-2-ylmethyl)urea

Trifluoroacetic acid (5 mL) was added to a solution of the product from Example 50B (1.6670 g, 3.85 mmol) in dichloromethane (50 mL) and stirred for 20 hours at ambient temperature. The reaction solution was concentrated in vaco, and the residue taken up in ethyl acetate, washed with aqueous saturated $NaHCO_3$ solution and water, and condensed in vacuo to a give the titled compound (1.1384 g, 89%) as a white solid. $^1$H NMR (300 MHz, DMSO-$d_6$) δ ppm 9.26 (s, 1 H) 8.74 (s, 1 H) 8.53 (d, J=6.10 Hz, 1 H) 8.31 (m, 1 H) 7.95 (d, J=6.10 Hz, 1 H) 7.72 (d, J=8.14 Hz, 1 H) 7.59 (t, J=7.97 Hz, 1 H) 6.84 (m, 3 H) 6.51 (d, J=7.12 Hz, 1 H) 6.44 (t, J=6.78 Hz, 1 H) 5.70 (s, 1 H) 3.38 (m, 2 H) 3.18 (m, 1 H) 2.69 (m, 2 H) 1.87 (m, 1 H) 1.63 (m, 1 H). MS (DCI) m/z 163 (100%, (M−169)$^+$), 333 (10%, (M+H)$^+$). Calcd For $C_{20}H_{20}N_4O.0.05$; $C_2HF_3O_2$: C, 71.40; H, 5.98; N, 16.57. Found C, 71.69; H, 5.95; N, 16.53.

Example 60

N-1H-indazol-4-yl-N'-({1-[2-(trifluoromethyl)benzyl]-1,2,3,4-tetrahydroquinolin-2-yl}methyl)urea

Example 60A methyl 4-({[({1-[2-(trifluoromethyl)benzyl]-1,2,3,4-tetrahydroquinolin-2-yl}methyl)amino]carbonyl}amino)-1H-indazole-1-carboxylate The titled compound was prepared using the procedure as described in Example 22C, substituting 2-trifluoromethylbenzyl bromide for benzyl bromide. $^1$H NMR (300 MHz, $d_6$-DMSO) 9.03 (s, 1H), 8.42 (s, 1H), 7.77 (m, 2H), 7.70 (d, J=7.5 Hz, 1H), 7.58 (m, 1H), 7.48 (m, 2H), 7.37 (d, J=7.5 Hz, 1H), 7.00 (d, J=7.5 Hz, 1H), 6.83 (m, 1H), 6.58 (m, 2H), 6.10 (d, J=7.5 Hz, 1H), 4.79 (m, 2H), 4.01 (s, 3H), 3.57 (m, 1H), 3.41-3.22 (m, 2H), 2.90 (m, 1H), 2.65 (m, 1H), 2.03 (m, 1H), 1.82 (m, 1H); MS (DCI/$NH_3$) m/e 538 (M+H)$^+$.

Example 60B

N-1H-indazol-4-yl-N'-({1-[2-(trifluoromethyl)benzyl]-1,2,3,4-tetrahydroquinolin-2-yl}methyl)urea The title compound was prepared using the procedure as described in Example 22D, substituting Example 60A for Example 22C. $^1$H NMR (300 MHz, DMSO-$d_6$) δ 13.00 (broad s, 1H), 8.78 (s, 1H), 8.09 (s, 1H), 7.78 (d, J=7.5 Hz, 1H), 7.60 (m, 2H), 7.45 (m, 1H), 7.38 (d, J=7.5 Hz, 1H), 7.19 (m, 1H), 7.04 (m, 2H), 6.83 (m, 1H), 6.60 (t, J=6.0 Hz, 1H), 6.48 (m, 1H), 6.10 (d, J=7.5 Hz, 1H), 4.79 (m, 2H), 3.57 (m, 1H), 3.41-3.20 (m, 2H), 2.92 (m, 1H), 2.71 (m, 1H), 2.10 (m, 1H), 1.96 (m, 1H); MS (ESI/NH$_3$) m/e 480 (M+H)$^+$. Anal. Calc'd. For $C_{26}H_{24}N_5F_3O.0.5$; $H_2O$: C, 63.93; H, 5.16; N, 14.34. Found: C, 63.71; H, 5.07; N, 14.23.

Example 61

N-1H-indazol-4-yl-N'-({1-[3-(trifluoromethyl)benzyl]-1,2,3,4-tetrahydroquinolin-2-yl}methyl)urea

Example 61A methyl 4-({[({1-[3-(trifluoromethyl)benzyl]-1,2,3,4-tetrahydroquinolin-2-yl}methyl)amino]carbonyl}amino)-1H-indazole-1-carboxylate The titled compound was prepared using the procedure as described in Example 22C, substituting 3-trifluoromethyl-benzyl bromide for benzyl bromide. $^1$H NMR (300 MHz, d$_6$-DMSO) 9.02 (s, 1H), 8.42 (s, 1H), 7.78 (d, J=7.5 Hz, 1H), 7.70 (d, J=7.5 Hz, 1H), 7.58 (m, 4H), 7.46 (t, J=7.5 Hz, 1H), 7.00 (d, J=7.5 Hz, 1H), 6.86 (m, 1H), 6.55 (m, 2H), 6.34 (d, J=7.5 Hz, 1H), 4.77 (m, 2H), 4.01 (s, 3H), 3.58 (m, 1H), 3.41-3.22 (m, 2H), 2.90 (m, 1H), 2.65 (m, 1H), 2.03 (m, 1H), 1.82 (m, 1H); MS (DCI/NH$_3$) m/e 538 (M+H)$^+$.

Example 61B

N-1H-indazol-4-yl-N'-({1-[3-(trifluoromethyl)benzyl]-1,2,3,4-tetrahydroquinolin-2-yl}methyl)urea The title compound was prepared using the procedure as described in Example 22D, substituting Example 61A for Example 22C. $^1$H NMR (300 MHz, DMSO-d$_6$) δ 13.00 (broad s, 1H), 8.76 (s, 1H), 8.09 (s, 1H), 7.58 (m, 5H), 7.18 (t, J=7.5 Hz, 1H), 7.08 (d, J=7.5 Hz, 1H), 6.93 (d, J=7.5 Hz, 1H), 6.83 (m, 1H), 6.60 (t, J=6.0 Hz, 1H), 6.52 (t, J=7.5 Hz, 1H), 6.35 (d, J=7.5 Hz, 1H), 4.75 (m, 2H), 3.57 (m, 1H), 3.41-3.17 (m, 2H), 2.95 (m, 1H), 2.70 (m, 1H), 2.09 (m, 1H), 1.86 (m, 1H); MS (ESI/NH$_3$) m/e 480 (M+H)$^+$. Anal. Calc'd. For $C_{26}H_{24}N_5F_3O.0.4$; $H_2O$: C, 65.13; H, 5.14; N, 14.39. Found: C, 63.90; H, 5.09; N, 14.16.

Example 62

N-1H-indazol-4-yl-N'-({1-[4-(trifluoromethyl)benzyl]-1,2,3,4-tetrahydroquinolin-2-yl}methyl)urea

Example 62A methyl 4-({[({1-[4-(trifluoromethyl)benzyl]-1,2,3,4-tetrahydroquinolin-2-yl}methyl)amino]carbonyl}amino)-1H-indazole-1-carboxylate The titled compound was prepared using the procedure as described in Example 22C, substituting 4-trifluoromethyl-benzyl bromide for benzyl bromide. $^1$H NMR (300 MHz, d$_6$-DMSO) 9.02 (s, 1H), 8.42 (s, 1H), 7.78 (d, J=7.5 Hz, 1H), 7.68 (m, 3H), 7.48 (m, 3H), 6.98 (d, J=7.5 Hz, 1H), 6.86 (m, 1H), 6.55 (m, 2H), 6.30 (d, J=7.5 Hz, 1H), 4.76 (m, 2H), 4.01 (s, 3H), 3.58 (m, 1H), 3.41-3.20 (m, 2H), 2.91 (m, 1H), 2.69 (m, 1H), 2.03 (m, 1H), 1.86 (m, 1H); MS (DCI/NH$_3$) m/e 538 (M+H)$^+$.

Example 62B

N-1H-indazol-4-yl-N'-({1-[4-(trifluoromethyl)benzyl]-1,2,3,4-tetrahydroquinolin-2-yl}methyl)urea The title compound was prepared using the procedure as described in Example 22D, substituting Example 62A for Example 22C. $^1$H NMR (300 MHz, DMSO-d$_6$) δ 13.00 (broad s, 1H), 8.76 (s, 1H), 8.09 (s, 1H), 7.68 (m, 2H), 7.58 (d, J=7.5 Hz, 1H), 7.46 (m, 2H), 7.18 (t, J=7.5 Hz, 1H), 7.08 (d, J=7.5 Hz, 1H), 6.99 (d, J=7.5 Hz, 1H), 6.86 (m, 1H), 6.60 (t, J=6.0 Hz, 1H), 6.52 (t, J=7.5 Hz, 1H), 6.30 (d, J=7.5 Hz, 1H), 4.75 (m, 2H), 3.57 (m, 1H), 3.41-3.17 (m, 2H), 2.95 (m, 1H), 2.70 (m, 1H), 2.07 (m, 1H), 1.87 (m, 1H); MS (ESI/NH$_3$) m/e 480 (M+H)$^+$. Anal. Calc'd. For $C_{26}H_{24}N_5F_3O.0.7$; $H_2O$: C, 63.46; H, 5.20; N, 14.23. Found: C, 63.59; H, 4.73; N, 13.87.

Example 63

(−)—N-[(1-benzyl-1,2,3,4-tetrahydroquinolin-2-yl)methyl]-N'-1H-indazol-4-ylurea

The title compound was prepared by chiral separation of Example 22D on the column Chiralcel OD (5 cm ID×50 cm, mobile phase ethanol-methanol-Hexane, 12.5:12.5:75, flow rate 50 mL/min, loading 60 mg in 2 mL of methanol). [α]$_D$−30.0° (c 0.725, methanol). $^1$H NMR (300 MHz, DMSO-d$_6$) δ 13.00 (broad s, 1H), 8.75 (s, 1H), 8.10 (s, 1H), 7.59 (d, J=7.5 Hz, 1H), 7.25 (m, 6H), 7.03 (d, J=7.5 Hz, 1H), 6.95 (d, J=7.5 Hz, 1H), 6.83 (m, 1H), 6.60 (m, J=6.0 Hz, 1H), 6.48 (m, 1H), 6.36 (d, J=7.5 Hz, 1H), 4.64 (m, 2H), 3.57 (m, 1H), 3.41-3.20 (m, 2H), 2.92 (m, 1H), 2.67 (m, 1H), 2.05 (m, 1H), 1.82 (m, 1H); MS (DCI/NH$_3$) m/e 412 (M+H)$^+$.

Example 64

(+)—N-[(-1-benzyl-1,2,3,4-tetrahydroquinolin-2-yl)methyl]-N'-1H-indazol-4-ylurea The title compound was prepared by chiral separation of Example 22D on the column Chiralcel OD (5 cm ID×50 cm, mobile phase ethanol-methanol-Hexane, 12.5:12.5:75, flow rate 50 mL/min, loading 60 mg in 2 mL of methanol). [α]$_D$+33.6° (c 0.725, methanol). $^1$H NMR (300 MHz, DMSO-d$_6$) δ 13.00 (broad s, 1H), 8.75 (s, 1H), 8.10 (s, 1H), 7.59 (d, J=7.5 Hz, 1H), 7.25 (m, 6H), 7.03 (d, J=7.5 Hz, 1H), 6.95 (d, J=7.5 Hz, 1H), 6.83 (m, 1H), 6.60 (m, J=6.0 Hz, 1H), 6.48 (m, 1H), 6.36 (d, J=7.5 Hz, 1H), 4.64 (m, 2H), 3.57 (m, 1H), 3.41-3.20 (m, 2H), 2.92 (m, 1H), 2.67 (m, 1H), 2.05 (m, 1H), 1.82 (m, 1H); MS (DCI/NH$_3$) m/e 412 (M+H)$^+$.

Example 65

(−)—N-1H-indazol-4-yl-N'-({1-[3-(trifluoromethyl)benzyl]-1,2,3,4-tetrahydroquinolin-2-yl}methyl)urea The title compound was prepared by chiral separation of Example 61B on the column Chiralcel OD (5 cm ID×50 cm, mobile phase ethanol-methanol-Hexane, 12.5:12.5:75, flow rate 50 mL/min, loading 80 mg in 1 mL of methanol). [α]$_D$−24.1° (c 0.52, methanol). $^1$H NMR (300 MHz, DMSO-d$_6$) δ 13.00 (broad s, 1H), 8.76 (s, 1H), 8.09 (s, 1H), 7.58 (m, 5H), 7.18 (t, J=7.5 Hz, 1H), 7.08 (d, J=7.5 Hz, 1H), 6.93 (d, J=7.5 Hz, 1H), 6.83 (m, 1H), 6.60 (t, J=6.0 Hz, 1H), 6.52 (t, J=7.5 Hz, 1H), 6.35 (d, J=7.5 Hz, 1H), 4.75 (m, 2H), 3.57 (m, 1H), 3.41-3.17 (m, 2H), 2.95 (m, 1H), 2.70 (m, 1H), 2.09 (m, 1H), 1.86 (m, 1H); MS (ESI/NH$_3$) m/e 480 (M+H)$^+$.

Example 66

(+)—N-1H-indazol-4-yl-N'-({1-[3-(trifluoromethyl) benzyl]-1,2,3,4-tetrahydroquinolin-2-yl}methyl)urea The title compound was prepared by chiral separation of Example 61B on the column Chiralcel OD (5 cm ID×50 cm, mobile phase ethanol-methanol-Hexane, 12.5:12.5:75, flow rate 50 mL/min, loading 80 mg in 1 mL of methanol). [α]$_D$+ 25.8° (c 0.48, methanol). $^1$H NMR (300 MHz, DMSO-d$_6$) δ 13.00 (broad s, 1H), 8.76 (s, 1H), 8.09 (s, 1H), 7.58 (m, 5H), 7.18 (t, J=7.5 Hz, 1H), 7.08 (d, J=7.5 Hz, 1H), 6.93 (d, J=7.5 Hz, 1H), 6.83 (m, 1H), 6.60 (t, J=6.0 Hz, 1H), 6.52 (t, J=7.5 Hz, 1H), 6.35 (d, J=7.5 Hz, 1H), 4.75 (m, 2H), 3.57 (m, 1H), 3.41-3.17 (m, 2H), 2.95 (m, 1H), 2.70 (m, 1H), 2.09 (m, 1H), 1.86 (m, 1H); MS (ESI/NH$_3$) m/e 480 (M+H)$^+$.

Example 67

N-1H-indazol-4-yl-N'-{1-[3-(trifluoromethyl)benzyl]-1,2,3,4-tetrahydroquinolin-3-yl}urea Example 67A To a solution of commercially available (1,2,3,4-tetrahydro-quinolin-3-yl)-carbamic acid tert-butyl ester (0.63 g, 2.54 mmol) in ethanol (10 mL) was added K$_2$CO$_3$ (0.53 g, 3.8 mmol) and 3-trifluoromethylbenzyl bromide (0.58 mL, 3.8 mmol). Resulting mixture was stirred at ambient temperature for 16 h, then more of 3-trifluoromethylbenzyl bromide (0.58 mL, 3.8 mmol) was added and the mixture was refluxed for additional 3 h. After cooling to ambient temperature diethyl ether was added to the reaction mixture and washed with water. Organic phase was separated and concentrated. The residue was chromatographed on silica gel (ethyl acetate-hexanes, 10:90 to 15:85) to isolate Example 67A (0.91 g, 88%) as a clear oil. $^1$H NMR (300 MHz, DMSO-d$_6$) δ 7.58 (m, 3H), 6.90 (m, 3H), 6.52 (m, 2H), 4.57 (m, 2H), 3.83 (s, 1H), 3.40 (m, 1H), 3.18 (m, 1H), 2.90 (dd, J=4.5 and 15.0 Hz, 1H), 2.71 (dd, J=9.0 and 15 Hz, 1H), 1.39 (s, 9H). MS (DCI/NH$_3$) m/e 407 (M+H)$^+$.

Example 67B

To a solution of example 67A (0.90 g, 2.22 mmol) in dichloromethane (10 mL) at 0° C. was added trifluoroacetic acid (2 mL) and mixture stirred at ambient temperature for 16 h. The mixture was concentrated under vacuum, added toluene and the solvent evaporated to obtain crude Example 67B (1.1 g) that was directly used in the next step without further purification. $^1$H NMR (300 MHz, DMSO-d$_6$) δ 8.08 (broad s, 2H), 7.66 (m, 4H), 6.98 (m, 2H), 6.65 (m, 2H), 4.63 (m, 2H), 3.72 (m, 1H), 3.55 (dd, J=1.5 and 9.0 Hz, 1H), 3.30 (dd, J=7.5 and 9.0 Hz, 1H), 3.13 (dd, J=4.5 and 15 Hz, 1H), 2.84 (dd, J=7.5 and 15 Hz, 1H). MS (DCI/NH$_3$) m/e 307 (M+H)$^+$.

Example 67C methyl 4-{[({1-[3-(trifluoromethyl)benzyl]-1,2,3,4-tetrahydroquinolin-3-yl}amino)carbonyl]amino}-1-1H-indazole-1-carboxylate The titled compound was prepared using the procedure as described in Example 22A, substituting Example 67B for 2-aminomethyl-3,4-dihydro-2H-quinoline-1-carboxylic acid tert-butyl ester. $^1$H NMR (300 MHz, d$_6$-DMSO) δ 9.02 (s, 1H), 8.39 (s, 1H), 7.86 (d, J=7.5 Hz, 1H), 7.70-7.44 (m, 6H), 7.00 (m, 2H), 6.57 (m, 3H), 4.63 (s, 2H), 4.28 (m, 1H), 4.01 (s, 3H), 3.58 (dd, J=1.5 and 9.0 Hz, 1H), 3.34 (m, 1H), 3.17 (dd, J=4.5 and 15.0 Hz, 1H), 2.72 (dd, J=4.5 and 15.0 Hz, 1H). MS (DCI/NH$_3$) m/e 524 (M+H)$^+$.

Example 67D

N-1H-indazol-4-yl-N'-{1-[3-(trifluoromethyl)benzyl]-1,2,3,4-tetrahydroquinolin-3-yl}urea The title compound was prepared using the procedure as described in Example 22D, substituting Example 67C for Example 22C. $^1$H NMR (300 MHz, DMSO-d$_6$) δ 13.00 (broad s, 1H), 8.80 (s, 1H), 8.09 (s, 1H), 7.68-7.47 (m, 5H), 7.19 (t, J=7.5 Hz, 1H), 7.00 (m, 3H), 6.60 (m, 3H), 4.64 (s, 2H), 4.26 (m, 1H), 3.55 (dd, J=1.5 and 9.0 Hz, 1H), 3.33 (m, 1H), 3.16 (dd, J=4.5 and 15 Hz, 1H), 2.72 (dd, J=1.5 and 15 Hz, 1H), MS (ESI/NH$_3$) m/e 466 (M+H)$^+$. Anal. Calc'd. For C$_{25}$H$_{22}$N$_5$F$_3$O.0.5; H$_2$O: C, 63.04; H, 4.91; N, 14.70. Found: C, 63.29; H, 4.73; N, 14.25.

Example 68

N-[(1-benzyl-6-fluoro-1,2,3,4-tetrahydroquinolin-2-yl)methyl]-N'-1H-indazol-4-ylurea Example 68A Example 68A was prepared from commercially available 6-fluoro-2-methyl-quinoline using a procedure described in *Chem. Pharm. Bull.* 2001, 49 (4), 480-483.

Example 68B

To a solution of Example 68A and benzylamine in dichloromethane was added sodium triacetoxy borohydride and the mixture was stirred 16 h at ambient temperature. The mixture was diluted with diethyl ether, washed with aq. NaOH and water. Organic phase was separated, concentrated in vacuum and the residue chromatographed on silica gel (ethyl acetate-Hexanes, 60%-100%) to isolate Example 68B (0.56 g, 88%) as a viscous oil. $^1$H NMR (300 MHz, DMSO-d$_6$) δ 8.31 (d, J=9.0 Hz, 1H), 8.03 (dd, J=6.0 and 9.0 Hz, 1H), 7.80-7.60 (m, 3H), 7.40-7.20 (m, 5H), 3.97 (s, 2H), 3.77 (s, 2H), 2.90 (broad s, 1H). MS (ESI/NH$_3$) m/e 267 (M+H)$^+$.

Example 68C

A solution of Example 68B (0.405 g, 1.52 mmol) in ethanol (4 mL) was hydrogenated in the presence of 20% Pd(OH)$_2$/C (40 mg) at 50° C. under pressure 30 psi for 3 h. Reaction mixture was filtered and the filtrate concentrated to obtain the crude Example 68C that was used directly in the next step without further purification.

Example 68D

To a solution of the crude mixture from Example 68C in tetrahydrofuran (15 mL) and triethylamine (1.0 mL) was added di-tert-butyl dicarbonate (0.43 g, 2.00 mmol). After stirring for 2 h at ambient temperature the mixture was concentrated and the residue chromatographed on silica gel (ethyl acetate:Hexane, 3:7 to 1:1) to obtain Example 68D (60 mg, 15% for 2 steps). $^1$H NMR (300 MHz, DMSO-d$_6$) δ 8.31

(d, J=9.0 Hz, 1H), 8.03 (dd, J=6.0 and 9.0 Hz, 1H), 7.75 (dd, J=3.0 and 9.0 Hz, 1H), 7.68 (m, 1H), 7.50 (m, 2H), 4.39 (d, J=6.0 Hz, 2H), 1.40 (s, 9H). MS (ESI/NH$_3$) m/e 277 (M+H)$^+$.

Example 68E

A solution of Example 68D (60 mg, 0.22 mmol) in ethanol (2 mL) was hydrogenated in the presence of 20% Pd(OH)$_2$/C (40 mg) at 50° C. under pressure 30 psi for 4 h. The reaction mixture was filtered and the filtrate concentrated to obtain crude Example 68E. MS (DCI/NH$_3$) m/e 281 (M+H)$^+$.

Example 68F

Example 68F was prepared using the procedure as described in Example 22C, substituting Example 68E for Example 22B and running the reaction under reflux instead of ambient temperature. $^1$H NMR (300 MHz, DMSO-d$_6$) δ 7.30 (m, 2H), 7.20 (m, 3H), 7.00 (t, J=6.0 Hz, 1H), 6.81 (dd, J=3.0 and 9.0 Hz, 1H), 6.68 (m, 1H), 6.21 (dd, J=4.5 and 9.0 Hz, 1H), 4.52 (m, 2H), 3.40 (m, 1H), 3.05 (m, 1H), 3.00-2.54 (m, 3H), 1.98 (m, 1H), 1.77 (m, 1H), 1.38 (s, 9H). MS (DCI/NH$_3$) m/e 371 (M+H)$^+$.

Example 68G

Example 68G was prepared using the procedure as described in Example 67B, substituting Example 68F for Example 67A. Crude mixture of the title compound was used in the next step. MS (DCI/NH$_3$) m/e 271 (M+H)$^+$.

Example 68H methyl 4-[({[(1-benzyl-6-fluoro-1,2,3,4-tetrahydro-quinolin-2-yl)methyl]amino}carbonyl)amino]-1H-indazole-1-carboxylate The titled compound was prepared using the procedure as described in Example 22A, substituting Example 68G for 2-aminomethyl-3,4-dihydro-2H-quinoline-1-carboxylic acid tert-butyl ester. $^1$H NMR (300 MHz, d$_6$-DMSO) δ 9.0 (s, 1H), 8.43 (s, 1H), 7.79 (d, J=7.5 Hz, 1H), 7.69 (d, J=7.5 Hz, 1H), 7.47 (t, J=7.5 Hz, 1H), 7.25 (m, 5H), 6.84 (dd, J=3.0 and 9.0 Hz, 1H), 6.70 (m, 1H), 6.53 (t, J=6.0 Hz, 1H), 6.30 (dd, J=4.5 and 9.0 Hz, 1H), 4.63 (m, 2H), 4.01 (s, 3H), 3.58 (m, 1H), 3.34 (m, 3H), 2.90 (m, 1H), 2.70 (m, 1H), 2.03 (m, 1H), 1.93 (m, 1H). MS (DCI/NH$_3$) m/e 488 (M+H)$^+$.

Example 68I

N-[(1-benzyl-6-fluoro-1,2,3,4-tetrahydroquinolin-2-yl)methyl]-N'-1H-indazol-4-ylurea The title compound was prepared using the procedure as described in Example 22D, substituting Example 68H for Example 22C. $^1$H NMR (300 MHz, DMSO-d$_6$) δ 13.00 (broad s, 1H), 8.76 (s, 1H), 8.09 (s, 1H), 7.58 (d, J=7.5 Hz, 1H), 7.35-7.13 (m, 6H), 7.04 (d, J=7.5 Hz, 1H), 6.84 (m, 1H), 6.70 (m, 1H), 6.57 (t, J=6.0 Hz, 1H), 6.30 (dd, J=4.5 and 9.0 Hz, 1H), 4.62 (m, 2H), 3.55 (m, 1H), 3.33-3.10 (m, 2H), 2.90 (m, 1H), 2.72 (m, 1H), 2.05 (m, 1H), 1.93 (m, 1H). MS (DCI/NH$_3$) m/e 430 (M+H)$^+$. Anal. Calc'd. For C$_{25}$H$_{24}$N$_5$FO.0.4; H$_2$O: C, 68.76; H, 5.72; N, 16.04. Found: C, 68.44; H, 5.53; N, 15.83.

Example 69

N-(6-fluoro-2-methyl-3,4-dihydro-2H-chromen-4-yl)-N'-1H-indazol-4-ylurea

A mixture of methoxylamine hydrochloride (0.137 g, 1.64 mmol) and commercially available 6-fluoro-2-methyl-4-chromanone (0.269 g, 1.49 mmol) in pyridine (3 mL) was stirred overnight at 65 C. The reaction mixture was cooled, concentrated, diluted with ethyl acetate, washed with saturated aqueous NaHCO$_3$, and saturated aqueous NH$_4$Cl. The organic layer was dried (Na$_2$SO$_4$), filtered and the solvent evaporated to give 0.306 g of a clear oil. The oil was dissolved in methanol (10 mL) and shaken with Raney Ni (cat. amount) under H$_2$ (60 psi) overnight. The mixture was filtered and concentrated to afford the corresponding amine used without further purification (243 mg, 1.34 mmol, 90%). The amine was stirred with Example 24D (445 mg, 1.34 mmol) and diisopropyl ethyl amine (0.28 mL, 1.6 mmol) in 2.5 mL N,N-dimethylformamide at room temperature for 45 min. The mixture was diluted with water, filtered, and the solid collected was air-dried to afford the indazolylurea as a tan solid, which was used without further purification. The solid was suspended in methanol (4 mL) and treated with 1N aq NaOH (1.8 mL, 1.8 mmol). The mixture was stirred at room temperature for 5 h, diluted with H$_2$O (4 mL), filtered and washed with 50% aqueous methanol, and dried (vac oven) to give the title compound as a tan solid (340 mg, 1.00 mmol, 67% overall): $^1$H NMR (300 MHz, DMSO-d$_6$) δ 13.00 (br s, 2H), 8.73 (s, 1H), 8.49 (s, 2H), 8.09 (s, 1H), 7.67 (t, 2H), 7.21 (m, 4H), 7.11-6.93 (m, 6H), 6.87 (dd, 1H), 6.81 (d, 1H), 6.77 (dd, 1H), 5.07 (m, 1H), 4.84 (m, 1H), 4.35 (m, 1H), 2.29 (dd, 1H), 2.11 (dt, 1H), 1.81 (m, 1H), 1.64 (q, 1H), 1.39 (d, 3H), 1.36 (d, 3H). MS (ESI) m/z 341.1 (M+H).

Example 70

N-1H-indazol-4-yl-N'-(7-methoxy-2-phenyl-3,4-dihydro-2H-chromen-4-yl)urea

The title compound was prepared using the procedure as described in Example 69, substituting commercially available 7-methoxyflavanone for 6-fluoro-2-methyl-4-chromanone $^1$H NMR (300 MHz, DMSO-d$_6$) δ 13.00 (br s, 1.7H), 8.74 (s, 1H), 8.57 (s, 0.7H), 8.08 (s, 1H), 8.04 (s, 0.7 H), 7.68 (d, 0.7H), 7.67 (d, 1H), 7.54-7.17 (m, 11.9H), 7.08 (d, 1H), 7.07 (d, 0.7H), 6.98 (d, 0.7H), 6.70 (d, 1H), 6.62 (m, 1.7H), 6.51 (d, 0.7H), 6.45 (d, 1H), 5.34 (d, 1H), 5.23 (m, 1H), 5.17 (d, 0.7H), 4.83 (m, 0.7H), 3.74 (s, 2H), 3.71 (s, 3H), 2.48-2.21 (m, 2.4H), 1.97 (q, 1H); MS (ESI) m/z 415.1 (M+H).

Example 71

N-1H-indazol-4-yl-N'-(7-methoxy-2,2-dimethyl-3,4-dihydro-2H-chromen-4-yl)urea

Example 71A

A mixture of commercially available 7-hydroxy-2,2-dimethyl-2,3-dihydro-4H-chromen-4-one (320 mg, 1.67 mmol), hydroxylamine hydrochloride (173 mg, 2.49 mmol), and pyridine (0.4 mL, 4.95 mmol) in methanol (5 mL) was stirred overnight at ambient temperature, concentrated, diluted with ethyl acetate, and washed with saturated aqueous NaHCO$_3$. The organic layer was dried (Na$_2$SO$_4$), filtered and the solvent evaporated to give Example 71A as a white solid (161 mg, 0.778 mmol, 47%): $^1$H NMR (300 MHz, DMSO-d$_6$) δ 10.78

(s, 1H), 9.66 (br s, 1H), 7.54 (d, 1H), 6.34 (dd, 1H), 6.17 (d, 1H), 2.70 (s, 2H), 1.27 (s, 6H); MS (ESI) m/z 208.1 (M+H).

Example 71B

A mixture of Example 71A (140 mg, 0.676 mmol), $K_2CO_3$ (279 mg, 2.02 mmol), and iodomethane (42 µL, 0.67 mmol) in acetone (2 mL) was stirred at 65° C. for 8 hrs, diluted with ethyl acetate, and washed successively with 1 N aq NaOH and brine. The organic layer was dried, filtered and the filtrate concentrated to give 163 mg of a yellow gum, which was dissolved in methanol (8 mL) and shaken with Raney Ni (0.3 g) under $H_2$ (60 psi) for 6 hrs at ambient temperature. The mixture was filtered and the solvent evaporated and purified by flash chromatography (6% methanol/dichloromethane) to give Example 71B as a clear film (82 mg, 0.40 mmol, 59%): $^1$H NMR (300 MHz, CDCl$_3$) δ 7.39 (d, 1H), 6.51 (dd, 1H), 6.34 (d, 1H), 4.12 (dd, 1H), 3.80 (s, 3H), 2.16 (dd, 1H), 1.75 (dd, 1H), 1.44 (s, 3H), 1.27 (s, 3H).

Example 71C

N-1H-indazol-4-yl-N'-(7-methoxy-2,2-dimethyl-3,4-dihydro-2H-chromen-4-yl)urea

Example 71B was stirred with Example 24D (131 mg, 0.394 mmol) and diisopropyl ethyl amine (0.10 mL, 0.57 mmol) in N,N-dimethylformamide (1.2 mL) at room temperature for 90 min. The mixture was diluted with water, filtered, and air-dried. The solid was suspended in methanol (1.2 mL) and tetrahydrofuran (3.6 mL), and treated with 1N aq NaOH (0.5 mL, 0.5 mmol). The mixture was stirred at rt for 90 min, diluted with $H_2O$ (2 mL), filtered, washed with 50% aq methanol, and flash chromatographed on silica gel (50% ethyl acetate/hexane) to give the title compound as a white solid (82 mg, 0.22 mmol, 57% overall): $^1$H NMR (300 MHz, DMSO-d$_6$) δ 13.01 (br s, 1H), 8.67 (s, 1H), 8.06 (s, 1H), 7.68 (s, 1H), 7.22 (t, 1H), 7.21 (d, 1H), 7.06 (d, 1H), 6.65 (d, 1H), 6.51 (dd, 1H), 6.33 (d, 1H), 4.93 (ddd, 1H), 3.70 (s, 3H), 2.17 (dd, 1H), 1.72 (dd, 1H), 1.39 (s, 3H), 1.29 (s, 3H); MS (ESI) m/z 367.2 (M+H).

Example 72

N-1H-indazol-4-yl-N'-(7-methoxy-2,2,8-trimethyl-3,4-dihydro-2H-chromen-4-yl)urea Example 72A A mixture of commercially available 7-hydroxy-2,2,8-trimethyl-2,3-dihydro-4H-chromen-4-one (2.01 g, 9.77 mmol) and methoxylamine hydrochloride (0.898 g, 10.8 mmol) in pyridine (20 mL) was stirred at 65 C. for 5 h, concentrated, diluted with ethyl acetate, and washed successively with sat aq NaHCO$_3$ and sat aq NH$_4$Cl. The organic layer was dried (Na$_2$SO$_4$), filtered and the solvent evaporated to give Example 72A as a red gum (3.10 g), which was used without further purification: $^1$H NMR (300 MHz, CDCl$_3$) δ 8.65 (br s, 2H), 7.79 (tt, 1H), 7.39 (dd, 2H), 7.61 (d, 1H), 6.42 (d, 1H), 3.94 (s, 3H), 2.76 (s, 2H), 2.08 (s, 3H), 1.36 (s, 6H).

Example 72B

A mixture of Example 72A (211 mg, 0.673 mmol), $K_2CO_3$ (183 mg, 1.32 mmol), and iodomethane (0.16 mL, 2.5 mmol) in acetone (2 mL) was stirred at 65 C. overnight, diluted with ethyl acetate, and washed successively with water and brine. The organic layer was dried (Na$_2$SO$_4$), filtered and concentrated. The residue was flash chromatographed (10% diethyl ether/hexane) to give the corresponding methyl ether as a clear film (115 mg, 0.461 mmol, 69%).

Example 72C

N-1H-indazol-4-yl-N'-(7-methoxy-2,2,8-trimethyl-3,4-dihydro-2H-chromen-4-yl)urea Example 72B (115 mg, 0.461 mmol) was dissolved in methanol (5 mL) and shaken with Raney Ni (catalytic amount) under $H_2$ (60 psi) for 3 h, filtered, and concentrated to give the corresponding amine as a clear oil (103 mg), which was used without further purification. The amine was stirred with Example 24D (137 mg, 0.412 mmol) and diisopropyl ethyl amine (0.10 mL, 0.57 mmol) in N,N-dimethylformamide (1.5 mL) at rt for 90 min. The mixture was diluted with water, filtered, and air-dried to afford the indazolylurea as a tan solid, which was used without further purification. The solid was suspended in methanol (1.2 mL) and tetrahydrofuran (3.6 mL), and treated with 1N aq NaOH (0.5 mL, 0.5 mmol). The mixture was stirred at rt for 90 min, concentrated, diluted with ethyl acetate, and washed successively with water and brine. The organic layer was dried (Na$_2$SO$_4$), filtered and concentrated to give the title compound as a white solid (169 mg, 0.444 mg, 66%): $^1$H NMR (300 MHz, DMSO-d$_6$) δ 13.01 (br s, 1H), 8.69 (s, 1H), 8.07 (s, 1H), 7.67 (d, 1H), 7.22 (t, 1H), 7.12 (d, 1H), 7.07 (d, 1H), 6.62 (d, 1H), 6.58 (d, 1H), 4.96 (ddd, 1H), 3.74 (s, 3H), 2.17 (dd, 1H), 1.96 (s, 3H), 1.71 (dd, 1H), 1.41 (s, 3H), 1.28 (s, 3H); MS (ESI) m/z 381.1 (M+H).

Example 73

N-1H-indazol-4-yl-N'-(2,2,8-trimethyl-3,4-dihydro-2H-chromen-4-yl)urea

Example 73A

A mixture of Example 72A (430 mg, 1.37 mmol), N-phenyltriflimide (535 mg, 1.50 mmol), and triethylamine (0.23 mL, 1.6 mmol) in dichloromethane (4 mL) was stirred for 4 h, diluted with sat aq NaHCO$_3$, and extracted with dichloromethane. The organic layer was dried (Na$_2$SO$_4$), filtered and concentrated, and the residue flash chromatographed (5% diethyl ether/hexane) to give Example 73A as a clear oil (449 mg, 1.33 mmol, 97%): $^1$H NMR (300 MHz, CDCl$_3$) δ 7.77 (d, 1H), 6.80 (d, 1H), 3.98 (s, 3H), 2.78 (s, 2H), 2.18 (s, 3H), 1.38 (s, 6H).

Example 73B

N-1H-indazol-4-yl-N'-(2,2,8-trimethyl-3,4-dihydro-2H-chromen-4-yl)urea

The title compound was prepared using the procedure as described in Example 72C, substituting the triflate from Example 73A for the methyl oxime from Example 72B $^1$H NMR (300 MHz, DMSO-d$_6$) δ 13.00 (br s, 1H), 8.70 (s, 1H), 8.07 (s, 1H), 7.88 (s, 1H), 7.22 (t, 1H), 7.15 (d, 1H), 7.08 (d, 1H), 7.03 (d, 1H), 6.79 (t, 1H), 6.68 (d, 1H), 5.00 (ddd, 1H), 2.19 (dd, 1H), 2.11 (dd, s, 3H), 1.76 (dd, 1H), 1.42 (s, 3H), 1.29 (s, 3H); MS (ESI) m/z 351.1 (M+H).

Example 74

N-1H-indazol-4-yl-N'-(7-methoxy-2,2-dimethyl-8-propyl-3,4-dihydro-2H-chromen-4-yl)urea

Example 74A

A mixture of 2,4-dihydroxy-3-propylacetophenone (1.94 g, 10 mmol), acetone (0.95 mL, 12.9 mmol), and pyrrolidine (1.7 mL, 20.4 mmol) was stirred in 3 mL toluene at rt for 1 h and at reflux (Dean-Stark trap) for 4 h. After cooling to rt, the mixture was diluted with ether (30 mL) and was washed with 2N HCl (10 mL) and $H_2O$ (10 mL). Drying over $Na_2SO_4$, filtered and evaporation of volatiles in vacuo afforded the crude title compound, which was used without further purification.

Example 74B

A solution of the product of Example 74A (10 mmol) in acetone (60 mL) was stirred overnight with $K_2CO_3$ (6.9 g, 50 mmol) and iodomethane (6.2 mL, 99.4 mmol) at room temperature. The mixture was evaporated in vacuo, and the residue was partitioned between ether and $H_2O$. The ethereal layer was dried ($Na_2SO_4$), filtered and concentrated in vacuo, to afford a crude product, which was purified by silica gel chromatography, using 95:5 hexane-ethyl acetate to 90:10 hexane-ethyl acetate (gradient) as eluent. Example 74B was obtained as a thick yellow oil that solidified upon standing, 563 mg (23%). $^1$H NMR (300 MHz, DMSO-$d_6$) δ ppm 7.63 (d, J=8.5 Hz, 1H), 6.74 (d, J=7.8 Hz, 1H), 3.84 (s, 3H), 2.69 (s, 2H), 2.50 (t, J=2.0 Hz, 2H), 1.45 (m, 2H), 1.37 (s, 6H), 0.87 (t, J=3.7 Hz, 3H). MS (ESI) m/z 249 (M+H).

Example 74C

To a solution of Example 74B (563 mg, 2.27 mmol) in methanol (12 mL) was added methoxylamine hydrochloride (0.19 g, 2.28 mmol) and pyridine (0.92 mL, 11.4 mmol). The mixture was stirred overnight at rt and was then evaporated in vacuo. The residue was partitioned between ethyl acetate and $H_2O$, and the organic layer was dried over $Na_2SO_4$, filtered and was evaporated in vacuo. The residue thus obtained was dissolved in methanol (8 mL) and was hydrogenated (balloon) over 10% Pd—C in the presence of 4 drops of conc. HCl overnight at room temperature. After this time, the catalyst was filtered off (Celite), and the filtrate was evaporated in vacuo. The residue was taken up in ether (20 mL) and was extracted with 1N HCl (3×10 mL). These acidic extracts were then basified to pH 10 with 2N NaOH and were extracted with ethyl acetate (3×10 mL). The organic phase was dried over $Na_2SO_4$, filtered and concentrated in vacuo, yielded Example 74C as a yellow oil, 205 mg (36%). $^1$H NMR (300 MHz, DMSO-$d_6$) δ ppm 7.31 (d, J=8.8 Hz, 1H), 6.51 (d, J=8.4 Hz, 1H), 3.81 (m, 2H), 3.71 (s, 3H), 2.47 (t, J=1.7 Hz, 2H), 2.46 (m, 1H), 1.44 (m, 2H), 1.34 (s, 3H), 1.16 (s, 3H), 0.84 (t, J=7.3 Hz, 3H). MS (ESI) m/z 250 (M+H).

Example 74D methyl 4-({[(7-methoxy-2,2-dimethyl-8-propyl-3,4-dihydro-2H-chromen-4-yl)amino]carbonyl}amino)-1H-indazole-1-carboxylate Example 74C (54 mg, 0.217 mmol) was stirred with Example 24D (72 mg, 0.217 mmol) and diisopropyl ethyl amine (0.06 mL, 0.345 mmol) in 1 mL N,N-dimethylformamide at rt for 2 h. After this time, most of the N,N-dimethylformamide was removed in vacuo, and the residue was diluted with $H_2O$. The precipitate thus formed was collected by filtration and was air-dried to afford the titled compound as a tan solid, which was used without further purification.

Example 74E

N-1H-indazol-4-yl-N'-(7-methoxy-2,2-dimethyl-8-propyl-3,4-dihydro-2H-chromen-4-yl)urea Example 74D (0.217 mmol) was suspended in methanol (2 mL) and was treated with 5N methanolic NaOH (0.2 mL, 1 mmol). The mixture was stirred at rt for 45 min, then it was poured into $H_2O$ (20 mL). The precipitate which formed was collected by filtration and was air-dried to afford the title compound as an off-white solid, 38 mg (43%). $^1$H NMR (300 MHz, DMSO-$d_6$) δ ppm 13.00 (br, 1H), 8.65 (s, 1H), 8.06 (s, 1H), 7.68 (d, J=7.1 Hz, 1H), 7.22 (t, J=7.5 Hz, 1H), 7.06-7.13 (m, 2H), 6.57-6.67 (m, 2H), 4.95 (m, 1H), 3.73 (s, 3H), 2.16 (m, 2H), 1.69 (m, 2H), 1.46 (m, 2H), 1.40 (s, 3H), 1.27 (s, 3H), 0.86 (t, J=7.5 Hz, 3H). MS (ESI) m/z 409 (M+H).

Example 75

N-(2,2-dimethyl-3,4-dihydro-2H-chromen-4-yl)-N'-1H-indazol-4-ylurea

Example 75A

The title compound was prepared using the procedure as described in Example 74A, substituting 2-hydroxyacetophenone for 2,4-dihydroxy-3-propylacetophenone. Chromatography on silica gel (95:5 hexane-ethyl acetate to 4:1 hexane-ethyl acetate, gradient eluent) afforded Example 75A as a yellow solid, 193 mg. $^1$H NMR (300 MHz, DMSO-$d_6$) δ ppm 7.72 (dd, J=7.8, 1.3 Hz, 1H), 7.55 (m, 1H), 6.74-6.96 (m, 2H), 2.79 (s, 2H), 1.39 (s, 6H). MS (ESI) m/z 177 (M+H), 194 (M+NH$_4$).

Example 75B

Example 75B was prepared using the procedure as described in Example 74C, substituting Example 75A for Example 74B, affording a colorless oil. $^1$H NMR (300 MHz, DMSO-$d_6$) δ ppm 7.54 (d, J=7.4 Hz, 1H), 7.05 (m, 1H), 6.83 (t, J=7.2 hz, 1H), 6.65 (m, 1H), 3.82 (m, 1H), 2.01 (m, 2H), 1.34 (s, 3H), 1.19 (s, 3H). MS (ESI) m/z 178 (M+H).

Example 75C

Example 75C was prepared using the procedure as described in Example 74D, substituting Example 75B for Example 74C. The crude compound was used without further purification.

Example 75D

N-(2,2-dimethyl-3,4-dihydro-2H-chromen-4-yl)-N'-1H-indazol-4-ylurea

The title compound was prepared using the procedure as described in Example 74E, substituting Example 75C for Example 74D. $^1$H NMR (300 MHz, DMSO-$d_6$) δ ppm 13.00 (br, 1H), 8.69 (s, 1H), 8.07 (s, 1H), 7.68 (d, J=7.8 Hz, 1H), 7.07-7.33 (m, 4H), 6.90 (t, J=7.5 Hz, 1H), 6.71-6.77 (m, 2H), 4.99 (m, 1H), 2.19 (m, 1H), 1.77 (m, 1H), 1.41 (s, 3H), 1.30 (s, 3H). MS (ESI) m/z 337 (M+H).

Example 76

N-(7-fluoro-2,2-dimethyl-3,4-dihydro-2H-chromen-4-yl)-N'-1H-indazol-4-ylurea

Example 76A

The title compound was prepared using the procedure as described in Example 74A, substituting 4-fluoro-2-hydroxyacetophenone for 2,4-dihydroxy-3-propylacetophenone. Chromatography on silica gel (95:5 hexane-ethyl acetate to 4:1 hexane-ethyl acetate, eluent gradient) afforded Example 76A as a yellow oil. $^1$H NMR (300 MHz, DMSO-d$_6$) δ ppm 7.80 (m 1H), 6.84-6.91 (m, 2H), 2.80 (s, 2H), 1.40 (s, 6H). MS (ESI) m/z 195 (M+H).

Example 76B

Example 76B was prepared using the procedure as described in Example 74C, substituting Example 76A for Example 74B, affording a colorless oil. $^1$H NMR (300 MHz, DMSO-d$_6$) δ ppm 7.56 (m, 1H), 6.66 (m, 1H), 6.48 (m, 1H), 3.81 (m, 1H), 2.02 (m, 2H), 1.35 (s, 3H), 1.20 (s, 3H). MS (ESI) m/z 196 (M+H).

Example 76C

Example 76C was prepared using the procedure as described in Example 74D, substituting Example 76B for Example 74C. The crude compound was used without further purification.

Example 76D

N-(7-fluoro-2,2-dimethyl-3,4-dihydro-2H-chromen-4-yl)-N'-1H-indazol-4-ylurea

The title compound was prepared using the procedure as described in Example 74E, substituting Example 76C for Example 74D. $^1$H NMR (300 MHz, DMSO-d$_6$) δ ppm 13.02 (br, 1H), 8.72 (s, 1H), 8.31 (s, 1H), 7.67 (d, J=6.8 Hz, 1H), 7.36 (m, 1H), 7.22 (m, 1H), 7.09 (m, 1H), 6.59-6.72 (m, 3H), 4.97 (m, 1H), 2.22 (m, 1H), 1.78 (m, 1H), 1.42 (s, 3H), 1.30 (s, 3H). MS (ESI) m/z 355 (M+H).

Example 77

N-(7-fluoro-2,2-diethyl-3,4-dihydro-2H-chromen-4-yl)-N'-1H-indazol-4-ylurea

Example 77A

The title compound was prepared using the procedure as described in Example 74A, substituting 4-fluoro-2-hydroxyacetophenone for 2,4-dihydroxy-3-propylacetophenone and 3-pentanone for acetone. Chromatography on silica gel (95:5 hexane-ethyl acetate to 85:15 hexane-ethyl acetate, eluent gradient) afforded Example 77A as a yellow oil. $^1$H NMR (300 MHz, DMSO-d$_6$) δ ppm 7.76 (m, 1H), 6.87 (m, 1H), 2.78 (s, 2H), 1.71 (m, 4H), 0.87 (m, 6H). MS (ESI) m/z 223 (M+H).

Example 77B

Example 77B was prepared using the procedure as described in Example 74C, substituting Example 77A for Example 74B, affording a colorless oil. $^1$H NMR (300 MHz, DMSO-d$_6$) δ ppm 7.55 (t, J=7.5 Hz, 1H), 6.65 (m, 1H), 6.49 (dd, J=10.9, 2.7 Hz, 1H), 2.02 (m, 1H), 1.91 (br, 2H), 1.64 (m, 4H), 1.51 (m, 1H), 0.85 (m, 6H). MS (ESI) m/z 224 (M+H).

Example 77C

Example 77C was prepared using the procedure as described in Example 74D, substituting Example 77B for Example 74C. The crude compound was used without further purification.

Example 77D

N-(7-fluoro-2,2-diethyl-3,4-dihydro-2H-chromen-4-yl)-N'-1H-indazol-4-ylurea

The title compound was prepared using the procedure as described in Example 74E, substituting Example 77C for Example 74D. $^1$H NMR (300 MHz, DMSO-d$_6$) δ ppm 13.00 (br, 1H), 8.73 (s, 1H), 8.08 (s, 1H), 7.67 (d, J=6.8 Hz, 1H), 7.07-7.36 (m, 3H), 6.72-6.78 (m, 2H), 6.63 (dd, J=10.5, 2.7 Hz, 1H), 4.96 (m, 1H), 2.26 (m, 2H), 1.67 (m, 4H), 0.92 (m, 6H). MS (ESI) m/z 383 (M+H).

Example 78

N-(7,8-difluoro-2,2-dimethyl-3,4-dihydro-2H-chromen-4-yl)-N'-1H-indazol-4-ylurea

Example 78A

A mixture of 2,3-difluorophenol (4.66 g, 35.8 mmol) and sodium acetate (7.2 g) was refluxed in acetic anhydride (30 mL) for 2.5 h. After cooling to rt, the mixture was poured into water and extracted with ether. The ethereal extracts were then stirred vigorously with solid K$_2$CO$_3$ overnight. Filtration, followed by drying over Na$_2$SO$_4$ and evaporation in vacuo, afforded the corresponding crude acetate as a pale yellow oil, which was used directly without further purification.

The acetate (5.225 g, 30.4 mmol) and AlCl$_3$ (7.0 g, 52.5 mmol) were heated at 120° for 2.5 h. The reaction mixture was cooled to rt and was quenched carefully with H$_2$O and 6N HCl. Extraction with ether, followed by silica gel chromatography (9:1 hexane-ethyl acetate to 4:1 hexane-ethyl acetate, eluent gradient), afforded Example 78A as a white solid, 2.349 g (45%). $^1$H NMR (300 MHz, DMSO-d$_6$) δ ppm 12.32 (br, 1H), 7.80 (m, 1H), 7.02 (m, 1H), 2.65 (s, 3H).

Example 78B

The title compound was prepared using the procedure as described in Example 74A, substituting Example 78A for 2,4-dihydroxy-3-propylacetophenone. Chromatography on silica gel (95:5 hexane-ethyl acetate to 4:1 hexane-ethyl acetate, eluent gradient) afforded Example 78B as a yellow oil. $^1$H NMR (300 MHz, DMSO-d$_6$) δ ppm 7.61 (m, 1H), 7.11 (m, 1H), 2.89 (s, 2H), 1.45 (s, 6H). MS (ESI) m/z 214 (M+H).

Example 78C

Example 78C was prepared using the procedure as described in Example 74C, substituting Example 78B for Example 74B, affording a colorless oil. $^1$H NMR (300 MHz, DMSO-d$_6$) δ ppm 7.38 (m, 1H), 6.86 (m, 1H), 3.84 (m, 1H), 2.04 (br, 2H), 2.06 (m, 1H), 1.57 (m, 1H), 1.41 (s, 3H), 1.24 (s, 3H). MS (ESI) m/z 214 (M+H).

Example 78D

Example 78D was prepared using the procedure as described in Example 74D, substituting Example 78C for Example 74C. The crude compound was used without further purification.

Example 78E

N-(7,8-difluoro-2,2-dimethyl-3,4-dihydro-2H-chromen-4-yl)-N'-1H-indazol-4-ylurea The title compound was prepared using the procedure as described in Example 74E, substituting Example 78D for Example 74D. $^1$H NMR (300 MHz, DMSO-$d_6$) δ ppm 13.02 (br, 1H), 8.78 (s, 1H), 8.08 (s, 1H), 7.66 (m, 1H), 6.90-7.25 (m, 4H), 6.77 (m, 1H), 5.00 (m, 1H), 2.24 (m, 1H), 1.85 (m, 1H), 1.47 (s, 3H), 1.35 (s, 3H). MS (ESI) m/z 373 (M+H).

Example 79

N-[7-(3,3-dimethylbutyl)-3,4-dihydro-2H-chromen-4-yl]-N'-1H-indazol-4-ylurea

Example 79A

A mixture of 3-bromophenol (10 g, 57.8 mmol), $K_2CO_3$ (10.4 g, 75.4 mmol), and propargyl bromide (80% solution by weight in toluene, 11.2 g of solution, 75.2 mmol) in $CH_3CN$ (150 mL) was stirred at rt for 42 h. The volatiles were evaporated in vacuo, then the residue was dissolved in ether and washed with saturated $NaHCO_3$ solution and water. The ethereal layer was dried ($Na_2SO_4$) and concentrated in vacuo to afford the crude terminal alkyne as a gold oil, 11.54 g (95%), which was used without further purification.

A solution of the above alkyne (11.54 g, 54.7 mmol) in acetone (200 mL) was refluxed with N-chlorosuccinimide (9.13 g, 68.4 mmol) and silver acetate (0.91 g, 5.45 mmol) for 5 h. The mixture was cooled to rt and filtered. Evaporation of the filtrate in vacuo, followed by silica gel chromatography (97:3 hexane-ethyl acetate to 94:6 hexane-ethyl acetate, eluent gradient), afforded Example 79A as a yellow oil, 7.937 g (59%). $^1$H NMR (300 MHz, DMSO-$d_6$) δ ppm 7.17-7.31 (m, 3H), 7.01 (m, 1H), 4.91 (s, 2H).

Example 79B

The product from Example 79A (7.935 g, 32.3 mmol) was refluxed in ethylene glycol for 4 h. The solution was then cooled to rt and poured into water. The mixture was extracted with ether, then the extracts were washed with water and brine. Concentration in vacuo, followed by silica gel chromatography (9:1 hexane-ethyl acetate to 65:35 hexane-ethyl acetate, eluent gradient), afforded Example 79B as a thick yellow oil, 979 mg (13%). $^1$H NMR (300 MHz, DMSO-$d_6$) δ ppm 7.67 (d, J=8.5 Hz, 1H), 7.24-7.39 (m, 2H), 4.55 (m, 2H), 2.81 (m, 2H). MS (ESI) m/z 227 (M+H).

Example 79C

A mixture of the product from Example 79B (979 mg, 4.33 mmol), tert-butylacetylene (3 mL, 24.4 mmol), CuI (166 mg, 0.872 mmol), triphenyl phosphine (304 mg, 1.16 mmol), and tris(dibenzylideneacetone)dipalladium(0) (789 mg, 0.862 mmol) was heated in triethylamine (8 mL) under microwave power at 140° for 20 min. Evaporation of the volatiles in vacuo, followed by silica gel chromatography, afforded Example 79C as a yellow oil, 741 mg (75%). $^1$H NMR (300 MHz, DMSO-$d_6$) δ ppm 7.70 (d, J=7.8 Hz, 1H), 6.97-7.02 (m, 2H), 4.53 (m, 2H), 2.80 (m, 2H), 1.30 (s, 9H). MS (ESI) m/z 229 (M+H).

Example 79D

Example 79D was prepared using the procedure as described in Example 74C, substituting Example 79C for Example 74B, affording a colorless oil. $^1$H NMR (300 MHz, DMSO-$d_6$) δ ppm 7.01 (t, J=7.8 Hz, 1H), 6.67 (m, 1H), 6.53 (m, 1H), 4.16 (m, 2H), 3.83 (m, 1H), 2.67 (m, 2H), 1.50-1.92 (m, 4H), 0.96 (s, 9H). MS (ESI) m/z 234 (M+H).

Example 79E

Example 79E was prepared using the procedure as described in Example 74D, substituting Example 79D for Example 74C. The crude compound was used without further purification.

Example 79F

N-[7-(3,3-dimethylbutyl)-3,4-dihydro-2H-chromen-4-yl]-N'-1H-indazol-4-ylurea

The title compound was prepared using the procedure as described in Example 74E, substituting Example 79E for Example 74D. $^1$H NMR (300 MHz, DMSO-$d_6$) δ ppm 12.98 (br, 1H), 8.61 (s, 1H), 8.02 (s, 1H), 7.67 (m, 1H), 6.64-7.30 (m, 6H), 4.93 (m, 1H), 4.05-4.29 (m, 2H), 2.64 (m, 2H), 1.71-2.04 (m, 2H), 1.43 (m, 2H), 0.93 (s, 9H). MS (ESI) m/z 393 (M+H).

Example 80

N-(7-tert-butyl-2,2-dimethyl-3,4-dihydro-2H-chromen-4-yl)-N'-1H-indazol-4-ylurea Example 80A The title compound was prepared according to the procedure as described in Example 78A, substituting 3-tert-butylphenol for 2,3-difluorophenol. Chromatography (95:5 hexane-ethyl acetate-hexane to 9:1 ethyl acetate-hexane, eluent gradient) afforded Example 80A as a thick yellow oil. $^1$H NMR (300 MHz, DMSO-$d_6$) δ ppm 12.01 (br, 1H), 7.81 (d, J=8.5 Hz, 1H), 7.01 (dd, J=8.5, 2.0 Hz, 1H), 6.91 (d, J=2.0 Hz, 1H), 2.61 (s, 2H), 1.27 (s, 9H). MS (ESI) m/z 193 (M+H).

Example 80B

Example 80B was prepared using the procedure as described in Example 74A, substituting Example 80A for 2,4-dihydroxy-3-propylacetophenone. Chromatography on silica gel (92:8 hexane-ethyl acetate to 4:1 hexane-ethyl acetate, eluent gradient) afforded Example 80B as a pale yellow oil. $^1$H NMR (300 MHz, DMSO-$d_6$) δ ppm 7.64 (d, J=8.1 Hz, 1H), 7.07 (dd, J=8.1, 1.7 Hz, 1H), 6.92 (d, J=1.7 Hz, 1H), 2.74 (s, 2H), 1.39 (s, 6H), 1.26 (s, 9H). MS (ESI) m/z 233 (M+H).

Example 80C

Example 80C was prepared using the procedure as described in Example 74C, substituting Example 80B for Example 74B, affording a pale yellow oil. The crude compound was used without further purification.

Example 80D

Example 80D was prepared using the procedure as described in Example 74D, substituting Example 80C for Example 74C. The crude compound was used without further purification.

Example 80E

N-(7-tert-butyl-2,2-dimethyl-3,4-dihydro-2H-chromen-4-yl)-N'-1H-indazol-4-ylurea The title compound was prepared using the procedure as described in Example 74E, substituting Example 80D for Example 74D. $^1$H NMR (300 MHz, DMSO-$d_6$) δ ppm 12.99 (br, 1H), 8.67 (s, 1H), 8.06 (d, J=0.7 Hz, 1H), 7.68 (d, J=7.5 Hz, 1H), 7.20-7.25 (m, 2H), 7.08 (d, J=8.5 Hz, 1H), 6.95 (dd, J=8.1, 2.0 Hz, 1H), 6.73 (d, J=1.7 Hz, 1H), 6.71 (s, 1H), 4.97 (m, 1H), 2.17 (m, 1H), 1.74 (m, 1H), 1.40 (s, 3H), 1.29 (s, 3H), 1.24 (s, 9H). MS (ESI) m/z 415 (M+NH$_4$)

Example 81

N-(2,2-diethyl-7-fluoro-3,4-dihydro-2H-chromen-4-yl)-N'-(1-methyl-1H-indazol-4-yl)urea A solution of Example 77D (212 mg, 0.554 mmol) in N,N-dimethylformamide (2.2 mL) was treated with 60% NaH (28 mg, 0.7 mmol), and the mixture was stirred at rt for 45 min. Dimethyl sulfate (0.06 mL, 0.634 mmol) was then added, and the reaction was allowed to stir for 1 h. Concentration in vacuo, followed by silica gel chromatography (98:2 dichloromethane-methanol, eluent) afforded the title compound as a tan foamy solid, 109 mg (50%). $^1$H NMR (300 MHz, DMSO-$d_6$) δ ppm 8.72 (s, 1H), 8.03 (s, 1H), 7.70 (d, J=7.1 Hz, 1H), 7.25-7.36 (m, 2H), 7.17 (m, 1H), 6.70-6.77 (m, 2H), 6.63 (dd, J=10.5, 2.7 Hz, 1H), 4.94 (m, 1H), 4.00 (s, 3H), 2.19 (m, 1H), 1.58-1.77 (m, 5H), 0.84-0.94 (m, 6H). MS (ESI) m/z 397 (M+H).

Example 82

N-(7,8-difluoro-3,4-dihydro-2H-chromen-4-yl)-N'-1H-indazol-4-ylurea

Example 82A

Example 82A was prepared according to the procedure described for Example 79A, substituting 2,3-difluorophenol for 3-bromophenol. $^1$H NMR (300 MHz, DMSO-$d_6$) δ ppm 7.01-7.23 (m, 2H), 5.02 (s, 2H).

Example 82B

The product from Example 82A (707 mg, 3.49 mmol) was stirred overnight at rt in a mixture of methanesulfonic acid (1 mL) and conc. H$_2$SO$_4$ (1 mL). The mixture was quenched with H$_2$O and extracted with ether. The ethereal extracts were washed with saturated NaHCO$_3$ solution and brine and then were dried (Na$_2$SO$_4$). Concentration in vacuo afforded Example 82B as a tan solid, 351 mg (55%). $^1$H NMR (300 MHz, DMSO-$d_6$) δ ppm 7.63 (m, 1H), 7.14 (m, 1H), 4.70 (t, J=6.4 Hz, 2H), 2.86 (t, J=6.4 Hz, 2H). MS (ESI) m/z 185 (M+H).

Example 82C

Example 82C was prepared according to the procedure described in Example 74C, substituting Example 82B for Example 74B. $^1$H NMR (300 MHz, DMSO-$d_6$) δ ppm 7.20 (m, 1H), 6.85 (m, 1H), 4.22-4.38 (m, 3H), 2.03 (m, 1H), 1.79 (m, 1H). MS (ESI) m/z 186 (M+H).

Example 82D

Example 82D was prepared using the procedure as described in Example 74D, substituting Example 82C for Example 74C. The crude compound was used without further purification.

Example 82E

N-(7,8-difluoro-3,4-dihydro-2H-chromen-4-yl)-N'-1H-indazol-4-ylurea

The title compound was prepared using the procedure as described in Example 74E, substituting Example 82D for Example 74D. $^1$H NMR (300 MHz, DMSO-$d_6$) δ ppm 13.01 (br, 1H), 8.64 (s, 1H), 8.04 (s, 1H), 7.66 (d, J=7.5 Hz, 1H), 7.09-7.22 (m, 2H), 7.06 (d, J=8.1 Hz, 1H), 6.97 (m, 1H), 6.90 (d, J=7.8 Hz, 1H), 4.96 (m, 1H), 4.44 (m, 1H), 4.29 (m, 1H), 2.08-2.15 (m, 2H). MS (ESI) m/z 345 (M+H).

Example 83

N-(7-fluoro-2,2-dipropyl-3,4-dihydro-2H-chromen-4-yl)-N'-1H-indazol-4-ylurea

Example 83A

The title compound was prepared using the procedure as described in Example 74A, substituting 4-fluoro-2-hydroxyacetophenone for 2,4-dihydroxy-3-propylacetophenone and 4-heptanone for acetone. Chromatography on silica gel (95:5 hexane-ethyl acetate to 4:1 hexane-ethyl acetate, gradient eluent) afforded Example 83A as a yellow oil. $^1$H NMR (300 MHz, DMSO-$d_6$) δ ppm 7.78 (m, 1H), 6.84-6.89 (m, 2H), 2.78 (s, 2H), 1.64 (m, 4H), 1.33 (m, 4H), 0.85 (t, J=7.3 Hz, 6H). MS (ESI) m/z 251 (M+H), 268 (M+NH$_4$).

Example 83B

Example 83B was prepared according to the procedure described in Example 74C, substituting Example 83A for Example 74B. $^1$H NMR (300 MHz, DMSO-$d_6$) δ ppm 7.54 (m, 1H), 6.65 (td, J=8.4, 2.7 Hz, 1H), 6.48 (dd, J=10.8, 2.8 Hz, 1H), 3.77 (m, 1H), 1.89-2.07 (m, 4H), 1.26-1.58 (m, 8H), 0.91 (t, J=7.3 Hz, 3H), 0.83 (t, J=7.1 Hz, 3H). MS (ESI) m/z 252 (M+H).

Example 83C

Example 83C was prepared using the procedure as described in Example 74D, substituting Example 83B for Example 74C. The crude compound was used without further purification.

Example 83D

N-(7-fluoro-2,2-dipropyl-3,4-dihydro-2H-chromen-4-yl)-N'-1H-indazol-4-ylurea

The title compound was prepared using the procedure as described in Example 74E, substituting Example 83C for Example 74D. ¹H NMR (300 MHz, DMSO-d₆) δ ppm 13.01 (br, 1H), 8.72 (m, 1H), 8.07 (s, 1H), 7.67 (m, 1H), 7.33 (m, 1H), 7.22 (m, 1H), 7.09 (m, 1H), 6.76 (m, 2H), 6.60 (dd, J=10.5, 2.7 Hz, 1H), 4.94 (m, 1H), 2.18 (m, 1H), 1.77 (m, 1H), 1.53-1.66 (m, 4H), 1.37 (m, 4H), 0.91 (m, 6H). MS (ESI) m/z 411 (M+H).

Example 84

N-(2,2-dibutyl-7-fluoro-3,4-dihydro-2H-chromen-4-yl)-N'-1H-indazol-4-ylurea

Example 84A

Example 84A was prepared using the procedure as described in Example 74A, substituting 4-fluoro-2-hydroxy-acetophenone for 2,4-dihydroxy-3-propylacetophenone and 5-nonanone for acetone. Chromatography on silica gel (95:5 hexane-ethyl acetate to 4:1 hexane-ethyl acetate, gradient eluent) afforded Example 84A as a yellow oil. ¹H NMR (300 MHz, DMSO-d₆) δ ppm 7.77 (m, 1H), 6.83-6.89 (m, 2H), 2.79 (s, 2H), 1.66 (m, 4H), 1.43 (m, 4H), 1.24 (m, 4H), 0.85 (m, 6H). MS (ESI) m/z 279 (M+H).

Example 84B

Example 84B was prepared according to the procedure described in Example 74C, substituting Example 84A for Example 74B. ¹H NMR (300 MHz, DMSO-d₆) δ ppm 7.54 (t, J=8.0 Hz, 1H), 6.65 (td, J=8.4, 2.7 Hz, 1H), 6.48 (dd, J=10.5, 2.4 Hz, 1H), 3.77 (m, 1H), 2.03 (m, 1H), 1.79 (m, 1H), 1.46-1.63 (m, 4H), 1.22-1.35 (m, 8H), 0.90 (t, J=6.7 Hz, 3H), 0.83 (t, J=6.9 Hz, 3H).

Example 84C

Example 84C was prepared using the procedure as described in Example 74D, substituting Example 84B for Example 74C. The crude compound was used without further purification.

Example 84D

N-(2,2-dibutyl-7-fluoro-3,4-dihydro-2H-chromen-4-yl)-N'-1H-indazol-4-ylurea

The title compound was prepared using the procedure as described in Example 74E, substituting Example 84C for Example 74D. ¹H NMR (300 MHz, DMSO-d₆) δ ppm 12.98 (br, 1H), 8.73 (s, 1H), 8.07 (s, 1H), 7.67 (d, J=7.8 Hz, 1H), 7.33 (m, 1H), 7.22 (t, J=7.8 Hz, 1H), 7.09 (d, J=8.5 Hz, 1H), 6.72-6.77 (m, 2H), 6.61 (dd, J=10.5, 2.7 Hz, 1H), 4.94 (m, 1H), 2.17 (m, 1H), 1.76 (m, 1H), 1.61 (m, 4H), 1.32 (m, 8H), 0.87 (m, 6H). MS (ESI) m/z 439 (M+H).

Example 85

N-(2-tert-butyl-7-fluoro-3,4-dihydro-2H-chromen-4-yl)-N'-1H-indazol-4-ylurea

Example 85A

The title compound was prepared using the procedure as described in Example 74A, substituting 4-fluoro-2-hydroxy-acetophenone for 2,4-dihydroxy-3-propylacetophenone and pivaldehyde for acetone. Chromatography on silica gel (95:5 hexane-ethyl acetate to 4:1 hexane-ethyl acetate, gradient eluent) afforded Example 85A as a yellow oil. ¹H NMR (300 MHz, DMSO-d₆) δ ppm 7.81 (m, 1H), 6.91 (m, 2H), 4.24 (dd, J=13.9, 2.4 Hz, 1H), 2.80 (m, 1H), 2.57 (m, 1H), 1.01 (s, 9H). MS (ESI) m/z 223 (M+H), 240 (M+NH₄).

Example 85B

Example 85B was prepared according to the procedure described in Example 74C, substituting Example 85A for Example 74B. ¹H NMR (300 MHz, DMSO-d₆) δ ppm 7.27 and 7.54 (2m, 1H), 6.49-6.69 (m, 2H), 3.84 (m, 1H), 1.93 (br, 2H), 1.83 and 2.12 (2m, 1H), 1.38 and 1.58 (2m, 1H), 0.96 and 0.98 (2s, 9H). MS (ESI) m/z 224 (M+H).

Example 85C

Example 85C was prepared using the procedure as described in Example 74D, substituting Example 85B for Example 74C. The crude compound was used without further purification.

Example 85D

N-(2-tert-butyl-7-fluoro-3,4-dihydro-2H-chromen-4-yl)-N'-1H-indazol-4-ylurea

The title compound was prepared using the procedure as described in Example 74E, substituting Example 85C for Example 74D. ¹H NMR (300 MHz, DMSO-d₆) δ ppm 13.01 (br, 1H), 8.50 and 8.79 (2s, 1H), 8.01 and 8.10 (2s, 1H), 7.69 (m, 1H), 7.19-7.42 (m, 2H), 7.08 (m, 1H), 6.61-6.95 (m, 3H), 4.89 and 5.04 (2m, 1H), 3.73 and 3.94 (2d, J=10.8 Hz, 1H), 2.17 (m, 1H), 1.69 (m, 1H), 1.00 (2s, 9H). MS (ESI) m/z 383 (M+H), 405 (M+Na).

Example 86

N-(1-ethyl-1H-indazol-4-yl)-N'-(7-fluoro-2,2-dimethyl-3,4-dihydro-2H-chromen-4-yl)urea The title compound was prepared according to the procedure described for Example 81, substituting Example 76D for Example 77D and iodoethane for dimethyl sulfate. ¹H NMR (300 MHz, DMSO-d₆) δ ppm 8.73 (s, 1H), 8.05 (s, 1H), 7.70 (d, J=8.1 Hz, 1H), 7.18-7.36 (m, 3H), 6.75 (td, J=8.5, 2.7 Hz, 2H), 6.61 (dd, J=10.5, 2.4 Hz, 1H), 4.97 (m, 1H), 4.39 (q, J=7.2 Hz, 2H), 2.19 (m, 1H), 1.79 (m, 1H), 1.41 (s, 3H), 1.38 (t, J=7.3 Hz, 3H), 1.30 (s, 3H). MS (ESI) m/z 383 (M+H), 405 (M+Na).

Example 87

N-(2-tert-butyl-7-fluoro-3,4-dihydro-2H-chromen-4-yl)-N'-(1-methyl-1H-indazol-4-yl)urea The title compound was prepared according to the procedure described for Example 81, substituting Example 85D for Example 77D. ¹H NMR (300 MHz, DMSO-d₆) δ ppm 8.49 and 8.75 (2s, 1H), 8.01 (2d, J=0.7 Hz, 1H), 7.70 (m, 1H), 7.24-7.41 (m, 2H), 7.16 (m, 1H), 6.61-6.89 (m, 3H), 4.89 and 5.04 (2m, 1H), 3.99 and 4.01 (2s, 3H), 3.73 and 3.94 (2d, J=10.5 Hz, 1H), 2.13-2.33 (2m, 1H), 1.52-1.81 (2m, 1H), 1.00 (2s, 9H). MS (ESI) m/z 397 (M+H), 419 (M+Na).

Example 88

N-(2-ethyl-2H-indazol-4-yl)-N'-(7-fluoro-2,2-dimethyl-3,4-dihydro-2H-chromen-4-yl)urea The title compound was prepared according to the procedure described for Example 86, being obtained as a side product from the reaction. $^1$H NMR (300 MHz, DMSO-d$_6$) δ 8.60 (s, 1H), 8.25 (d, J=0.7 Hz, 1H), 7.48 (dd, J=7.1, 1.4 Hz, 1H), 7.32 (m, 1H), 7.09-7.18 (m, 2H), 6.73 (td, J=8.5, 2.7 Hz, 1H), 6.58-6.65 (m, 2H), 4.94 (m, 1H), 4.45 (q, J=7.1 Hz, 2H), 2.20 (m, 1H), 1.78 (m, 1H), 1.51 (t, J=7.1 Hz, 3H), 1.41 (s, 3H), 1.30 (s, 3H). MS (ESI) m/z 382 (M+H), 405 (M+Na).

Example 89

N-(7-fluoro-2,2-dimethyl-3,4-dihydro-2H-chromen-4-yl)-N'-[1-(2-methoxyethyl)-1H-indazol-4-yl]urea The title compound was prepared according to the procedure described for Example 81, substituting Example 76D for Example 77D and 2-bromoethyl methyl ether for dimethyl sulfate. $^1$H NMR (300 MHz, DMSO-d$_6$) δ 8.73 (s, 1H), 8.07 (s, 1H), 7.69 (dd, J=7.4, 1.0 Hz, 1H), 7.19-7.36 (m, 3H), 6.72-6.78 (m, 2H), 6.61 (dd, J=10.8, 2.7 Hz, 1H), 4.97 (m, 1H), 4.51 (t, J=5.4 Hz, 2H), 3.75 (t, J=5.4 Hz, 2H), 3.18 (s, 3H), 2.20 (m, 1H), 1.78 (m, 1H), 1.41 (s, 3H), 1.30 (s, 3H). MS (ESI) m/z 413 (M+H), 435 (M+Na).

Example 90

N-1H-indazol-4-yl-N'-[1-(3-phenylpropyl)-7-(trifluoromethyl)-1,2,3,4-tetrahydroquinolin-3-yl]urea

Example 90A

To a flask containing 4-Hydroxy-7-trifluoromethyl-quinoline-3-carboxylic acid ethyl ester (17.50 mmol, 5.0 g) (Aldrich) was added POCl$_3$ (45 mL) (Aldrich) and the reaction was heated to 115° C. for 2 hours. The material was poured over 600 g of ice and stirred vigorously for 1 hour. The reaction was neutralized with aqueous NH$_4$OH and extracted with ethyl acetate (250 mL), dried (Na$_2$SO$_4$), filtered and concentrated in vacuo. The material was purified on SiO$_2$ and eluted with ethyl acetate/hexane (1/1) to afford a white solid (4.6 g) in 87% yield. $^1$H NMR (300 MHz, CDCl$_3$) δ ppm 9.28 (s, 1H), 8.73 (d, J=7.65 Hz, 1H), 8.45 (s, 1H), 7.79 (d, J=7.68 Hz, 1H), 4.39-4.60 (m, 2H), 1.50 (t, J=14.50, 7.50 Hz, 3H). MS (DCI) m/e 304 (M+H)$^+$

Example 90B

To an Example 90A (16.50 mmol, 5.0 g) in a hydrogenation flask was added ethanol (100 mL), 10% Pd/C (1.0 g) (Aldrich). The reaction was charged with H$_2$ at 60 psi and was shaken for 12 hours at room temperature. The mixture was filtered and concentrated in vacuo. The product was purified on SiO$_2$ and eluted with ethyl acetate/hexane (1/1) to give Example 90B as a yellow solid (3.12 g) in 69% yield. $^1$H NMR (300 MHz, CD$_3$OD) δ ppm 7.06 (d, J=7.0 Hz, 1H), 6.85 (d, J=7.0 Hz, 1H), 6.70 (s, 1H), 4.25-4.10 (m, 2H), 3.62-3.55 (m, 1H), 3.40 (t, J=14.62, 7.23 Hz, 1H), 3.10 (d, J=7.65 Hz, 2H), 2.95-2.80 (m, 1H), 1.25 (t, J=14.0, 7.50 Hz, 3H). MS (DCI) m/e 274 (M+H)$^+$

Example 90C

To an Example 90B (2.40 mmol, 0.6 g) in a flask was added dichloroethane (15 mL), 3-phenyl-propionaldehyde (4.50 mmol, 0.60 mL) and the reaction was stirred at room temperature for 1 hour. To the mixture was added triacetoxyborohydride (5.20 mmol, 1.10 g), acetic acid (14.50 mmol, 0.85 mL) and the reaction was stirred at room temperature for 2 hours. The reaction was quenched with water (10 mL) and extracted with ethyl acetate (100 mL), dried (Na$_2$SO$_4$) and concentrated in vacuo. The material was purified on SiO$_2$ and eluted with ethylacetate/hexane (4/1 to 1/1) to provide a colorless oil (0.27 g) in 29% yield. $^1$H NMR (300 MHz, CD$_3$OD) δ ppm 7.34-7.17 (m, 5H), 7.13 (d, J=7.84 Hz, 1H), 6.98 (d, J=7.81 Hz, 1H), 6.79 (s, 1H), 4.23-4.11 (m, 2H), 3.51-3.19 (m, 4H), 3.05-2.82 (m, 2H), 2.73-2.65 (m, 1H), 2.27 (t, J=14.94, 7.65 Hz, 2H), 2.01-1.89 (m, 2H), 1.52 (t, J=14.0, 7.68 Hz, 3H). MS (DCI) m/e 392 (M+H)$^+$

Example 90D

To an Example 90C (1.0 mmol, 0.39 g) in a flask was added tetrahydrofuran (40 mL) and 1M LiOH (20 mL) and the reaction was stirred at room temperature for 4 hours. The material was neutralized with citric acid and extracted with ethyl acetate (200 mL), dried (Na$_2$SO$_4$) and concentrated in vacuo to give a white solid (0.26 g) in 72% yield. $^1$H NMR (300 MHz, CD$_3$OD) δ ppm 7.34-7.17 (m, 5H), 7.04 (d, J=7.84 Hz, 1H), 6.81 (d, J=7.81 Hz, 1H), 6.64 (s, 1H), 4.23-4.11 (m, 2H), 3.51-3.19 (m, 2H), 3.05-2.82 (m, 2H), 2.75-2.68 (m, 1H), 2.63 (t, J=14.94, 7.63 Hz, 2H), 2.01-1.89 (m2H). MS (DCI) m/e 364 (M+H)$^+$.

Example 90E

To a flask containing Example 90D (0.80 mmol, 0.275 g) was added t-butanol (10 mL), triethyl amine (0.90 mmol, 0.12 mL) (Aldrich) and diphenylphosphorazide (0.80 mmol, 0.18 mL) (Aldrich) and the reaction was heated at reflux for 1.5 hours. The reaction was cooled and concentrated in vacuo. The mixture was purified on SiO$_2$ and eluted with ethyl acetate/hexane (4/1) to give a yellow oil (0.24 g) in 73% yield. $^1$H NMR (300 MHz, CD$_3$OD) δ ppm 7.30-7.08 (m, 5H), 7.04 (d, J=7.46 Hz, 1H), 6.75 (d, J=7.80 Hz, 1H), 6.61 (s, 1H), 3.93-3.90 (m, 1H), 3.44-3.38 (m, 1H), 3.31-3.26 (m, 3H), 3.18-3.12 (m, 1H), 3.12-2.95 (m, 1H), 2.85 (t, J=14.92, 7.49 Hz, 2H), 1.96-1.88 (m, 1H), 1.43 (s, 9H). MS (DCI) m/e 435 (M+H)$^+$.

Example 90F methyl 4-[({[1-(3-phenylpropyl)-7-(trifluoromethyl)-1,2,3,4-tetrahydroquinolin-3-yl]amino}carbonyl)amino]-1H-indazole-1-carboxylate To a flask containing Example 90E (1.60 mmol, 0.68 g) was added methylene chloride (10 mL), trifluoroacetic acid (2 mL) and the reaction was stirred at room temperature for 1 hour. The mixture was concentrated in vacuo. The residue was taken up in N,N-dimethylformamide (10 mL) and diisopropylethylamine (3.30 mmol, 0.57 mL) was added along with Example 24D (1.60 mmol, 0.52 g) and the reaction was stirred at room temperature for 1 hour and concentrated in vacuo. The material was purified on SiO$_2$ with ethyl acetate/hexane (3/1) to give a yellow solid (0.56 g) in 64% yield. $^1$H NMR (300 MHz, CD$_3$OD) δ ppm 8.22 (s, 1H), 7.72-7.81 (m, 2H), 7.48 (t, J=16.28, 8.48 Hz, 1H), 7.10-7.22 (m, 6H), 6.80 (d, J=7.80 Hz, 1H), 6.69 (s, 1H), 4.31-4.34 (m, 1H), 4.10 (s, 3H), 3.55-3.59 (m, 1H), 3.29-3.39 (m, 3H), 3.11-2.82 (m, 1H), 2.71-2.82 (m, 1H), 2.69 (t, J=14.92, 7.46 Hz, 2H), 1.96-1.91 (m, 2H). MS (DCI) m/e 552 (M+H)+

Example 90G

N-1H-indazol-4-yl-N'-[1-(3-phenylpropyl)-7-(trifluoromethyl)-1,2,3,4-tetrahydroquinolin-3-yl]urea To a flask containing Example 90F (1.0 mmol, 0.56 g) was added methanol (20 mL), 5N NaOH in methanol (1 mL) and the reaction was stirred at room temperature for 2 hours. The reaction mixture was diluted with water (75 mL) and filtered. The solid was washed with hexane (30 mL) and dried in a vacuum oven at 50° C. for 16 hours to give a brown solid (0.26 g) in 38% yield. $^1$H NMR (300 MHz, $CD_3OD$) δ ppm 7.98 (s, 1H), 7.57 (d, J=7.46 Hz, 1H), 7.24 (t, J=8.14, 15.94 Hz, 1H), 7.09-7.21 (m, 7H), 6.79 (d, J=7.80 Hz, 1H), 6.68 (s, 1H), 4.29-4.34 (m, 1H), 3.57 (d, J=13.90 Hz, 1H), 3.25-3.35 (m, 3H), 3.10 (d, J=13.0 Hz, 1H), 2.81 (d, J=13.0 Hz, 1H), 2.66 (t, J=15.60, 8.60 Hz, 2H), 1.85-2.01 (m, 2H). MS (APCI) m/e 494 (M+H)+. Calcd. For $C_{27}H_{26}N_5OCF_3$: C, 65.71; H, 5.31; N, 14.19. Found C, 65.31; H, 5.64; N, 14.12.

Example 91

N-(1-benzyl-7-fluoro-1,2,3,4-tetrahydroquinolin-3-yl)-N'-1H-indazol-4-ylurea

Example 91A

Example 91A was prepared using the procedure as described in Example 90A, substituting 7-Fluoro-4-hydroxy-quinoline-3-carboxylic acid ethyl ester for 4-Hydroxy-7-trifluoromethyl-quinoline-3-carboxylic acid ethyl ester. The product was a yellow solid (3.6 g) which was obtained in 66%. $^1$H NMR (300 Mz, $CDCl_3$) δ ppm 7.12 (d, J=7.80 Hz, 1H), 6.95 (d, J=8.0 Hz, 1H), 6.90 (s, 1H), 4.20-4.11 (m, 2H), 3.60-3.50 (m, 1H), 3.45 (t, J=14.00, 7.03 Hz, 1H), 3.05 (d, J=7.60 Hz, 2H), 2.95-2.75 (m, 1H), 1.30 (t, J=14.0, 7.50 Hz, 3H). MS (DCI) m/e 220 (M+H)+.

Example 91B

Example 91B was prepared using the procedure as described in Example 90B, substituting Example 91A for Example 90A. The product was an orange solid (3.82 g) which was obtained in 74%. $^1$H NMR (300 Mz, $CDCl_3$) δ ppm 7.12 (d, J=7.80 Hz, 1H), 6.95 (d, J=8.0 Hz, 1H), 6.90 (s, 1H), 4.20-4.11 (m, 2H), 3.60-3.50 (m, 1H), 3.45 (t, J=14.00, 7.03 Hz, 1H), 3.05 (d, J=7.60 Hz, 2H), 2.95-2.75 (m, 1H), 1.30 (t, J=14.0, 7.50 Hz, 3H). MS (DCI) m/e 220 (M+H)+.

Example 91C

Example 91C was prepared using the procedure as described in Example 90C and substituting benzaldehyde for 3-Phenyl-propionaldehyde and substituting Example 91B for Example 90B. The product was a white solid (1.2 g) which was obtained in 42% yield. $^1$H NMR (300 Mz, $CDCl_3$) δ ppm 7.35-7.21 (m, 5H), 6.70-6.65 (m, 2H), 6.47-6.42 (m, 1H), 4.39 (s, 2H), 4.22-4.11 (m, 2H), 3.56-3.43 (m, 2H), 3.10-2.94 (m, 3H), 1.30-1.22 (m, 3H). MS (DCI) m/e 314 (M+H)+.

Example 91D

Example 91D was prepared using the procedure as described in Example 90D, substituting Example 91C for Example 90C. The product was a colorless oil (0.25 g) which was obtained in 72%. $^1$H NMR (300 Mz, $CDCl_3$) δ ppm 7.30-7.19 (m, 5H), 6.72-6.64 (m, 2H), 6.44-6.39 (m, 1H), 4.39 (s, 2H), 3.49-3.38 (m, 2H), 3.03-2.94 (m, 3H) MS (DCI) m/e 286 (M+H)+.

Example 91E

Example 91E was prepared using the procedure as described in Example 90E, substituting Example 91D for Example 90D. The product was a colorless oil (0.35 g) which was obtained in 58%. $^1$H NMR (300 MHz, $CDCl_3$) δ ppm 7.35-7.22 (m, 5H), 6.75-6.68 (m, 2H), 6.49-6.45 (m, 1H), 4.45 (s, 2H), 4.20-4.09 (m, 1H), 3.47 (d, J=8.18 Hz, 1H), 3.51-3.28 (m, 1H), 3.12 (dd, J=16.61, 8.15 Hz, 1H), 2.69 (dd, J=17.30, 4.75 Hz, 1H), 1.43 (s, 9H). MS (DCI) m/e 357 (M+H)+.

Example 91F methyl 4-({[(1-benzyl-7-fluoro-1,2,3,4-tetrahydro-quinolin-3-yl)amino]carbonyl}amino)-1H-indazole-1-carboxylate Example 91F was prepared using the procedure as described in Example 90F, substituting Example 91E for Example 90E. The product was a white solid (0.16 g) which was obtained in 34%. $^1$H NMR (300 MHz, DMSO-$d_6$) δ ppm 7.64 (d, J=7.40 Hz, 1H), 7.35-7.16 (m, 5H), 7.20 (d, J=7.80 Hz, 1H), 6.94 (dd, J=9.40, 3.10 Hz, 1H), 6.80 (t, J=8.40, 3.0 Hz, 1H), 6.58-6.53 (m, 2H), 4.60-4.40 (m, 2H), 4.21-4.14 (m, 2H), 4.05 (s, 3H), 3.50 (d, J=11.50 Hz, 1H), 3.35-3.20 (m, 1H), 3.18 (dd, J=8.40, 16.28 Hz, 1H), 2.79 (dd, J=8.28, 16.62 Hz, 1H). MS (DCI) m/e 474 (M+H)+.

Example 91G

N-(1-benzyl-7-fluoro-1,2,3,4-tetrahydroquinolin-3-yl)-N'-1H-indazol-4-ylurea

The title compound was prepared using the procedure as described in Example 90G, substituting Example 91F for Example 90F. The product was a white solid (0.12 g) which was obtained in 68%. $^1$H NMR (300 MHz, DMSO-$d_6$) δ ppm 12.98 (s, 1H), 8.78 (s, 1H), 8.06 (s, 1H), 7.64 (d, J=7.46 Hz, 1H), 7.32-7.12 (m, 5H), 7.17 (d, J=7.80 Hz, 1H), 6.90 (dd, J=9.50, 3.06 Hz, 1H), 6.85 (t, J=8.48, 3.06 Hz, 1H), 6.56-6.51 (m, 2H), 4.59-4.44 (m, 2H), 4.25-4.18 (m, 2H), 3.55 (d, J=11.50 Hz, 1H), 3.31-3.23 (m, 1H), 3.16 (dd, J=8.40, 16.28 Hz, 1H), 2.76 (dd, J=8.28, 16.62 Hz, 1H). MS (ESI) m/e 416 (M+H)+. Calcd. For $C_{24}H_{22}N_5OF$: C, 69.38; H, 5.34; N, 16.86. Found C, 69.77; H, 4.98; N, 16.63.

Example 92

N-[1-benzyl-7-(trifluoromethoxy)-1,2,3,4-tetrahydroquinolin-3-yl]-N'-1H-indazol-4-ylurea

Example 92A

Example 92A was prepared using the procedure as described in Example 90A, substituting 4-Hydroxy-7-trifluoromethoxy-quinoline-3-carboxylic acid ethyl ester for 4-Hydroxy-7-trifluoromethyl-quinoline-3-carboxylic acid ethyl ester. The product was a white solid (3.18 g) which was obtained in 60%. $^1$H NMR (300 MHz, CDCL3) δ ppm 9.19 (s, 1H), 8.25-8.17 (m, 2H), 7.70 (d, J=8.30 Hz, 1H), 4.56-4.47 (m, 2H), 1.47 (t, J=12.0 Hz, 3H). MS (DCI) m/e 320 (M+H)+.

Example 92B

Example 92B was prepared using the procedure as described in Example 90B, substituting Example 92A for Example 90A. The product was a white solid (1.62 g) which was obtained in 70%. $^1$H NMR (300 MHz, CD$_3$OD) δ ppm 7.35-7.15 (m, 3H), 4.38-4.35 (m, 2H), 4.30-4.11 (m, 1H), 3.81-3.70 (m, 1H), 3.10-3.35 (m, 3H), 1.05-1.40 (m, 3H). MS (DCI) m/e 289 (M+H)+.

Example 92C

Example 92C was prepared using the procedure as described in Example 90C, substituting Example 92B for Example 90B, and substituting benzaldehyde for 3-Phenylpropionaldehyde. The product was a white solid (1.62 g) which was obtained in 71%. $^1$H NMR (300 MHz, CD$_3$OD) δ ppm 7.36-7.22 (m, 5H), 6.90-6.86 (m, 1H), 6.84 (d, J=11.87 Hz, 1H), 6.47 (d, J=8.82 Hz, 1H), 4.49 (s, 2H), 4.22-4.11 (m, 2H), 3.58-3.48 (m, 2H), 3.08-2.88 (m, 3H), 1.23 (t, J=3.39, 7.12 Hz, 3H). MS (DCI) m/e 380 (M+H)+.

Example 92D

Example 92D was prepared using the procedure as described in Example 90D, substituting Example 92C for Example 90C. The product was a white solid (1.82 g) which was obtained in 72%. $^1$H NMR (300 MHz, CD$_3$OD) δ ppm 7.72-7.34 (m, 5H), 6.91-6.85 (m, 1H), 6.81 (d, J=8.81 Hz, 1H), 6.51 (d, J=19.15 Hz, 1H), 4.52 (s, 2H), 3.62-3.30 (m, 2H), 3.04-2.97 (m, 3H). MS (DCI) m/e 352 (M+H)+.

Example 92E

Example 92E was prepared using the procedure as described in Example 90E, substituting Example 92D for Example 90D. The product was a white solid (0.92 g) which was obtained in 56%. $^1$H NMR (300 MHz, CD$_3$OD) δ ppm 7.42-7.22 (m, 5H), 6.91-6.85 (m, 2H), 6.51-6.48 (m, 1H), 4.47 (s, 2H), 4.16-4.09 (m, 1H), 3.53 (d, J=12.21 Hz, 1H), 3.33-3.25 (m, 1H), 3.10 (dd, J=3.73, 15.94 Hz, 1H), 2.73 (dd, J=3.05, 15.94 Hz, 1H), 1.44 (s, 9H). MS (DCI) m/e 423 (M+H)+.

Example 92F methyl 4-[({[1-benzyl-7-(trifluoromethoxy)-1,2,3,4-tetrahydroquinolin-3-yl]amino}carbonyl)amino]-1H-indazole-1-carboxylate The titled compound was prepared using the procedure as described in Example 90F, substituting Example 92E for Example 90E. The product was a white solid (0.82 g) which was obtained in 61%. $^1$H NMR (300 MHz, CD$_3$OD) δ ppm 8.19 (s, 1H), 7.09-7.95 (m, 1H), 7.43 (t, J=7.80, 15.94 Hz, 1H), 7.12-7.31 (m, 6H), 6.91-6.87 (m, 2H), 6.54-6.87 (m, 1H), 5.38-5.25 (m, 1H), 4.50-4.45 (m, 3H), 4.16-4.11 (m, 2H), 3.58 (dd, J=2.37, 11.87 Hz, 1H), 3.40-3.38 (m, 1H), 3.14 (dd, J=4.41, 11.62 Hz, 1H), 2.96-2.86 (m, 1H). MS (DCI) m/e 540 (M+H)+.

Example 92G

N-[1-benzyl-7-(trifluoromethoxy)-1,2,3,4-tetrahydroquinolin-3-yl]-N'-1H-indazol-4-ylurea The title compound was prepared using the procedure as described in Example 90G, substituting Example 92F for Example 90F. The product was a tan solid (0.62 g) which was obtained in 70%. $^1$H NMR (300 MHz, DMSO-d$_6$) δ ppm 13.03 (s, 1H), 8.82 (s, 1H), 8.08 (s, 1H), 7.65 (d, J=7.40 Hz, 1H), 7.34-7.13 (m, 5H), 7.08 (d, J=7.80 Hz, 1H), 6.98-6.91 (m, 1H), 6.65-6.50 (m, 2H), 4.59-4.41 (m, 2H), 4.31-4.22 (m, 2H), 4.01-4.04 (m, 1H), 3.63-3.56 (m, 1H), 3.11-3.42 (m, 2H), 2.76 (dd, J=8.30, 16.50 Hz, 1H). MS (ESI) m/e 465 (M+H)+. Calcd. For C$_{25}$H$_{22}$N$_5$OF$_3$: C, 64.51; H, 4.76; N, 15.05. Found C, 61.90; H, 4.82; N, 15.16.

Example 93

N-(1-benzyl-6-tert-butyl-1,2,3,4-tetrahydroquinolin-3-yl)-N'-1H-indazol-4-ylurea

Example 93A

Example 93A was prepared using the procedure as described in Example 90A, substituting 6-tert-butyl-4-hydroxy-quinoline-3-carboxylic acid ethyl ester for 4-Hydroxy-7-trifluoromethyl-quinoline-3-carboxylic acid ethyl ester. The product was a yellow oil (3.17 g) which was obtained in 69%. $^1$H NMR (300 MHz, CDCl$_3$) δ ppm 9.10 (s, 1H), 8.21-8.15 (m, 2H), 7.71 (d, J=8.00 Hz, 1H), 4.56-4.47 (m, 2H), 1.47 (m, 3H). MS (APCI) m/e 292 (M+H)+.

Example 93B

Example 93B was prepared using the procedure as described in Example 90B, substituting Example 93A for Example 90A. The product was a white solid (1.62 g) which was obtained in 58%. $^1$H NMR (300 MHz, CDCl$_3$) δ ppm 7.04 (s, 1H), 6.97 (d, J=7.80 Hz, 1H), 6.40 (d, J=7.80 Hz, 1H), 4.41-4.34 (m, 2H), 3.58-3.36 (m, 2H), 3.03-2.90 (m, 3H), 1.26 (s, 9H), 1.23 (m, 3H). MS (APCI) m/e 262 (M+H)+.

Example 93C

Example 93C was prepared using the procedure as described in Example 90C, substituting Example 93B for Example 90B, and substituting benzaldehyde for 3-Phenylpropionaldehyde. The product was a white solid (1.12 g) which was obtained in 64%. $^1$H NMR (300 MHz, CDCl$_3$) δ ppm 7.35-7.14 (m, 5H), 7.04 (s, 1H), 6.97 (d, J=7.80 Hz, 1H), 6.42 (d, J=7.80 Hz, 1H), 4.43 (s, 2H), 4.38-4.35 (m, 2H), 3.56-3.37 (m, 2H), 3.05-2.90 (m, 3H), 1.27 (s, 9H), 1.23 (m, 3H). MS (APCI) m/e 352 (M+H)+.

Example 93D

Example 93D was prepared using the procedure as described in Example 90D, substituting Example 93C for Example 90C. The product was a white solid (1.02 g) which was obtained in 96%. $^1$H NMR (300 MHz, CDCl$_3$) δ ppm 7.40-7.16 (m, 5H), 7.01 (s, 1H), 6.95 (d, J=7.80 Hz, 1H), 6.48 (d, J=7.80 Hz, 1H), 4.45 (s, 2H), 3.54-3.39 (m, 2H), 3.03-2.90 (m, 3H), 1.26 (s, 9H). MS (APCI) m/e 324 (M+H)+.

Example 93E

Example 93E was prepared using the procedure as described in Example 90E, substituting Example 93D for Example 90D. The product was a white solid (0.42 g) which was obtained in 53%. $^1$H NMR (300 MHz, CDCl$_3$) δ ppm 7.40-7.22 (m, 5H), 6.94-6.87 (m, 2H), 6.50-6.46 (m, 1H), 4.45 (s, 2H), 4.17-4.09 (m, 1H), 3.50 (d, J=12.20 Hz, 1H), 3.35-3.23 (m, 1H), 3.11 (dd, J=3.80, 16.0 Hz, 1H), 2.78 (dd, J=3.80, 16.0 Hz, 1H), 1.44 (s, 9H), 1.26 (s, 9H). MS (DCI) m/e 423 (M+H)$^+$.

Example 93F methyl 4-({[(1-benzyl-6-tert-butyl-1,2,3,4-tetrahydroquinolin-3-yl)amino]carbonyl}amino)-1H-indazole-1-carboxylate The titled compound was prepared using the procedure as described in Example 90F, substituting Example 93E for Example 90E. The product was a white solid (0.26 g) which was obtained in 42%. $^1$H NMR (300 MHz, DMSO-d$_6$) δ ppm 12.93 (s, 1H), 8.80 (s, 1H), 8.12 (s, 1H), 7.62 (d, J=7.84 Hz, 1H), 7.35-7.18 (m, 5H), 7.00-6.99 (m, 3H), 6.60-6.48 (m, 2H), 4.50-4.42 (m, 2H), 4.36-4.24 (m, 1H), 4.10 (s, 3H), 3.39 (dd, J=7.80, 16.20 Hz, 1H), 3.27 (dd, J=7.80, 16.20 Hz, 1H), 3.14 (dd, J=7.80, 16.20 Hz, 1H), 2.71 (dd, J=7.80, 16.20 Hz, 1H), 1.29 (s, 9H). MS (APCI) m/e 512 (M+H)$^+$.

Example 93G

N-(1-benzyl-6-tert-butyl-1,2,3,4-tetrahydroquinolin-3-yl)-N'-1H-indazol-4-ylurea The title compound was prepared using the procedure as described in Example 90G, substituting Example 93F for Example 90F. The product was a tan solid (0.16 g) which was obtained in 71%. $^1$H NMR (300 MHz, DMSO-d$_6$) δ ppm 12.98 (s, 1H), 8.84 (s, 1H), 8.06 (s, 1H), 7.66 (d, J=7.80 Hz, 1H), 7.34-7.15 (m, 5H), 7.06-6.96 (m, 3H), 6.57-6.45 (m, 2H), 4.56-4.48 (m, 2H), 4.32-4.26 (m, 2H), 3.37 (dd, J=7.80, 16.20 Hz, 1H), 3.26-3.38 (m, 1H), 3.14 (dd, J=7.82, 16.27 Hz, 1H), 2.71 (dd, J=7.81, 16.17 Hz, 1H), 1.26 (s, 9H). MS (APCI) m/e 454 (M+H)$^+$. Calcd. For C$_{28}$H$_{31}$N$_5$O: C, 74.14; H, 6.89; N, 15.44. Found C, 74.32; H, 6.64; N, 15.12.

Example 94

N-1H-indazol-4-yl-N'-[1-(3-phenylpropyl)-7-(trifluoromethoxy)-1,2,3,4-tetrahydroquinolin-3-yl]urea Example 94A Example 94A was prepared using the procedure as described in Example 90C, substituting Example 92B for Example 90B. The product was a colorless oil (0.94) which was obtained in 48%. $^1$H NMR (300 MHz, CDCl$_3$) δ ppm 7.32-7.18 (m, 5H), 6.91-6.85 (m, 2H), 6.41 (d, J=11.53 Hz, 1H), 4.21-4.09 (m, 2H), 3.47-3.17 (m, 4H), 2.99-2.88 (m, 3H), 2.68 (t, J=7.12, 11.47 Hz, 2H), 1.97-1.87 (m, 2H), 1.27 (t, J=4.07, 7.12 Hz, 3H). MS (DCI) m/e 408 (M+H)$^+$.

Example 94B

Example 94B was prepared using the procedure as described in Example 90D, substituting Example 94A for Example 90C. The product was a white solid (1.24 g) which was obtained in 84%. $^1$H NMR (300 MHz, CDCl$_3$) δ ppm 7.32-7.18 (m, 5H), 6.91-6.86 (m, 2H), 6.42 (d, J=8.82, 1H), 3.49-3.42 (m, 2H), 3.38-3.19 (m, 2H), 3.02-2.93 (m, 3H), 2.67 (t, J=7.12, 15.46 Hz, 2H), 1.97-1.87 (m, 2H). MS (DCI) m/e 380 (M+H)$^+$.

Example 94C

Example 94C was prepared using the procedure as described in Example 90E, substituting Example 94B for Example 90D. The product was a yellow oil (0.92 g) which was obtained in 72%. $^1$H NMR (300 MHz, CD$_3$OD) δ ppm 7.25-76.98 (m, 5H), 7.01 (d, J=7.80 Hz, 1H), 6.72 (d, J=7.80 Hz, 1H), 6.61 (s, 1H), 3.96-3.92 (m, 1H), 3.45-3.35 (m, 1H), 3.30-3.24 (m, 3H), 3.21-3.17 (m, 2H), 3.10-2.93 (m, 1H), 2.85-2.81 (m, 2H), 1.96-1.88 (m, 1H), 1.40 (s, 9H). MS (DCI) m/e 451 (M+H)$^+$.

Example 94D methyl 4-[({[1-(3-phenylpropyl)-7-(trifluoromethoxy)-1,2,3,4-tetrahydroquinolin-3-yl]amino}carbonyl)amino]-1H-indazole-1-carboxylate The titled compound was prepared using the procedure as described in Example 90F, substituting Example 94C for Example 90E. The product was a yellow solid (0.65 g) which was obtained in 42%. $^1$H NMR (300 MHz, DMSO) δ ppm 8.16 (s, 1H), 7.84 (d, J=8.0 Hz, 1H), 7.14-7.41 (m, 7H), 6.85 (d, J=7.0 Hz, 1H), 6.78 (s, 1H), 6.34 (d, J=8.0 Hz, 1H), 4.43-4.40 (m, 1H), 4.15-4.07 (m, 5H), 3.44 (dd, J=3.0, 12.0 Hz, 1H), 3.26-3.06 (m, 2H), 2.73 (d, J=12.0 Hz, 1H), 2.62-2.57 (m, 2H), 1.88-1.78 (m, 2H). MS (DCI) m/e 568 (M+H)$^+$.

Example 94E

N-1H-indazol-4-yl-N'-[1-(3-phenylpropyl)-7-(trifluoromethoxy)-1,2,3,4-tetrahydroquinolin-3-yl]urea The title compound was prepared using the procedure as described in Example 90G, substituting Example 94D for Example 90F. The product was a tan solid (0.36 g) which was obtained in 71%. $^1$H NMR (300 MHz, DMSO-d$_6$) δ ppm 12.84 (s, 1H), 8.69 (s, 1H), 8.02 (s, 1H), 7.67 (d, J=7.45 Hz, 1H), 7.23-7.10 (m, 5H), 7.03 (d, J=8.47 Hz, 1H), 6.93-6.91 (m, 2H), 6.65 (d, J=7.79 Hz, 1H), 6.45 (d, J=7.80 Hz, 1H), 4.30-4.26 (m, 1H), 3.50 (dd, J=2.03, 11.19 Hz, 1H), 3.34-3.21 (m, 4H), 3.13 (dd, J=5.08, 16.61 Hz, 1H), 2.76-2.63 (m, 4H), 1.93-1.83 (m, 2H). MS (DCI) m/e 510 (M+H)$^+$. Calcd. For C$_{27}$H$_{27}$N$_5$O$_2$F$_3$: C, 63.52; H, 5.33; N, 13.72. Found C, 63.19; H, 5.42; N, 13.54.

Example 95

N-1H-indazol-4-yl-N'-(1-methyl-1,2,3,4-tetrahydroquinolin-4-yl)urea

Example 95A

Boc-4-amino-1,2,3,4 tetrahydroquinoline (0.9 g, 3.6 mMol) was dissolved in 25 mls of acetonitrile, 1.9 mls of 37% aqueous formaldehyde (25.5 mMol), and 3.8 g of sodium triacetoxyborohydride (17.9 mMol) were added and the reaction mixture stirred at room temperature for 18 hours. 100 mls of diethyl ether was added and the reaction mixture extracted with 25 mls of water. The organic phase was dried with MgSO$_4$ and filtered through a silica plug. The solvent was removed by evaporation under vacuum. The residue was dissolved in 5 mls trifluoroacetic acid stirred at room temperature for 20 minutes, dichloromethane was added and the solvent evaporated to provide Example 95A. $^1$H NMR (300 MHz, DMSO-d$_6$) δ ppm 8.17 (s, 2 H) 7.11-7.25 (m, 2 H) 6.70 (d, J=8.14 Hz, 1 H) 6.61-6.68 (m, 1 H) 4.35-4.45 (m, 1 H) 3.18-3.35 (m, 2 H) 2.88 (s, 3 H) 1.98-2.19 (m, 2 H) MS (DCI/NH3) m/z 163.0 (M+H)$^+$.

Example 95B methyl 4-({[(1-methyl-1,2,3,4-tetrahydroquinolin-4-yl)amino]carbonyl}amino)-1H-indazole-1-carboxylate A mixture of 0.23 g (1.4 mMol) of the compound from example 95A, 0.48 g (1.4 mMol) of the compound from example 24D in 2 mls of N,N-dimethylformamide and 0.5 mls (2.8 mMol) of N,N-diisopropylethylamine were stirred at room temperature for 2 hours. The reaction was precipitated with water, the solids collected by filtration, resuspended in 10% methanol in dichloromethane and purified by flash chromatography on silica using a gradient from dichloromethane to 20% methanol in dichloromethane with a few drops of NH$_4$OH as the solvents to provide the titled compound. $^1$H NMR (300 MHz, DMSO-d$_6$) δ ppm 8.79 (s, 1 H) 8.36 (s, 1 H) 7.91 (dd, J=7.80, 0.68 Hz, 1 H) 7.68 (d, J=8.48 Hz, 1 H) 7.50 (t, J=8.14 Hz, 1 H) 7.08-7.17 (m, 2 H) 6.59-6.71 (m, 3 H) 4.74-4.85 (m, 1 H) 4.03 (s, 3 H) 3.18-3.29 (m, 2 H) 2.89 (s, 3 H) 1.94-2.06 (m, 2 H).

Example 95C

N-1H-indazol-4-yl-N'-(1-methyl-1,2,3,4-tetrahydroquinolin-4-yl)urea

The compound obtained in example 95B was dissolved in 2 mls of 5N NaOH in methanol and stirred for 2 hours at ambient temperature. Water was added to the reaction mixture and the precipitate was collected. The precipitated compound was redissolved in 10% methanol in dichloromethane and purified by flash chromatography on silica using a gradient from dichloromethane to 20% methanol in dichloromethane with a few drops of NH$_4$OH as the solvents to provide the titled compound. $^1$H NMR (300 MHz, DMSO-d$_6$) δ ppm 12.99 (s, 1 H) 8.53 (s, 1 H) 8.01 (s, 1 H) 7.70 (d, J=7.46 Hz, 1 H) 7.21 (t, J=7.97 Hz, 1 H) 7.11-7.17 (m, 2 H) 7.07 (t, J=8.48 Hz, 1 H) 6.58-6.72 (m, 3 H) 4.76-4.85 (m, 1H) 3.15-3.29 (m, 2 H) 2.89 (s, 3 H) 1.99 (s, 2 H). MS (DCI/NH3) m/z 322.0 (M+H)$^+$.

Example 96

N-(1-benzyl-6-tert-butyl-1,2,3,4-tetrahydroquinolin-4-yl)-N'-1H-indazol-4-ylurea Example 96A A solution of 24.7 g (0.14 Mol) of 3-bromopropionyl chloride in 50 mls of dichloromethane was added dropwise to a mixture of 21.5 g (0.14 Mol) 4-tert-butylaniline and 39.8 g (0.29 Mol) of K$_2$CO$_3$ in 150 mls of dichloromethane and the reaction mixture was stirred for 18 hours at ambient temperature. 100 mls of water was added slowly, the organic layer was separated and washed twice with water dried with MgSO$_4$, and the solvent removed to provide Example 96A. $^1$H NMR (300 MHz, DMSO-d$_6$) δ ppm 9.96 (s, 1 H) 7.48-7.53 (m, 2 H) 7.29-7.34 (m, 2 H) 3.73 (t, J=6.27 Hz, 2 H) 2.93 (t, J=6.44 Hz, 2 H) 1.25 (s, 9 H). MS (DCI/NH3) m/z 283.9 (M+H)$^+$.

Example 96B 33 mls (33 mMol) of 1M potassium tert-butoxide in tetrahydrofuran was added to a mixture of 9.2 g (32.4 mMol) of the compound from example 96A in 50 mls of N,N-dimethylformamide and the reaction was stirred for 2 hours at ambient temperature. 150 mls of diethyl ether was added and the organic phase was washed with water, saturated NaCl, dried with MgSO$_4$, filtered and the solvent evaporated to provide Example 96B. $^1$H NMR (300 MHz, DMSO-d$_6$) δ ppm 7.34-7.41 (m, 2 H) 7.23-7.29 (m, 2 H) 3.59 (t, J=4.41 Hz, 2 H) 3.05 (t, J=4.41 Hz, 2 H) 1.26 (s, 9 H). MS (DCI/NH3) m/z 204.0 (M+H)$^+$.

Example 96C 5.0 g (33 mMol) of trifluoromethanesulfonic acid [CAS number 1493-13-6] was added to a solution of 7.0 g (35 mMol) of the compound from example 96B in 200 mls of dichloroethane and the solution was heated to 60° C. for 1 hour. The reaction was washed with 10% NaHCO$_3$, water, and saturated NaCl, the organic layer was dried with MgSO$_4$, filtered and the solvent evaporated. The resulting oil was further purified by flash chromatography using a gradient from hexane to 35% ethyl acetate in hexane to provide Example 96C. $^1$H NMR (300 MHz, DMSO-d$_6$) δ ppm 7.56 (d, J=2.37 Hz, 1 H) 7.37 (dd, J=8.82, 2.37 Hz, 1 H) 6.72 (d, J=8.48 Hz, 1 H) 6.60 (s, 1 H) 3.39 (t, J=6.95 Hz, 2 H) 2.45-2.52 (m, 2 H) 1.21 (s, 9 H). MS (DCI/NH3) m/z 204.0 (M+H)$^+$.

Example 96D

A reaction mixture of 0.25 g (1.2 mMol) of the compound from example 96C, 0.32 g (1.8 mMol) of benzyl bromide, 0.3 mls (1.8 mMol) N,N-diisopropylethylamine in 2.0 mls of N-methyl-2-pyrrolidinone was heated at 60° C. in a sealed tube for 18 hours. 50 mls of dichloromethane was added and washed with water and saturated NaCl, the organic phase was dried with MgSO$_4$, filtered and the solvent evaporated. The residue was purified by flash chromatography using a gradient from hexane to 25% ethyl acetate in hexane to provide Example 96D. $^1$H NMR (300 MHz, DMSO-d$_6$) δ ppm 7.68 (t, J=2.54 Hz, 1 H) 7.40 (dt, J=8.90, 2.84 Hz, 1 H) 7.31-7.36 (m, 4 H) 7.22-7.30 (m, 1 H) 6.69-6.76 (m, 1 H) 4.60 (s, 2 H) 3.55-3.62 (m, 2 H) 2.62-2.69 (m, 2 H) 1.19-1.22 (m, 9 H). MS (DCI/NH3) m/z 294.1 (M+H)$^+$.

Example 96E

A reaction mixture of 0.22 g (0.75 mMol) of the compound from example 96D, 0.3 g (3.75 mMol) of methoxylamine hydrochloride in 1.5 mls of pyridine was stirred for 2 hours at room temperature. 100 mls of ethyl acetate was added and the organic layer washed with water, the organic layer was dried with MgSO$_4$, filtered and the solvent was evaporated. The residue resuspended in 30% ethyl acetate in hexane and filtered through a silica plug to provide Example 96E. $^1$H NMR (300 MHz, DMSO-d$_6$) δ ppm 7.76 (d, J=2.71 Hz, 1 H) 7.28-7.36 (m, 4 H) 7.21-7.26 (m, 1 H) 7.17 (dd, J=8.82, 2.37 Hz, 1 H) 6.62 (d, J=8.82 Hz, 1 H) 4.46 (s, 2 H) 3.89 (s, 3 H) 3.26 (t, J=6.61 Hz, 2 H) 2.78 (t, J=6.44 Hz, 2 H) 1.21 (s, 9 H). MS (DCI/NH3) m/z 323.1 (M+H)$^+$.

Example 96F 0.25 g (0.75 mMol) of the compound from example 96E in 20 mls of 7N $NH_3$ in methanol and 2 g of Raney-Nickel were reacted in a Parr shaker under 60 psi of $H_2$ for 18 hours at ambient temperature. The catalyst was filtered from the reaction and was washed with methanol, the solvent was evaporated and the compound used without further purification.

Example 96G

N-(1-benzyl-6-tert-butyl-1,2,3,4-tetrahydroquinolin-4-yl)-N'-1H-indazol-4-ylurea A reaction mixture of 0.2 g (0.75 mMol) of the compound from example 96F in 2 mls of N,N-dimethylformamide, 0.26 mls (1.5 mMol) of N,N-diisopropylethylamine and 0.25 g (0.75 mMol) of the compound from example 24D was stirred for 18 hours at ambient temperature. 50 mls of water was added to the reaction and the precipitate collected by filtration. The precipitate was solubilized in ethyl acetate and the organic phase extracted with water and saturated NaCl. The organic phase was dried with $MgSO_4$, filtered and the solvent evaporated. 2 mls of 5N NaOH in methanol was added to the residue and stirred at room temperature for 1 hour. 100 mls of ethyl acetate was added and the organic phase extracted with water and saturated NaCl. The organic phase was dried with $MgSO_4$, filtered and the solvent removed, and the final compound purified by flash chromatography using a gradient from dichloromethane to 20% methanol in dichloromethane with a few drops of $NH_4OH$ as the solvent system to provide the titled compound. $^1H$ NMR (300 MHz, DMSO-$d_6$) δ ppm 8.58 (s, 1 H) 8.03 (s, 1 H) 7.70 (d, J=7.46 Hz, 1 H) 7.26-7.38 (m, 5 H) 7.21-7.25 (m, 1 H) 7.16-7.20 (m, 1 H) 7.02-7.09 (m, 2 H) 6.75 (d, J=7.12 Hz, 1 H) 6.51 (d, J=8.82 Hz, 1 H) 4.78-4.85 (m, 1 H) 4.44-4.61 (m, 2 H) 3.33-3.47 (m, 2 H) 3.17 (s, 1 H) 1.97-2.13 (m, 2 H) 1.20 (s, 9 H). MS (DCI/NH3) m/z 454.2 (M+H)$^+$

Example 97

N-(1-benzyl-6-methoxy-1,2,3,4-tetrahydroquinolin-4-yl)-N'-1H-indazol-4-ylurea

Example 97A

A mixture of 24.7 g (0.14 Mol) of 3-bromopropionyl chloride in 50 mls of dichloromethane was added dropwise to a mixture of 17.2 g (0.14 Mol) 4-methoxyaniline and 39.8 g (0.29 Mol) of $K_2CO_3$ in 150 mls of dichloromethane and the reaction was stirred for 18 hours. 100 mls of water was added slowly, the organic layer was separated and washed twice with water dried with $MgSO_4$, filtered and the solvent removed to provide Example 97A. $^1H$ NMR (300 MHz, DMSO-$d_6$) δ ppm 9.90 (s, 1 H) 7.47-7.53 (m, 2 H) 6.84-6.91 (m, 2 H) 3.69-3.75 (m, 5 H) 2.91 (t, J=6.44 Hz, 2 H). MS (DCI/NH3) m/z 257.9 (M+H)$^+$.

Example 97B 33 mls (33 mMol) of 1M potassium tert-butoxide in tetrahydrofuran was added to a mixture of 8.5 g (33 mMol) of the compound from example 97A in 50 mls of N,N-dimethylformamide and the reaction was stirred for 2 hours. 150 mls of diethyl ether was added and the organic phase was washed with water, saturated NaCl, dried with $MgSO_4$, filtered and the solvent evaporated to provide Example 97B. $^1H$ NMR (300 MHz, DMSO-$d_6$) δ ppm 7.26-7.31 (m, 2 H) 6.91-6.96 (m, 2 H) 3.72 (s, 3 H) 3.58 (t, J=4.41 Hz, 2 H) 3.03 (t, J=4.41 Hz, 2 H). MS (DCI/NH3) m/z 177.9 (M+H)$^+$.

Example 97C 5.0 g (33 mMol) of trifluoromethanesulfonic acid [CAS No. 1493-13-6] was added to a solution of 6.2 g (35 mMol) of the compound from example 97B in 200 mls of dichloroethane and the solution was heated to 60° C. for 1 hour. The reaction was washed with 10% $NaHCO_3$, water, and saturated NaCl. The organic layer was dried with $MgSO_4$, filtered and the solvent evaporated. The resulting oil was further purified by flash chromatography with a gradient from hexane to 50% ethyl acetate in hexane to provide Example 97C. $^1H$ NMR (300 MHz, DMSO-$d_6$) δ ppm 7.07 (d, J=3.05 Hz, 1 H) 6.98 (dd, J=8.82, 3.05 Hz, 1 H) 6.75 (d, J=8.48 Hz, 1 H) 6.43 (s, 1 H) 3.67 (s, 3 H) 3.33-3.43 (m, 2 H) 2.39-2.60 (m, 2 H). MS (DCI/NH3) m/z 178.0 (M+H)$^+$.

Example 97D

A reaction mixture of 0.4 g (2.4 mMol) of the compound from example 97C, 0.6 g (3.6 mMol) of benzyl bromide, 0.6 mls (3.4 mMol) N,N-diisopropylethylamine in 2.0 mls of N-methyl-2-pyrrolidinone was heated at 60° C. in a sealed tube for 18 hours. 50 mls of dichloromethane was added and washed with water and saturated NaCl, the organic phase was dried with $MgSO_4$, filtered and the solvent evaporated. The residue was purified by flash chromatography using a gradient from hexane to 30% ethyl acetate in hexane to provide Example 97D. $^1H$ NMR (300 MHz, DMSO-$d_6$) δ ppm 7.31-7.37 (m, 4 H) 7.23-7.30 (m, 1 H) 7.21 (d, J=3.39 Hz, 1 H) 7.02 (dd, J=9.16, 3.39 Hz, 1 H) 6.78 (d, J=9.49 Hz, 1 H) 4.58 (s, 2 H) 3.68 (s, 3 H) 3.51-3.57 (m, 2 H) 2.63-2.69 (m, 2 H). MS (DCI/NH3) m/z 268.0 (M+H)$^+$.

Example 97E

A reaction mixture of 0.5 g (1.9 mMol) of the compound from example 97D, 0.8 g (9.4 mMol) of methoxylamine hydrochloride in 3.0 mls of pyridine was stirred for 2 hours at room temperature. 100 mls of ethyl acetate was added and the organic layer extracted with water, organic layer was dried with $MgSO_4$, filtered, and the solvent was evaporated. The residue was resuspended in 30% ethyl acetate in hexane and filtered through a silica plug to provide Example 97E. $^1H$ NMR (300 MHz, DMSO-$d_6$) δ ppm 7.28-7.35 (m, 5 H) 7.20-7.27 (m, 1 H) 6.79 (dd, J=8.82, 3.05 Hz, 1 H) 6.62-6.69 (m, 1H) 4.43 (s, 2 H) 3.89 (s, 3 H) 3.66 (s, 3 H) 3.20 (t, J=6.44 Hz, 2 H) 2.77 (t, J=6.61 Hz, 2 H). MS (DCI/NH3) m/z 297.1 (M+H)$^+$.

Example 97F 0.4 g (1.4 mMol) of the compound from example 97E in 20 mls of 7N $NH_3$ in methanol and 2 g of Raney-Nickel are reacted in a Parr shaker under 60 psi of $H_2$ for 18 hours at ambient temperature. The catalyst was filtered from the reaction, washed with methanol, the solvent was evaporated and the compound used without further purification. MS (DCI/NH3) m/z 269.0 (M+H)$^+$.

Example 97G

N-(1-benzyl-6-methoxy-1,2,3,4-tetrahydroquinolin-4-yl)-N'-1H-indazol-4-ylurea A reaction mixture of 0.34 g (1.3 mMol) of the compound from example 97F in 2 mls of N,N-dimethylformamide, 0.5 mls (2.9 mMol) of N,N-diisopropylethylamine and 0.46 g (1.4 mMol) of the compound from example 24D and allowed to react for 18 hours at ambient temperature. 50 mls of water was added to the reaction and the precipitate collected by filtration. The precipitate was solubilized in ethyl acetate and the organic phase extracted with water and saturated NaCl. The organic phase was dried with MgSO$_4$, filtered and the solvent evaporated. 2 mls of 5N NaOH in methanol was added to the residue and stirred at room temperature for 1 hour. 100 mls of ethyl acetate was added and the organic phase washed with water and saturated NaCl. The organic phase was dried with MgSO$_4$, filtered and the solvent removed. The residue was purified by flash chromatography using a gradient from dichloromethane to 20% methanol in dichloromethane with a few drops of NH$_4$OH as the solvent system to provide the titled compound. $^1$H NMR (300 MHz, DMSO-d$_6$) δ ppm 12.99 (s, 1 H) 8.58 (s, 1 H) 8.03 (s, 1 H) 7.70 (d, J=7.46 Hz, 1 H) 7.21-7.37 (m, 6 H) 7.06 (d, J=8.48 Hz, 1 H) 6.82 (d, J=2.71 Hz, 1 H) 6.75 (d, J=7.12 Hz, 1 H) 6.65-6.71 (m, 1 H) 6.52 (d, J=8.82 Hz, 1H) 4.77-4.88 (m, 1 H) 4.48 (s, 2 H) 3.63 (s, 3 H) 3.32-3.39 (m, 2 H) 1.99-2.08 (m, 2 H). MS (DCI/NH3) m/z 428.0 (M+H)$^+$.

Example 98

N-[1-(cyclohexylmethyl)-6-methoxy-1,2,3,4-tetrahydroquinolin-4-yl]-N'-1H-indazol-4-ylurea Example 98A In 2 mls of dichloroethane, 0.4 g (2.3 mMol) of the compound obtained from example 97C with 0.8 g (6.8 mMol) of cyclohexanecarboxaldehyde and 1 drop of glacial acetic acid were allowed to stir at room temperature for 30 minutes. 1.4 g (6.6 mMol) of sodium triacetoxyborohydride was added and the reaction continued for 18 hours. 100 mls of dichloromethane was added and then washed with 10% NaHCO$_3$, water, the organic layer dried with MgSO$_4$, filtered and the solvent evaporated. The residue was purified by flash chromatography using a gradient from hexane to 30% ethyl acetate in hexane to provide Example 98A. $^1$H NMR (300 MHz, DMSO-d$_6$) δ ppm 7.16 (d, J=3.39 Hz, 1 H) 7.06 (dd, 1 H) 6.80 (d, J=9.49 Hz, 1 H) 3.68 (s, 3 H) 3.40-3.47 (m, 2 H) 3.11 (d, J=7.12 Hz, 2 H) 2.52-2.59 (m, 2 H) 1.62-1.78 (m, 6 H) 1.10-1.25 (m, 3 H) 0.91-1.05 (m, 2 H)). MS (DCI/NH3) m/z 274.1 (M+H)$^+$.

Example 98B

A reaction mixture of 0.4 g (1.5 mMol) of the compound from example 98A, 0.6 g (7.5 mMol) of methoxylamine hydrochloride in 2.0 mls of pyridine was stirred for 2 hours at room temperature. 100 mls of ethyl acetate was added and the organic layer washed with water. The organic layer was dried with MgSO$_4$, filtered and the solvent was evaporated. The residue was resuspended in 30% ethyl acetate in hexane and filtered through a silica plug to provide Example 98B. $^1$H NMR (300 MHz, DMSO-d$_6$) δ ppm 7.25 (d, J=3.05 Hz, 1 H) 6.85 (dd, J=8.99, 3.22 Hz, 1 H) 6.66 (d, J=9.16 Hz, 1 H) 3.87 (s, 3 H) 3.66 (s, 3 H) 3.13 (t, J=6.61 Hz, 2 H) 2.98 (d, J=6.78 Hz, 2 H) 2.68 (t, J=6.44 Hz, 2 H) 1.51-1.79 (m, 6 H) 1.06-1.30 (m, 3 H) 0.76-1.04 (m, 2 H). MS (DCI/NH3) m/z 303.1 (M+H)$^+$.

Example 98C 0.4 g (1.3 mMol) of the compound from example 98B in 20 mls of 7N NH$_3$ in methanol and 2 g of Raney-Nickel are reacted in a Parr shaker under 60 psi of H$_2$ for 18 hours at ambient temperature. The catalyst was filtered from the reaction and was washed with methanol. The solvent was evaporated and the compound used without further purification. MS (DCI/NH3) m/z 275.2 (M+H)$^+$.

Example 98D

N-[1-(cyclohexylmethyl)-6-methoxy-1,2,3,4-tetrahydroquinolin-4-yl]-N'-1H-indazol-4-ylurea A reaction mixture of 0.25 g (0.9 mMol) of the compound from example 98C in 2 mls of N,N-dimethylformamide, 0.3 mls (1.7 mMol) of N,N-diisopropylethylamine and 0.3 g (0.9 mMol) of the compound from example 24D was stirred for 18 hours at ambient temperature 50 mls of water was added to the reaction and the precipitate collected by filtration. The precipitate was solubilized in ethyl acetate and the organic phase extracted with water and saturated NaCl. The organic phase was dried with MgSO$_4$, filtered and the solvent evaporated. 2 mls of 5N NaOH in methanol was added to the residue and stirred at room temperature for 1 hour. 100 mls of ethyl acetate was added and the organic phase extracted with water and saturated NaCl. The organic phase was dried with MgSO$_4$, filtered and the solvent removed, and the residue purified by flash chromatography using a gradient from dichloromethane to 20% methanol in dichloromethane with a few drops of NH$_4$OH as the solvent system to provide the titled compound. $^1$H NMR (300 MHz, DMSO-d$_6$) δ ppm 12.99 (s, 1 H) 8.54 (s, 1 H) 8.02 (s, 1 H) 7.69 (d, J=7.12 Hz, 1 H) 7.17-7.24 (m, 1 H) 7.05 (d, J=8.14 Hz, 1 H) 6.68-6.78 (m, 3 H) 6.54 (d, J=8.48 Hz, 1 H) 4.76 (ddd, J=7.29, 4.24, 4.07 Hz, 1 H) 3.64 (s, 3 H) 3.20-3.29 (m, 2 H) 3.03 (t, J=6.27 Hz, 2 H) 1.85-2.00 (m, 2 H) 1.62-1.78 (m, 6 H) 1.13-1.26 (m, 3 H) 0.88-1.03 (m, 2 H). MS (DCI/NH3) m/z 434.1 (M+H)$^+$.

Example 99

N-(1-benzyl-6-fluoro-1,2,3,4-tetrahydroquinolin-4-yl)-N'-1H-indazol-4-ylurea

Example 99A

A mixture of 27.7 g (0.16 Mol) of 3-bromopropionyl chloride in 50 mls of dichloromethane was added dropwise to a mixture of 18.0 g (0.16 Mol) 4-fluoroaniline and 45.0 g (0.33 Mol) of K$_2$CO$_3$ in 150 mls of dichloromethane and the reaction was stirred for 18 hours. 100 mls of water was added slowly, the organic layer was separated and washed twice with water dried with MgSO$_4$, filtered and the solvent removed to provide Example 99A. $^1$H NMR (300 MHz, DMSO-d$_6$) δ ppm 10.10 (s, 1 H) 7.58-7.66 (m, 2 H) 7.10-7.20 (m, 2 H) 3.73 (t, J=6.27 Hz, 2 H) 2.94 (t, J=6.27 Hz, 2 H). MS (DCI/NH3) m/z 245.8 (M+H)$^+$.

Example 99B 12 mls (12 mMol) of 1M potassium tert-butoxide in tetrahydrofuran was added to a mixture of 2.9 g (12 mMol) of the compound from example 99A in 20 mls of N,N-dimethylformamide and the reaction was stirred for 2 hours. 100 mls of diethyl ether was added and the organic phase was washed with water, saturated NaCl, dried with MgSO$_4$, filtered and the solvent evaporated to provide Example 99B. $^1$H NMR (300 MHz, DMSO-d$_6$) δ ppm 7.33-7.42 (m, 2 H) 7.16-7.27

(m, 2 H) 3.62 (t, J=4.41 Hz, 2 H) 3.08 (t, J=4.58 Hz, 2 H). MS (DCI/NH3) m/z 165.9 (M+H)$^+$.

Example 99C 5.0 g (33 mMol) of trifluoromethanesulfonic acid [CAS No. 1493-13-6] was added to a solution of 5.0 g (30 mMol) of the compound from example 99B in 200 mls of dichloroethane and the solution was heated to 60° C. for 1 hour. The reaction was washed with 10% NaHCO$_3$, water, and saturated NaCl. The organic layer was dried with MgSO$_4$, filtered and the solvent evaporated. The resulting oil was further purified by flash chromatography using a gradient from hexane to 35% ethyl acetate in hexane to provide Example 99C. $^1$H NMR (300 MHz, DMSO-d$_6$) δ ppm 7.16-7.27 (m, 2 H) 6.78-6.83 (m, 1 H) 6.76 (s, 1 H) 3.37-3.44 (m, 2 H) 2.52-2.55 (m, 2 H). MS (DCI/NH3) m/z 165.9 (M+H)$^+$.

Example 99D

A reaction mixture of 0.2 g (1.2 mMol) of the compound from example 99C, 0.32 g (1.8 mMol) of benzyl bromide, 0.3 mls (1.8 mMol) N,N-diisopropylethylamine in 2.0 mls of N-methyl-2-pyrrolidinone was heated at 60° C. in a sealed tube for 18 hours. 50 mls of dichloromethane was added, extracted with water and saturated NaCl, the organic phase was dried with MgSO$_4$, filtered and the solvent evaporated. The residue was purified by flash chromatography using a gradient from hexane to 40% ethyl acetate in hexane to provide Example 99D. $^1$H NMR (300 MHz, DMSO-d$_6$) δ ppm 7.31-7.40 (m, 5 H) 7.21-7.30 (m, 2 H) 6.81 (dd, J=9.32, 4.24 Hz, 1 H) 4.63 (s, 2 H) 3.58-3.65 (m, 2 H) 2.67-2.73 (m, 2 H). MS (DCI/NH3) m/z 256.0 (M+H)$^+$.

Example 99E

A reaction mixture of 0.25 g (1.0 mMol) of the compound from example 99D, 0.35 g (5.0 mMol) of hydroxylamine hydrochloride in 1.5 mls of pyridine was stirred for 2 hours at room temperature. 100 mls of ethyl acetate was added and the organic layer extracted with water, organic layer was dried with MgSO$_4$, filtered and the solvent was evaporated and the residue resuspended in 30% ethyl acetate in hexane and filtered through a silica plug. The solvent was evaporated and the residue dissolved in 1 mls of pyridine and 0.1 mls of acetic anhydride was added and the reaction stirred for 18 hours at ambient temperature. The solvent was removed the residue dissolved in 30% ethyl acetate in hexane and filtered through a silica plug to provide Example 99E. $^1$H NMR (300 MHz, DMSO-d$_6$) δ ppm 7.55 (dd, J=9.83, 3.05 Hz, 1 H) 7.22-7.37 (m, 5 H) 7.13 (ddd, J=9.32, 8.14, 3.22 Hz, 1 H) 6.75 (dd, J=9.16, 4.75 Hz, 1 H) 4.54 (s, 2 H) 3.37 (t, J=6.61 Hz, 2 H) 2.96 (t, J=6.78 Hz, 2 H) 2.21 (s, 3 H). MS (DCI/NH3) m/z 313.0 (M+H)$^+$.

Example 99F 0.25 g (0.8 mMol) of the compound from example 99E in 20 mls of 7N NH$_3$ in methanol and 2 g of Raney-Nickel are reacted in a Parr shaker under 60 psi of H$_2$ for 4 hours at ambient temperature. The catalyst was filtered from the reaction and was washed with methanol, the solvent was evaporated and the compound used without further purification. MS (DCI/NH3) m/z 257.1 (M+H)$^+$.

Example 99G

N-(1-benzyl-6-fluoro-1,2,3,4-tetrahydroquinolin-4-yl)-N'-1H-indazol-4-ylurea

A reaction mixture of 0.2 g (0.8 mMol) of the compound from example 99F in 2 mls of N,N-dimethylformamide, 0.26 mls (1.5 mMol) of N,N-diisopropylethylamine and 0.25 g (0.75 mMol) of the compound from example 24D was stirred for 18 hours at ambient temperature. 50 mls of water was added to the reaction and the precipitate collected by filtration. The precipitate was solubilized in ethyl acetate and the organic phase extracted with water and saturated NaCl. The organic phase was dried with MgSO$_4$, filtered and the solvent evaporated. 2 mls of 5N NaOH in methanol was added to the residue and stirred at room temperature for 1 hour. 100 mls of ethyl acetate was added and the organic phase extracted with water and saturated NaCl. The organic phase was dried with MgSO$_4$, filtered and the solvent removed, and the residue purified by flash chromatography using a gradient from dichloromethane to 20% methanol in dichloromethane with a few drops of NH$_4$OH as the solvent system to provide the titled compound. $^1$H NMR (300 MHz, DMSO-d$_6$) δ ppm 13.01 (s, 1 H) 8.61 (s, 1 H) 8.05 (s, 1 H) 7.69 (d, J=7.46 Hz, 1 H) 7.22-7.38 (m, 6 H) 7.07 (d, J=8.48 Hz, 1 H) 7.02 (dd, J=9.49, 3.05 Hz, 1 H) 6.87 (td, J=8.82, 3.05 Hz, 1 H) 6.79 (d, J=7.46 Hz, 1 H) 6.52 (dd, J=9.16, 4.75 Hz, 1 H) 4.83-4.90 (m, 1 H) 4.53 (s, 2 H) 3.37-3.46 (m, 2 H) 2.01-2.10 (m, 2 H). MS ESI m/z 416.1 (M+H)$^+$.

Example 100

N-[8-chloro-1-(3-methylbutyl)-1,2,3,4-tetrahydroquinolin-4-yl]-N'-1H-indazol-4-ylurea Example 100A A mixture of 7.1 g (0.04 Mol) of 3-bromopropionyl chloride in 50 mls of dichloromethane was added dropwise to a mixture of 5.0 g (0.04 Mol) 2-chloroaniline and 11.0 g (0.08 Mol) of K$_2$CO$_3$ in 100 mls of dichloromethane and the reaction was stirred for 18 hours at ambient temperature. 100 mls of water was added slowly, the organic layer was separated and washed twice with water dried with MgSO$_4$, filtered and the solvent evaporated to provide Example 100A. $^1$H NMR (300 MHz, CDCl$_3$) δ ppm 8.37 (d, J=8.14 Hz, 1 H) 7.70 (s, 1 H) 7.38 (dd, J=8.14, 1.36 Hz, 1 H) 7.23-7.32 (m, 1 H) 7.06 (td, J=7.71, 1.53 Hz, 1 H) 3.72 (t, J=6.61 Hz, 2 H) 3.02 (t, J=6.61 Hz, 2 H). MS (DCI/NH3) m/z 261.9 (M+H)$^+$.

Example 100B 35 mls (35 mMol) of 1M potassium tert-butoxide in tetrahydrofuran was added to a mixture of 9.0 g (34 mMol) of the compound from example 100A in 20 mls of N,N-dimethylformamide and the reaction was stirred for 2 hours at ambient temperature. 100 mls of diethyl ether was added and the organic phase was washed with water, saturated NaCl, dried with MgSO$_4$, filtered and the solvent evaporated to provide Example 100B. $^1$H NMR (300 MHz, CDCl$_3$) δ ppm 7.93 (dd, J=8.14, 1.70 Hz, 1 H) 7.33 (dd, J=8.14, 1.36 Hz, 1 H) 7.19-7.28 (m, 1 H) 7.02-7.11 (m, 1 H) 4.04 (t, J=4.75 Hz, 2 H) 3.12-3.17 (m, 2 H). MS (DCI/NH3) m/z 181.9 (M+H)$^+$.

Example 100C 5.0 g (33 mMol) of trifluoromethanesulfonic acid [1493-13-6] was added to a solution of 6.0 g (33 mMol) of the compound from example 100B in 200 mls of dichloroethane and the solution was stirred for 1 hour. The reaction was washed with NaHCO$_3$, water, and saturated NaCl the organic layer was dried with MgSO$_4$ and the solvent evaporated. The resulting oil was further purified by flash chromatography with a gradient from hexane to 30% ethyl acetate in hexane to provide Example 100C. $^1$H NMR (300 MHz, DMSO-d$_6$) δ ppm 7.59 (ddd, J=7.80, 1.36, 0.68 Hz, 1 H) 7.48 (dd, J=7.63, 1.53 Hz, 1 H) 6.58-6.67 (m, 2 H) 3.51 (td, J=7.12, 2.37 Hz, 2 H) 2.54-2.62 (m, 2 H). MS (DCI/NH3) m/z 181.9 (M+H)$^+$.

Example 100D

In 2 mls of dichloroethane, 0.15 g (0.8 mMol) of the compound obtained from example 100C with 0.2 g (2.4 mMol) of isovaleraldehyde and 1 drop of glacial acetic acid were allowed to mix at room temperature for 30 minutes. 0.8 g (4 mMol) of sodium triacetoxyborohydride was added and the reaction continued for 18 hours at 55° C. 100 mls of dichloromethane was added and then washed with 10% NaHCO$_3$, 5% citric acid, saturated NaCl, the organic layer dried with MgSO$_4$, filtered and the solvent evaporated. The residue was purified by flash chromatography using a gradient from hexane to 50% ethyl acetate in hexane to provide Example 100D. $^1$H NMR (300 MHz, DMSO-d$_6$) δ ppm 7.73 (dd, J=7.80, 1.70 Hz, 1 H) 7.61 (dd, J=7.80, 1.70 Hz, 1 H) 6.98 (t, J=7.80 Hz, 1 H) 3.46-3.54 (m, 2 H) 3.24-3.31 (m, 2H) 2.65-2.73 (m, 2 H) 1.53-1.67 (m, 3 H) 0.92 (d, J=6.44 Hz, 6 H). MS (DCI/NH3) m/z 252.0 (M+H)$^+$.

Example 100E

A reaction mixture of 0.25 g (1.0 mMol) of the compound from example 100D, 0.35 g (5.0 mMol) of hydroxylamine hydrochloride in 2.0 mls of pyridine was stirred for 2 hours at room temperature. 100 mls of ethyl acetate was added and the organic layer extracted with water, organic layer was dried with MgSO$_4$, filtered, and the solvent was evaporated. The residue dissolved in dichloromethane and filtered through a silica plug. The solvent was evaporated and the residue dissolved in 1 mls of pyridine and 0.1 mls of acetic anhydride was added and the reaction stirred for 18 hours at ambient temperature. The solvent was removed and the residue dissolved in dichloromethane and filtered through a silica plug to provide Example 100E. $^1$H NMR (300 MHz, DMSO-d$_6$) δ ppm 7.90 (dd, J=7.97, 1.53 Hz, 1 H) 7.52 (dd, J=7.97, 1.53 Hz, 1 H) 7.03 (t, J=7.97 Hz, 1 H) 3.22 (t, J=6.27 Hz, 2 H) 3.00-3.09 (m, 2 H) 2.92 (t, J=6.27 Hz, 2 H) 2.22 (s, 3H) 1.50-1.64 (m, 3 H) 0.90 (d, J=6.44 Hz, 6 H). MS (DCI/NH3) m/z 309.1 (M+H)$^+$.

Example 100F 0.25 g (0.8 mMol) of the compound from example 100E in 20 mls of 7N NH$_3$ in methanol and 2 g of Raney-Nickel are reacted in a Parr shaker under 60 psi of H$_2$ for 4 hours at ambient temperature. The catalyst was filtered from the reaction and was washed with methanol, the solvent was evaporated and the compound used without further purification. MS (DCI/NH3) m/z 253.0 (M+H)$^+$.

Example 100G

N-[8-chloro-1-(3-methylbutyl)-1,2,3,4-tetrahydro-quinolin-4-yl]-N'-1H-indazol-4-ylurea A reaction mixture of 0.2 g (0.8 mMol) of the compound from example 100F in 2 mls of N,N-dimethylformamide, 0.26 mls (1.5 mMol) of N,N-diisopropylethylamine and 0.25 g (0.75 mMol) of the compound from example 24D was stirred for 18 hours at ambient temperature. 50 mls of water was added to the reaction and the precipitate collected by filtration. The precipitate was solubilized in ethyl acetate and the organic phase extracted with water and saturated NaCl. The organic phase was dried with MgSO$_4$, filtered and the solvent evaporated. 2 mls of 5N NaOH in methanol was added to the residue and stirred at room temperature for 1 hour. 100 mls of ethyl acetate was added and the organic phase extracted with water and saturated NaCl. The organic phase was dried with MgSO$_4$, filtered and the solvent removed. The residue purified by flash chromatography using a gradient from dichloromethane to 20% methanol in dichloromethane with a few drops of NH$_4$OH as the solvent system to provide the titled compound. $^1$H NMR (300 MHz, DMSO-d$_6$) δ ppm 13.00 (s, 1 H) 8.51 (s, 1 H) 8.01 (s, 1 H) 7.68 (d, J=7.46 Hz, 1 H) 7.25-7.33 (m, 2 H) 7.18-7.25 (m, 1 H) 7.06 (d, J=8.14 Hz, 1 H) 6.92 (t, J=7.80 Hz, 1 H) 6.82 (d, J=8.14 Hz, 1 H) 4.84-4.91 (m, 1 H) 3.16-3.21 (m, 1 H) 2.97-3.12 (m, 3 H) 1.94-2.07 (m, 1 H) 1.77-1.90 (m, 1 H) 1.52-1.68 (m, 3 H) 0.92 (dd, J=6.44, 1.36 Hz, 6 H). MS ESI m/z 412.1 (M+H)$^+$.

Example 101

N-1H-indazol-4-yl-N'-[1-methyl-7-(trifluoromethyl)-1,2,3,4-tetrahydroquinolin-4-yl]urea

Example 101A 4.0 g (18.9 mMol) of 7-trifluoromethyl-quinolin-4-ylamine, 6.2 g (28.4 mMol) of di-tert-butyl dicarbonate, 10 mls of 2N NaOH in 50 mls of tetrahydrofuran was stirred at room temperature for 18 hours. 100 mls of diethyl ether was added and extracted with water and saturated NaCl solution then dried with MgSO$_4$, filtered and the solvent removed. The compound was purified by flash chromatography using a gradient from hexane to 50% ethyl acetate in hexane as solvents to provide Example 101A. $^1$H NMR (300 MHz, DMSO-d$_6$) δ ppm 10.01 (s, 1 H) 8.89 (d, J=5.43 Hz, 1 H) 8.63 (d, J=8.82 Hz, 1 H) 8.29 (s, 1 H) 8.08 (d, J=5.43 Hz, 1 H) 7.83 (dd, J=8.99, 1.87 Hz, 1 H) 1.56 (s, 9 H). MS (DCI/NH3) m/z 313.0 (M+H)$^+$.

Example 101B 2.7 g (8.7 mMol) of the compound from example 101A in 135 mls of methanol with 27 g Raney-Nickel was reacted in a Parr shaker under 45 psi H$_2$. The catalyst was filtered, washed with methanol and the solvent evaporated. $^1$H NMR (300 MHz, DMSO-d$_6$) δ ppm 7.23 (d, J=8.48 Hz, 1 H) 7.11 (d, J=7.80 Hz, 1 H) 6.68-6.77 (m, 2 H) 6.27 (s, 1 H) 4.56-4.70 (m, 1H) 3.22 (td, J=5.68, 1.86 Hz, 2H) 1.70-1.90 (m, 2 H) 1.42 (s, 9 H). MS (DCI/NH3) m/z 317.0 (M+H)$^+$.

Example 101C

A mixture of 0.3 g (0.95 mMol) of the compound from example 101B, 0.5 mls (6.6 mMol) 37% aqueous formaldehyde, 1.0 g (4.7 mMol) of sodium triacetoxyborohydride in 3 mls of acetonitrile was stirred for 2 hours at ambient temperature. The reaction was diluted with 7:1 hexane:ethyl acetate and filtered through a silica plug. The solvent was evaporated and 1 mls of 4N HCl in dioxane was added to the residue and stirred for 1 hour at ambient temperature, methanol was added and the solvent evaporated to provide Example 101C. $^1$H NMR (300 MHz, METHANOL-D4) δ ppm 7.32-7.39 (m, 1 H) 6.90-6.95 (m, 2 H) 4.54 (t, J=4.24 Hz, 1H) 3.37-3.44 (m, 2 H) 3.01 (s, 3 H) 2.10-2.36 (m, 2 H).

Example 101D

N-1H-indazol-4-yl-N'-[1-methyl-7-(trifluoromethyl)-1,2,3,4-tetrahydroquinolin-4-yl]urea A reaction mixture of 0.2 g (0.8 mMol) of the compound from example 101C in 2 mls of N,N-dimethylformamide, 0.26 mls (1.5 mMol) of N,N-diisopropylethylamine and 0.25 g (0.75 mMol) of the compound from example 24D was stirred for 18 hours at ambient temperature 50 mls of water was added to the reaction and the precipitate collected by filtration. The precipitate was solubilized in ethyl acetate and the organic phase extracted with water and saturated NaCl. The organic phase was dried with $MgSO_4$, filtered and the solvent evaporated. 2 mls of 5N NaOH in methanol was added to the residue and stirred at room temperature for 1 hour. 100 mls of ethyl acetate was added and the organic phase extracted with water and saturated NaCl. The organic phase was dried with $MgSO_4$, filtered and the solvent removed, and the final compound purified by flash chromatography using a gradient from dichloromethane to 20% methanol in dichloromethane with a few drops of $NH_4OH$ as the solvent system to provide the titled compound. $^1H$ NMR (300 MHz, $CD_3OD$) δ ppm 8.06 (d, J=0.68 Hz, 1 H) 7.59 (d, J=7.80 Hz, 1 H) 7.36 (d, J=7.80 Hz, 1 H) 7.28-7.33 (m, 1 H) 7.14-7.19 (m, 1 H) 6.88 (d, J=8.14 Hz, 1 H) 6.84 (s, 1 H) 5.00 (t, J=5.26 Hz, 1 H) 3.34-3.41 (m, 2 H) 2.98 (s, 3 H) 2.08-2.17 (m, 2H). MS ESI m/z 390.1 $(M+H)^+$.

Example 102

N-[7-(3,3-dimethylbutyl)-1-methyl-1,2,3,4-tetrahydroquinolin-4-yl]-N'-1H-indazol-4-ylurea Example 102A A mixture of 25.5 g (0.15 Mol) of 3-bromopropionyl chloride in 50 mls of dichloromethane was added dropwise to a mixture of 25.0 g (0.15 Mol) 3-bromoaniline and 41.0 g (0.30 Mol) of $K_2CO_3$ in 150 mls of dichloromethane and the reaction was stirred for 18 hours at ambient temperature. 100 mls of water was added slowly, the organic layer was separated and washed twice with water dried with $MgSO_4$, filtered and the solvent removed to provide Example 102A. $^1H$ NMR (300 MHz, $CDCl_3$) δ ppm 7.78 (s, 1 H) 7.58 (s, 1 H) 7.41 (d, J=8.14 Hz, 1 H) 7.23-7.28 (m, 1 H) 7.17 (t, J=7.97 Hz, 1H) 3.69 (t, J=6.44 Hz, 2 H) 2.94 (t, J=6.44 Hz, 2 H). MS (DCI/NH3) m/z 305.9 $(M+H)^+$.

Example 102B 28 mls (28 mMol) of 1M potassium tert-butoxide in tetrahydrofuran was added to a mixture of 8.5 g (28 mMol) of the compound from example 102A in 50 mls of N,N-dimethylformamide and the reaction was stirred for 2 hours. 150 mls of diethyl ether was added and the organic phase was washed with water, saturated NaCl, dried with $MgSO_4$ and the solvent evaporated to provide Example 102B. $^1H$ NMR (300 MHz, DMSO-$d_6$) δ ppm 7.53-7.56 (m, 1 H) 7.22-7.35 (m, 3 H) 3.65 (t, J=4.58 Hz, 2 H) 3.09 (t, J=4.58 Hz, 2 H). MS (DCI/NH3) m/z 225.7 $(M+H)^+$.

Example 102C 5.0 g (33 mMol) of trifluoromethanesulfonic acid [CAS No. 1493-13-6] was added to a solution of 28 mMol of the compound from example 102B in 250 mls of dichloroethane and the solution was stirred for 1 hour at ambient temperature. The reaction was washed with 10% $NaHCO_3$, water, and saturated NaCl the organic layer was dried with $MgSO_4$, filtered and the solvent evaporated. The resulting oil was further purified by flash chromatography using a gradient from hexane to 40% ethyl acetate in hexane then 100% ethyl acetate to provide Example 102C. $^1H$ NMR (300 MHz, DMSO-$d_6$) δ ppm 7.48 (d, J=8.48 Hz, 1 H) 7.00 (s, 1 H) 6.98 (d, J=1.70 Hz, 1 H) 6.72 (dd, J=8.48, 2.03 Hz, 1 H) 3.44 (td, J=7.12, 2.03 Hz, 2 H) 2.52-2.57 (m, 2 H). MS (DCI/NH3) m/z 225.9 $(M+H)^+$.

Example 102D

A mixture of 0.25 g (1.1 mMol) of the product from example 102C, 0.23 g (7.7 mMol) of paraformaldehyde and a drop of glacial acetic acid in 1 mls of dichloroethane was stirred for 30 minutes at ambient temperature. 1.1 g (5.5 mMol) of sodium triacetoxyborohydride was added and the reaction stirred for 18 hours at ambient temperature. 100 mls of ethyl acetate was added and then washed with 10% $NaHCO_3$, 5% citric acid, saturated NaCl, the organic layer dried with $MgSO_4$, filtered, and the solvent evaporated. The residue was purified by flash chromatography using a gradient from hexane to 50% ethyl acetate in hexane to provide Example 102D.

Example 102E

A mixture of 0.3 g (1.3 mMol) of the compound from example 102D, 0.16 g (2 mMol) of 3,3 dimethyl-1-butyne, 46 mg (0.07 mMol) bis(triphenylphosphine)palladium(II) dichloride, 12 mg (0.07 mMol) CuCl, 68 mg (0.26 mMol) triphenylphosphine, 1.5 mls triethylamine in 0.5 mls N,N-dimethylformamide was heated under microwave irradiation at 130° C. for 40 minutes. The reaction was cooled, diluted with 50% ethyl acetate in hexane and filtered through a silica plug. The solvent was evaporated and the residue purified by flash chromatography using a gradient from hexane to 50% ethyl acetate in hexane to provide Example 102E. $^1H$ NMR (300 MHz, $CD_3OD$) δ ppm 7.71 (d, J=8.14 Hz, 1 H) 6.77 (d, J=1.36 Hz, 1 H) 6.66 (dd, J=7.80, 1.36 Hz, 1 H) 3.44-3.51 (m, 2 H) 2.98 (s, 3 H) 2.65-2.71 (m, 2 H) 1.32 (s, 9 H). MS (DCI/NH3) m/z 242.0 $(M+H)^+$.

Example 102F

A mixture of 0.2 g (0.9 mMol) of the compound from example 102E and 0.4 g (5 mMol) of methoxylamine hydrochloride in 4 mls of pyridine was stirred for 18 hours at ambient temperature. The reaction was diluted with dichloromethane and filtered through a silica plug. The solvent was evaporated and Example 102F was used without further purification. LCMS m/z 271.0 $(M+H)^+$.

Example 102G 0.15 g (0.6 mMol) of the compound from example 102F in 10 mls of 7N $NH_3$ in methanol and 1.0 g of Raney-Nickel are reacted for 16 hours under 60 psi $H_2$ at room temperature. The catalyst was filtered, washed with methanol and the solvent removed. The compound was used without further purification. LCMS m/z 247.3 $(M+H)^+$.

Example 102H

N-[7-(3,3-dimethylbutyl)-1-methyl-1,2,3,4-tetrahydroquinolin-4-yl]-N'-1H-indazol-4-ylurea A reaction mixture of 0.15 g (0.6 mMol) of the compound from example 102G in 2 mls of N,N-dimethylformamide, 0.26 mls (1.5 mMol) of N,N-diisopropylethylamine and 0.2 g (0.6 mMol) of the compound from example 24D was stirred for 18 hours at ambient temperature. 50 mls of water was added to the reaction and the precipitate collected by filtration. The precipitate was solubilized in ethyl acetate and the organic phase extracted with water and saturated NaCl. The organic phase was dried with $MgSO_4$, filtered and the solvent evaporated. 2 mls of 5N NaOH in methanol was added to the residue and stirred at room temperature for 1 hour. 100 mls of ethyl acetate was added and the organic phase extracted with water and saturated NaCl. The organic phase was dried with $MgSO_4$, filtered and the solvent removed, and the residue purified by flash chromatography using 2% methanol in dichloromethane with a few drops of $NH_4OH$ as the solvent system to provide the titled compound. $^1H$ NMR (300 MHz, DMSO-$d_6$) δ ppm 12.99 (s, 1 H) 8.51 (s, 1 H) 8.00 (s, 1 H) 7.70 (d, J=7.46 Hz, 1 H) 7.21 (t, J=7.97 Hz, 1 H) 7.04 (dd, J=8.14, 3.39 Hz, 2 H) 6.65 (d, J=7.46 Hz, 1H) 6.43-6.50 (m, 2 H) 4.72-4.82 (m, 1 H) 3.15-3.28 (m, 2 H) 2.88 (s, 3 H) 2.40-2.48 (m, 2 H) 1.91-2.03 (m, 2 H) 1.42 (ddd, J=8.48, 4.75, 4.41 Hz, 2 H) 0.94 (s, 9 H). MS ESI m/z 406.2 $(M+H)^+$.

Example 103

N-(7-fluoro-1-methyl-1,2,3,4-tetrahydroquinolin-4-yl)-N'-1H-indazol-4-ylurea

Example 103A

A mixture of 35.0 g (0.2 Mol) of 3-bromopropionyl chloride in 50 mls of dichloromethane was added dropwise to a mixture of 22.7 g (0.2 Mol) 3-fluoroaniline and 55.0 g (0.4 Mol) of $K_2CO_3$ in 150 mls of dichloromethane and the reaction was stirred for 18 hours at ambient temperature. 100 mls of water was added slowly, the organic layer was separated and washed twice with water dried with $MgSO_4$, filtered and the solvent removed to provide Example 103A. $^1H$ NMR (300 MHz, DMSO-$d_6$) δ ppm 10.27 (s, 1 H) 7.61 (dt, J=11.78, 2.08 Hz, 1 H) 7.27-7.39 (m, 2 H) 6.84-6.92 (m, 1 H) 3.73 (t, J=6.44 Hz, 2 H) 2.97 (t, J=6.27 Hz, 2 H). MS (DCI/NH3) m/z 245.8 $(M+H)^+$.

Example 103B 15 mls (15 mMol) of 1M potassium tert-butoxide in tetrahydrofuran was added to a mixture of 3.7 g (15 mMol) of the compound from example 103A in 50 mls of N,N-dimethylformamide and the reaction was stirred for 2 hours. 150 mls of diethyl ether was added and the organic phase was washed with water, saturated NaCl, dried with $MgSO_4$ and the solvent evaporated. The compound was used without further purification.

Example 103C 2.0 g (13.3 mMol) of trifluoromethanesulfonic acid [CAS No. 1493-13-6] was added to a solution of 2.3 g (14 mMol) of the compound from example 103B in 200 mls of dichloroethane and the solution was stirred at room temperature for 18 hours at ambient temperature. The reaction was washed with 10% $NaHCO_3$, water, and saturated NaCl the organic layer was dried with $MgSO_4$, filtered and the solvent evaporated. The resulting oil was further purified by flash chromatography using a gradient from hexane to 40% ethyl acetate in hexane then 100% ethyl acetate to provide Example 103C. $^1H$ NMR (300 MHz, DMSO-$d_6$) δ ppm 7.64 (dd, J=8.82, 6.78 Hz, 1 H) 7.03 (s, 1 H) 6.50 (dd, J=11.53, 2.37 Hz, 1 H) 6.39 (td, J=8.73, 2.54 Hz, 1 H) 3.44 (td, J=7.12, 2.03 Hz, 2 H) 2.49-2.54 (m, 2 H). MS (DCI/NH3) m/z 166.0 $(M+H)^+$.

Example 103D

A mixture of 0.35 g (2.0 mMol) of the product from example 103C, 0.4 g (13.3 mMol) of paraformaldehyde and a drop of glacial acetic acid in 1 mls of dichloroethane was stirred for 30 minutes at ambient temperature. 2.1 g (10 mMol) of sodium triacetoxyborohydride was added and the reaction stirred for 18 hours at ambient temperature. 100 mls of ethyl acetate was added and then washed with 10% $NaHCO_3$, 5% citric acid, saturated NaCl, the organic layer dried with $MgSO_4$, filtered and the solvent evaporated. The residue was purified by flash chromatography using a gradient from hexane to 50% ethyl acetate in hexane to provide Example 103D. LCMS m/z 180.0 $(M+H)^+$.

Example 103E

A reaction mixture of 0.35 g (2.0 mMol) of the compound from example 103D, 0.85 g (10 mMol) of methoxylamine hydrochloride in 2.0 mls of pyridine was stirred for 2 hours at room temperature. 100 mls of ethyl acetate was added and the organic layer extracted with water, organic layer was dried with $MgSO_4$, filtered and the solvent was evaporated. The residue was resuspended in 50% ethyl acetate in hexane and filtered through a silica plug to provide Example 103E. $^1H$ NMR (300 MHz, $CDCl_3$) δ ppm 7.87 (dd, J=8.65, 6.95 Hz, 1 H) 6.39-6.46 (m, 1 H) 6.35 (dd, J=12.04, 2.54 Hz, 1 H) 3.95 (s, 3 H) 3.17 (t, J=6.61 Hz, 2 H) 2.87 (s, 3 H) 2.86 (t, J=6.44 Hz, 2 H). MS (DCI/NH3) m/z 209.0 $(M+H)^+$.

Example 103F 0.4 g (2.0 mMol) of the compound from example 103E in 20 mls of 7N $NH_3$ in methanol and 4 g of Raney-Nickel are reacted in a Parr shaker under 60 psi of $H_2$ for 1.5 hours. The catalyst was filtered from the reaction and was washed with methanol, the solvent was evaporated and the compound used without further purification.

Example 103G

N-(7-fluoro-1-methyl-1,2,3,4-tetrahydroquinolin-4-yl)-N'-1H-indazol-4-ylurea

A reaction mixture of 0.3 g (1.7 mMol) of the compound from example 103F in 2 mls of N,N-dimethylformamide, 0.58 mls (3.3 mMol) of N,N-diisopropylethylamine and 0.5 g (1.7 mMol) of the compound from example 24D was stirred for 18 hours at ambient temperature. 50 mls of water was added to the reaction and the precipitate collected by filtration. The precipitate was solubilized in ethyl acetate and the organic phase extracted with water and saturated NaCl. The organic phase was dried with $MgSO_4$, filtered and the solvent evaporated. 2 mls of 5N NaOH in methanol was added to the residue and stirred at room temperature for 1 hour. 100 mls of ethyl acetate was added and the organic phase extracted with water and saturated NaCl. The organic phase was dried with MgSO$_4$, filtered and the solvent removed, and the residue purified by flash chromatography using 2% methanol in dichloromethane with a few drops of NH$_4$OH as the solvent system to provide the titled compound. $^1$H NMR (400 MHz, PYRIDINE-D5) δ ppm 14.36 (s, 1 H) 9.29 (s, 1 H) 8.47 (d, J=7.67 Hz, 1 H) 8.41 (s, 1 H) 7.46 (t, J=7.82 Hz, 1 H) 7.32-7.39 (m, 2 H) 7.08 (d, J=7.67 Hz, 1 H) 6.45 (td, J=8.29, 2.15 Hz, 1 H) 6.37 (dd, J=12.43, 1.99 Hz, 1 H) 5.27-5.35 (m, 1 H) 2.98-3.07 (m, 2 H) 2.57 (s, 3 H) 2.09-2.18 (m, 1 H) 1.97-2.07 (m, 1 H). MS ESI m/z 340.1 (M+H)$^+$.

Example 104

N-1H-indazol-4-yl-N'-[(6-methyl-3,4-dihydro-2H-chromen-2-yl)methyl]urea

Example 104A

A mixture of 11.8 g (80.6 mMol) of diethyl oxalate and 5.5 g (36.6 mMol) of 2'-hydroxy-5'-methylacetophenone was added dropwise to 56 mls of a 13% sodium ethoxidet/ethanol (110 mMol) over 20 minutes. The solution was heated to 80° C. for 1 hour then cooled to room temperature. 50 mls of water and 50 mls of diethyl ether were added and the suspension stirred, concentrated HCl (8-10 mls) was added to adjust the pH to about 2. The organic phase was separated, washed twice with saturated NaCl and dried with MgSO$_4$ and filtered. The solvent was evaporated and the oil redried from ethyl acetate to give a yellow solid. The solid was dissolved in 44 mls of glacial acetic acid and 12 mls of concentrated HCl then heated at 85° C. for 18 hours. The reaction was cooled, water was added and the reaction filtered to give a grey solid. $^1$H NMR (300 MHz, DMSO-d$_6$) δ ppm 7.83-7.85 (m, 1 H) 7.67-7.72 (m, 1 H) 7.61-7.66 (m, 1 H) 6.89 (s, 1 H) 2.44 (s, 3 H). MS ESI m/z 205.0 (M+H)$^+$.

Example 104B 3.5 g (17.1 mMol) of the compound from 104A was dissolved in 50 mls of glacial acetic acid with 0.35 g of 10% Pd/C and was hydrogenated at 70° C., 60 psi H$_2$ for 2.5 hours. The catalyst was filtered and washed and the solvent was evaporated. $^1$H NMR (300 MHz, CDCl$_3$) δ ppm 6.90-6.96 (m, 1 H) 6.83 (t, J=8.65 Hz, 2 H) 4.71 (dd, J=8.48, 3.39 Hz, 1 H) 2.72-2.86 (m, 2 H) 2.28-2.40 (m, 1 H) 2.25 (s, 3 H) 2.09-2.23 (m, 1 H). MS ESI m/z 210.1 (M+NH$_4$)$^+$.

Example 104C 3.3 g (17 mMol) of the compound from 104B was dissolved in 60 mls of dichloromethane, 0.1 mls of N,N-dimethylformamide then 4.5 mls of oxalyl chloride was added and the solution stirred for 30 minutes at ambient temperature. The solvent was evaporated and the residue dissolved in 30 mls of dichloromethane, 100 mls of 0.5 M NH$_3$ in dioxane was added and the reaction stirred for 18 hours at ambient temperature. The solution was filtered, the solvent evaporated, the residue dissolved in ethyl acetate and filtered through a silica plug and the solvent evaporated to provide Example 104C. $^1$H NMR (300 MHz, DMSO-d$_6$) δ ppm 7.35 (d, J=6.10 Hz, 2 H) 6.84-6.91 (m, 2 H) 6.73 (d, J=8.14 Hz, 1 H) 4.41 (dd, J=8.99, 3.22 Hz, 1 H) 2.70-2.82 (m, 1 H) 2.62 (dt, J=16.53, 5.30 Hz, 1 H) 2.19 (s, 3 H) 2.07-2.17 (m, 1 H) 1.79-1.94 (m, 1 H). MS ESI m/z 192.1 (M+H)$^+$.

Example 104D 1.0 g (5.2 mMol) of the compound from example 104C was dissolved in 20 mls of tetrahydrofuran, 16 mls (16 mMol) of 1.0 M LiAlH$_4$ in tetrahydrofuran was added slowly, the reaction was stirred for 3 hours at room temperature then was heated at 65° C. for 2 hours, then stirred 18 hours at room temperature. 1 mls of water was added dropwise, 30 mls of tetrahydrofuran, then 3 mls of 5% NaOH. The solution was filtered and the solvent evaporated. 50 mls of diethyl ether was added to the residue, dried over Na$_2$SO$_4$, filtered and the solvent evaporated to provide Example 104D. $^1$H NMR (300 MHz, DMSO-d$_6$) δ ppm 6.80-6.86 (m, 2 H) 6.58-6.63 (m, 1 H) 3.76-3.87 (m, 1 H) 3.33 (s, 2 H) 2.64-2.82 (m, 4 H) 2.17 (s, 3 H) 1.92-2.04 (m, 1 H) 1.50-1.68 (m, 1 H). MS ESI m/z 178.1 (M+H)$^+$.

Example 104E

N-1H-indazol-4-yl-N'-[(6-methyl-3,4-dihydro-2H-chromen-2-yl)methyl]urea

A reaction mixture of 0.4 g (2.3 mMol) of the compound from example 104D in 4 mls of N,N-dimethylformamide, 0.85 mls (4.8 mMol) of N,N-diisopropylethylamine and 0.8 g (2.3 mMol) of the compound from example 24D was stirred at ambient temperature for 18 hours. 50 mls of water was added to the reaction and the precipitate collected by filtration. The precipitate was solubilized in ethyl acetate and the organic phase extracted with water and saturated NaCl. The organic phase was dried with MgSO$_4$, filtered and the solvent evaporated. 2 mls of 5N NaOH in methanol was added to the residue and stirred at room temperature for 1 hour. 100 mls of ethyl acetate was added and the organic phase extracted with water and saturated NaCl. The organic phase was dried with MgSO$_4$, filtered and the solvent removed, and the residue purified by flash chromatography using a gradient from dichloromethane to 10% methanol in dichloromethane with a few drops of NH$_4$OH as the solvent system to provide the titled compound. $^1$H NMR (300 MHz, DMSO-d$_6$) δ ppm 12.98 (s, 1 H) 8.78 (s, 1 H) 8.09 (s, 1 H) 7.64 (d, J=7.12 Hz, 1 H) 7.20 (t, J=7.97 Hz, 1 H) 7.05 (d, J=8.14 Hz, 1 H) 6.84-6.91 (m, 2 H) 6.59-6.71 (m, 2 H) 4.02-4.11 (m, 1 H) 3.36-3.51 (m, 2 H) 2.74-2.88 (m, 1 H) 2.62-2.74 (m, 1 H) 2.19 (s, 3 H) 1.91-2.04 (m, 1 H) 1.61-1.76 (m, 1 H). MS ESI m/z 337.1 (M+H)$^+$.

(5) Determination of Biological Activity (a) In Vitro Data—Determination of Inhibition Potencies Dulbecco's modified Eagle medium (D-MEM) (with 4.5 mg/mL glucose) and fetal bovine serum were obtained from Hyclone Laboratories, Inc. (Logan, Utah). Dulbecco's phosphate-buffered saline (D-PBS) (with 1 mg/mL glucose and 3.6 mg/l Na pyruvate) (without phenol red), L-glutamine, hygromycin B, and Lipofectamine™ were obtained from Life Technologies (Grand Island, N.Y.). G418 sulfate was obtained from Calbiochem-Novabiochem Corp. (San Diego, Calif.). Capsaicin (8-methyl-N-vanillyl-6-nonenamide) was obtained from Sigma-Aldrich, Co. (St. Louis, Mo.). Fluo-4 AM (N-[4-[6-[(acetyloxy)methoxy]-2,7-difluoro-3-oxo-3H-xanthen-9-yl]-2-[2-[2-[bis[2-[(acetyloxy)methoxy]-2-oxyethyl]amino]-5-methylphenoxy]ethoxy]phenyl]-N-[2-[(acetyloxy)methoxy]-2-oxyethyl]-glycine, (acetyloxy) methyl ester) was purchased from Molecular Probes (Eugene, Oreg.).

The cDNAs for the human VR1 receptor were isolated by reverse transcriptase-polymerase chain reaction (RT-PCR) from human small intestine poly A+RNA supplied by Clontech (Palo Alto, Calif.) using primers designed surrounding the initiation and termination codons identical to the published sequences (Hayes et al. *Pain* Vol 88, pages 205-215, 2000). The resulting cDNA PCR products were subcloned into pCIneo mammalian expression vector (Promega) and fully sequenced using fluorescent dye-terminator reagents (Prism, Perkin-Elmer Applied Biosystems Division) and a Perkin-Elmer Applied Biosystems Model 373 DNA sequencer or Model 310 genetic analyzer. Expression plasmids encoding the hVR1 cDNA were transfected individually into 1321N1 human astrocytoma cells using Lipofectamine™. Forty-eight hours after transfection, the neomycin-resistant cells were selected with growth medium containing 800 µg/mL Geneticin (Gibco BRL). Surviving individual colonies were isolated and screened for VR1 receptor activity. Cells expressing recombinant homomeric VR1 receptors were maintained at 37° C. in D-MEM containing 4 mM L-glutamine, 300 µg/mL G418 (Cal-biochem) and 10% fetal bovine serum under a humidified 5% $CO_2$ atmosphere.

The functional activity of compounds at the VR1 receptor was determined with a $Ca^{2+}$ influx assay and measurement of intracellular $Ca^{2+}$ levels ($[Ca^2]i$). All compounds were tested over an 11-point half-log concentration range. Compound solutions were prepared in D-PBS (4× final concentration), and diluted serially across 96-well v-bottom tissue culture plates using a Biomek 2000 robotic automation workstation (Beckman-Coulter, Inc., Fullerton, Calif.). A 0.2 µM solution of the VR1 agonist capsaicin was also prepared in D-PBS. The fluorescent $Ca^{2+}$ chelating dye fluo-4 was used as an indicator of the relative levels of $[Ca^{2+}]i$ in a 96-well format using a Fluorescence Imaging Plate Reader (FLIPR) (Molecular Devices, Sunnyvale, Calif.). Cells were grown to confluence in 96-well black-walled tissue culture plates. Then, prior to the assay, the cells were loaded with 100 µL per well of fluo-4 AM (2 µM, in D-PBS) for 1-2 hours at 23° C. Washing of the cells was performed to remove extracellular fluo-4 AM (2×1 mL D-PBS per well), and afterward, the cells were placed in the reading chamber of the FLIPR instrument. 50 µL of the compound solutions were added to the cells at the 10th second time mark of the experimental run. Then, after a 3-minute time delay, 50 µL of the capsaicin solution was added at the 190-second time mark (0.05 µM final concentration) (final volume=200 µL) to challenge the VR1 receptor. Time length of the experimental run was 240 seconds. Fluorescence readings were made at 1 to 5 second intervals over the course of the experimental run. The peak increase in relative fluorescence units (minus baseline) was calculated from the 190th second time mark to the end of the experimental run, and expressed as a percentage of the 0.05 µM capsaicin (control) response. Curve-fits of the data were solved using a four-parameter logistic Hill equation in GraphPad Prism®(GraphPad Software, Inc., San Diego, Calif.), and $IC_{50}$ values were calculated.

The compounds of the present invention were found to be antagonists of the vanilloid receptor subtype 1 (VR1) receptor with $IC_{50s}$ from 6000 nM to 1 nM.

(b) In Vivo Data—Determination of Antinociceptive Effect

Experiments were performed on adult male 129J mice (Jackson laboratories, Bar Harbor, Me.), weighing 20-25 g. Mice were kept in a vivarium, maintained at 22° C., with a 12 hour alternating light-dark cycle with food and water available ad libitum. All experiments were performed during the light cycle. Animals were randomly divided into separate groups of 10 mice each. Each animal was used in one experiment only and was sacrificed immediately following the completion of the experiment. All animal handling and experimental procedures were approved by an IACUC Committee.

The antinociceptive test used was a modification of the abdominal constriction assay described in Collier, et al., *Br. J. Pharmacol. Chemother.* Vol. 32 pages 295-310 (1968). Each animal received an intraperitoneal (i.p.) injection of 0.3 mL of 0.6% acetic acid in normal saline to evoke writhing. Animals were placed separately under clear cylinders for the observation and quantification of abdominal constriction. Abdominal constriction was defined as a mild constriction and elongation passing caudally along the abdominal wall, accompanied by a slight twisting of the trunk and followed by bilateral extension of the hind limbs. The total number of abdominal constrictions was recorded from 5 to 20 minutes after acetic acid injection. The $ED_{50s}$ were determined based on the i.p. injection.

The other antinociceptive test used was Complete Freund's Adjuvant-induced Thermal Hyperalgesia (CFA) assay described in Pircio et al. *Eur J. Pharmacol.* Vol. 31 (2) pages 207-215 (1975). Chronic inflammatory hyperalgesia was induced in one group of rats following the injection of complete Freund's adjuvant (CFA, 50%, 150 µL) into the plantar surface of the right hindpaw 48 hours prior to testing. Thermal nociceptive thresholds were measured in three different groups of rats. The $ED_{50s}$ were determined based on the oral administration. The $ED_{50}$ values for two compounds tested were 30 and 70 µmol/kg.

The in vitro and in vivo data demonstrates that compounds of the present invention antagonize the VR1 receptor and are useful for treating pain.

Compounds of the present invention, as VR1 antagonists, are also useful for ameliorating or preventing additional disorders that are affected by the VR1 receptors such as, but not limited to, inflammatory thermal hyperalgesia, bladder overactivity, and urinary incontinence.

Compounds of the present invention, including but not limited to those specified in the examples, can be used to treat pain as demonstrated by Nolano, M. et al., *Pain* Vol. 81 pages 135-145 (1999); Caterina, M. J. and Julius, D., *Annu. Rev. Neurosci.* Vol. 24, pages 487-517 (2001); Caterina, M. J. et al., *Science* Vol. 288 pages 306-313 (2000); Caterina, M. J. et al., *Nature* Vol. 389, pages 816-824 (1997).

Compounds of the present invention, including but not limited to those specified in the examples, can be used to treat bladder overactivity and/or urinary incontinence as demonstrated by Fowler, C. *Urology* Vol. 55 pages 60-64 (2000).

Compounds of the present invention, including but not limited to those specified in the examples, can be used to treat inflammatory thermal hyperalgesia as demonstrated by Davis, J. et al., *Nature* Vol. 405 pages 183-187 (2000).

The present invention also provides pharmaceutical compositions that comprise compounds of the present invention. The pharmaceutical compositions comprise compounds of the present invention formulated together with one or more non-toxic pharmaceutically acceptable carriers. The pharmaceutical compositions can be specially formulated for oral administration in solid or liquid form, for parenteral injection or for rectal administration.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous and intraarticular injection and infusion.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions that can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals, which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), Poste et al., Chapter 4, p. 33 et seq.

Dosage forms for topical administration of a compound of this invention include powders, sprays, ointments and inhalants. The active compound may be mixed under sterile conditions with a pharmaceutically acceptable carrier and any needed preservatives, buffers or propellants that may be required. Ophthalmic formulations, eye ointments, powders and solutions are also contemplated as being within the scope of this invention.

Actual dosage levels of active ingredients in the pharmaceutical compositions of this invention can be varied so as to obtain an amount of the active compound(s), which is effective to achieve the desired therapeutic response for a particular patient, compositions and mode of administration. The selected dosage level will depend upon the activity of the particular compound, the route of administration, the severity of the condition being treated and the condition and prior medical history of the patient being treated.

When used in the above or other treatments, a therapeutically effective amount of one of the compounds of the present invention can be employed in pure form or, where such forms exist, in pharmaceutically acceptable salt, ester or prodrug form. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The compounds of the present invention can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well-known in the art. For example, S. M. Berge et al. describe pharmaceutically acceptable salts in detail in (*J. Pharmaceutical Sciences* Vol. 66, pages 1 et seq (1977). The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

The term "pharmaceutically acceptable prodrug" or "prodrug," as used herein, represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the present invention may be rapidly transformed in vivo to compounds of formula (I), for example, by hydrolysis in blood.

The present invention contemplates compounds of formula I formed by synthetic means or formed by in vivo biotransformation.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

The total daily dose of the compounds of this invention administered to a human or lower animal may range from about 0.01 to about 100 mg/kg/day. For purposes of oral administration, more preferable doses can be in the range of from about 0.1 to about 25 mg/kg/day. If desired, the effective daily dose can be divided into multiple doses for purposes of administration; consequently, single dose compositions may contain such amounts or submultiples thereof to make up the daily dose.

Compounds of the present invention were named by ACD/ChemSketch version 5.0 (developed by Advanced Chemistry Development, Inc., Toronto, ON, Canada) or were given names, which appeared to be consistent with ACD nomenclature.

What is claimed is:

1. A compound having formula (I):

(I)

or a pharmaceutically acceptable salt thereof, wherein:
$A_1$ is $CR^1$;
$A_2$ is $CR^2$;
$A_3$ is $CR^3$;
$A_4$ is $CR^4$;
$R^1$, $R^2$, $R^3$ and $R^4$ are each independently selected from the group consisting of alkyl, alkenyl alkynyl haloalkyl, halogen, hydrogen hydroxy, alkoxy, —$OR_c$, haloakoxy, —$NR_AR_B$, —$C(O)R_a$, —$C(O)OH$, —$C(O)Oalkyl$, —$S(alkyl)$, —$S(O)alkyl$, —$S(O)_2R_a$, $R_c$, —O-alkyl-$R_c$ and -alkyl-$R_c$;
X is $NR^5$;
Y is a bond;
L is $C_{1-10}$ alkyl;
$R^5$ is selected from the group consisting of hydrogen, alkyl, alkenyl, haloalkyl, —$C(O)R_a$, —$S(O)_2R_a$, $R_c$, and -alkyl-$R_c$;
$R_a$, is alkyl, haloalkyl, —$NH_2$, —$N(H)(alkyl)$, —$N(alkyl)_2$, $R_c$, or -alkyl-$R_c$;
m is 2;
n is 0;
$R^7$ and $R^8$, at each occurrence, are independently selected from the group consisting of hydrogen, alkyl, alkenyl, aryl, heteroaryl, cycloalkyl, cycloalkenyl, and -alkyl-$R_c$, wherein the aryl, heteroaryl, cycloalkyl and cycloalkenyl are each independently unsubstituted or substituted with 1, 2, 3 or 4 substituents selected from the group consisting of alkyl, haloalkyl, halogen, hydroxy, alkoxy, haloalkoxy, —$NH_2$, —$N(H)(alkyl)$, —$N(alkyl)_2$, —$N(H)C(O)alkyl$, —$N(alkyl)C(O)alkyl$, —$N(H)C(O))Oalkyl$, —$N(alkyl)C(O)Oalkyl$, —$C(O)alkyl$, —$C(O)OH$, —$C(O)Oalkyl$, —$C(O)NH_2$, —$C(O)N(H)(alkyl)$, —$C(O)N(alkyl)_2$, —$S(alkyl)$, —$S(O)alkyl$, —$S(O)_2alkyl$, —$S(O)_2N(H)_2$, —$S(O)_2N(H)(alkyl)$ and —$S(O)_2N(alkyl)_2$;
$R^9$ is hydrogen, alkyl, haloalkyl, hydroxy, alkoxy or haloalkoxy;
$R_A$ and $R_B$ are independently selected from the group consisting of hydrogen, alkyl, haloalkyl, $R_c$ and -alkyl-$R_c$,
Z is indazolyl that is unsubstituted or substituted with 1, 2, 3 or 4 substituents selected from the group consisting of alkyl, haloalkyl, halogen, hydroxy, alkoxy, haloalkoxy, —$NH_2$, —$N(H)(alkyl)$, —$N(alkyl)_2$, —$C(O)alkyl$, —$C(O)OH$, —$C(O)Oalkyl$, —$C(O)NH_2$, —$C(O)N(H)(alkyl)$, —$C(O)N(alkyl)_2$, —$S(alkyl)$, —$S(O)alkyl$, —$S(O)_2alkyl$, —$S(O)_2N(H)_2$, —$S(O)_2N(H)(alkyl)$, —$S(O)_2N(alkyl)_2$, $R_c$, and alkoxyalkyl; and
$R_c$ at each occurrence is independently a monocyclic or bicyclic ring, independently selected from the group consisting of cycloalkyl, cycloalkenyl, heterocycle, heteroarly and aryl; wherein each $R_c$ is independently unsubstituted or substituted with 1, 2, 3 or 4 substituents selected from the group consisting of alkyl, haloalkyl, halogen, oxo, hydroxy, alkoxy, haloalkoxy, —$NH_2$, —$N(H)(alkyl)$, —$N(alkyl)_2$, —$N(H)C(O)alkyl$, —$N(alkyl)C(O)alkyl$, —$N(H)C(O)Oalkyl$, —$N(alkyl)C(O)Oalkyl$, —$C(O)alkyl$, —$C(O)OH$, —$C(O)Oalkyl$, —$C(O)NH_2$, —$C(O)N(H)(alkyl)$, —$C(O)N(alkyl)_2$, —$S(alkyl)$, —$S(O)alkyl$, —$S(O)_2alkyl$, —$S(O)_2N(H)_2$, —$S(O)_2N(H)(alkyl)$ and —$S(O)_2N(alkyl)_2$.

2. The compound of claim 1, or a pharmaceutically acceptable salt thereof, wherein the compound is selected from the group consisting of:
N-[(1-benzyl-1,2,3,4-tetrahydroquinolin-2-yl)methyl]-N'-1H-indazol-4-ylurea;
methyl 4-{[({[1-(2-phenylethyl)-1,2,3,4-tetrahydroquinolin-2-yl]methyl}amino)-carbonyl]amino}-1H-indazole-1-carboxylate;
N-1H-indazol-4-yl-N'-{[1-(2-phenylethyl)-1,2,3,4-tetrahydroquinolin-2-yl]-methyl}urea;
N-1H-indazol-4-yl-N'-{[1-(3-phenylpropyl)-1,2,3,4-tetrahydroquinolin-2-yl]-methyl}urea;
methyl 4-{[({[1-(3-phenylpropyl)-1,2,3,4-tetrahydroquinolin-2-yl]methyl}amino)-carbonyl]amino}-1-1H-indazole-1-carboxylate;
N-1H-indazol-4-yl-N'-({1-[(trifluoromethyl)sulfonyl]-1,2,3,4-tetrahydroquinolin-2-yl}methyl)urea;
methyl 4-({[({1-[(trifluoromethyl)sulfonyl]-1,2,3,4-tetrahydroquinolin-2-yl}methyl)amino]carbonyl}amino)-1H-indazole-1-carboxylate;
N-{[1-(cyclohexylmethyl)-1,2,3,4-tetrahydroquinolin-2-yl]methyl}-N'-1H-indazol-4-ylurea;
methyl 4-{[({[1-(cyclohexylmethyl)-1,2,3,4-tetrahydroquinolin-2-yl]methyl}amino)carbonyl]amino}-1-H-indazole-1-carboxylate;
N-1H-indazol-4-yl-N'-[(1-propyl-1,2,3,4-tetrahydroquinolin-2-yl)methyl]urea;
methyl 4-[({[(1-propyl-1,2,3,4-tetrahydroquinolin-2-yl)methyl]amino}carbonyl)amino]-1H-indazole-1-carboxylate;
N-1H-indazol-4-yl-N'-{[1-(pyridin-2-ylmethyl)-1,2,3,4-tetrahydroquinolin-2-yl]methyl}urea;
methyl 4-({[({1-[2-(trifluoromethyl)benzyl]-1,2,3,4-tetrahydroquinolin-2-yl}methyl)amino]carbonyl}amino)-1H-indazole-1-carboxylate;
N-1H-indazol-4-yl-N'-({1-[2-(trifluoromethyl)benzyl]-1,2,3,4-tetrahydroquinolin-2-yl}methyl)urea;
N-1H-indazol-4-yl-N'-({1-[3-(trifluoromethyl)benzyl]-1,2,3,4-tetrahydroquinolin-2-yl}methyl)urea;
methyl 4-({[({1-[3-(trifluoromethyl)benzyl]-1,2,3,4-tetrahydroquinolin-2-yl}methyl)amino]carbonyl}amino)-1H-indazole-1-carboxylate;
N-1H-indazol-4-yl-N'-({1-[4-(trifluoromethyl)benzyl]-1,2,3,4-tetrahydroquinolin-2-yl}methyl)urea;
methyl 4-({[({1-[4-(trifluoromethyl)benzyl]-1,2,3,4-tetrahydroquinolin-2-yl}methyl)amino]carbonyl}amino)-1H-indazole-1-carboxylate;
(−)—N-[(1-benzyl-1,2,3,4-tetrahydroquinolin-2-yl)methyl]-N'-1H-indazol-4-ylurea;
(+)—N-[(1H-benzyl-1,2,3,4-tetrahydroquinolin-2-yl)methyl]-N'-1H-indazol-4-ylurea;

(−)—N-1H-indazol-4-yl-N'-({1-[3-(trifluoromethyl)benzyl]-1,2,3,4-tetrahydroquinolin-2-yl}methyl)urea;
(+)—N-1H-indazol-4-yl-N'-({1-[3-(trifluoromethyl)benzyl]-1,2,3,4-tetrahydroquinolin-2-yl}methyl)urea;
methyl 4-[({[(1-benzyl-6-fluoro-1,2,3,4-tetrahydroquinolin-2-yl)methyl]amino}-carbonyl)amino]-1H-indazole-1-carboxylate; and
N-[(1-benzyl-6-fluoro-1,2,3,4-tetrahydroquinolin-2-yl)methyl]-N'-1H-indazol-4-ylurea.

3. A compound having formula (I):

$$\text{(I)}$$

or a pharmaceutically acceptable salt thereof, wherein:
$A_1$ is $CR^1$;
$A_2$ is $CR^2$;
$A_3$ is $CR^3$;
$A_4$ is $CR^4$;
$R^1$, $R^2$, $R^3$ and $R^4$ are each independently selected from the group consisting of alkyl, alkenyl alkynyl haloalkyl, halogen, hydrogen hydroxy, alkoxy, —$OR_c$, haloakoxy, —$NR_AR_B$, —C(O)$R_a$, —C(O)OH, —C(O)Oalky, —S(alkyl), —S(O)alkyl —S(O)$_2R_a$, $R_c$, —O-alkyl-$R_c$ and -alkyl-$R_c$;
X is $NR^5$;
Y is a bond;
L is $C_{1-10}$ alkyl;
$R^5$ is selected from the group consisting of hydrogen, alkyl, alkenyl, haloalkyl, —C(O)$R_a$, —S(O)$_2R_a$, $R_c$, and -alkyl-$R_c$;
$R_a$, is alkyl, haloalkyl, —$NH_2$, —N(H)(alkyl), —N(alkyl)$_2$, $R_c$, or -alkyl-$R_c$;
m is 2;
n is 0;
$R^7$ and $R^8$, at each occurrence, are independently selected from the group consisting of hydrogen, alkyl, alkenyl, aryl, heteroaryl, cycloalkyl, cycloalkenyl, and -alkyl-$R_c$, wherein the aryl, heteroaryl, cycloalkyl and cycloalkenyl are each independently unsubstituted or substituted with 1, 2, 3 or 4 substituents selected from the group consisting of alkyl, haloalkyl, halogen, haydroxy, alkoxy, haloalkoxy, —$NH_2$, —N(H)(alkyl), —N(alkyl)$_2$, —N(H)C(O)alkyl, —N(alkyl)C(O)alkyl, —N(H)C(O))Oalkyl, —N(alkyl)C(O)Oalkyl, —C(O)alkyl, —C(O)OH, —C(O)Oalkyl, —C(O)$NH_2$, —C(O)N(H)(alkyl), —C(O)N(alkyl)$_2$, —S(alkyl), —S(O)alkyl, —S(O)$_2$alkyl, —S(O)$_2$N(H)$_2$, —S(O)$_2$N(H)(alkyl) and —S(O)$_2$N(alkyl)$_2$;
$R^9$ is hydrogen, alkyl, haloalkyl, hydroxy, alkoxy or haloalkoxy;
$R_A$ and $R_B$ are independently selected from the group consisting of hydrogen, alkyl, haloalkyl, $R_c$ and -alkyl-$R_c$,
Z is isoquinoliny that is unsubstituted or substituted with 1, 2, 3 or 4 substituents selected from the group consisting of alkyl, haloalkyl, halogen, hydroxy, alkoxy, haloalkoxy, —$NH_2$, —N(H)(alkyl), —N(alkyl)$_2$, —C(O)alkyl, —C(O)OH, —C(O)Oalkyl, —C(O)$NH_2$, —C(O)N(H)(alkyl), —C(O)N(alkyl)$_2$, —S(alkyl), —S(O)alkyl, —S(O)$_2$alkyl, —S(O)$_2$N(H)$_2$, —S(O)$_2$N(H)(alkyl), —S(O)$_2$N(alkyl)$_2$, $R_c$, and alkoxyalkyl; and
$R_c$ at each occurrence is independently a monocyclic or bicyclic ring, independently selected from the group consisting of cycloalkyl, cycloalkenyl, heterocycle, heteroarly and aryl; wherein each $R_c$ is independently unsubstituted or substituted with 1, 2, 3 or 4 substituents selected from the group consisting of alkyl, haloalkyl, halogen, oxo, hydroxy, alkoxy, haloalkoxy, —$NH_2$, —N(H)(alkyl), —N(alkyl)$_2$—N(H)C(O)alkyl, —N(alkyl)C(O)alkyl, —N(H)C(O)Oalkyl, —N(alkyl)C(O)Oalkyl, —C(O)alkyl, —C(O)OH, —C(O)Oalkyl, —C(O)$NH_2$, —C(O)N(H)(alkyl), —C(O)N(alkyl)$_2$, —S(alkyl), —S(O)alkyl, —S(O)$_2$alkyl, —S(O)$_2$N(H)$_2$, —S(O)$_2$N(H)(alkyl) and —S(O)$_2$N(alkyl)$_2$.

4. The compound of claim 3, or a pharmaceutically acceptable salt thereof, wherein the compund is selected from the group consisting of:
N-isoquinolin-5-yl-N'-{[1-(2-phenylethyl)-1,2,3,4-tetrahydroquinolin-2-yl]methyl}urea;
N-[(1-benzyl-1,2,3,4-tetrahydroquinolin-2-yl)methyl]-N'-isoquinolin-5-ylurea;
N-isoquinolin-5-yl-N'-{[1-(3-phenylpropyl)-1,2,3,4-tetrahydroquinolin-2-yl]methyl}urea; and
N-isoquinolin-5-yl-N'-(1,2,3,4-tetrahydroquinolin-2-ylmethyl)urea.

5. A pharmaceutical composition comprising a therapeutically effective amount of a compound of formula (I) as defined in claim 1 or a pharmaceutically acceptable salt thereof.

6. A method of treating a disorder wherein the disorder is ameliorated by inhibiting vanilloid receptor subtype 1 (VR1) receptor in a host mammal in need of such treatment comprising administering a therapeutically effective amount of a compound of formula (I) as defined in claim 1 or a pharmaceutically acceptable salt thereof, and wherein the disorder is selected form the group consisting of pain and urinary disorders.

7. The method of claim 6 wherein the disorder is selected from the group consisting of acute pain, chronic pain, inflammatory pain, osteoarthritic pain, cancer pain, lower back pain, bladder overactivity and urinary incontinence.

8. The method of claim 6 wherein the disorder is bladder overactivity.

9. The method of claim 6 wherein the disorder is urinary incontinence.

10. The method of claim 6 wherein the disorder is osteoarthritic pain.

11. The method of claim 6 wherein the disorder is inflammatory pain.

12. A pharmaceutical composition comprising a therapeutically effective amount of a compound of formula (I) as defined in claim 3 or a pharmaceutically acceptable salt thereof.

13. A method of treating a disorder wherein the disorder is ameliorated by inhibiting vanilloid receptor subtype 1 (VR1) receptor in a host mammal in need of such treatment comprising administering a therapeutically effective amount of a compound of formula (I) as defined in claim 3 or a pharmaceutically acceptable salt thereof, and wherein the disorder is selected form the group consisting of pain and urinary disorders.

14. The method of claim 13 wherein the disorder is selected form the group consisting of acute pain, chronic pain, inflammatory pain, osteoarthritic pain, cancer pain, lower back pain, bladder overactivity and urinary incontinence.

15. The method of claim 13 wherein the disorder is bladder overactivity.

16. The method of claim 13 wherein the disorder is urinary incontinence.

17. The method of claim 13 wherein the disorder is osteoarthritic pain.

18. The method of claim 13 wherein the disorder is inflammatory pain.

\* \* \* \* \*